US005882879A

United States Patent [19]
Veenstra et al.

[11] Patent Number: 5,882,879
[45] Date of Patent: Mar. 16, 1999

[54] METHOD FOR INFLUENCING β-LACTAM ANTIBIOTIC PRODUCTION AND FOR ISOLATION OF LARGE QUANTITIES OF ACV SYNTHETASE

[75] Inventors: Annemarie Veenstra, Nieuw Vennep, Netherlands; Juan Francisco Martin, Leon, Spain; Bruno Diez Garcia, San Sebastian, Spain; Santiago Gutierez, Leon, Spain; Jose Luis Barredo, Burgos, Spain; Eduardo Montenegro Prieto, Leon, Spain; Hans Von Doehren, Berlin, Germany; Harriet Palissa, Berlin, Germany; Henk Van Liempt, Berlin, Germany

[73] Assignee: Gist-Brocades, N.V., Delft, Netherlands

[21] Appl. No.: 222,617

[22] Filed: Apr. 4, 1994

Related U.S. Application Data

[63] Continuation-in-part of Ser. No. 658,398, Feb. 19, 1991, abandoned.

[30] Foreign Application Priority Data

| Feb. 28, 1990 | [EP] | European Pat. Off. ........... 90200475.3 |
| Feb. 28, 1990 | [EP] | European Pat. Off. ........... 90200488.6 |
| Jul. 2, 1990 | [EP] | European Pat. Off. ........... 90201768.0 |
| Oct. 3, 1990 | [EP] | European Pat. Off. ........... 90202628.5 |

[51] Int. Cl.⁶ ............................. C12P 37/00; C12N 15/31
[52] U.S. Cl. ........................ 435/43; 435/69.1; 435/252.3; 435/252.33; 435/252.35; 435/254.3; 435/254.11; 435/320.1; 435/254.5; 536/23.2
[58] Field of Search ........................ 435/43, 69.1, 172.3, 435/320.1, 252.3–252.35, 243, 254.1, 254.11, 254.5, 14.6, 254.3; 536/23.2, 23.7

[56] References Cited

FOREIGN PATENT DOCUMENTS

| 0 233 715 | 8/1987 | European Pat. Off. . |
| 0 260 762 | 3/1988 | European Pat. Off. . |
| 0 280 051 | 8/1988 | European Pat. Off. . |
| 0 320 272 | 6/1989 | European Pat. Off. . |
| 0 336 446 | 10/1989 | European Pat. Off. . |

OTHER PUBLICATIONS

*The Molecular Biology of the Cell* 2nd ed., Garland Publishing Inc., New York (1989) pp. 194–196.
Van Liempt et al., "(L–alpha–Aminoadipyl)–L–cysteinyl–D–valine Synthetase from *Aspergillus nidulans*", *J. Biol. Chem.* (1989) 264:3680–3684.
Banko et al., "(L–alpha–Aminoadipyl)–L–cysteinyl–D–valine Synthetase (ACV Synthetase): A Multifunctional Enzyme with Broad Substrate . . . ", *J. Amer. Chem. Soc.* (1987) 109:2858–2860.
MacCabe et al., "The *Aspergillus nidulans* npeA Locus Consists of Three Contiguous Genes Required for Penicillin Biosynthesis", *EMBO J.* (1990) 9:279–287.
Smith et al., "Cloning and Heterologous Expression of the Penicillin Biosynthetic Gene Cluster from *Penicillium Chrysogenum*", *Bio/Technology* (1990) 8:39–41.

Adlington et al., "A Study of the Biosynthesis of the Tripeptide (L–alpha–aminoadipyl)–L–cysteinyl–D–valine in a Beta–lactum Negative Mutant . . . " *Biochem J.* (1983) 213:573–576.
Jensen and Westlake, "Immobilization of Beta–lactum Synthesizing Enzymes", *Developments in Industrial Microbiology* (1989) 30:113–119.
Skatrud et al., "Use of Recombinant DNA to Improve Production of Cephalosporin C by *Cephalosporium Acremonium*", *Bio/Technology* (1989) 7:477–485.
Chen et al., "Cloning and Expression of a DNA Sequence Conferring Cephamycin C Production", *Bio/Technology* (1988) 6:1222–1224.
Miller and Ingolia, "Cloning and Characterization of Beta–lactum Biosynthetic Genes", *Mol. Microbiol.* (1989) 3:689–695.
Martin and Liras, "Enzymes Involved in Penicillin, Cephalosporin and Cephamycin Biosynthesis", *Advance in Biochemical Engineering/Biotechnology* (1989) 39:153–187.
Alvarez et al., "Purification to Homogeneity and Characterization of Acyl Coenzyme A:6–Aminopenicillanic Acid . . . " *Antimicrob. Agents and Chemother.* (1987) 31:1675–1682.
Veenstra et al., "Cloning of Penicillin Biosynthetic Genes", *Genetics and Mol. Biol. of Industrial Microorganisms* (1989) pp. 262–269.
Barredo et al., "Cloning and Characterization of the Acyl–coenzyme A:6–aminopenicillanic–acid–acyltransferase Gene of *Penicillium chrysogenum*", *Gene* (1989) 83:291–300.
Diez et al., "Two Genes Involved in Penicillin Biosynthesis are Linked in a 5.1 kb SalI Fragment in the Genome of *Penicillium chrysogenum*", *Mol. Gen. Genet.* (1989) 218:572–576.
Usui and Yu, "Purification and Properties of Isopenicillin N Epimerase from *Streptomyces clavuligerus*", *Biochimica et Biophysica* (1989) 999:78–85.
Kupka et al., "Partial Purification and Properties of the alpha–ketoglutarate–linked–ring–expansion Enzyme of Beta–lactam Biosynthesis of *Cephalosporium acremonium*", *FEMS Microbiol. Letters* (1983) 16:1–6.
Dotzlaf and Yeh, "Copurification and Characterization of Deacetoxycephalosporin C Synthetase/Hydroxylase from *Cephalosporium acremonium*", *J. Bacteriol.* (1987) 169:1611–1618.
Rollins et al., "Purification and Initial Characterization of Deacetoxycephalosporin C Synthase from *Streptomyces clavuligerus*", *Can. J. Microbiol.* (1988) 34:1196–1202.

(List continued on next page.)

Primary Examiner—James Martinell
Attorney, Agent, or Firm—McDonnell Boehnen Hulbert & Berghoff

[57] ABSTRACT

Novel methods and compositions are provided for the enhanced production of β-lactam antibiotics. The process is exemplified by the production of penicillin. In addition, the *P. chrysogenum* and *A. chrysogenum* δ-(L-α-aminoadipyl)-L-cysteinyl-D-valine synthetase genes have been isolated and sequenced. Also methods are provided for the production of δ-(L-α-aminoadipyl)-L-cysteinyl-D-valine synthetase using recombined DNA techniques.

30 Claims, 32 Drawing Sheets

OTHER PUBLICATIONS

Cortes et al., "Purification and Characterization of a 2–Oxoglutarate–linked ATP–independent Deacetoxycephalosporin C Synthase of *Streptomyces lactamdurans*", *J. Gen. Microbiol.* (1987) 133:3165–3174.

Samson et al., "Cloning and Expression of the Fungal Expandase/Hydroxylase Gene Involved in Cephalosporin Biosynthesis", *Bio/Technology* (1987) 5:1207–1214.

Kovacevic et al., "Cloning, Characterization, and Expression in *Escherichia coli* of the *Streptomyces clavuligerus* Gene Encoding Deacetoxycephalosporin C Synthetase", *J. Bacteriol.* (1989) 171:754–760.

von Dohren, "Applications of Multienzyme Systems in the Production of Peptide Antibiotics", *Peptide Antibiotics*, W. de Gruyter & Co., Berlin (1982) pp. 169–182.

Kratzschmar et al., "Gramicidin S Biosynthesis Operon Containing the Structural Genes grsA and grsB Has an Open Reading Frame . . . ", *Journ. of Bacteriol.* (1989) 171:5422–5429.

Ingolia and Queener, "Beta–Lactom Biosynthetic Genes", *Medicinal Research Reviews* (1989) 9:245–264.

Martin and Liras, "Biosynthesis of Beta–lactam Antibiotics:Design and Construction of Overproducing Strains", *Trends in Biotechnology* (1985) 3:39–44.

Revilla et al., "Glucose Represses Formation of (L–alpha–Aminoadipyl)–L–Cysteinyl–D–Valine and Isopenicillin N Synthase . . . "*J. Bacteriol.* (1986) 168:947–952.

Somerville, "The trp Promoter of *Escherichia coli* and its Exploitation in the Design of Efficient Protein Production Systems", *Biotechnology and Gen. Eng. Reviews* (1988) 6:1–41.

Luengo et al., "Lysine Regulation and Penicillin Biosynthesis in Low–producing and Industrial Strains of *Penicillium chrysogenum*", *J. Gen. Microbiol.* (1979) 115:207–211.

Barredo et al., "Glucokinase–Deficient Mutant of *Penicillium chrysogenum* Is Derepressed in Glucose Catabolite Regulation . . . ", *Antimicrob. Agents and Chemother.* (1988) 32:1061–1067.

Queener and Swartz, "Penicillins:Biosynthetic and Semisynthetic", *Secondary Products of Metabolism*, Rose (ed) Academic Press, London (1979) pp. 35–122.

Queener et al., "Cephalosporin C Fermentation:Biochemical and Regulatory Aspects of Sulfur Metabolism", *Biotech. of Indust. Antibiotics*, Vandamme (ed), Marcel Dekker Inc., New York, Basel (1984) pp. 141–170.

Zhang and Demain, "Purification from *Cephalosporium acremonium* of the Initial Enzyme Unique to the Biosynthesis of Penicillins and Cephalosporins", *Biochem. Biophys. Res. Comm.* (1990) 169:1145–1152.

Jhang et al., "Phosphate Regulation of ACV Synthetase and Cephalosporin Biosynthesis in *Streptomyces clavuligerus*", *FEMS Microbiol. Letters* (1989) 57:145–150.

Cohen et al., "Microbial Isopenicillin N Synthase Genes: Structure, Function, Diversity and Evolution", *Trends in Biotechnology* (1990) 8:105–111.

Weckermann et al., "Complete Nucleotide Sequence of the tycA Gene Coding the Tyrodcidine Synthetase 1 from *Bacillus brevis*", *Nucleic Acids Research* (1988) 16:11841.

Schweizer et al., "Rat Mammary Gland Fatty Acid Synthase: Localization of the Constituent Domains and Two Functional Polyadenylation/termination Signals in the cDNA", *Nucleic Acids Research* (1989) 17:567–586.

Yuan et al., "Molecular Cloning and Sequencing of DNA Complementary to Chicken Liver Fatty Acid Synthase mRNA", *PNAS* (1988) 85:6328–6331.

Dobson et al., "Conservation of High Efficiency Promoter Sequences in *Saccharomyces cerevisiae*", *Nucleic Acids Research* (1982) 10:2625–2637.

van Solingen et al., "Sequence of the *Penicillium chrysogenum* Phosphoglycerate Kinase Gene", *Nucleic Acids Research* (1988) 16:11823.

Thompson et al., "Physical Analysis of Antibiotic–resistance Genes from Streptomyces and Their Use in Vector Construction", *Gene* (1982) 20:51–62.

Katz et al., "Cloning and Expression of the Tyrosinase Gene from *Streptomyces antibioticus* in *Streptomyces lividans*", *Journal Gen. Microbiol.* (1983) 129:2703–2714.

De Boer, et al., "Construction of a Tandem trp–lac Promoter and a Hybrid trp–lac Promoter for Efficient and Controlled Expression of the Human Growth Hormone Gene in *Escherichia Coli,*" *Praeger Publishers* (1982) 462–481.

Diez, et al., "The Cluster of Penicillin Biosynthetic Genes", *The Journal of Biological Chemistry* (1990) 265:16358–16365.

Smith et al., "The Multifunctional Peptide Synthetase Performing the First Step of Penicilin Biosynthesis in *Penicillium Crysogenum* is a 421 073 Dalton Protein Similar to *Bacillus brevis* Peptide Antibiotic Synthetases", *The EMBO Journal* (1990) 9:2743–2750.

DISTRIBUTION OF β-LACTAM PRODUCING MICROORGANISMS

| Class of β-lactams | Fungi | Bacteria Gram positive | Bacteria Gram negative |
|---|---|---|---|
| PENAM | *Aspergillus*<br>*Penicillium*<br>*Epidemophyton*<br>*Trichophyton*<br>*Polypaecillum*<br>*Malbranchea*<br>*Pleurophomopsis* | | |
| CEPHEM | *Cephalosporium*<br>*Spiroidium*<br>*Scopulariopsis*<br>*Diheterospora*<br>*Peacilomyces* | *Streptomyces*<br>*Nocardia* | *Flavobacterium*<br>*Xanthomonas*<br>*Lysobacter* |
| CLAVAM | | *Streptomyces* | |
| CARBAPENEM | | *Streptomyces* | *Serratia*<br>*Erwinia* |
| MONOBACTAM | | *Nocardia* | *Pseudomonas*<br>*Gluconobacter*<br>*Chromobacterium*<br>*Agrobacterium*<br>*Acetobacter* |

FIG. 1

| | | |
|---|---|---|
| P. chrysogenum ACV Synthetase A(301-1068) | -----S | 301 |
| P. chrysogenum ACV Synthetase B(1397-2154) | -----S | 1397 |
| P. chrysogenum ACV Synthetase C(2474-3295) | RPTENG | 2479 |
| B. brevis Tyrocidine Synthetase I (1-798) | MLANQA | 6 |
| B. brevis Gramicidine Synthetase I(13-809) | QNKNGT | 18 |

| | |
|---|---|
| AEQKQ-QLEEWNNTDGEYPSSKRLHHLIEEVVERHEDKIAVVCDERELTY | 350 |
| SIQLE-QLAAWNATEAEFPDTT-LHEMFENEASQKPDKIAVVYEETSLTY | 1445 |
| DLHLPLAQSPLATTAEEQKVAS-LNQAFEREAFLAAEKIAVVQGDRALSY | 2528 |
| NLIDNKRELEQHALVPYAQGKS-IHQLFEEQAEAFPDRVAIVFENRRLSY | 55 |
| HEEEQYLFAVNNTKAEYPRDKT-IHQLFEEQVSKRPNNVAIVCENEQLTY | 67 |

| | |
|---|---|
| GELNAQGNSLARYLRS-IGILPEQLVALFLDKSEKLIVTILGVWKSGAAY | 399 |
| RELNERANRMAHQLRSDVSPNPNEVIALVMDKSEHMIVNILAVWKSGGAY | 1495 |
| ADLNGQANQLARYIQSVSCIGADDGIALMLEKSIDTIICILAIWKAGAAY | 2578 |
| QELNRKANQLARALLEKG-VQTDSIVGVMMEKSIENVIAILAVLKAGGAY | 104 |
| HELNVKANQLARIFIEKG-IGKDTLVGIMMEKSIDLFIGILAVLKAGGAY | 116 |

| | |
|---|---|
| VPIDPTYPDERVRFVLDDTKARAIIASNQHVERLQREVIGDRNLCIIRLE | 449 |
| VPIDPGYPNDRIQYILEDTQALAVIADSCYLPRI-KGMAASGTL----LY | 1540 |
| VPLDPTYPPGRVQLILEEIKAKAVLVHSSHASKC-ERHGAKVIA----VD | 2623 |
| VPIDIEYPRDRIQYILQDSQTKIVLTQKS-VSQ--LVHDVGYSG----EV | 147 |
| VPIDIEYPKERIQYILDDSQARMLLTQKH-LVH--LIHNIQFNG----QV | 159 |

| | |
|---|---|
| PLLASLAQDSSKFPAHNLDDLPLTSQQLAYVTYTSGTTGFPKGIFKQHTN | 499 |
| PSVLPANPDS-KWSVSNPSPLS-RSTDLAYIIYTSGTTGRPKGVTVEHHG | 1588 |
| SPAIETAVSQ-Q-SAADLPTIA-SLGNLAYIIFTSGTSGKPKGVLVEQKA | 2670 |
| VVLDEEQLDA--RETANLHQPS-KPTDLAYVIYTSGTTGKPKGTMLEHKG | 194 |
| EIFEEDTIKI--REGTNLHVPS-KSTDLAYVIYTSGTTGNPKGTMLEHKG | 206 |

| | |
|---|---|
| VVNSITDLSARYGVAG-QHHEA-ILLFSACVFEPFVRQTLMALVNGHLLA | 547 |
| VVNLQVSLSKVFGLRD-TDDEV-ILSFSNYVFDHFVEQMTDAILNGQTLL | 1636 |
| VLLLRDALRERYFGRDCTKHHG-VLFLSNYVFDFSVEQLVLSVLSGHKLI | 2719 |
| I-AICNPFSKIRLASPSKTGSG-FLPACRSTHPFGKCSW-LCCL-APRVH | 240 |
| I-SNLKVFFENSLNVTEKDRIGQFASISFDASVWEMFMA-LLTG-ASLYI | 253 |

FIG. 13A

```
VINDVEKYDADTLLPFIRRHSITYLNGTASVLQEYDFSDCP-SLNRIILV    596
VLNDGMRGDKERLYRYIEKNRVTYLSGTPSVVSMYEFSRFKDHLRRVDCV   1686
VPPAEFVADDE-FYRMASTHGLSYLSGTPSLLQKIDLARL-DHLQVVTAA   2767
PSKQTIHDFAA-FEHYLSENELTIITLPPTYLTHLTPERI-TSLRIMITA    288
ILKDTINDFVK-FEQYINQKEITVITLPPTIVVHLDPERI-LSIQTLITA    301

GENLTEARYLALRQRFKNRILNEYGFTESAFVTALKIFDPESTRKDTSLG    646
GEAFSEPVFDKIRETFHGLVINGYGPTEVSITTHKRLYPFPERRMDKSIG   1736
GEELHATQYEKMRRRFNGPIYNAYGVTETTVYNIIAEFT-TNSIFENALR   2816
GSASSAPLVNKWKDKL--RYINAYGPTETSICATIWEAP-SNQLSVQSVP    335
GSATSPSLVNKWKEKV--TYINAYGPTETTICATTWVAT-KETIG-HSVP    347

--RPVRNVKCYILNPSLKRVPIGATGELHIGGLGISKGYLNRPELTPHRF    694
--QQVHNSTSYVLNEDMKRTPIGAVGELYLGGEGVVRGYHNRADVTAERF   1784
--EVLPGTRAYVLNAALQPVPFDAVGELYLAGDSVTRGYLNQPLLTDQRF   2864
IGKPIQNTHIYIVNEDLQLLPTADEGELCIGGVGLARGYWNRPDLTAEKF    385
IGAPIQNTQIYIVDENLQLKSVGEAGELCIGGEGLARGYWKRPELTSQKF    397

IPNPFQTDCEKQLGINSLMYKTGDLAR--WLP--NGEVEYLGRADFQIKL    740
IPNPFQSEEDKREGRNSRLYKTGDLVR--WIPGSSGEVEYLGRNDFQVKI   1832
IPNPFCKEEDIAMGRFARLYKTGDLVRSRFNRQQQPQLEYLGRGDLQIKM   2914
VDNPF-------VPGEKMYRTGDL----AKWLTDGTIEFLGRIDHQVKI    423
VDNPF-------VPGEKLYKTGDQ----ARWLSDGNIEYLGRIDNQVKI    435

RGIRIEPGEIETMLAMYPRVRTSLVVSKKLRNGPEETTNEHLVGYYVCDS    790
RGLRIELGEIEAILSSYHGIKQSVVIAKDCREG----AQKFLVGYYVADA   1878
RGYRIEISEVQNVLTSSPGVREGAVVAKYENNDTYSRTAHSLVGYYTTDN   2964
RGHRIELGEIESVLLAHEHITEAVVIAR-----EDQHAGQYLCAYYISQQ    468
RGHRVELEEVESILLKHMYISETAVSVH-----KDHQEQPYLCAYFVSEK    480

ASVSEADLLSFLEKKLPRYMIPTRLV-QLSQIPVNVNGKADLRALPAV--    837
A-LPSAAIRRFMQSRLPGYMVPSRLI-LVSKFPVTPSGKLDTKALPPA--   1924
ETVSEADILTFMKARLPTYMVPSHLCCLEGALPVTINGKLDVRRLPE--I   3012
EATP-AQLRDYAAQKLPAYMLPSYFVKLD-KMPLTPNDKIDRKALPEPDL    516
HIPL-EQLRQFSSEELPTYMIPSYFIQLD-KMPLTSNGKIDRKQLPEPDL    528
```

FIG. 13B

```
-DISNSTEVRSDLRGDTEIALGEIWADVLGARQRSVSRNDNFFRLGGHSI    886
-EEESEIDVVPP-RSEIERSLCDIWAELLEMHPEEIGIYSDFFSLGGDSL   1972
INDSAQSSYSPP-RNIIEAKMCRLWESALGM--ERCGIDDDLFKLGGDSI   3059
TANQSQAAYHPP-RTETESILVSIWQNVLGI--EKIGIRDNFYSLGGDSI    563
TFGM-RVDYEAP-RNEIEETLVTIWQDVLGI--EKIGIKDNFYALGGDSI    574

TCIQLIARIRQRQRLSVSISVEDVFATRTLERMADLLQNKQQEKCD-KPH    935
KSTKL--SFMIHESFNRAVSVSALFCHRTVEAQTHLILNDAADVHEITPI   2020
TSLHL--VAQIHNQVGCKITVRDIFEHRTARALHDVFMKDSDRSNVTQF   3107
QAIQV--VARLHS-YQLKLETKDLLNYPTIEQV--ALFVKSTTRKSDQGI    608
KAIQV--AARLHS-YQLKLETKDLLKYPTIDQL--VHYIKDSKRRSEQGI    619

E-APTELL---EENAATDNIYLANSLQQGFVYHYLKSMEQSDAYVMQSVL    981
DCNDTQMI---PVSRAQERLLFIHEFENGSNAYNIDAAFELPGSVDASLL   2067
RTEQGPVIGEAPLLPIQDWFL-SKALQH--PMYWNHTFYVRTPELDVDSL   3154
IAGNVPLTPIQKWF-----FG-KNFTNT--GHWNQSSVLYRPEGFDPKVI    650
VEGEIGLTPIQHWF-----FE-QQFTNM--HHWNQSYMLYRPNGFDKEIL    661

RYNTTLSPDLFQRAWKHAQQSFPALR--LRFSWEKEVFQLLDQDP-PLDW   1028
EQALRGNLARHEALRTLLVKDHATGI--YLQKVLSPDEAQGMFSV-NVDT   2114
SAAVRDLQQYHDVFRMRLKREEVGFVQ-SFAEDFSPAQLRVLNVK-DVDG   3202
QSVMDKIIEHHDAVRMVYQHENGNVVQHNRGLGGQLYDFFSYNLTAQPDV    700
LRVFNKIVEHHDALRMIYKHHNGKIVQINRGLEGTLFDFYTFDLTANDNE    711

RFLYFTDVAAGAVEDRKLEDLRRQDLTERFKLDVGRLFRV             1068
AKQVERLDQEIASLSQHVFRLDDELPWEARILKLESGGLY             2154
SAAVNEILDGWQSGFNLENGPIGSIGYLHGYEDRSARVWFSVHHMAIDTV   3252
QQAIEAETQRLHSSMNLQEGPLVKVALFQTL--HGDHFFLAIHHLVVDGI    748
QQVICEESARLQNSINLEVGPLVKIALFHTQ--NGDHLFMAIHHLVVDGI    759

SWQILVRDLQTLYRNGSLGSKGSSFRQWA---EAIQNYKASDSERN----   3295
SWRILFKIWQPDTRRHLQGKRSVCPKKRILFKAGHNGCKNNANEADLLSE    798
SWRILFEDLATAYEQAMHQQTIALPEKTDSFKDWSIELEKYANSELFLEE    809
```

FIG. 13C

```
Pc ACVS P                                                    LIMITS:    3563   364
ratfas 3563  E  R  P  L  F  L  L  P  P  P  G  E  G  G  A  E  S  Y  F  N
  1   E  I  .. L  F  .. .. V  H  P  I  E  -- S  A  T  V  H  -- H 3580  L  V  K  R  L  L  R  Q  T  N  M  Y  G  F  N  N  Y  Y  L  S
 21   .. .. A  A  K  .. S  V  P  .. Y  .. V  -- I  .. C  -- H  ..

3600  K  R  L  L  D  T  F  E  P  E  L  A  Y  Y  Q  C  D  Q  T  A
 38   A  P  -- L  L  S  T  E  N  L  -- A  M  -- L  -- I  -- R  ..

3620  Q  P  H  G  P  Y  H  R  V  A  F  I  G  Y  G  G  I  V  K  I
 58   Q  P  E  G  P  Y  .. R  V  A  Y  S  -- S  G  A  C  L  .. ..

3640  M  S  R  R  L  V  A  S  Q  A  Q  Q
 78   M  C  S  Q  L  Q  A  Q                                  LIMITS:   3563   364

Matches = 27        Mismatches = 55       Unmatched = 7
Length = 89         Matches/length = 30.3 perc

DOMAINS AND SUBDOMAINS WITHIN THE ACVS PROTEIN

| Domain | Position (amino acid) | Function | Subdomains |
|---|---|---|---|
| I. | 301-1068 | activation of amino acid substrate | 374- 423<br>474- 501<br>655- 699<br>725- 754 |
| II. | 1392-2154 | idem | 1470-1518<br>1564-1590<br>1745-1789<br>1817-1846 |
| III. | 2474-3295 | idem | 2554-2603<br>2647-2673<br>2827-2871<br>2899-2928 |
| IV. | 3560-3647 | thioesterase | |

FIG. 15

|  | Hybridization with the | |
|---|---|---|
| Probes | 11.4-kb transcript (pcbAB) | 1.15-kb transcript (pcbC) |
| $P_1$ SalI 3.2-kb | + | − |
| $P_2$ SalI 6.2-kb | + | − |
| $P_3$ SalI 7.3-kb | − | + |
| $P_4$ SalI-BamHI 1.7-kb | − | + |
| $P_5$ SalI-BamHI 0.75-kb | + | − |
| $P_6$ XhoI 0.9-kb | + | − |
| $P_7$ AccI 0.5-kb | + | − |
| $P_8$ BamHI-BstXI 0.5-kb | − | − |

FIG. 17B

```
A.chrysogenum ACV Synthetase  (1,3665)                    VA          02
P.chrysogenum ACV Synthetase  (62,3727)              RVRFRGG          68

LEQWKTTVQSVSERCDLSGLSQHPTDYQLASTGVKGAGGSSIEERSAIVS               52
IERWKECVNQVPERCDLSGLTTDSTRYQLASTGF-GDASAAYQERLMTVP              117

DELFSSLRDVCSQRQLDPRSLMLFSVHQMLKRFGNGSHTVVASLVTSSEG              102
VDVHAALQELCLERRVSVGSVINFSVHQMLKGFGNGTHTITASLHREQNL              167

CPSTSAWRAIPSVIHHIEGGDNNNTVASAVEQAANLLNSEGSGQDLLIPI              152
QNSSPSWVVSPTIVTH--ENRDGWSVAQAVE---SIEAGRGSEKESVTAI              212

GL-TELVKSELIDLLVIFDDETNNIRLP-QDFPLILRIHQRQDHWQLSVR              200
DSGSSLVKMGLFDLLVSFVD-ADDARIPCFDFPLAVIVRECDANLSLTLR              261

YPSPLFDTMVIDSFLSALHNLLS-AVTKPSQLVRDIELLPEYQVAQLEKW              249
FSDCLFNEETICNFTDALNILLAEAVIGRVTPVADIELLSAEQKQQLEEW              311

NNTDGDYPTEKRLHHLFEEAAVRRPQHVALICGDKRITYEELNAMANRLA              299
NNTDGEYPSSKRLHHLIEEVVERHEDKIAVVCDERELTYGELNAQGNSLA              361

HHLVSSGIQTEQLVGLFLDKTELMIATILGIWKSGAAHVPIDPGYPDERV              349
RYLRSIGILPEQLVALFLDKSEKLIVTILGVWKSGAAYVPIDPTYPDERV              411

KFVLNDTKAQVVIASQRHVDRLRAEAVGGQHLRIIGLESLFDNLAQQTQH              399
RFVLDDTKARAIIASNQHVERLQREVIGDRNLCIIRLEPLLASLAQDSSK              461

SPETSGNLTHLPLNSKQLAYVTYTSGTTGFPKGIYKEHTSVVNSITDLSA              449
FP--AHNLDDLPLTSQQLAYVTYTSGTTGFPKGIFKQHTNVVNSITDLSA              509
```

FIG. 18A

```
RYGVAGEDDEVILVFSAYVFEPFVRQMLMALTTGNSLAIISDEDKFDPDT    499
RYGVAGQHHEAILLFSACVFEPFVRQTLMALVNGHLLAVINDVEKYDADT    559

LIPFIQKHKVTYIHATSSVLQEYDFGSCPSLKRMILVGENLTEPRYEALR    549
LLPFIRRHSITYLNGTASVLQEYDFSDCPSLNRIILVGENLTEARYLALR    609

QRFKSRILNEYGFTESAFVTALNIFEPTSQRKDMSLGRPVRNVKCYILDA    599
QRFKNRILNEYGFTESAFVTALKIFDPESTRKDTSLGRPVRNVKCYILNP    659

NLKRVPIGVTGELHIGGLGISRGYMNREELTRQKFLPNPYQTDKERQRGV    649
SLKRVPIGATGELHIGGLGISKGYLNRPELTPHRFIPNPFQTDCEKQLGI    709

NSTMYKTGDLARWLPSGEVEYLGRADFQIKLRGIRIEPGEIESTLAMYPG    699
NSLMYKTGDLARWLPNGEVEYLGRADFQIKLRGIRIEPGEIETMLAMYPR    759

IRASIVVSKKLLSQGQETIQDHLVGYYVCDEGHIPEGDLLSFLEKKLPRY    749
VRTSLVVSKKLRNGPEETTNEHLVGYYVCDSASVSEADLLSFLEKKLPRY    809

MVPTRLVQLAQIPTNINGKADLRALPAVEVAVAPTHKQDGERGNQLESDL    799
MIPTRLVQLSQIPVNVNGKADLRALPAVDIS-NSTEVRSDLRGDT-EIAL    857

AAIWGNILSVPAQDIGSESNFFRLGGHSIACIQLIARV--RQQLGQGITL    847
GEIWADVLGARQRSVSRNDNFFRLGGHSITCIQLIARIRQRQRLSVSISV    907

EEVFQTKTLRAMAALLSEKYTKASNGTNGVTNGTAHVNGHAANGHVSDSY    897
EDVFATRTLERMADLLQNK--QQEKCDKPHEAPTELLEENAATDNI---Y    952

VASSLQQGFVYHSLKN-ELSEAYTMQSMIHYGVPLKRDIYQAAWQRVQGE    946
LANSLQQGFVYHYLKSMEQSDAYVMQSVLRYNTTLSPDLFQRAWKHAQQS   1002
```

FIG. 18B

```
HPALRLRFTWEAEVMQIVDPKSELDWRVVDWTDVSSREKQLVALEQLQTE          996
FPALRLRFSWEKEVFQLLDQDPPLDWRFLYFTDVAAGAVEDRKLEDLRRQ         1052

DLAKVYHLDKGPLMRLYLILLPDSKYSCLFSCHHAILDGWSLPLLFNNVH         1046
DLTERFKLDVGRLFRVYLIKHSENRFTCLFSCHHAILDGWSLPLLFEKVH         1102

QAYLDLVEGTASPVEQDATYLLGQQYLQSHRDDHLDFWAEQIGRIEERCD         1096
ETYLQLLHGDNLTSSMDDPYTRTQRYLHAHREDHLDFWAGVVQKINERCD         1152

MNALLNEASRYKVPLADYDQVREQRQQTISLPWNNSMDAGVREELSSRGI         1146
MNALLNERSRYKVQLADYDQVQEQRQLTIALSGDAWL-ADLRQTCSAQGI         1201

TLHSILQTVWHLVLHSYGGGTHTITGTTISGRHLPVPGIERSVGLFINTL         1196
TLHSILQFVWHAVLHAYGGGTHTITGTTISGRNLPILGIERAVGPYINTL         1251

PMIFDHTVCQDMTALEAIEHVQGQVNAMNSRGNVELGRMSKNDLKHGLFD         1246
PLVLDHSTFKDKTIMEAIEDVQAKVNVMNSRGNVELGRLHKTDLKHGLFD         1301

TLFVLENYPNLDTEQREKHEEKLKFTIKGGTEKLSYPLAVIAQE-DGDSG         1295
SLFVLENYPNLDKSRTLEHQTELGYSIEGGTEKLNYPLAVIAREVETTGG         1351

CSFTLCYAGELFTDESIQALLDTVRDTLSDILGNIHAPIRNMEYLSSNQT         1345
FTVSICYASELFEEVMISELLHMVQDTLMQVARGLNEPVGSLEYLSSIQL         1401

AQLDKWNATAFEYPNTTLHAMFESEAQQKPDKVAVVYEDIRLTYRELNSR         1395
EQLAAWNATEAEFPDTTLHEMFENEASQKPDKIAVVYEETSLTYRELNER         1451

ANALAFYLLSQAAIQPNKLVGLIMDKSEHMITSILAVWKTGGAYVPIDPR         1445
ANRMAHQLRSDVSPNPNEVIALVMDKSEHMIVNILAVWKSGGAYVPIDPG         1501
```

FIG. 18C

```
YPDQRIQYILEDTAALAVITDSPHIDRLRSITNNRLPVIQSDFALQLPPS           1495
YPNDRIQYILEDTQALAVIADSCYLPRIKGMAASGTLLYPSVLPANPDSK           1551

--PVHPVSNCKPSDLAYIMYTSGTTGNPKGVMVEHHGVVNLCVSLCRLFG           1543
WSVSNPSPLSRSTDLAYIIYTSGTTGRPKGVTVEHHGVVNLQVSLSKVFG           1601

LRNTDDEVILSFSNYVFDHFVEQMTDALLNGQTLVVLNDEMRGDKERLYR           1593
LRDTDDEVILSFSNYVFDHFVEQMTDAILNGQTLLVLNDGMRGDKERLYR           1651

YIETNRVTYLSGTPSVISMYEFDRFRDHLRRVDCVGEAFSEPVFDKIRET           1643
YIEKNRVTYLSGTPSVVSMYEFSRFKDHLRRVDCVGEAFSEPVFDKIRET           1701

FPGLIINGYGPTEVSITTHKRPYPFPERRTDKSIGCQLDNSTSYVLNDDM           1693
FHGLVINGYGPTEVSITTHKRLYPFPERRMDKSIGQQVHNSTSYVLNEDM           1751

KRVPIGAVGELYLGGDGVARGYHNRPDLTADRFPANPFQTEQERLEGRNA           1743
KRTPIGAVGELYLGGEGVVRGYHNRADVTAERFIPNPFQSEEDKREGRNS           1801

RLYKTGDLVRWIHNANGDGEIEYLGRNDFQVKIRGQRIELGEIEAVLSSY           1793
RLYKTGDLVRWIPGSSG--EVEYLGRNDFQVKIRGLRIELGEIEAILSSY           1849

PGIKQSVVLAKDRKNDGQKYLVGYFVSSAGSLSAQAIRRFMLTSLPDYMV           1843
HGIKQSVVIAKDCREGAQKFLVGYYVADAA-LPSAAIRRFMQSRLPGYMV           1898

PAQLVPIAKFPVTVSGKLDAKALPVPDDTVEDDIVPPRTEVERILAGIWS           1893
PSRLILVSKFPVTPSGKLDTKALPPAEEESEIDVVPPRSEIERSLCDIWA           1948

ELLEIPVDRISIYSDFFSLGGDSLKSTKLSFAATRALGVAVSVRNLFSHP           1943
ELLEMHPEETGIYSDFFSLGGDSLKSTKLSFMIHESFNRAVSVSALFCHR           1998
```

FIG. 18D

```
TIEALSQWIIRGSNEVKDVAVVKGGASLDIPLSPAQERLMFIHEFGHSGE      1993
TVEAQTHLILNDAADVHEITPIDCNDTQMIPVSRAQERLLFIHEF---EN      2045

DTGAYNVPLQLQLHHDVCLESLEKALRDVVSRHEALRTLITRTQKSSVHC      2043
GSNAYNIDAAFELPGSVDASLLEQALRGNLARHEALRTLLVKDHATGIYL      2095

QKILDAEEAQKLFSVDVLRLTSETEMQGRMAESTAHAFKLDEELPIHVRL      2093
QKVLSPDEAKGMFSVNVDTAKQVERLDQEIASLSQHVFRLDDELPWEARI      2145

YQVVRDGRTLSFASIVCHHLAFDAWSWDVFQRDLDAFYAVHTKHKAAANL      2143
LKLESGG--L-YLILAFHHTCFDAWSLKVFEQELRALYAALQKTKSAANL      2192

PTLRVQYKEYAIEHRRALRAEQHRVLADYWLRKLSDMEASYLVPDRPRPA      2193
PALKAQYKEYALYHRRQLSGDRMRNLSDFWLRKLIGLEPLQLITDRPRPV      2242

QFDYTGNDLQFSTTPETTAQLKELAKREGSSLYTVVAAAYFLLLYVYTNQ      2243
QFKYDGDDLSIELSKKETENLRGVAKRCKSSLYVVLVSVYCVMLASYANQ      2292

RDITIGIPVAHRNHPDFESVVGFFVNLLPLRVNVSQSDIHGLIQAVQKEL      2293
SDVSVGIPVSHRTHPQFQSVIGFFVNLVVLRVDISQSAICGLIRRVMKEL      2342

VDAQIHQDLPFQEITKLLHVQHDPSRHPLLQAVFNWENVPANVH------      2337
VDAQLHQDMPFQEVTKLLQVDNDPSRHPLVQNVFNFESRANGEHDARSED      2392

EEQL-LQEYKPPSPLPSAAKFDLNVTVKESVNSLNVNFNYPTSLFEEETV      2386
EGSLAFNQYRPVQPVDSVAKFDLNATVTELESGLRVNFNYATSLFNKSTI      2442

QGFMETFHLLLRQLAH-----NKASTSLSKL-SVEDGVLN---PEPTNLQ      2427
QGFLHTYEYLLRQLSELSAEGINEDTQLSLVRPTENGDLHLPLAQSPLAT      2492
```

FIG. 18E

```
PSSRDSGNSLHGLFEDIVASTPDRIAIADGTRSLSYSELNERANQLVHLI     2477
TAEEQKVASLNQAFEREAFLAAEKIAVVQGDRALSYADLNGQANQLARYI     2542

ISSASIVADDRIALLLDKSIDMVIALLAVWKAGAAYVPLDPTYPSQRTEL     2527
QSVSCIGADDGIALMLEKSIDTIICILAIWKAGAAYVPLDPTYPPGRVQL     2592

ILEESSARTLITTRKHTPRGGTVANVPSVVLDSPETLACLNQQSKENPTT     2577
ILEEIKAKAVLVHSSHASKCERHGA-KVIAVDSPAIETAVSQQSAADLPT     2641

STQKPSDLAYVIFTSGTTGKPKGVLVEHQSVVQLRNSLIERYFG-ETNGS     2626
IA-SLGNLAYIIFTSGTSGKPKGVLVEQKAVLLLRDALRERYFGRDCTKH     2690

HAVLFLSNYVFDFSLEQLCLSVLGGNKLIIPPEEGLTHEAFYDIGRREKL     2676
HGVLFLSNYVFDFSVEQLVLSVLSGHKLIVPPAEFVADDEFYRMASTHGL     2740

SYLSGTPSVLQQIELSRLPHLHMVTAAGEEFHASQFEKMRSQFAGQINNA     2726
SYLSGTPSLLQKIDLARLDHLQVVTAAGEELHATQYEKMRRRFNGPIYNA     2790

YGITETTVYNIITTFKGDAPFTKALCHGIPGSHVYVLNDRLQRVPFNAVG     2776
YGVTETTVYNIIAEFTTNSIFENALREVLPGTRAYVLNAALQPVPFDAVG     2840

ELYLGGDCLARGYLNQDALTNERFIPNPFYEPKQASDSRPQRLYKTGDLV     2826
ELYLAGDSVTRGYLNQPLLTDQRFIPNPFCKEEDIAMGRFARLYKTGDLV     2890

--RF--RGPHHLEYLGRKDQQVKLRGFRIELSEVRDAVLAISAVKEAAVI     2872
RSRFNRQQQPQLEYLGRGDLQIKMRGYRIEISEVQNVLTSSPGVREGAVV     2940

PKYDEDGSDSRRVSAIVCYYTLNAGTVCEASSIRDHLHANLPPYMVPSQI     2922
AKYENNDTYSRTAHSLVGYYTTDNETVSEADIL-TFMKARLPTYMVPSHL     2989
```

FIG. 18F

```
HQLEGSLPVTVNGKLDLNRLS-TTQVSQPELYTAPRNSTEETLCQLWASL      2971
CCLEGALPVTINGKLDVRRLPEIINDSAQSSYSPPRNIIEAKMCRLWESA      3039

LGVDHCGIDDDLFARGGDSISSLRLVGDIYRALGRKVTVKDIYLHRSVRA      3021
LGMERCGIDDDLFKLGGDSITSLHLVAQIHNQVGCKITVRDIFEHRTARA      3089

LSENVLTDQKDKGTLPASPPLQRAEQGQVEGDAPLLPIQDWFLSKPLDNP      3071
LHDHVFMKDSDRSNV---TQF-RTEQGPVIGEAPLLPIQDWFLSKALQHP      3135

AYWNHCFTIRTGALSVEGLRGALKLLQERHDVLRLRLQRRDEGRHVQTFA      3121
MYWNHTFYVRTPELDVDSLSAAVRDLQQYHDVFRMRLKREEVG-FVQSFA      3184

RDCAQPRLTVLDRRSFEDAEDVQEALCEIQSHFDLENGPLYTVAYIHGYE      3171
EDFSPAQLRVLNVKDVDGSAAVNEILDGWQSGFNLENGPIGSIGYLHGYE      3234

DGSARVWFACHHVMVDTVSWNIILQDLQALYHGDSLGPKSSSVQQWSLAV      3221
DRSARVWFSVHHMAIDTVSWQILVRDLQTLYRNGSLGSKGSSFRQWAEAI      3284

SDYKMPLSERAHWNVLRKTVAQSFETLPICMGGVLQCQEKFSRETTTALL      3271
QNYKASDSERNHWNKLVMETASSISALPTSTGSRVRLSRSLSPEKTASLI      3334

SKACPALDSGMHEILLMAVGSALQKAAGDVPQVVTIEGHGREDTIDATLD      3321
QGGIDRQDVSVYDSLLTSVGLALQHIAPTGPSMVTIEGHGREE-VDQTLD      3383

VSRTVGWFTSMYPFEIPKV--TDPAQGVVDVKEAMRRVPNRGVGYGPAYG      3369
VSRTMGWFTTMYPFEIPRLSTENIVQGVVAVSERFRQVPARGVGYGTLYG      3433

YGGSCLPAVSFNYLGRLDQASSGAQRDWTLVMDEDEYPVGLCTSAEDSGR      3419
YTQHPLPQVTVNYLGQLARKQSKP-KEWVLAVGDNEFEYGLMTSPEDKDR      3482
```

FIG. 18G

```
SSSMVDFTFSISGGQLVMDMSSSWGHGARNEFVRTVRNTLDDLIKTTSSR    3469
SSSAVDVTAVCIDGTMIIDVDSAWSLEESEQFISSIEEGLNKILDGRASQ    3532

DFSAPLPPSDQESSFTPYFVFEEGERHGAPLFLLPPGEGGAESYFHNIVK    3519
QTSRFPDVPQPAETYTPYFEYLEPPRQGPTLFLLPPGEGGAESYFNNIVK    3582

GLPNRNLVVFNNHYREEKTLRTIEALAEYYLSHIRSIQPEGPYHILGWSF    3569
RLRQTNMVVFNNYYLHSKRLRTFEELAEMYLDQVRGIQPHGPYHFIGWSF    3632

GGILGLEAAKRLTGEGHKIATLALIDPYFDIPSASKAIGQPDDACVLDPI    3619
GGILAMEMSRRLVASDEKIGFLGIIDTYFNVRGATRTIGLGDTE-ILDPI    3681

YHVYHPSPESFRTVSSLTNHIALFKATETNDQHGNATQQALYEWFA       3665
HHIYNPDPANFQRLPSATDRIVLFKAMRPNNKYESENQRRLYEYYD       3727
```

FIG. 18H

METHOD FOR INFLUENCING β-LACTAM ANTIBIOTIC PRODUCTION AND FOR ISOLATION OF LARGE QUANTITIES OF ACV SYNTHETASE

CROSS REFERENCE TO RELATED APPLICATION

This is a request for filing a Continuation-In-Part application of pending application, Ser. No. 07/658,398 filed on Feb. 19, 1991, now abandoned.

INTRODUCTION

1. Technical Field

This invention relates to methods and compositions to enhance the in vivo and in vitro production of fermentable or known and new secondary metabolites, particularly β-lactams and their biosynthetic intermediates using recombinant DNA techniques.

2. Background

β-Lactam antibiotics are the largest family of secondary metabolites produced in nature by microorganisms. The most important classes of the β-lactam antibiotics both clinically and economically are the penicillins (penam) and cephalosporins (cephem). Their biosynthesis occurs via a complex pathway of enzymatic steps; the unravelling of this pathway has been the subject of many studies during the last few decades. The first two steps are the key steps in the biosynthetic pathways of the penam and cephem classes of β-lactam antibiotics. After these two steps the biosynthetic pathways to the penicillins and cephalosporins diverge.

The first step in the biosynthesis of the penicillin, cephalosporin and cephamycin antibiotics is the condensation of the L-isomers of three amino acids, L-α-amino adipic acid (A), L-cysteine (C) and L-valine (V) into a tripeptide, δ-(L-α-aminoadipyl)-L-cysteinyl-D-valine or ACV. This step is catalyzed by 67 -(L-α-aminoadipyl)L-cysteinyl-D-valine synthetase or ACVS. In the second step, the tripeptide ACV is oxidatively cyclised by the action of the Isopenicillin N synthase (hereinafter referred to as IPNS) or cyclase. The product of this reaction is Isopenicillin N; this compound contains the typical β-lactam and thiazolidine ring structures and possesses antibacterial activity. From Isopenicillin N the penicillins G or V are formed by exchange of the hydrophilic A side chain by a hydrophobic side chain. The side chains commonly used in industrial processes are either phenylacetic acid (PA), yielding penicillin G, or phenoxyacetic acid (POA), yielding penicillin V; this exchange reaction is catalyzed by the enzyme acyltransferase (hereinafter referred to as AT).

From Isopenicillin N the route to cephalosporin and the cephamycins proceeds via racemization of the A side chain, forming penicillin N. This reaction is catalyzed by an enzyme named epimerase or racemase. The five-membered ring in penicillin N is expanded into a six-membered ring by the action of the enzyme deacetoxy-cephalosporin C synthase or expandase. The fungal enzyme has been shown also to catalyze the next reaction in the pathway, the hydroxylation of the methyl group at the 3'-position of the six-membered ring, forming deacetylcephalosporin C. In Streptomycetes this latter enzyme activity is encoded by a separate gene. From deacetylcephalosporin C, Cephalosporin C is formed by acetylation of the 3'-position. The cephamycins are formed from the same compound by several enzymatic steps.

In vivo synthesis of β-lactams and their precursors can be increased by increasing the activity of enzymes involved in β-lactam biosynthetic pathways. This can be achieved by either increasing the amount of enzyme present or by improving the specific activity of the enzyme. However, obtaining enzymes having the desired activity has typically been limited by the availability of spontaneous mutations in enzymes which are active at points in the pathway.

Currently, the cost effectiveness of in vitro synthesis of β-lactam precursors in cell free extracts is poor in comparison to traditional fermentation processes. These in vitro processes are hampered by the limited amounts of enzyme present within the cell, and hence within the cell free extract, and by the presence of inhibitory factors such as proteases and enzyme inhibitors. In addition, the use of fermentable or known β-lactam antibiotics (i.e. can be produced by fermentation of (β-lactam producing) non-rec-DNA microorganisms) is complicated by a) the development of resistance or tolerance to fermentable or known β-lactam antibiotics by bacterial species, and b) the limitations in therapeutic use, such as, an allergy to penicillin. There is therefore, substantial interest in the development of systems which allow for the efficient and cost-effective production of β-lactam antibiotics (i.e. cannot be produced by fermentation of (β-lactam producing) non-rec-DNA microorganisms) and their precursors, both in vivo and in vitro.

Relevant Literature

Van Liempt et al., (*J. Biol. Chem.* 1989, 264:3680–3684) have shown in *Aspergillus nidulans* that the ACV condensation is carried out by a large multi-functional enzyme, ACV synthetase. Similar results have been obtained for the *Acremonium chrysogenum* ACV synthetase by Banko et al., (*J. Amer. Chem. Soc.* (1987), 109:2858). The gene encoding ACV synthetase (pcbAB) has been located on the genome of *A. nidulans* (MacCabe et al., *EMBO J.* (1990), 9:279–287) and *Penicillium chrysogenum* (EP-A-320272, published Jun. 14, 1989; U.S. Ser. No. 392,119; D. Smith et al., *Bio/Technology* (1990), 8:39–41). pcbAB is located just upstream of the gene encoding IPNS.

In vitro synthesis of the tripeptide ACV in cell free extracts (Adlington et al., *Biochem. J.* (1983), 213:573; G. Banko et al., *J. Am. Chem. Soc.* (1987), 109:2858; Jensen and Westlake, *Developments in Industrial Microbiology* (1989), 30:113–119; EP-A-280051) has been used to study parameters of the ACV synthetase-reaction and also to study the feasibility of commercial application of in vitro synthesis of β-lactam antibiotics such as compared to traditional fermentation processes these processes are not commercially attractive. (Jensen, supra.). Several inhibitory compounds for the ACV synthetase reaction have been disclosed (Adlington and Banko, supra). It has also been established that the ACV synthetase has a rather narrow substrate specificity. Only a few amino acids can be substituted for the native α-amino adipic acid, cysteine and valine.

Amplification of antibiotic biosynthetic genes by increased copy number resulting in an increase in the production of an antibiotic has been described by Skatrud et al., *Bio/technology* (1989), 7:477–485 and U.S. Ser. No. 392,119, supra). Increased cephalosporin production, using the cefEF gene (Skatrud et al., supra) or penicillin, using the pcbC-penDE gene cluster (U.S. Ser. No. 392,119) has been reported. Expression of β-lactam biosynthetic genes, other than the ACV synthetase gene, has been described in *Streptomyces lividans*. (Chen et al., *Bio/technology*, (1988) 6:1222–1224). Publications relating to enzymes included in β-lactam biosynthesis and the cloning of genes encoding these enzymes are as follows. The IPNS has been purified and the gene encoding this enzyme, pcbC, has been cloned from various organisms (reviewed in Miller and Ingolia,

*Molecular Microbiology* 1989, 3:689–695; Martin and Liras, *Advances in Biochemical Engineering/Biotechnology* (1989), 39:153–187).

The enzyme acyltransferase has been purified (Alvarez et al., *Antimicrob. Agents Chemother.* 1987, 31:1675–1682; EP-A-336446) and the gene encoding this enzyme (penDE) has been cloned (EP-A-336446; U.S. Pat. No. 5,108,918; Veenstra et al., in: C. L. Hershberger, S. W. Queener and G. Hegeman, eds: *Genetics and Molecular Biology of Industrial Microorganisms*, (1989), pp 262–269; Barredo et al., Gene 1989, 83:291–300). The pcbC and penDE genes are clustered in the genome of *Penicillium chrysogenum* (B. Diez et al., *Mol. Gen. Genet.* (1989), 218:572576; Veenstra, supra).

The epimerase has been purified from *Streptomyces clavuligerus* (Usui and C-A Yu, *Biochem. Biophys. Acta* (1989), 999:78–85); the presence of this gene on a large DNA fragment was suggested in EP-A-233715. The enzyme expandase has been isolated both from *Acremonium chrysogenum* (Kupta et al., *FEMS Microbiol. Letters* (1987), 169:1–6; Dotzlaf and Yeh, *J. Bacteriol.* (1986), 16:1611–1618) and from *Streptomyces clavuligerus* (Rollins et al., *Can. J. Microbiol.* (1988), 34:1196–1202) and *Streptomyces lactamdurans* (Cortes et al., *J. Gen. Microbiol.* (1987), 133:3165–3174). The expandase genes have been cloned from both *A. chrysogenum* (cefEF, Samson et al., *Bio/technology* (1987), 5:1207–1214) and from *Streptomyces clavuligerus* (cefE, Kovacevic et al., *J. Bacteriol.* (1989), 171:754–760).

SUMMARY OF THE INVENTION

Methods, and compositions for use therein, are provided for enhanced expression of β-lactam antibiotic biosynthetic genes, leading to increased production of β-lactam antibiotics and precursors thereto. The methods include the steps of stably transforming a host cell with an expression cassette containing at least one DNA sequence encoding an ACV synthetase (ACVS) or a biologically active mutant or ACV synthetase (ACV') and isolating transformants which produce an enhanced amount of ACV synthetase. The expression cassette includes transcriptional and translational initiation and termination regulatory regions, hereinafter defined as promoter, and transcriptional and translational termination regulatory regions, hereinafter defined as terminator, appropriate for the host cell. The promoter may also be heterologous to the open reading frame. The host cell may be a eukaryote or a prokaryote. Also included is the pcbAB gene from *P. chrysogenum* and *A. chrysogenum*, constructs and vectors comprising the pcbAB gene or a mutant thereof, and transformed cells comprising the pcbAB. The subject invention finds use particularly in improved production both in vivo and in vitro of fermentable or known and new β-lactam antibiotics and their precursors, particularly antibiotics of the penam and cephem classes.

BRIEF DESCRIPTION OF THE DRAWINGS

FIG. 1 shows a schematic of the distribution of β-lactam producing microorganisms.

FIGS. 13A–13C show a scheme that shows the sequence homology between domains I, II, and III (SEQ ID NO: 5, 6, and 7) found within the ACVS protein and Gramicidin and Tyrocidin Synthetases (SEQ ID NO: 8 and 9).

FIG. 14 shows a scheme that shows the sequence homology between the ACVS protein (SEQ ID NO: 10) and the thioesterase domain of rat fatty acid synthetase (SEQ ID NO: 11).

FIG. 15 shows a scheme listing the domains and subdomains within the ACVS protein.

FIGS. 17A–17B is a restriction site and functional map of the chromosomal region encoding the ACVS gene in *A. chrysogenum*. Probes that have been used in Northern Blot hybridizations, and the results obtained, are indicated.

FIGS. 18A–18H show the similarity between the deduced amino acid sequence from the ACVS genes from *P. chrysogenum* (SEQ ID NO: 2) and *A. chrysogenum* (SEQ ID NO: 4).

DESCRIPTION OF THE SPECIFIC EMBODIMENTS

Figure 2:
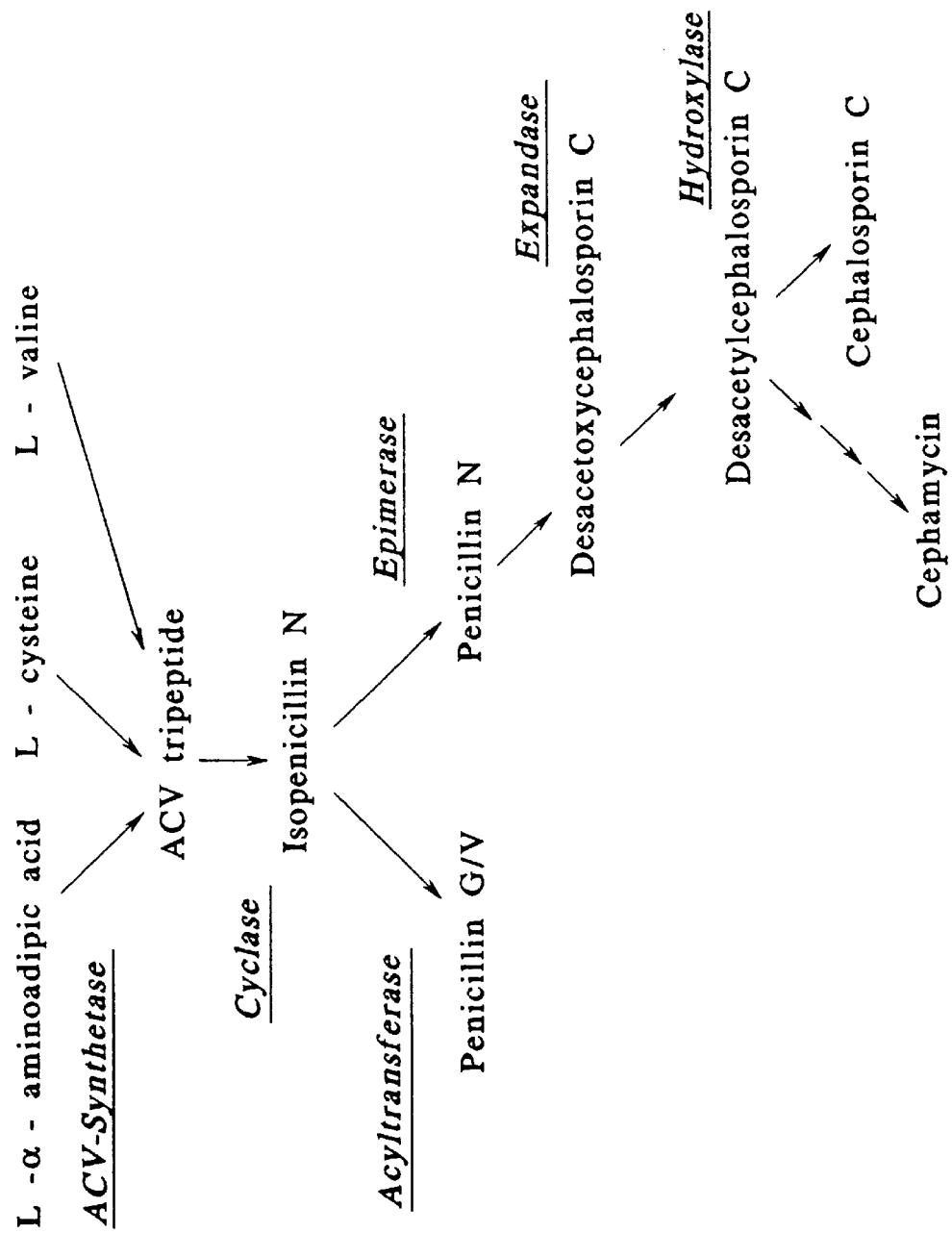
FIG. 2 shows a schematic representation of the biosynthetic pathways of the penicillins, cephalosporins and cephamycins.

In accordance with the subject invention, methods and compositions are provided which allow for increased, cost-effective production of fermentable or known and new β-lactam antibiotics and their precursors both in vivo and in vitro. The method includes the steps of transforming a host cell using an expression cassette which includes in the 5'-3' direction of transcription, a promoter, an open reading frame encoding an ACVS or ACVS', optionally having a signal sequence for secretion recognized by the host cell; and a terminator. The promoter and terminator are functional in the host cell and provide for efficient expression of ACVS or ACVS' without undesirable effects on the viability and proliferation of the host cell. Transcription and translation of the ACV synthetase DNA sequence will augment levels of ACV synthetase already present in the cell. Transcription and translation of the ACVS' DNA sequence will provide for expression of ACVS' in the host cell, which may have novel or enhanced properties as compared to the native enzyme.

Optionally, the expression cassette may include a transcription regulating sequence which is not subject to repression by substances present in the growth medium. The expression systems may be used to prepare β-lactam antibiotics directly or they may be used to prepare cell free extracts containing large quantities of ACVS or ACVS' for in vitro preparation of said antibiotics. Alternatively, the expression hosts may be used as a source of large quantities of enzyme which can be purified and used in in vitro systems.

In currently used systems, the first step in the in vitro synthesis of new β-lactams or their precursors has been the chemical synthesis of the desired new tripeptide; these modified tripeptides are subsequently cyclised by the action of the IPNS enzyme. The availability of ACVS' offers the advantage that the laborious chemical synthesis of new tripeptides can be avoided; the substantially more efficient and cost effective enzymatic synthesis of the desired tripeptides can be used instead. Additionally, by avoiding the use of harmful chemicals, solvents and the like, the subject invention causes less environmental problems when carried out at an industrial scale than do traditional methods of synthesis. Recognition of some of altered tripeptides as a substrate by IPNS, however, may in turn require the design and use of a modified IPNS enzyme.

Enhanced production of ACV synthetase is achieved by the introduction of extra copies of the gene encoding ACV synthetase (pcbAB gene) into a host cell by transformation: protoplasts are mixed with DNA constructs that contain at least one copy of the gene to be amplified linked to a selectable marker. By choosing the appropriate conditions, some protoplasts will take up the DNA construct which is thereafter stably maintained because the construct has become integrated into the host cell genome. Transformed cells can be selected from the background of so-called "non-transformed" cells by screening for expression of the selectable marker. Amplification of the pcbAB gene, which may be used to produce cephalosporin, penicillin, and cephamycin thus can be expected to result in an increase in intracellular enzyme activity, which in turn will be accompanied by an increase in production of the desired antibiotics. Since ACV synthetase forms part of the biosynthetic pathway of both the penam and the cephem classes of β-lactam anti-biotics, increased production of this enzyme has several applications. Production of ACVS' is achieved by the introduction of at least one copy of a mutant gene encoding ACV synthetase (pcbAB' gene) into a host cell by transformation, as described hereinabove.

Surprisingly, the data presented in the instant invention indicate that the coding region *P. chrysogenum* pcbAB gene is 11,337 nucleotides long and encodes a protein of 413 kDa. Based on the results obtained for *A. nidulans* (250 kDa enzyme: Van Liempt et al.) and *P. chrysogenum* (gene present on $8 \times 10^3$ nucleotide DNA fragment: EP-A-320272) a gene with a size of at most $8 \times 10^3$ nucleotides would be predicted. Moreover, these data obtained still allowed for the ACV synthetase activity to be encoded in more than one gene. Besides that, a significant amount of ACV synthetase can now be achieved by using the manipulated pcbAB genes of the present invention.

Only now it can be envisaged that all catalytic activities required for tripeptide formation (i.e. activation of three amino acids, racemization of valine, formation of dipeptide AC and tripeptide ACV, release of ACV) can indeed be present in one single polypeptide chain. ACVS this is a multifunctional enzyme. Multifunctional enzymes are defined herein to be enzymes that consist of one single polypeptide chain and that carry within their structure the ability to perform more than one catalytic reaction. In contrast, in the case of the biosynthesis of Gramicidin S, a peptide antibiotic consisting of two identical units of five amino acids, at least two, and probably three polypeptide chains are involved (e.g. von Dohren, 1982, In: *Peptide Antibiotics*, W. de Gruyter & Co., Berlin. pp 169–182; Kratzschmar et al., *Jour. of Bacteriol.* (1989) 171, 5422–5429).

In vitro synthesis of the ACV tripeptide has been described previously (Adlington and Banko, (supra). However, the only available systems up to now have been preparations comprising cell-free extracts of various organisms that possess ACV synthetase activity, followed by an in vitro reaction. The availability of an efficient expression system and the accompanying constructs, designed for high expression of the gene in suitable hosts is highly advantageous. It allows for the design of in vitro systems which do not have the disadvantages of a limited amount of enzyme present within the cell and hence within the cell free extract, or the presence of an excess of negative factors such as proteases or inhibitors or other similar effects. Increased productivity thus is obtained as a result of the enzyme being present in large quantities in the cell-free extracts prepared from the transformed host organisms as compared to the organisms used by for example Adlington and Banko, supra. Alternatively, large quantities of purified enzyme can be obtained and subsequently incubated in systems devoid of negative components.

For preparation of ACV and secondary metabolites, or for preparation of ACV synthetase by recombinant methods, genes encoding ACV synthetase (the pcbAB gene) may be obtained from a variety of sources including *Penicillium chrysogenum, Acremonium chrysogenum, Aspergillus nidulans,* Flavobacterium or Streptomycetes. The structural genes may be isolated by various techniques. These include isolating mRNA from a host organism which codes for the polypeptide of interest, the mRNA reverse transcribed, the resulting single stranded (ss) DNA used as a template to prepare double stranded (ds) DNA and the dsDNA gene isolated.

Another technique is to isolate the chromosomal DNA from the source organism of interest and, using a probe, appropriately degenerate, comprising a region of the most conserved sequences in the gene of interest, identify sequences encoding ACV synthetase in the genome. The probe can be considerably shorter than the entire sequence, but should be at least 10, preferably at least 14, more preferably at least 20 nucleotides in length. Longer nucleotides are also useful, up to about 100 nucleotides of the gene of interest. Both DNA and RNA probes can be used.

In use, the probe is typically labeled in a detectable manner (for example with $^{32}P$ or biotinylated nucleotides) and are incubated with ss DNA or RNA from the organism in which the gene is being sought after separation and/or immobilization of the ss or ds DNA, typically using nitrocellulose paper or nylon membranes. Hybridization is detected by means of autoradiography. Hybridization techniques suitable for use with oligonucleotides are well known to those skilled in the art. Although probes are normally used with a detectable label that allows for easy identification, unlabeled oligonucleotides are also useful, both as precursors of labeled probes and for use in methods that provide for direct detection of DNA or DNA/RNA. Accordingly, the term "oligonucleotide" refers to both labeled and unlabeled forms.

The gene encoding the ACVS can also be isolated from other organisms. For the gene encoding the IPNS, it has been shown (See for example, Ingolia and Queener, *Medicinal Research Reviews* (1989) 9:245–264) that genes isolated from different organisms show a high degree of homology, ranging from about 70% on the DNA level if two fungal or two Streptomyces genes are compared to 60% or more if a fungal and a Streptomycete gene are compared. Homologies on the protein level are 75% and 54%, respectively. Despite the differences on the DNA and protein level, all IPNS proteins catalyse the same reaction in a similar fashion. Therefore, ACVS sequences and enzymes can be identified that share a minimal homology of about 60% on the DNA level or 50% on the protein level.

Sequences that are at least substantially identical to the sequence given in SEQ ID NO: 1, SEQ ID NO: 2, SEQ ID NO: 3 or SEQ. ID. NO. 4 are of particular interest. SEQ ID NO: 1 and SEQ ID NO: 2 show a nucleotide sequence and deduced amino acid sequence respectively of the *P. chrysogenum* ACV synthetase gene. SEQ ID NO: 3 AND SEQ ID NO: 4 show the nucleotide sequence and deduced amino acid sequence of the *A. chrysogenum* ACV synthetase gene respectively. By "substantially identical" is intended sequences which can include conservative mutations, where the sequence encodes the same amino acid sequence, but may have as many as 30% different nucleic acid bases, more usually not more than 10% different bases, or mutations which are non-conservative, where fewer than about 10%, more usually fewer than about 5%, and preferably not more than 1% of the encoded amino acids are substituted or deleted, and there are fewer than 5% of inserted amino acids, where the percentage is based on the number of naturally occurring amino acids in the native enzyme. The degree of change which is acceptable can be determined by assessing the enzymatic activity of the expression product of the isolated gene, where the expression product should retain the ability to catalyze the formation of ACV from its constituting amino acids.

ACV synthetase genes can be isolated by using, for example, the sequence as given in SEQ ID NO: 1, or parts thereof as a probe in heterologous hybridization experiments. These probes can be restriction fragments derived from the ACVS encoding DNA isolated from *P. chrysogenum;* such restriction fragments can easily be selected and isolated using the restriction map as given in FIG. 4. Alternatively, synthetic oligonucleotide probes can be made based on the data given in SEQ ID NO: 1. In still another variation, oligonucleotides can be designed, based on the data in SEQ ID NO: 1, and used in a PCR reaction to generate a larger probe fragment. In this way, for example, the genes of *Acremonium chrysogenum* and *Aspergillus nidulans* can be readily isolated; also the genes from Streptomycetes can be isolated using less stringent hybridization conditions. The genes that are isolated in this fashion are also of interest. This procedure is exemplified by the isolation of the pcbAB gene from *A. chrysogenum*. The data obtained for this gene in their turn can be used for the gene-isolation procedure as described above. For example, using the data of the present invention, regions with a high homology can be identified, such as the domains of FIGS. 15 and 18 (SEQ ID NO: 12 and 13), and selected for use as a highly specific probe in the isolation of pcbAB genes from more distantly related organisms.

Alternatively, the DNA sequences encoding the ACV synthetase can be synthesized using conventional techniques such as PCR (Polymerase Chain Reactions) or by synthesis of overlapping single strands which may be ligated together to define the desired coding sequences. The termini can be designed to provide restriction sites or one or both termini may be blunt-ended for ligation to complementary ends of an expression vector. For expression of the sequence an initial methionine is provided. Expression vectors are generally available and are amply described in the literature.

For preparation of ACVS' and modified secondary metabolites, or for preparation of ACVS' by recombinant methods, genes encoding ACVS' may be obtained from spontaneous pcbAB' mutant from a variety of sources including *Penicillium chrysogenum, Acremonium chrysogenum, Aspergillus nidulans*, or from Flavobacterium or the Streptomycetes. Also, sequences that encode biologically active mutant ACV synthetase can be derived from sequences that are at least substantially identical to the sequence of a fermentable or known ACV synthetase or from spontaneous mutant pcbAB alleles. Mutant sequences can be "derived" by a variety of genetic and recombinant DNA techniques, such as in vitro mutagenesis and homologous recombination. The gene of interest encodes biologically active mutant ACV synthetase or a biologically active portion of ACV synthetase or a mutant thereof. A spontaneous mutant gene or a wild type gene (from which a mutant structural gene subsequently can be derived) can be isolated by various techniques using host organisms which are ACV synthetase mutants or wild type. These techniques have been described hereinabove.

Once the ACV synthetase DNA is obtained, mutations can be introduced by a number of in vitro mutagenesis techniques, either random or site-directed. Precise changes to the amino acid sequence are obtained by site-directed mutagenesis techniques which use synthetic oligonucleotides complementary to the region to be modified, except for the desired nucleotide(s) change. Regions are precisely deleted by "loop-out" mutagenesis techniques using synthetic oligonucleotides. Precise insertions are obtained using synthetic oligonucleotides to generate appropriate restriction sites. A series of mutations localized to a region of the ACV synthetase-encoding DNA sequence on a plasmid are generated by in vitro mutagenesis techniques and subsequently identified by cloning and sequencing the isolated mutagenized plasmids.

Once specific mutations have been generated and isolated to individual plasmids, "cassette" mutagenesis is applied to generate a series of new mutants by combining mutations into the same plasmid using appropriate restriction sites. Alternatively, mutagenesis using two or more oligonucleotides directed to different regions of the gene yields mutants with the desired multiple mutations.

Mutant proteins are also generated by the insertion, addition, or substitution of coding sequences from other proteins to ACV synthetase coding sequences. The source proteins may be ACV synthetases from other strains or species or may be unrelated proteins. Such amino acid sequences introduced into ACV synthetase will impart desirable properties or characteristics which originally belonged to the source protein.

Desirable properties are useful properties for activities and functions which include and are not limited to protein stability, secretion, isolation, purification, increased enzymatic activity, resistance to inhibitors, proteases and denaturants, solubility, and modified substrate specificity. Source proteins include those proteins involved in amino acid activation, amino acid racemization, peptide formation, thioesterase activity and the like. Preferred proteins include proteins involved in the biosynthesis of other antibiotic peptides, such as tyrocidin synthetase, gramicidin synthetase or proteins having enzymatic activities similar to those of ACVS, such as long chain fatty acid synthetases.

Although any region of the protein may be mutated, regions of the ACV synthetase protein which serve as candidates for mutagenesis are defined in order to minimize extensive screening of randomly generated mutants. The nucleotide and deduced amino acid sequences of ACV synthetase provided are a powerful tool with which to delineate such regions. Sequence homology comparisons, at both the DNA and amino acid level, identify protein regions with known function or structure.

Hydrophobicity profiles or related biophysical profiles, based on the amino acid sequence, with subsequent comparisons to profiles of other proteins may be used to identify additional protein regions of known structure and function. The finding of sequence or profile homologies indicates that the protein regions share a similar function, activity or enzymatic mechanism. Hydrophobicity or secondary structural profiles can indicate domain "linking" regions, "hinge" regions or "loops" which are candidates for restriction site insertions to generate domain "cassettes."

Regions for mutagenesis or replacement are also defined by correlation of a genetic map of ACV synthetase mutants alleles with a physical map, either at the restriction site or sequence level. Preferred regions for mutagenesis, either site-directed or via substitution include the functional domains and sub-domains of ACV synthetase as provided in FIGS. 13 (SEQ ID NO: 5, 6, and 7), 14 (SEQ ID NO: 10), and 15.

Mutant proteins also include functional proteins formed by various combinations or quarternery assemblies of discrete polypeptides. The polypeptides contain one or more enzymatic activities. Preferably the polypeptides are from the domains of ACV synthetase as defined in FIGS. 13 (SEQ ID NO: 5, 6, and 7), 14 (SEQ ID NO: 10), and 15. Polypeptides from regions of other proteins, as defined in the preceding sections, may also be combined with one or more ACV synthetase polypeptides in the same discrete fashion.

Once the desired DNA sequence has been obtained, it may be manipulated in a variety of ways to provide for expression. It is highly desirable that modifications of the nucleotide sequence, other than the modifications which result in the desired mutation(s), retain the three dimensional structure of the expression product, particularly that portion of the structure which may be responsible for the enzymatic activity of the resulting enzyme. Convenient restriction sites may be designed into the DNA sequence of interest; when possible the restriction site(s) leaves the amino acid sequence of the expression product unaltered. However, in some cases, incorporation of new restriction sites may yield an altered amino acid sequence.

Where the gene encoding ACVS or ACVS' is to be expressed in a host which recognizes the wild type promoter and terminator of the gene of interest, the entire gene with its wild type 5' and 3'-regulatory regions may be introduced into an appropriate expression vector. Where said gene is to be expressed in a host cell which does not recognize the naturally occurring wild type promoter and terminator, further manipulation may be required. Conveniently, a variety of 3'-transcriptional regulatory regions are known and may be inserted downstream from the stop codons. The non-coding 5'-region upstream from a structural gene may be removed by endonuclease restriction, Bal31 restriction or the like. Alternatively, where a convenient restriction site is present near the 5'-terminus of the structural gene, the structural gene may be restricted and an adaptor employed for linking the structural gene to the promoter region, where the adapter provides for the lost nucleotides of the structural gene.

The biosynthesis of β-lactam antibiotics in general, and of penicillin in particular, is subject to glucose repression (Martin and Liras, *TIBS* (1985), 3:39–44). This repression by glucose has been unequivocally established for the formation of the tripeptide by the ACV synthetase and for the activity of IPNS (Revilla et al., *J. Bacteriol.* (1986), 168:947–952). It is not known at which stage of expression repression by glucose is exerted; this can, for example, be at the transcriptional or at the translational level. If the former applies, constitutive expression of the pcbAB gene will result in an increase in enzyme activity followed by an increase in the production of ACV, and subsequently of the β-lactam antibiotic derived from it.

Increased expression of the gene in β-lactam producing bacterial or fungal hosts therefore can be obtained by changing the regulation of gene expression. Thus, the transcriptional regulatory region is preferably one which is not subject to repression by, for example, presence or absence of nutrients such as glucose, or expression products in the growth medium. The transcriptional regulatory region may additionally include regulatory sequences which terminate transcription and which provide sequences or structures which inhibit degradation of the mRNA.

Exemplary of changing the regulation of expression is modification of the pcbAB gene. The native sequence generally is replaced by a region which is functional in either the native or heterologous host and wherein expression is either inducible or constitutive. For example, the regulatory sequences can be changed by replacing the pcbAB promoter, which is strongly repressed by glucose, with a promoter which is insensitive to glucose or even is stimulated by it. In the latter situation, antibiotic will be produced during the early stages of the fermentation, when biomass is formed in high-glucose conditions. This modification may further increase the yield of the antibiotic during the fermentation. Expression of the gene may also be brought under control of other promoters, either promoters for which expression can be regulated in a different fashion or promoters that are expressed constitutively.

Illustrative promoters which find use in the subject invention, include, for prokaryotic cells, the lac, trp (Sommerville, *Biotechnology and Genetic Engineering Reviews* (1988), 6:1–41) or tac promoters of *E. coli*, or aph or tyrosine synthetase promoters of *S. lividans*. For filamentous fungi, illustrative promoters include the glyceraldehyde phosphate dehydrogenase (gapdh) promoter, the phosphoglycerate kinase (pgk) promoter, the nitrate reductase promoter and the like. A preferred embodiment of the present invention which is exemplified herein is the use of the pgk promoter of *P. chrysogenum*, which has been described in U.S. Pat. No. 5,108,918.

In eukaryotic cells, a terminator provides for proper maturation of the mRNA transcript and are necessary for efficient expression. In general, it is preferable to use the native polyadenylation signal associated with the gene of interest. In both eukaryotic and prokaryotic systems, termination regions can also contain sequences or structures which increase the stability of the mRNA species and allow for higher expression. Several examples of prokaryotic sequences are known, for example the trp terminator, the gene 32 (T4) terminator, or synthetic terminators which are similar in sequence to gene 32. For eukaryotes, terminators can be used that are isolated from cloned genes. For yeast, the terminator of the CYC1 gene or the actin gene can be used for example. For filamentous fungi, the terminators isolated from for example the trpC gene, the pgk gene or the penDE gene are useful.

Where it is desired to isolate the ACVS, secretion of the enzyme into the media or into the periplasmic space of the transformed microbial host can improve the efficiency of the isolation procedure. Secretion can be accomplished by using DNA expression cassettes as described herein, which further comprise a signal sequence (secretory leader) that is functional in the host cell. The signal sequence will be heterologous to the ACV synthetase gene and may be homologous or heterologous to the host cell, or may be a synthetic signal sequence. The signal sequence provides a peptide sequence that is in-frame with the enzyme sequence, and may be located 5' or 3' to the ACV synthetase sequence. The signal sequence can also be provided by joining, in-frame, an open reading frame of a protein that is secreted by the host cell and the open reading frame of the ACV synthetase. Illustrative secretory leaders include the secretory leaders of penicillinase, α-factor, immunoglobulin, T-cell receptors, outer membrane proteins, glucoamylase, fungal amylase and the like. By fusion in proper reading frame, the mature polypeptide may be secreted into the medium.

The promoter and terminator may be homologous (derived from the original host), or heterologous (derived from a foreign source or synthetic DNA sequences). The expression cassette thus may be wholly or partially derived from fermentable or known sources, and either wholly or partially derived from sources homologous to the host cell, or heterologous to the host cell. The various DNA constructs (DNA sequences, vectors, plasmids, expression cassettes) of the invention are isolated and/or purified, or synthesized and thus are not "naturally occurring."

The expression cassette may be included within a replication system for episomal maintenance in an appropriate cellular host or may be provided without a replication system, where it may become integrated into the host genome. Integration may be stimulated in yeast and bacteria by the inclusion of (parts of) ribosomal RNA genes or other yeast genes and subsequin thesearization in these genes.

The DNA may be introduced into the host cell in accordance with known techniques, such as transformation DNA, transfection by contacting the cells with a virus, microinjection of the DNA into cells, biolistic transformation and the like. Both prokaryotic and eukaryotic hosts may be employed, which may include bacteria and fungi, particularly filamentous fungi. Prokaryotic cells include *Escherichia coli*, Flavobacterium and Streptomyces spp. Eukaryotic cells include filamentous fungi such as *Penicillium chrysogenum, Acremonium chrysogenum, Aspergillus nidulans, niger* and *oryzae*; and yeasts such as *Saccharomyces cerevisiae, Kluyveromyces lactis*. Preferred host cells include *P. chrysogenum, A. chrysogenum, A. nidulans*. Replacement of the native ACVS gene by the mutant gene may result in in vivo synthesis of β-lactam derivatives. The presence of a wild type gene in these organisms indicates that they allow for efficient expression of the wild type ACVS gene and hence they are inferred to also express the mutant gene without too many difficulties.

Other preferred hosts include the Streptomycetes. Several Streptomycetes also synthesize β-lactams (see FIG. 1). They can be used for the same reasons as the above-mentioned fungi. On the other hand, a Streptomycete such as *S. lividans* is very amenable to genetic manipulation (Hopwood et al., (1985) Genetic Manipulation of Streptomyces: a Laboratory Manual, The John Innes Foundation, Norwich, U.K.). Moreover, it has been disclosed that β-lactam biosynthetic genes are actively expressed in *S. lividans* (Chen et al., supra). Therefore, *S. lividans* is a preferred host for expression of the gene, for isolation of the mutant protein, or to use for preparation of cell-free extracts. Expression of foreign genes in *E. coli* is very well known in the art. One disadvantage of this organism may be that the ACVS could be too large for production of active enzyme; inclusion bodies may be formed or (over) expression may be harmful to the cell. Yeasts, like *S. cerevisiae* or *K. lactis* are examples of frequently used hosts for expression of heterologous proteins.

Transformed host cells subsequently are grown under conditions that are suitable for the antibiotic production. These conditions have been amply described in the literature (Luengo et al., *J. Gen. Microbiol.* (1979), 115:207–211; Barredo et al., *Antimicrob. Agents Chemother.* (1988), 32:1061–1067; Queener and Schwartz, In: Rose AH (ed) *Secondary Products of Metabolism*, Academic Press, London (1979): 35–122; Queener et al., In: *Biotechnology of Industrial Antibiotics*, E. J. Candamme (ed) Marcel Dekker Inc., New York, Basel (1984): 141–170). Generally media for antibiotic production contain either a slow fermentable carbon source, like lactose, or are limited in the carbon source, e.g. glucose, in a so called fed-batch fermentation procedure. For the production of penicillin G or V the appropriate side chain precursor, as has been described hereinbefore, is added to the medium; for the production of cephalosporin the medium may be supplemented with DL methionine. Generally, Corn Steep Liquor or related compounds are supplied as a nitrogen source.

For prokaryotic hosts, the culture conditions are known in the art (e.g. Maniatis et al., Molecular Cloning, a Laboratory Manual, Cold Spring Harbor Laboratory (First edition, 1982 or second edition, 1989) and Hopwood (supra)); in this case it is advisable to maintain selective pressure by addition to the culture medium of the antibiotic that is used as a selective agent. The secondary metabolite is subsequently isolated from the cultured cells.

ACVS or ACVS' can be purified from the host cells that have been grown under these conditions or, alternatively, using the conditions that are most suited for the expression of the promoter used; preferably, cells are harvested early in the fermentation (2–4 days) for this purpose. For the isolation of ACVS or ACVS'. the procedures as described in Van Liempt et al. (supra) or Banko et al. (supra) can be used. For isolation of ACVS or ACVS' from transformed *E. coli*, the cells are grown overnight in e.g. TY or LB medium (Maniatis et al., supra) and can be lysed by treatment with lysozyme. Protease inhibitors, such as PMSF or α-2 macroglobulin can be included in the buffers used, in order to avoid degradation of the ACVS or ACVS' to be purified.

Cell-free extracts can be prepared from the various cultures using the procedures as they are described in Adlington et al. (supra), Banko et al. (supra), Jensen et al. (supra), Zhang an Demain (*Biochem. Biophys. Res. Comm.* (1990) 196:1145–1152); Jhang et al. (*FEMS Microbiol. Lett.* (1989) 57:145–150). In general, cells are harvested, washed in suitable buffer and disrupted in a French press, by grinding in liquid nitrogen or by sonication. The presence of glycerol (40–50%) as a stabilizer is crucial, both for isolation of large quantities of the enzyme and for isolation of an active cell-free extract.

The pcbAB genes of the present invention, and more particularly the DNA constructs derived thereof, can be used to transform suitable host cells, in order to increase the fermentable or known ACV synthetase activity present in the host cells. Cells with an increased level of ACV synthetase find their use in the production of increased amounts of β-lactam antibiotics. This increased production can be the result of the increased ACV synthetase activity by itself, or in combination with an increased activity of other enzymes, known in the art. For example, host cells that have been transformed with the pcbAB gene can be retransformed with a construct containing other β-lactam-biosynthetic genes, such as the construct pGJ02A that has been described before (U.S. Ser. No. 392,119). In this way the entire pathway leading to penicillin G or V formation can be amplified. Combined use of these two constructs can also confer the ability to synthesize penicillin to host organisms that by nature lack this ability.

Cells with increased ACV synthetase activity moreover find their use in the isolation of increased quantities of the ACV synthetase enzyme; the isolated enzyme can be used, for example, in in vitro reactions or for the further unraveling of the reaction mechanism.

Cells with increased ACV synthetase activity also find their use in the preparation of cell-free extracts with increased ACV synthetase activity, leading to improved yields—and hence an improved economy—of in vitro synthesis of β-lactam antibiotics and their precursors.

Amplification of the mutant pcbAB gene, particularly one with a phenotype of increased enzyme activity, will result in a further enhancement in intracellular enzyme activity, which in turn may be accompanied by an increase in productivity of the antibiotics of both the cephalosporin and penicillin pathways.

Expression of the mutant pcbAB gene, particularly the one with a phenotype of altered substrate specificity, will result in the synthesis of non-natural β-lactam antibiotics and their precursors.

Cells with increased ACVS' activity also find their use in the isolation of ACVS' enzyme or in the preparation of cell-free extracts with ACVS' activity.

The following examples are offered by way of illustration and not by way of limitation.

EXPERIMENTAL

General Methods

In all examples described herein, the experimental techniques mentioned are known in the art: these have been described e.g. in T. Maniatis et al., supra.

Deposits

The following organisms have been deposited with Centraal Bureau voor Schimmelcultures (CBS), Oosterstraat 1, 3742 SK Baarn, Netherlands:

E. coli WK6 containing plasmid pPCV01, Accession No. CBS 142.90, was deposited Feb. 28, 1990;

Cosmid HM193, Accession No. CBS 179.89, was deposited on Apr. 3, 1989 as a DNA sample (cosmid clone in E. coli unstable);

P. chrysogenum strain Wisconsin 54-1255 npe5 an ACV synthetase gene mutation, Accession No. CBS 178.89, was deposited on Apr. 3, 1989.

EXAMPLE 1

Characterization of the pcbAB gene from P. chrysogenum

A. Isolation of the pcbAB gene

Chromosomal DNA of P. chrysogenum was isolated and treated as described in U.S. Pat. No. 5,108,918. After partial digestion of the DNA, partials of 20–35 kb in size were isolated and ligated into the BamHI digested cosmid vector pPS07 (see EP-A-0260762) using standard protocols (e.g. Maniatis et al., supra). The ligation mixture was packaed in vitro and the phage lysate was transduced into E. coli HB101 (ATCC 33694), again using methods known in the art. Fresh transductant colonies were grown in 10 ml of L-broth (per litre 10 g of NaCl, 10 g of Bacto-tryptone and 5 g of Bacto-Yeast Extract) under ampicillin selection. Cosmid DNA was isolated and the presence of insert DNA was checked by Eco RI digestion. Insertion containing cosmids were stored in microtiterplates at −20° C.

To isolate cosmid clones containing the IPNS gene and a large amount of flanking regions, the cosmid library was screened for clones containing the IPNS gene. A cosmid library was used, as opposed to a phage lambda library, because cosmid vectors are known in the art to contain larger inserts (20–40 kb) than lambda vectors (9–23 kb). As probes were used two oligonucleotides based on the N-terminal amino acid sequence of the P. chrysogenum IPNS gene: 5'-TCC GGC GAT AAC ATG GAG-3' (SEQ ID NO: 22) and 5'-TCC GGC GAT AAT ATG GAG-3' (SEQ ID NO: 23). The probes were labelled using standard techniques known in the art (e.g. Maniatis et al., supra).

Cosmids hybridizing to the probes were isolated, and the presence of the IPNS gene was confirmed by subcloning, sequence analysis and comparison of the data to the sequence of the IPNS gene described in L. Carr et al., Gene, (1986) 48:57–266).

Cosmid HM193 contains one DNA fragment so identified. This cosmid clone contains about 23 kb of DNA upstream of the IPNS gene. Using parts of cosmid clone HM193 as a probe, cosmid clones containing similar or overlapping inserts have been isolated, using techniques known in the art. The presence of the pcbAB gene on the DNA fragments has been demonstrated in various ways. The DNA fragments were able to complement a mutation in the gene encoding ACV synthetase, which is present in the strain Wisconsin 54-1255 npe5, deposited as CBS 178.89. This is a mutant ACV synthetase-negative P. chrysogenum strain derived from Wis54-1255. Restoration of penicillin production by complementation was accompanied by the reappearance of in vitro ACV synthetase activity in cell free extracts. Moreover, restoration of penicillin production was also accompanied by reappearance of a large protein on SDS-PAGE gels.

B. Localization of the pcbAB gene

Northern hybridizations were performed using mRNA that was isolated from penicillin-producing cultures as described in U.S. Pat. No. 5,108,918. The subcloned SalI fragments indicated in FIG. 3 were used as probes. Using probes I, II, III and IV a large mRNA ($\geq 10 \times 10^3$ nucleotides) segment was detected in the Northern blot hybridizations. Probe V detected the mRNAs of the pcbC and penDE genes (about 1.5×103 nucleotides). Using smaller probes (A–D and E–H in FIG. 4), the positions of the putative 5'- and 3'-ends of the gene were located. The gene encoding the ACV synthetase is present on the chromosome of P. chrysogenum as indicated by the shaded region in the schematic of FIG. 3.

C. Polarity of the gene

The direction of transcription was determined by Northern hybridization of mRNA of P. chrysogenum using as a probe the following synthetic oligonucleotides that have been designed based on the nucleotide sequence surrounding the two HindIII sites located within the ACVS coding region (FIG. 4).

AB1504: 5'-CCC AGA CGC ACT TGA TCC TG-3' (SEQ ID NO: 14)

AB1505: 5'-GTC CCC GCT TGC GAC GAC TG-3' (SEQ ID NO: 15)

AB1549: 5'-CGG GAA TCA TCT GCG TAT C-3' (SEQ ID NO: 16)

AB1550: 5'-CGC GCT CAA AGG CCT GGT TC-3' (SEQ ID NO: 17)

Figure 5:
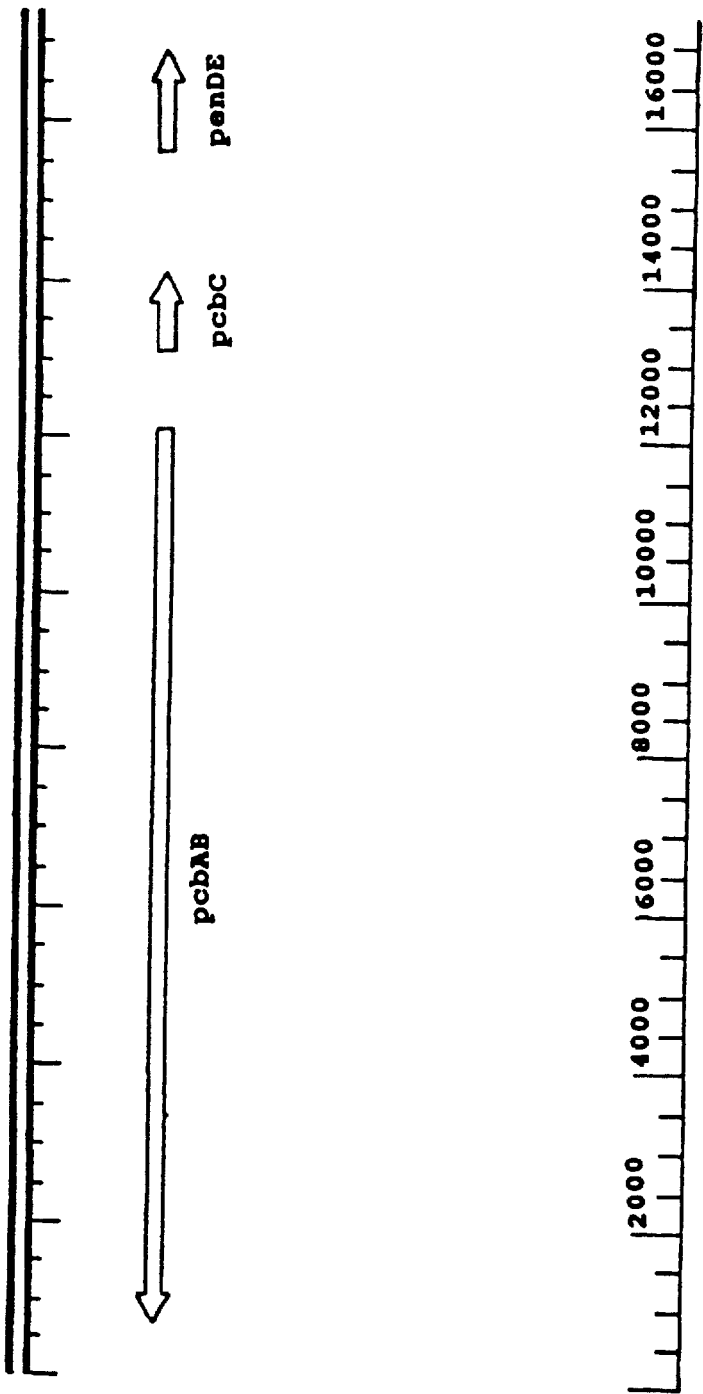
FIG. 5 shows a schematic representation of the cluster of penicillin biosynthetic genes present in the genome of *P. chrysogenum*.

Only probes AB1549 and AB1550 hybridized to the ACV synthetase mRNA and the deduced direction of transcription is indicated in FIG. 5. The direction of transcription of the ACV synthetase gene is in the opposite direction to the genes encoding IPNS and AT.

D. Determination of the nucleotide sequence

The nucleotide sequence of a DNA fragment contained in cosmid HM193 containing the ACV synthetase gene was determined by the dideoxy method (Sanger et al., *Proc. Natl. Acad. Sci. U.S.A.* (1977) 74:5463–5467) using the Sequenase system 2.0 (U.S. Biochemicals, Cleveland, Ohio). Double sequencing reactions with dGTP and dITP were used in some clones to avoid errors (Barnes et al., (1983) Methods in Enzymology 101, 98–122). The sequencing strategy is given in FIGS. 4A–4D. The nucleotide sequence of the 12,364 nucleotide DNA fragment is given in sequence 1 (SEQ ID NO: 1). In this sequence a long open reading frame (ORF) of 11,337 nucleotides was found from which a protein sequence (SEQ ID NO: 2) of 3778 amino acids was deduced.

E. Determination of partial protein sequence of ACV Synthetase

To further confirm that the gene cloned is indeed the gene encoding the *P. chrysogenum* ACV Synthetase, amino acid sequences have been obtained from ACV synthetase that has been purified from *Aspergillus nidulans*. The similarity between protein and nucleotide sequence data confirm the identity of the cloned gene.

ACV Synthetase was purified from *A. nidulans*, strain G-69, as has been described in Van Liempt et al., (supra).

The enzyme containing fractions from the DEAE column were applied to a Mono Q column on a FPLC apparatus (Pharmacia). ACV synthetase was eluted using a 0–300 mM NaCl gradient in Tris/HCl buffer (pH 7.5). The peak fraction, having a protein concentration of 0.5 mg/ml was shown to contain almost pure (over 90%) ACV synthetase; this was demonstrated by SDS-PAGE.

For digestion with protease, 1.25 ml (0.625 μg) of ACV synthetase from the Mono Q fraction was incubated with 62.5 μl (6.3 μg) of Subtilisin (Sigma) for 60 min. at room temperature. The reaction was terminated by the addition of trichloroacetic acid (10% final concentration). The precipitated protein was recovered by centrifugation, dissolved in approximately 200 μl of Laemmli sample buffer, and the mixture was neutralized by the addition of 4M Tris. The protein was dissolved and incubated for 5 min. at 95° C.

A slab gel of 140×170×1.5 mm of polyacrylamide (separating gel 5% T), with a 3% stacking gel (Laemmli) was allowed to polymerize overnight at 4° C. The digested protein was applied in several slots, and electrophoresis was carried out with 0.02% thioglycolic acid in the upper buffer compartment. After the Bromophenol Blue marker had migrated up to 70% of the gel length, the electrophoresis was terminated and the proteins were transferred electrophoretically onto a PVDF-membrane (Immobilon) in a semidry blotting apparatus (Sartorius). The transfer buffer was 25 mM Tris/HCl (pH 8.5), 0.5 mM dithioerythritol.

After transfer (approximately 2 hrs.) the membrane was washed with water, stained in 0.5% Coomassie R 250, 50% Methanol for 5 min., destained in 50% Methanol, 10% Acetic Acid, washed with water and air dried.

From the complex pattern of protein bands present on the membrane, the bands that were the most pronounced and least contaminated with other nearby bands were excised. The amino acid sequence of the peptides in the excised bands was determined using a gas-phase sequenator (Applied Biosystems model 470a). The following sequence was determined (in this notation amino acids separated by a slash indicates ambiguity of interpretation at this position while an amino acid in parentheses indicates uncertainty in the interpretation; Xxx indicates the presence of an unidentified amino acid):

band 3 (SEQ ID NO: 18): Asn Ala Asn Val Tyr Leu Ala Asn Ser Leu Gln Gln Gly Phe Val Tyr Gln Phe Leu Lys Asn Met Gly Asp/Arg Ser Gly/Trp Ala Asp/Tyr Asp/Val Met Gln Xxx Val (Thr) (Asp/Arg) Tyr band 9 (SEQ ID NO: 19): Gln Ser Val Gln Xxx Ala Lys Ser Val Ala Lys Phe Asp Leu Asn (Ala Thr) Ala Xxx (Glu) (Leu/Ser Asp/Gly Lys Ala)

band 12B (SEQ ID NO: 20): (Gln/Ser/Cys Gln Thr) Val Leu Gly Asp Ala Pro Leu Leu Pro Ile Gln (Thr/Gln His/Gln Phe)

F. Comparison of protein and nucleotide sequences

The amino acid sequences from Example 1E (*A. nidulans*) (SEQ ID NO: 18, 19, and 20) were compared with the deduced amino acid sequence from Example 1D (*P. chrysogenum*), which is shown in SEQ ID NO: 2. For this comparison the MicroGenie™ 6.0 program (Beckman) was used.

```
aa band 3     1   N A N V Y L A N S L Q Q G F V
                  | : | | | | | | | | | | | |
Pc ACVS     948   T D N I Y L A N S L Q Q G F V (D)*  (W)(D)(D)
aa band 3    16   Y Q F L K N M G (R) S (E) A (Y)(Y) M
                  | : | |       |     | : | | | |
Pc ACVS P   963   Y H Y L K S M E Q S D A Y V M (D)
aa band 3    31   Q X V T (R) Y
                  |   |     | |
Pc ACVS P   978   Q S V L R Y Matches = 22      (25) Mismatches    = 14 (11)
Length  = 36           Matches/Length = 61.1 (69.4) percent
```

```
aa band 9a    1   Q S V Q X I K S V A K F D L N
                  | |   :     | | | | | | | | |
           2402   R P V Q P V D S V A K F D L N (S) (E)
             16   [A T A X E (L)(D) K A]
                  | |       | |  :
           2417   A T V T E L E S G Matches = 12      (13)      Mismatches   = (7)
Length  = 24                Matches/Length = 50.0 (54.2) percent
```

```
                           (C)
                           (S)                              (T)(H)
aa band 12B   1   (Q) Q T V L G D A P L L P I Q (Q)(Q)(F)
                   |   | : | | | | | | | | | :   |
Pc ACVS P  3110   Q G P V I G E A P L L P I Q D W F Matches = 10      (11)      Mismatches   = 7 (6)
Length  = 17                Matches/Length = 58.8 (64.5) percent
```

| : Homologous residues
: : Similar residues (defined according to the Beckman standard:
A replacement is defined conservative when both amino acids belong to one of the following sets: (A, S, T), (N, Q), (D, E), (I, L, M, V), (R, H, K), OR (F, W, Y).
MicroGenie ™ Manual MG-IM-6.0, Dec. 1988).

The degree of homology found between *A. nidulans* and *P. chrysogenum* varies between 50 and 61%. This is very similar to the degree of homology between the IPNS proteins derived from both organisms (e.g. G. Cohen et al., 1990, Trends in Biotechnology 8:105–111); hence the protein data confirm the conclusion that the gene cloned is indeed the *P. chrysogenum* ACV synthetase gene.

G. Identification of distinct domains in the ACVS enzyme which are used to obtain ACVS' enzyme From the nucleotide sequence of the pcbAB gene an amino acid sequence has been deduced, as indicated in SEQ ID NO: 2. Upon matrix comparison of this protein sequence with itself, three distinct regions of homology are found: these regions are defined herein as domains. These domains are located between amino acid 301 and 1068 (domain I), 1392 and 2154 (domain II) and between amino acids 2474 and 3295 (Domain III; FIGS. 13A–13C). Similar domains were found in the pcbAB gene of *A. chrysogenum*. Within these domains, several even more conserved elements can be distinguished. A summary is given in FIG. 15. Since the ACVS enzyme synthesizes a tripeptide, which most probably requires the activation of three amino acids, a role of these three domains in the amino acid activation reactions seems likely. Therefore, the said domains are candidate regions for in vitro mutagenesis.

Comparison of the deduced amino acid sequence with the protein sequences known for other multifunctional enzymes reveals a significant homology with the *Bacillus brevis* tyrocidin synthetase I (SEQ ID NO: 8) (hereinafter referred to a TYI; Weckerman et al., *Nucleic Acids Research* (1988), 16:11841) and gramicidin synthetase I (SEQ ID NO: 9) (hereinafter referred to as GSI; Kratzschmar et al., supra; compare FIG. 13). Since both TYI and GSI are involved in activation and racemization of the amino acid phenylalanine, this homology supports the notion that these conserved sequences may represent centers involved in ATP-mediated activation of amino acids. If the mechanism of peptide synthesis by ACVS or Gramicidin Synthetase is comparable, the expected order of the domains in the enzyme is in the same order as that of the amino acids in the tripeptide (Kratzschmar, supra).

Upon comparison of the ACVS protein sequence with other known protein sequences of large enzymes, a significant homology is found with the Fatty Acid Synthetase (long chain) from rat and chicken (FIG. 14; M. Schweizer et al., *Nucleic Acids Research* (1989) 17:567–586; Z. Yuan et al., *PNAS* (1988), 85:6328–6331). The homology is found between the COOH-terminal part of the ACVS protein (SEQ ID NO: 10) (domain IV in FIG. 15) and the thioesterase domain (SEQ ID NO: 11) of the long chain Fatty Acid Synthetase proteins. Even the active site of the thioesterase, viz. G.X.S.X.G. (e.g. Kratzschmar, supra), is present in the ACVS protein sequence. A similar homology has been described for a subunit of gramicidin Synthetase; in this case the homology is found between the grsT subunit and the type II fatty acid synthetases. The demonstration of the said homology suggests that ACVS most probably also contains within its structure the ability to release the tripeptide, once it has been formed and bound to the enzyme by thioester bond formation, by the action of its thioesterase domain. This activity may form another target for in vitro mutagenesis, e.g. by increasing the efficiency of the release of the tripeptide, in case this part of the reaction is the rate determining step. However, in experiments designed to change substrate specificity, this domain preferably remains unchanged.

The functional domains of the ACVS protein being identified, it now is possible to construct modified peptide synthetases by the exchange of functional domains. This can be achieved e.g. by interchanging the three domains that have been identified within the ACVS protein. An alternative way is the exchange of ACVS specific domains with domains from other proteins known to have a similar function. Selected domains can be isolated by restriction enzyme digestion of clones containing the genes encoding the said proteins or domains thereof. However, suitable restriction sites at useful positions are seldom encountered. Therefore, the Polymerase Chain Reaction offers a good alternative for the isolation of suitable DNA fragments. In general, DNA fragments containing functional domains are prepared as follows: for each domain two oligonucleotides are designed, one starting at the N-terminal end of the selected domain, in the direction of the C-terminal end. The other oligonucleotide is derived from the C-terminal end of the domain and is designed in the opposite direction; consequently this oligonucleotide is derived from the other DNA strand. At the 5'-end of each oligonucleotide a suitable restriction site can be included in the oligonucleotide, in order to facilitate ligation of the domains after amplification. The DNA fragments between the two oligonucleotides are amplified using the polymerase chain reaction, thereby following the protocols known in the art (described e.g. in 'PCR-Technology', supra). Preferably, Taq DNA polymerase is used for the amplification reaction.

EXAMPLE 2

Expression of the pcbAB gene from *P. chrysogenum* in *P. chrysogenum*

Synthesis of pPCV01

This vector was derived from pBluescript II KS M13(+) (Stratagene, La Jolla, Calif.) and contains the phleomycin resistance gene under control of the *P. chrysogenum* pgk promoter. It moreover contains a synthetic multiple cloning site, including unique SpeI site. The *P. chrysogenum* pgk gene has been isolated from a genomic cosmid library. To construct the cosmid library, chromosomal DNA of *P. chrysogenum* was isolated by forming protoplasts from the mycelium as described in EP-A-260762. The protoplasts were analyzed by diluting the isotonic (0.7M KCL) suspension with four volumes of TES buffer (0.05MTris-Hcl pH 8.0, 0.1M EDTA, 0.15M NaCl). To the lysate, 1% sodium lauryl sulfate was added and the mixture was incubated at 55° C. for 30 minutes. After one extraction with phenol and two extractions with chloroform, the DNA was precipitated with ethanol, dried, and dissolved in TE buffer (10M Tris, 1M EDTA pH 8.0). The DNA solution was then treated with 100 μg/ml RNase at 37° C. for one hour and subsequently with 200 μg/ml proteinase K at 42° C. for one hour. The solution was extracted once with phenol and twice with chloroform. An equal volume of isopropanol was laid on top of the aqueous phase and the DNA was collected at the interface by spooling around a glass rod. After drying, the DNA was dissolved in TE buffer. The molecular weight of the DNA preparation obtained was about $10^8$. After partial digestion of the DNA with Sau 3A, particles of 20–35 kb in size were isolated and ligated into the BamHI digested cosmid vector PS07 (see EPA 0260762; cf. FIG. 4) using standard protocols (e.g., Maniatis et al. supra). The ligation mixture was packaged in vitro and the phage lysate was transduced into E. coli HB101 (ATCC 33694), again using methods known in the art. Fresh transductant colonies were grown in 10 ml of L-broth (per liter 10 g of NaCl, 10 g of Bacto-tryptone and 5 g of Bacto-yeast extract) on the ampicillin selection. Cosmid DNA was isolated and the presence of insert DNA was checked by EcoRI digestion. Insertion-containing cosmids were stored in microtiter plates at −20° C. The pgk gene was isolated using the corresponding gene of Saccharomyces cerevisiae (Dobson et al., Nucleic Acid Research (1982) 10:2625–2637) as a probe (Van Solingen et al., Nucleic Acid Research (1988) 16:11823). The sequence of part of the promoter is disclosed in U.S. Pat. No. 5,108,918. The promoter and a small part of the coding region can be isolated as a 1.5 kb HindIII fragment.

Synthesis of PCV02

Figure 8:
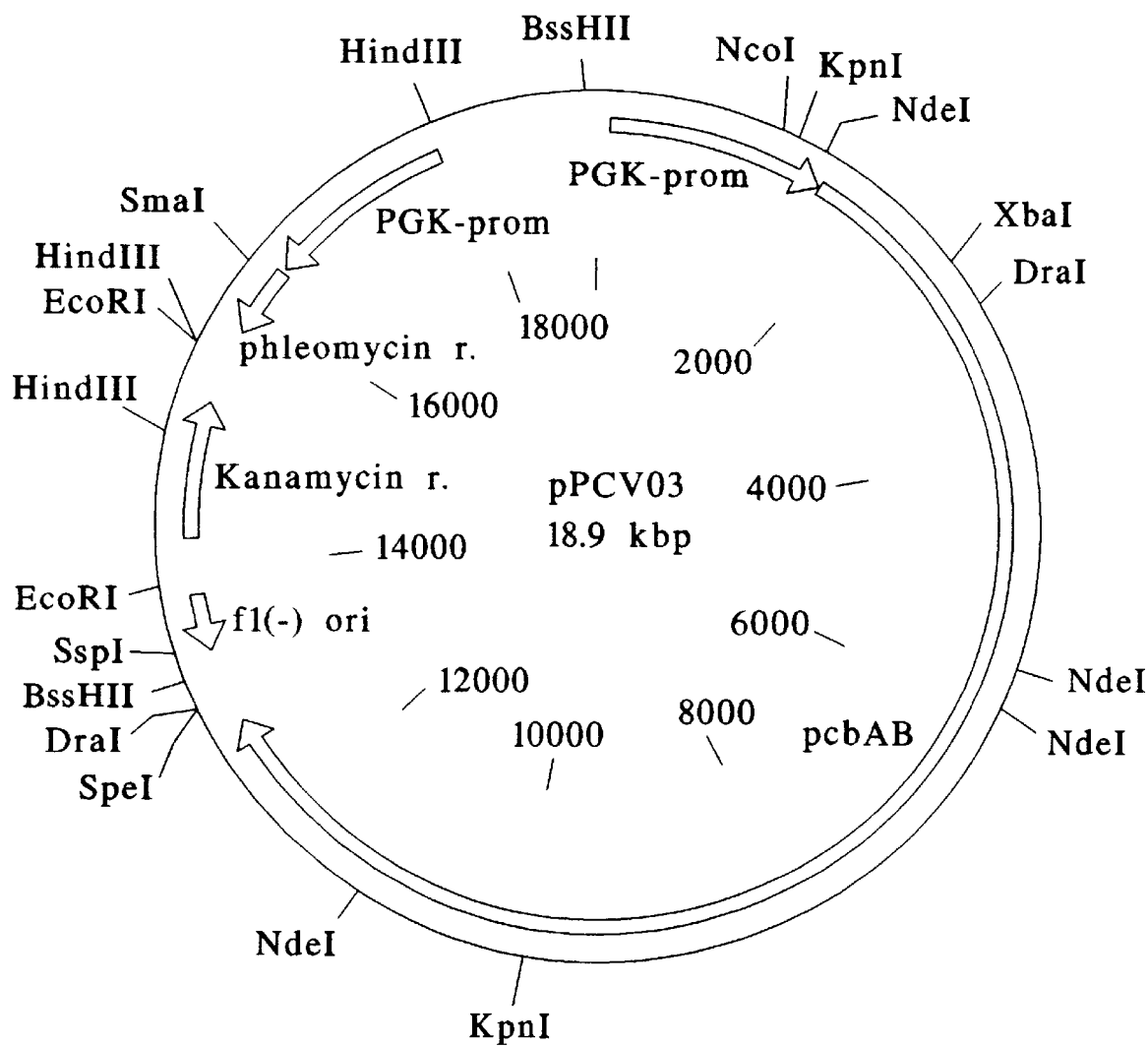
FIG. 8 shows a restriction site and functional map of construct pPCV03.

The pcbAB gene is isolated from cosmid clone HM193 as a $1.2 \times 10^4$ nucleotide SpeI fragment and was subcloned into the vector pPCV01, using the unique SpeI site. Conditions used were as disclosed in Maniatis et al. (supra) The resulting construct is named pPCV02 (FIG. 8). The orientation of the gene in the vector has been determined by digestion with restriction enzymes.

Transformation

The plasmid pPCV02 is transformed into P. chrysogenum Wis54-1255 npe5 (CBS 178.89) using the procedure described in copending application U.S. Ser. No. 097,455 filed Sep. 16, 1987. Strain npe5 is a non-producing mutant of Wis 45-1255; the npe phenotype is caused by the absence of ACV synthetase activity. Transformants are selected for resistance against 30 μg/ml of phleomycin. Isolated transformants have been tested in a bioassay, as described in U.S. Pat. No. 5,108,918, for a restoration of penicillin production. In a representative experiment penicillin production has been restored in 80% (8 out of 10) of the pPCV02-transformants analyzed; in transformants having received the vector pPCV01, without the ACV synthetase insert, a restoration of the penicillin production has not been demonstrated (0 out of 26).

The construct pPCV02 is also transformed into wild type P. chrysogenum. Selected transformants are assayed for an increased ACV synthetase activity, using cell-free extracts as described in U.S. Pat. No. 5,108,918, or for an increased penicillin productivity, using shake flask experiments, also described in U.S. Pat. No. 5,108,918.

EXAMPLE 3

Expression of the pcbAB gene from P. chrysogenum under control of the P. chrysogenum pgk promoter Transcription of the pcbAB gene is subject to glucose repression mRNA preparations, isolated from Penicillium cultures grown on either glucose- or lactose-containing media (U.S. Pat. No. 5,108,918, are transferred to GeneScreen-plus® (NEN/DuPont) and hybridized with the $1.5 \times 10^3$ nucleotide HindIII fragment, which is internal to the pcbAB gene (FIG. 4). In glucose-grown cultures, no pcbAB mRNA is detected, while in the lactose grown cultures, a large mRNA ($\geq 10 \times 10^3$ nucleotides) is detected.

Construction of pPCV03

The region surrounding the ATG start codon of the pcbAB gene is isolated as a $1.7 \times 10^3$ nucleotide SalI-DraI fragment. The vector pTZ18R (U.S. Biochemical Corporation, Cleveland, Ohio) is digested with SalI and SmaI restriction enzymes. The digested vector and the $1.7 \times 10^3$ fragment are ligated. A construct containing the pTZ18R vector bearing the $1.7 \times 10^3$ fragment insert is isolated. Into this construct, the P. chrysogenum pgk promoter is ligated as a $1.5 \times 10^3$ nucleotides HindIII fragment (U.S. Pat. No. 5,108,918). A construct containing the pgk promoter in the desired orientation (same polarity as the pcbAB fragment) is isolated. From this construct single stranded DNA is isolated by superinfection with the helper phage M13K07, (U.S. Biochemical Corporation, Cleveland, Ohio) using techniques known in the art or as prescribed by the supplier of the pTZ cloning vector. By in vitro mutagenesis using a synthetic oligonucleotide having the following sequence (SEQ. ID. NO. 21): 5'-TGG CTT CAG TTG AGT CAT ATG GGT AGT TAA TGG TAT-3', a DNA fragment containing the mature pgk region and the region upstream of the pcbAB ATG is looped out. This mutagenesis introduces an NdeI site at the position of the ATG (underlined in the oligonucleotide sequence). The construct is named pTZpgk::acvsl. This construct is digested with HindIII and XbaI and the promoter-gene fusion is isolated on a DNA fragment of $2.9 \times 10^3$ nucleotides as described by Maniatis et al., (supra). This fragment is ligated with the 16.3 kb DNA fragment containing the pcbAB gene, isolated after partial XbaI digestion of pPCV02, the remaining HindIII-XbaI sticky ends are filled in with T4 DNA polymerase and the construct is circularized by the addition of ligase.

The resulting construct, pPCV03 (FIG. 8), is isolated as follows. The ligation mixture is transformed into HB101 (ATCC 33694) using standard techniques. Plasmid DNA is isolated from several transformants and analyzed by restriction enzyme-digestion and agarose gel electrophoresis. Transformants containing the correct DNA constructs are grown on large scale (500 ml) and plasmid DNA is isolated using methods as disclosed in Maniatis et al., (supra) and transformed into P. chrysogenum. Expression of the pcbAB gene, enzyme activity and penicillin production of transformants is analyzed after growth in shaker flasks on both glucose- and lactose containing media; the data obtained are compared with those obtained for transformants containing pPCV02. In contrast to transformants containing pPCV02, transformants containing pPCV03 express the pcbAB gene in glucose-containing media: both an ACV synthetase-specific mRNA and ACV synthetase enzyme activity are detected.

EXAMPLE 4

Expression of the pcbAB gene in E. coli

For efficient production of ACV synthetase enzyme in E. coli it is necessary to place the pcbAB gene under control of a promoter which allows efficient gene expression in E. coli. Examples of such efficient promoters are the trp promoter, the lac promoter and the tac promoter. In this example the trp promoter is described, but it will be obvious to those skilled in the art that the experiments can be easily repeated with the lac and tac promoters, leading to similar results. If desired, a runaway replicon can be included in the construct; this will allow for controlled amplification of the plasmid copy number after a temperature shift.

Figure 9:
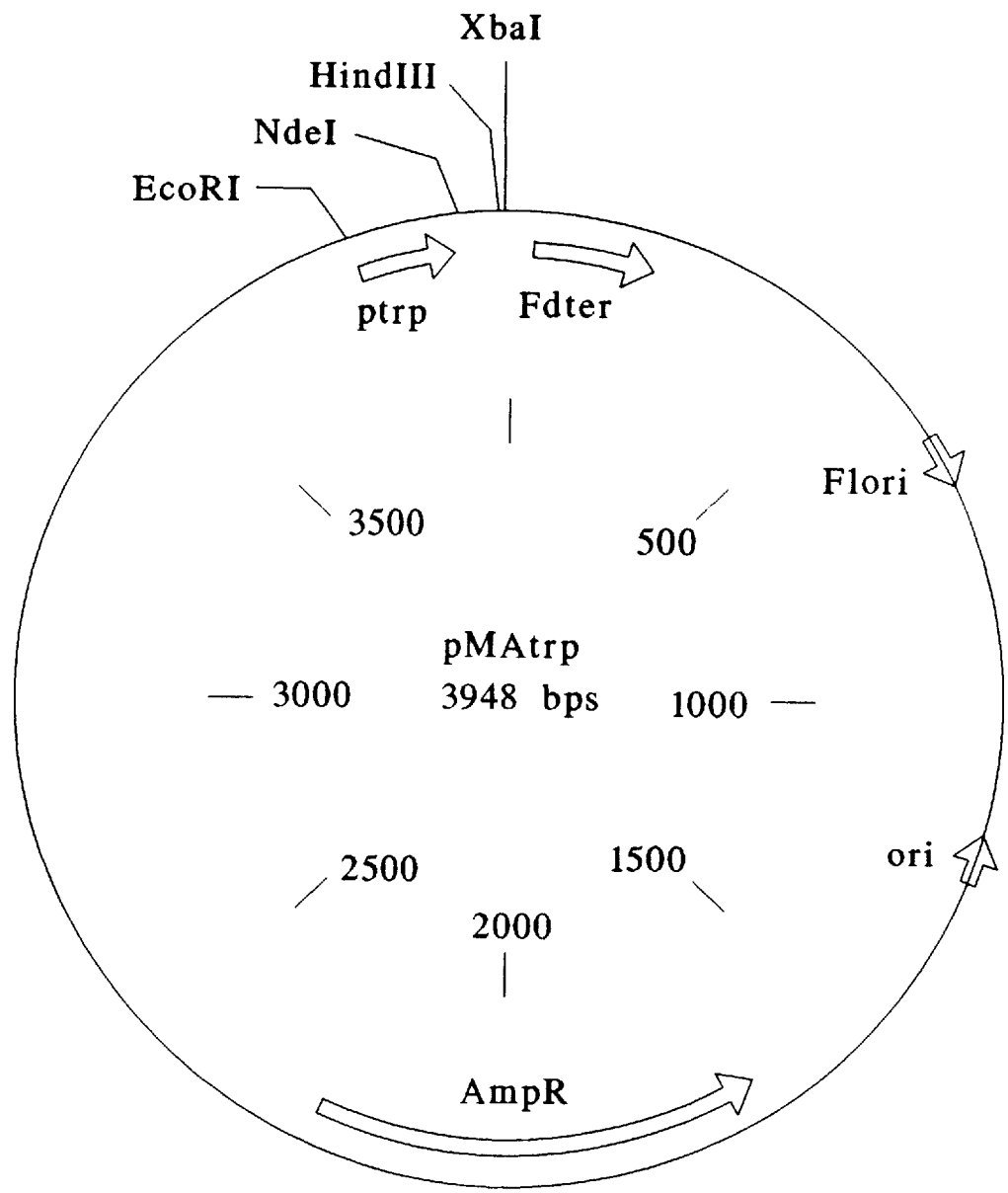
FIG. 9 shows a restriction site and functional map of the *E. coli* vector pMAtrp.
Figure 10:
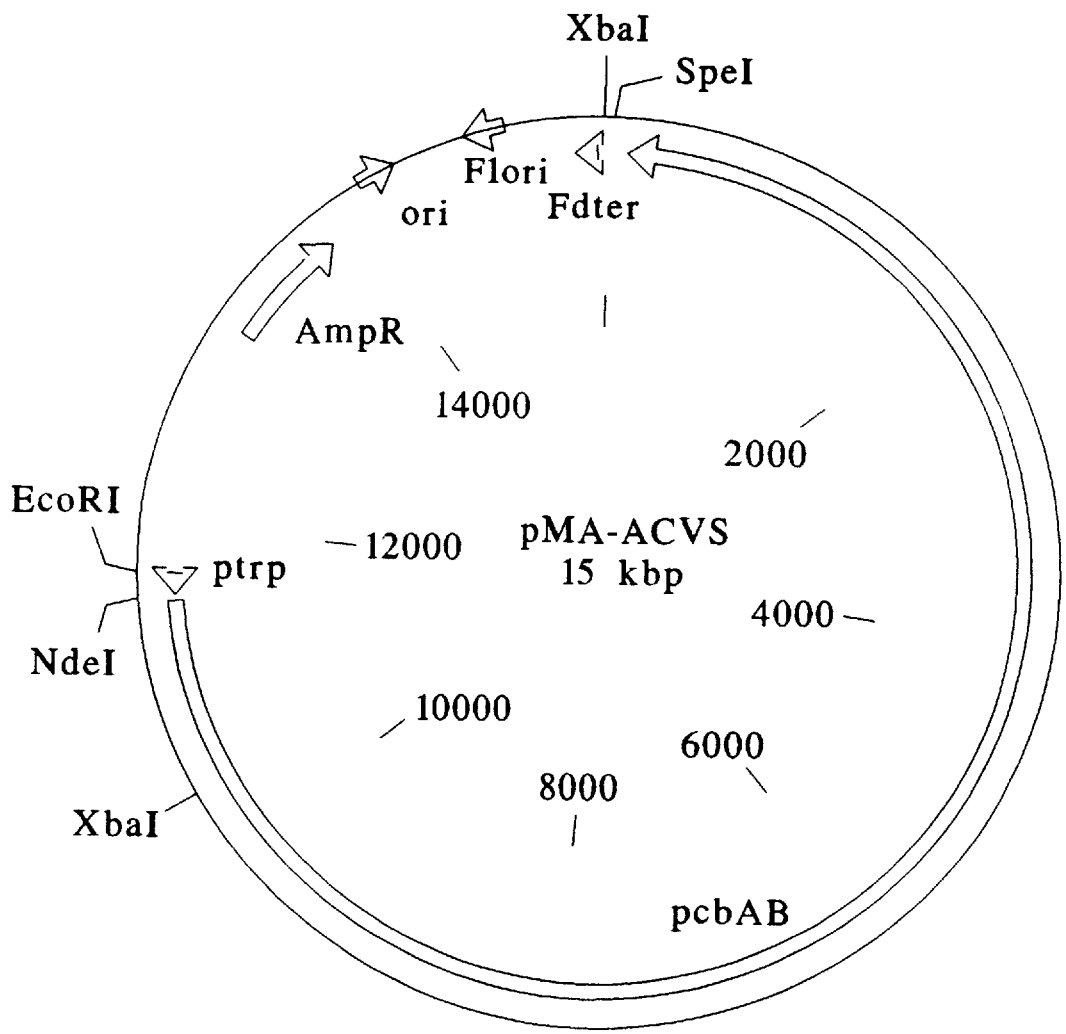
FIG. 10 shows a restriction site and functional map of pMA-ACV synthetase.

Synthesis of PMA-ACVS pMAtrp (FIG. 9), having the trp promoter region between −113 and the ATG transcription start flanked by an NdeI site at the position of the ATG (Sommerville, supra), is digested with SmaI and NdeI. From pPCV03 a $1.5 \times 10^3$ nucleotide NdeI-DraI fragment, containing the 5'-part of the pcbAB gene, is isolated and ligated into the SmaI, NdeI digested pMAtrp. Into the XbaI sites of the resulting construct, the 3'-part of the pcbAB gene was inserted as a $1.0\times10^4$ nucleotide XbaI fragment isolated from HM193 or pPCV02. Constructs are selected for the correct orientation of the inserted XbaI fragment; the construct containing the fragment in the correct orientation is named pMA-ACV synthetase (FIG. 10). Orientation is determined by digestion with various restriction enzymes.

pMA-ACV synthetase is isolated and used to transform a suitable E. coli host, such as, for example E. coli HB101, E. coli C600 or E. coli JM101. Transformants are analyzed by determination of ACV synthetase activity in cell free extracts, by electrophoresis of cell free extracts in 5% polyacrylamide gels (SDS-PAGE) and by immunoblotting, using a polyclonal antiserum which had been raised against purified ACV synthetase.

EXAMPLE 5

Expression of the pcbAB gene from P. chrysogenum in Streptomyces lividans

For expression in a Streptomyces host, several options are available. S. lividans is a preferred host because of the ease of transformation of this host, as compared to several other Streptomycetes.

Figure 11:
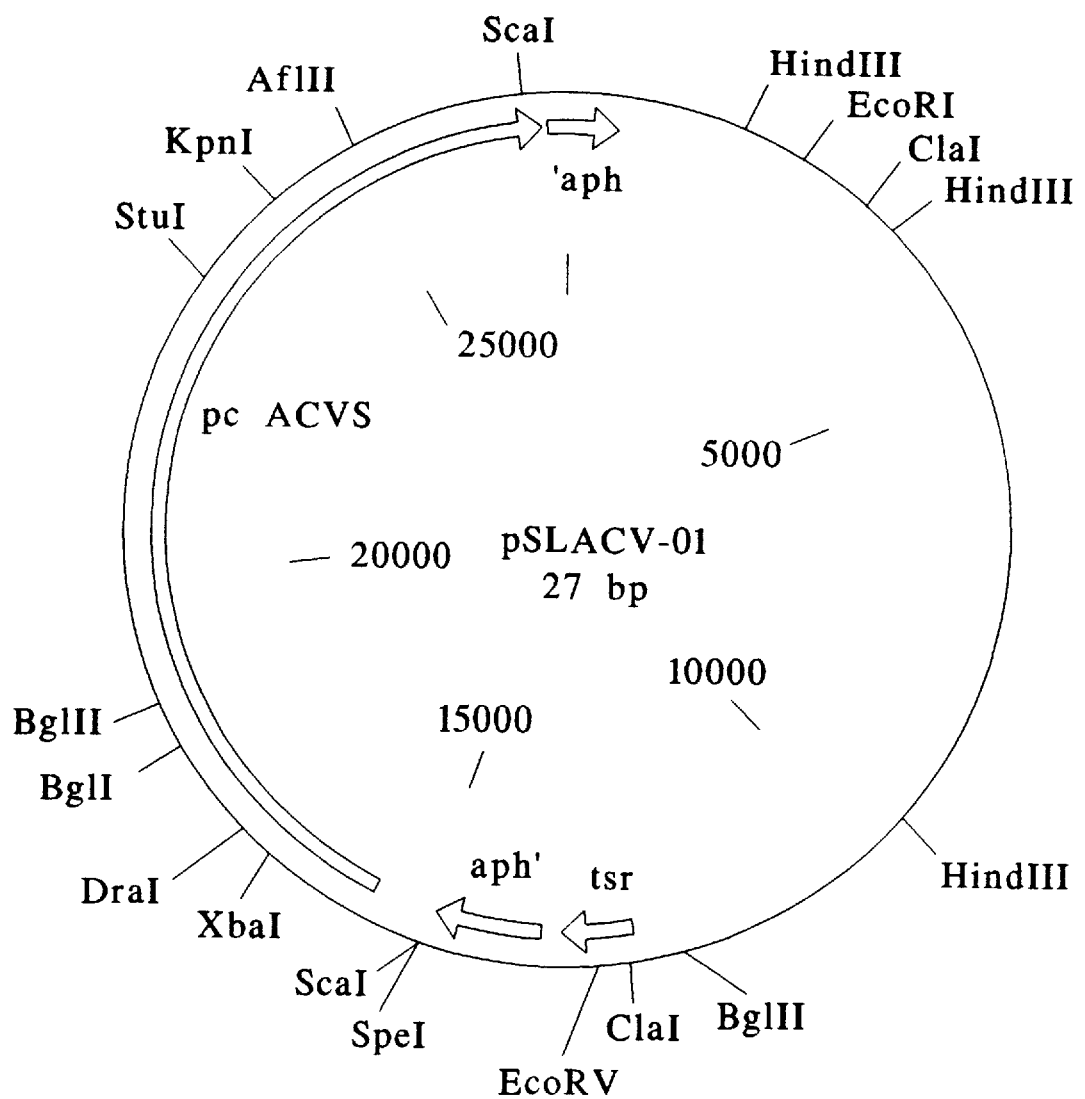
FIG. 11 shows a restriction site and functional map of pSLACV-01.

Expression of the P. chrysogenum ACV synthetase gene under control of the aph promoter The P. chrysogenum ACV synthetase gene is isolated as the $1.2\times10^4$ nucleotide SpeI fragment described in Example 2. The sticky ends of this fragment are made blunt by treatment with T4 DNA polymerase using the procedures known in the art. The vector pIJ61 has been described by C. J. Thompson et al., (1982) Gene 20, 51–62); reviewed in: D. A. Hopwood et al., supra; the vector can be obtained from D. A. Hopwood. The vector pIJ61 was digested with BamHI, and the ends were made blunt using T4 DNA polymerase. Subsequently, the blunt-ended $1.2\times10^4$ nucleotide SpeI fragment is inserted into the blunt-ended BamHI site via ligation, and the mixture is used to transform S. lividans 66, by the method of Hopwood et al. (D. A. Hopwood et al., 1985, supra). Transformants are selected for resistance to thiostrepton (50 µg/ml) and are subsequently analyzed for the orientation of the pcbAB gene in the same orientation as the aph gene is named pSLACV-01 (FIG. 11).

Selected transformants containing the plasmid pSLACV-01 were cultured as described in Chen et al., (supra). Cell free extracts are prepared and analyzed by SDS-PAGE or immunoblotting for the presence of a large (>250 kDa) protein; the ACV synthetase activity in the extracts is also determined using the procedure as described by Van Liempt (supra).

Figure 12A:
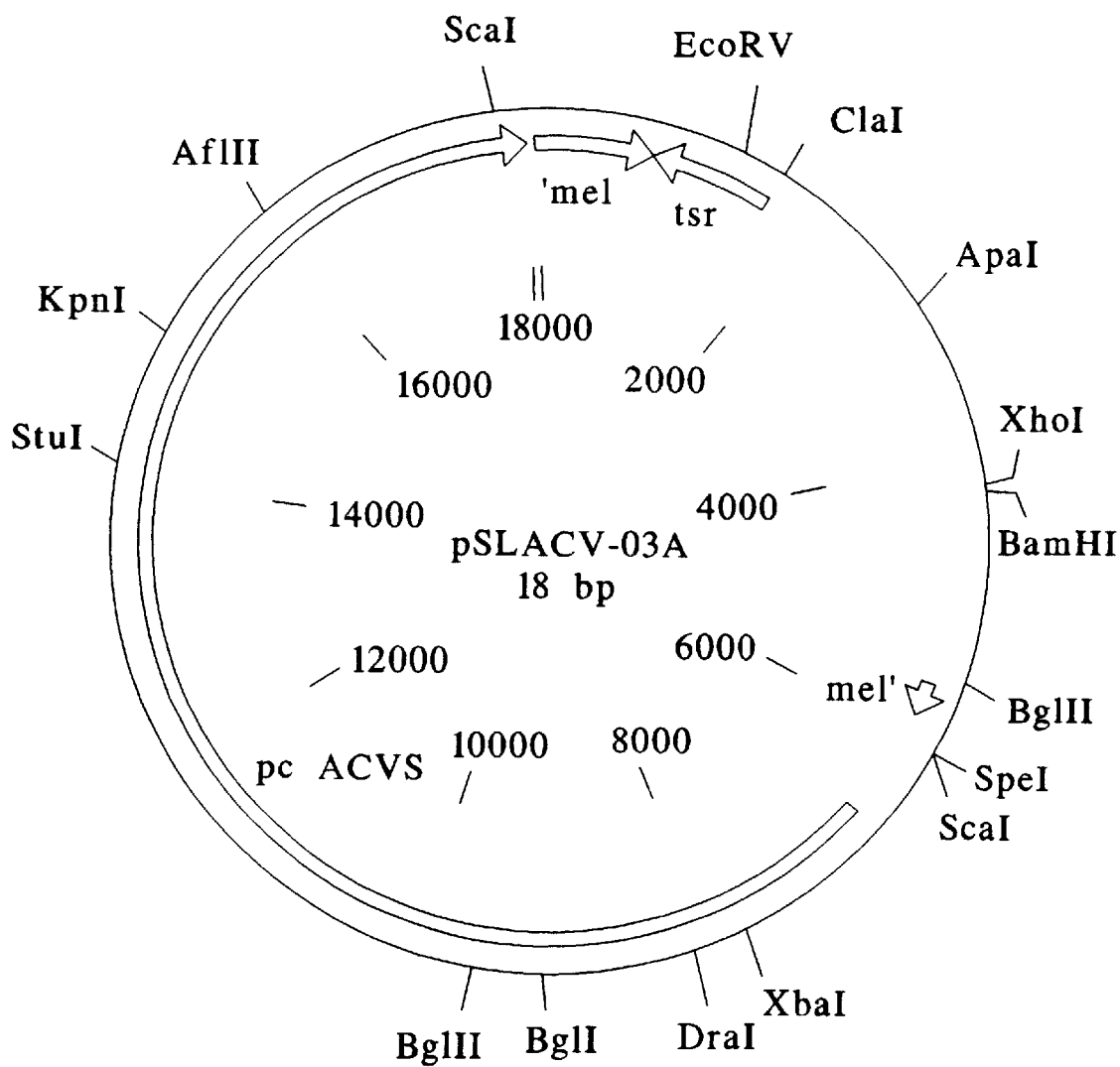
FIG. 12A shows a restriction site and functional map of pSLACV-03A.
Figure 12B:
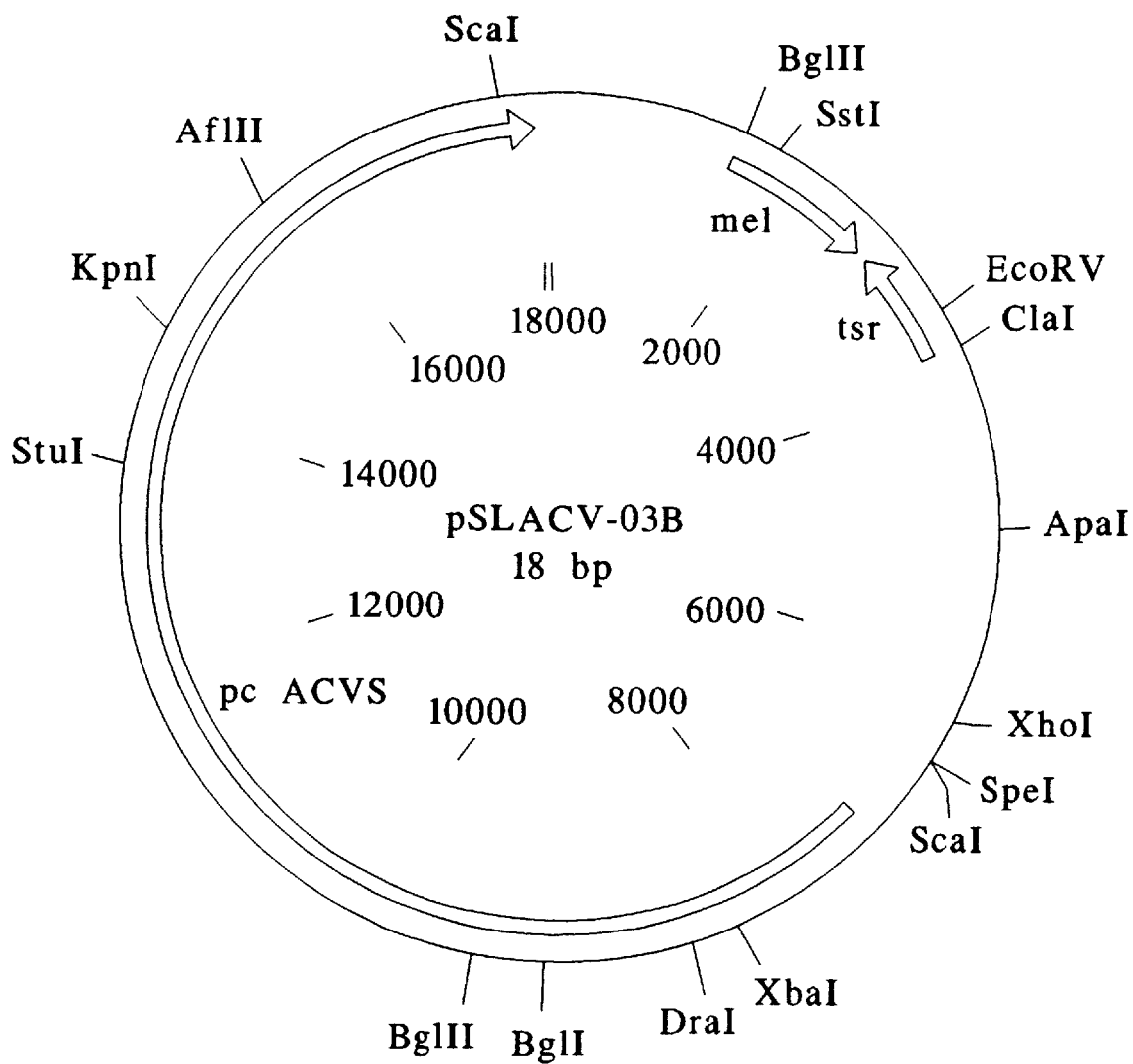
FIG. 12B shows a restriction site and functional map of pSLACV-03B.

Expression of the P. chrysogenum pcbAB gene in S. lividans under control of the tyrosinase promoter The vector pIJ702 is digested with either BglII or SstI. pIJ702 is described by E. Katz et al., Journ. Gen. Microbiol. (1983) 129:2703–2714; reviewed in: D. A. Hopwood et al., supra; obtainable from D. A. Hopwood. BglII digested pIJ702 was made blunt-ended by treatment with T4 DNA polymerase; SstI digested pIJ702 is treated with Mung bean nuclease in order to obtain blunt ends. The blunt-ended SpeI fragment containing the P. chrysogenum pcbAB gene as described hereinabove is inserted into both blunt-ended vectors via ligation. Thiostrepton resistant transformants are screened for a melanin-negative phenotype by application of a soft agar overlay containing tyrosine (0.1 mM) as described in Hopwood et al. (supra). Melanin-negative transformants contained an interrupted tyrosinase gene (by insertion of the ACV synthetase gene) and their colonies remained colorless upon addition of tyrosine, while wild-type colonies turn brown. Analysis by restriction enzyme digestion and agarose gel electrophoresis for the correct orientation of the inserts yielded plasmids pSLACV-03A (SstI site; FIG. 12A) and pSLACV-03B (BglII site; FIG. 12B).

Analysis of transformants is as described hereinabove. Induction of the tyrosinase promoter is established by the addition of methionine (10 mM) to the culture medium.

EXAMPLE 6

Isolation and characterization of the pcbAB gene from A. chrysogenum Isolation of the A. chrysogenum pcbAB gene A gene library of A. chrysogenum C10 (deposited with American Type Culture Collection, Rockville, Md., as ATCC 48272) has been constructed in the lambda cloning vector EMBL3. To this end, A. chrysogenum DNA has been partially digested with Sau3A and fragments ranging in size from 13 to $17\times10^3$ nucleotides have been isolated by sucrose gradient ultracentrifugation. The vector EMBL3 has been digested with BamHI and arms have been separated and purified by sucrose gradient centrifugation. About 0.4 µg of vector arms have been ligated with 0.5 µg of partially digested, purified A. chrysogenum DNA; the ligation mixture has been packaged in vitro using the lambda phage packaging system of Amersham (Buckinghamshire, UK), following the procedure provided by the supplier. The packaged mixture has been used to infect E. coli Q-359 (ATCC 47019); about 70,000 plaques have been obtained.

In order to isolate phages containing the A. chrysogenum pcbAB gene, the gene library first was screened using as a probe the isolated pcbc gene from P. chrysogenum, namely a $1\times10^3$ nucleotide NcoI fragment, carrying the promoterless gene (Barredo et al., (1989)b, Mol. Gen. Genet. 216, 91–98); conditions have been described in Barredo et al., 1989b (supra). Five phages, showing a positive hybridization signal have been purified and a restriction map has been constructed. The position of these phages (F1, F3, F4, F5 and F6) relative to a restriction map of the genomic region is given in FIG. 16.

Figure 16:
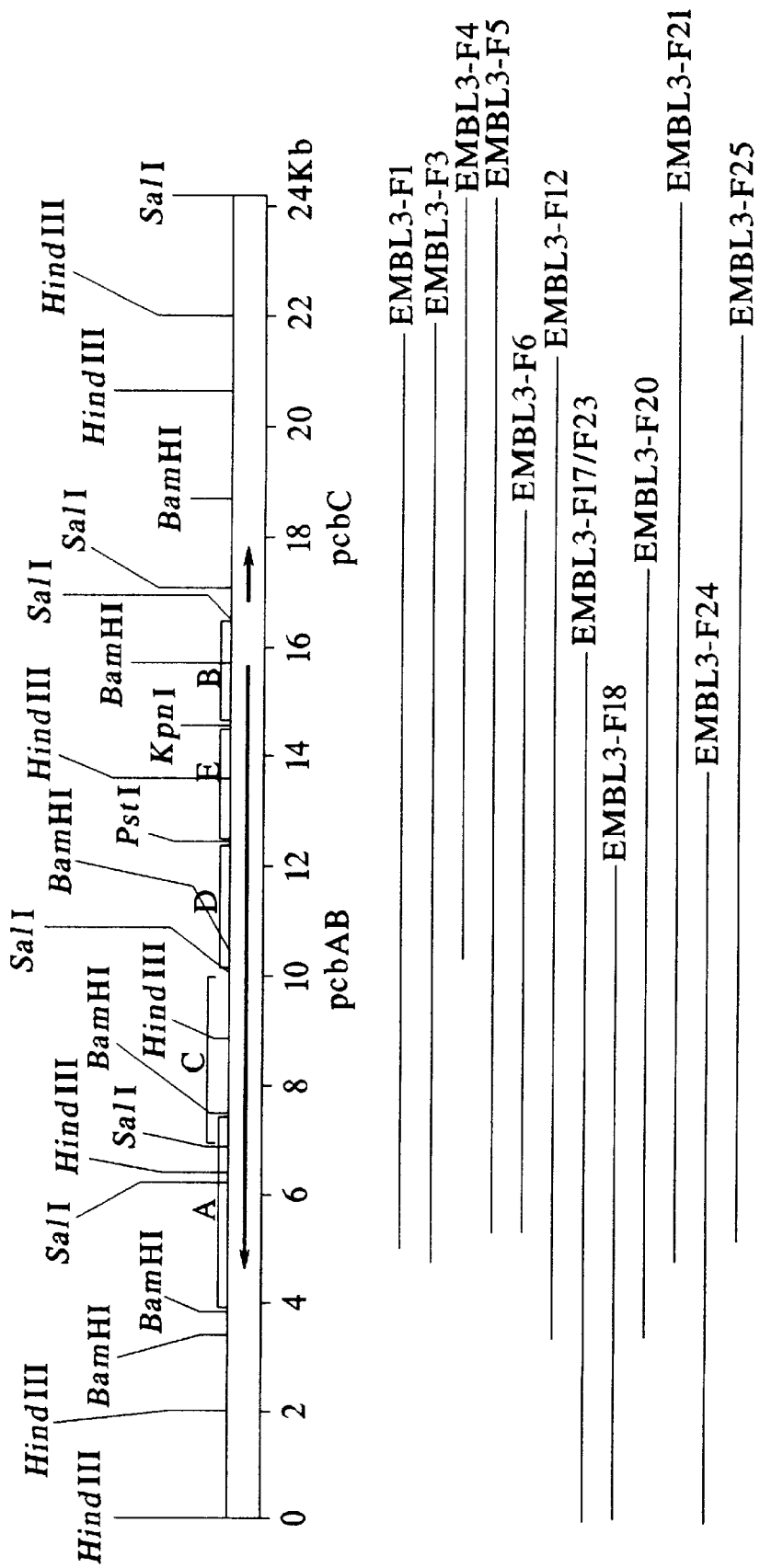
FIG. 16 is a restriction site and functional map of the chromosomal region encoding the ACVS gene in *A. chrysogenum*. Arrows indicate the positions of the IPNS-(pcbC) and ACVS-(pcbAB) genes. The position of phages which have been isolated from a gene library and which contain part of the region are indicated.

To identify the presence of another gene on the phages, the isolated DNA has also been hybridized with a $6.0\times10^3$ nucleotide SalI fragment (III in FIG. 3) derived from the P. chrysogenum pcbAB gene as it is present in, for example, HM193. All five phages showed a strong hybridization signal with this latter probe. This finding indicates that in A. chrysogenum the pcbC and pcbAB genes are linked, as they are in P. chrysogenum and as indicated in FIG. 16. To isolate phages with an insert containing more upstream sequences, as compared to the isolated phages (which extend a maximal $11.5\times10^3$ nucleotides upstream from the 5'-end of the pcbC gene) the library has been rescreened using as a probe a $0.9\times10^3$ nucleotide XhoI fragment (probe P6 in FIG. 17) isolated from, for example, phages F1, F3, F5 or F6. This rescreening has yielded another seventeen phages. Eight of these phages have been further purified and characterized; the position of the phages F12, F17, F18, F20, F21, F23, F24 and F25 relative to a restriction map of the genomic region is given in FIG. 14.

Localization of the pcbAB gene of A. chrysogenum

Figure 17A:
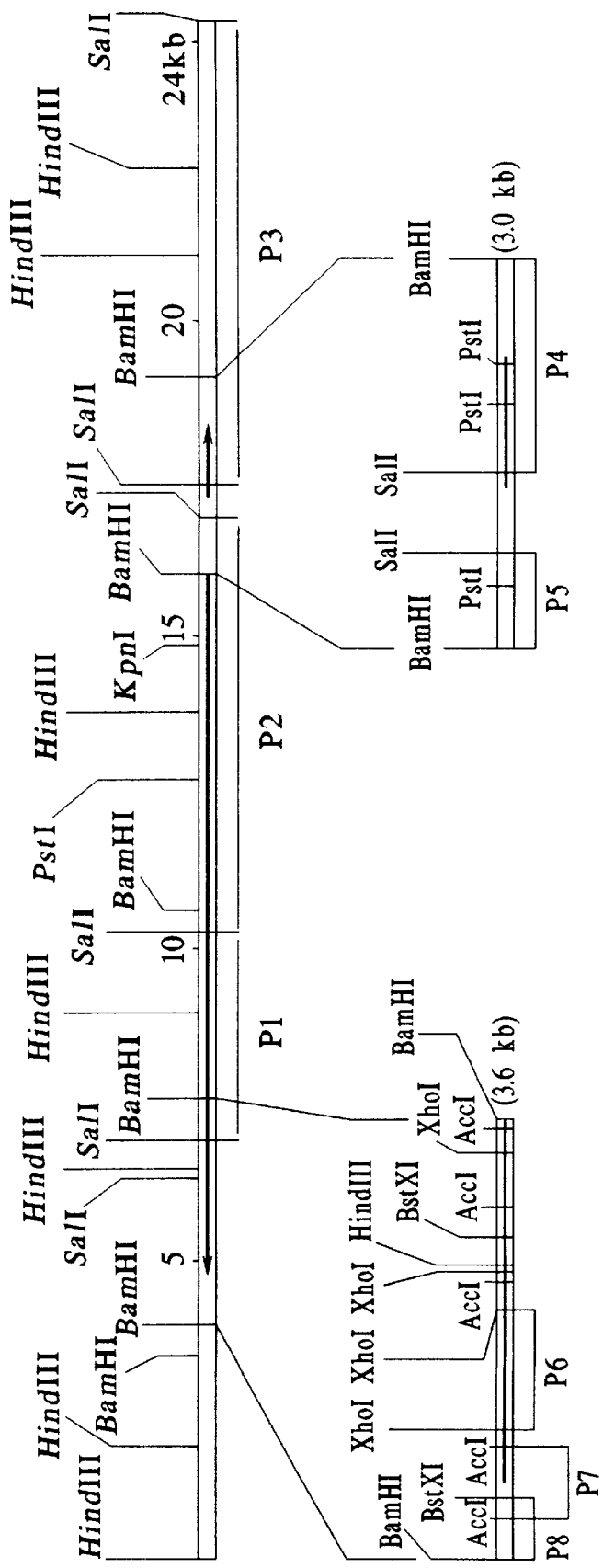

Northern blot hybridizations have been performed using mRNA that has been isolated from A. chrysogenum following the procedure described in Barredo et al., 1989b (supra). As probes, the fragments P1–P8 as indicated in FIG. 17 have been used. Probes P3 and P4 hybridize to a transcript of about $1.15 \times 10^3$ nucleotides; this transcript is derived from the pcbC gene and encodes the IPNS enzyme. Probes P1, P2, P5, P6 and P7 hybridize to a large mRNA, size $>11 \times 10^3$ nucleotides; this indicates the presence of a large gene in the region covered by these probes. Moreover, the ends of the large transcript have been more accurately mapped by the results using the small probes P5-P8: absence of hybridization using probe P8 indicates that the distal end of the putative pcbAB gene is located within the $0.5 \times 10^3$ nucleotide AccI fragment preceding P8 (namely in region P7 in FIG. 17) while the hybridization patterns of probes P4 and P5 indicate that the proximal end of the putative pcbAB gene has to be present outside region P4, most probably within region P5. The orientation of the gene has been established by homology with the *P. chrysogenum* gene; it is transcribed in the opposite direction to the pcbC gene (FIG. 16), which also occurs in *P. chrysogenum*.

Determination of the nucleotide sequence of the pcbAB gene from *A. chrysogenum*

The nucleotide sequence of the region encoding the putative pcbAB gene of *A. chrysogenum* has been determined. Five subclones have been constructed in pBluescript KS(+) (Stratagene, LaJolla, U.S.A.), starting from phage F12 (FIG. 16). The subclones contain the following fragments: A ($3.6 \times 10^3$ nucleotide BamHI), B ($1.7 \times 10^3$ nucleotide SalI-KpnI), C ($3.2 \times 10^3$ nucleotide SalI), D ($2.4 \times 10^3$ nucleotide SalI-PstI) and E ($2.0 \times 10^3$ nucleotide PstI-KpnI). Fragment A has been cloned in both orientations in pBluescript KS(+) which had been digested with BamHI; subsequently the fragment has been subcloned into 23 smaller, overlapping fragments, which have been sequenced using the dideoxy chain termination method (Sanger et al., *Proc. Natl. Acad. Sci.* (U.S.A.) (1977) 74:5463–5467), using either Sequenase (U.S. Biochemicals, Cleveland, Ohio) or Taq polymerase (Promega, Madison, Wis.). The sticky ends of fragment B have been made blunt, using standard techniques, and the blunt end fragment has been cloned into EcoRV digested pBluescript KS(+). Subsequently, the fragment has been subcloned into fourteen overlapping smaller fragments. These fragments have been sequenced using the dideoxy chain termination method.

Fragments C, D and E have been sequenced by generating sets of ordered deletion mutants using the "Erase-A-Base" system (Promega, Madison, Wis.). To this end, fragment C has been subcloned into SalI-digested pBluescript KS(+) in both orientations; the clones have been opened by digestion with BstXI and XbaI to obtain appropriate ends to generate the deletions. Fragment D has been subcloned in both orientations into EcoRV-digested pBluescript KS(+), after filling in the sticky ends of the fragment. For the generation of sets of deletion mutants, the clones have been opened by digestion with PstI and EcoRI. Fragment E (after filling in the sticky ends) has been subcloned into EcoRV digested pBluescript KS(+) in both orientations; clones have been opened for generation of sets of deletion mutants by digestion with EcoRI and PstI.

The digested clones of the fragments C, D and E have been treated with exonuclease III, followed by deletion of the remaining sticky ends with exonuclease S1. The gaps that have been introduced by both enzymes have been repaired with Klenow DNA polymerase, followed by ligation of the linear molecules and transformation into *E. coli*. For all treatments, the conditions recommended by the supplier of the "Erase-A-Base" system have been used. The resulting fragments have been sequenced using the dideoxy chain termination method. Clones overlapping the junctions of the five fragments have also been sequenced; the entire region has been sequenced in both strands. The nucleotide sequence of a $11.8 \times 10^3$ nucleotide DNA fragment is shown in FIG. 16 (SEQ ID NO:3). In this sequence a long open reading frame (ORF) of 11,139 bp has been demonstrated. From this ORF a protein sequence of 3712 amino acids has been deduced (SEQ ID NO:4).

Similarity with the *P. chrysogenum* pcbAB sequence

Figure 6:
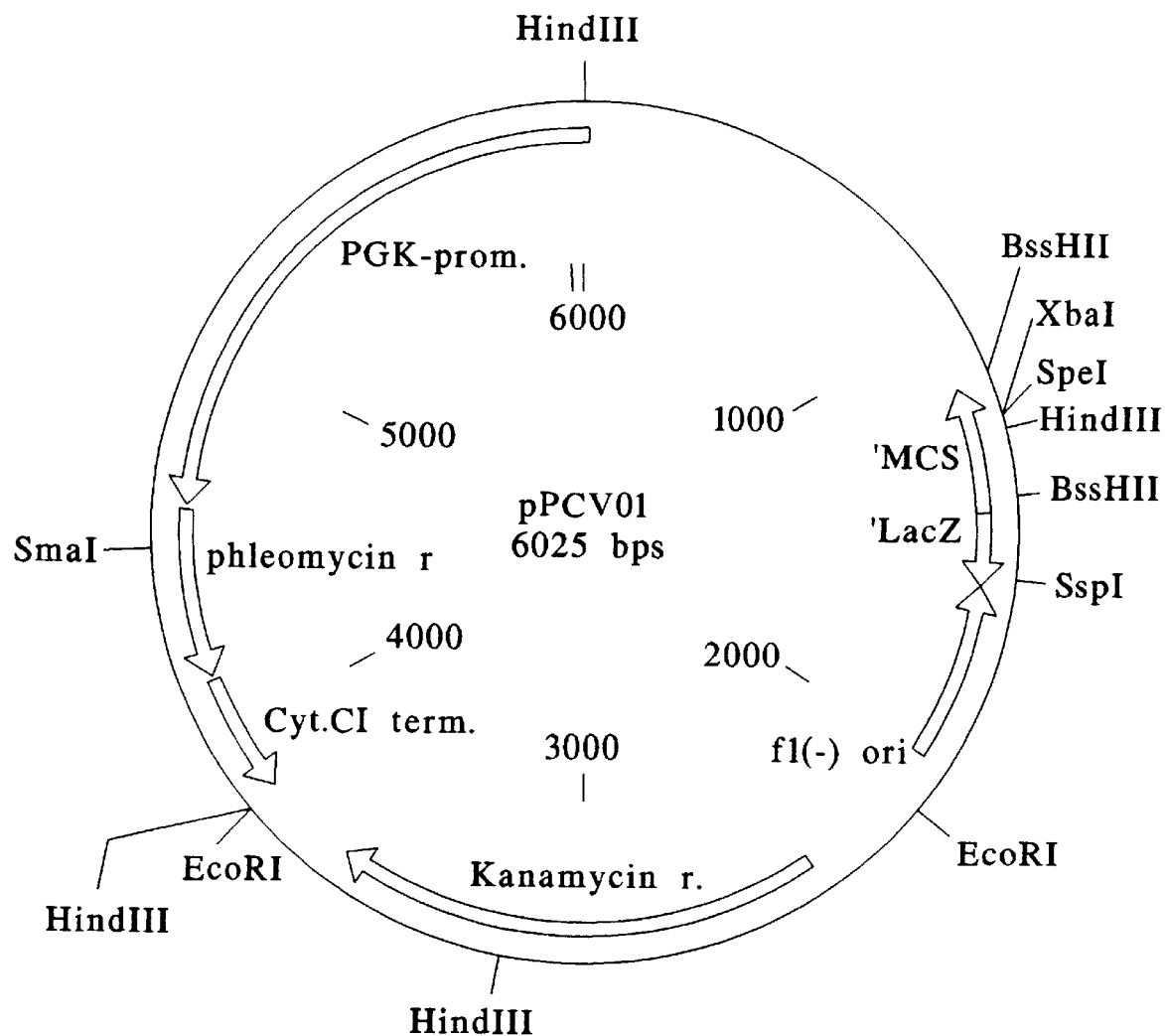
FIG. 6 shows a restriction site and functional map of construct pPCV01.
Figure 7:
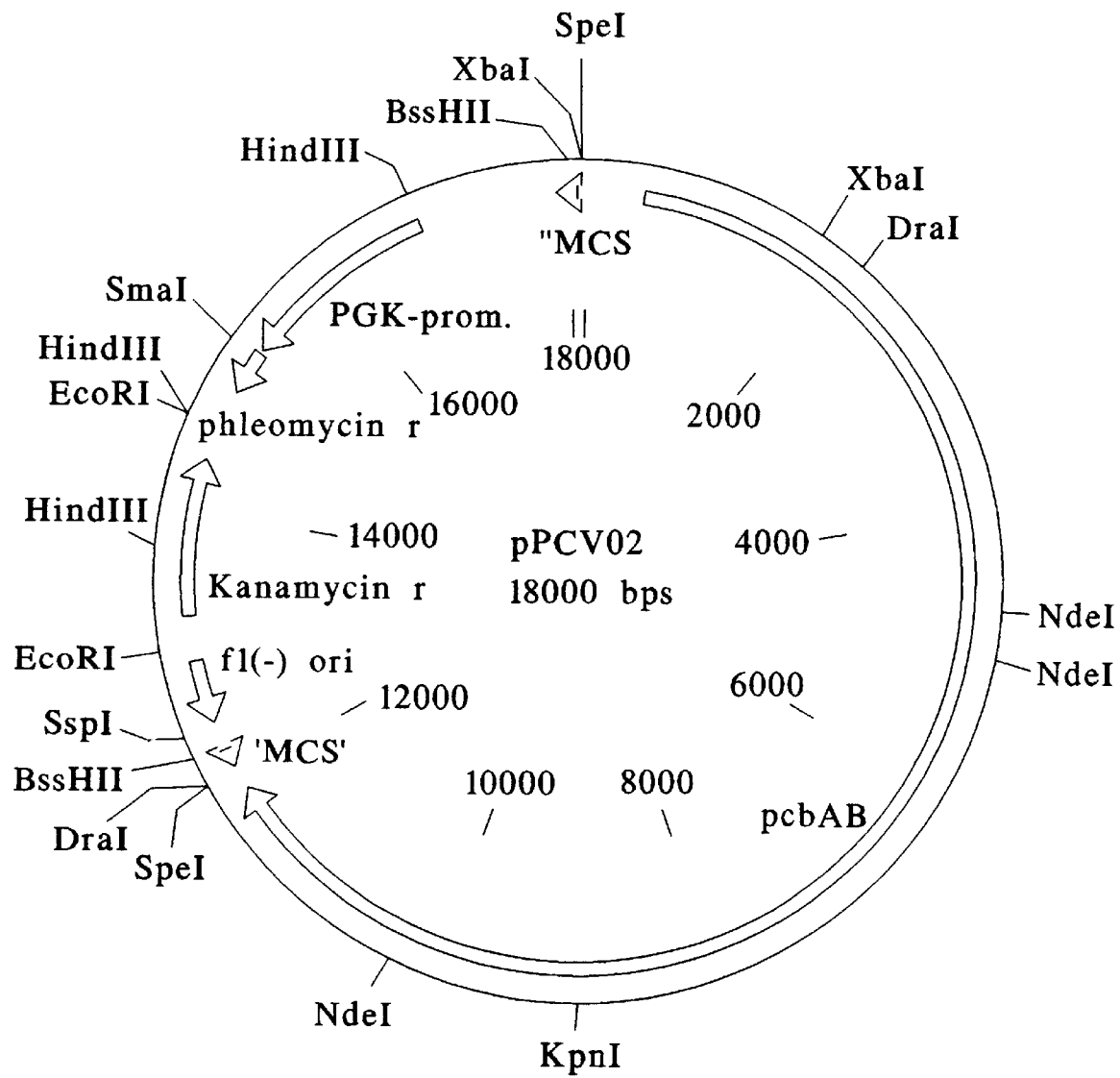
FIG. 7 shows a restriction site and functional map of construct pPCV02.

The nucleotide sequence of the *A. chrysogenum* pcbAB gene has been compared with the nucleotide sequence that has been determined for the *P. chrysogenum* pcbAB gene (Example 1; FIG. 6). A 62.9% homology has been determined at the nucleotide level. At the protein level the similarity is 54.9% (based on the deduced amino acid sequences); a comparison between the deduced amino acid sequences for the *P. chrysoqenum* (SEQ ID NO:2) and *A. chrysogenum* (SEQ ID NO:4) ACVS is given in FIGS. 18A–18H.

The ACV synthetase enzyme activities reside on a single gene in *P. chrysogenum* and *A. chrysogenum*. Elevated activity of this enzymes can be obtained in host cells using the recombinant compositions of the instant invention. Heterologous expression of ACV synthetase can provide a means of using more efficient and robust hosts for the commercial production of ACV synthetase and its secondary metabolites. Finally, the availability of large amounts of the ACV synthetase-enzyme, for example, by expression of the gene in a suitable host, will allow for better prospects for commercial application of in vitro synthesis of β-lactam antibiotics and their precursors.

All publications and patent applications cited in this specification are herein incorporated by reference as if each individual publication or patent application were specifically and individually indicated to be incorporated by reference.

The invention now being fully described, it will be apparent to one of ordinary skill in the art that many changes and modifications can be made thereto without departing from the spirit or scope of the appended claims.

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 12364 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (v) ORIGINAL SOURCE:
  (A) ORGANISM: Penicillium chrysogenum (ix) FEATURE:
  (A) NAME/KEY: CDS
  (B) LOCATION: 264..11600
  (D) OTHER INFORMATION: /function="enzyme"
      / product= "ACV Synthetase"

(xi) SEQUENCE DESCRIPTION: SEQ ID NO:1:

```
GTCGACAGTT  GACAGAGCCA  ATGGCATCGG  ATCTGCCCTA  GACCGTGCTA  GACGAAAGTC     60

TCCATCTTGT  CTGCGGGCAG  TTCTTCAGTC  GCCCAGATTC  TCGATGGAGA  TTGGCCAGGT    120

CAGCCATATA  TACCCTGCAA  TGGCAGACCA  ATGCAGCAGG  CCCAGTATAA  GGAATTCCCC    180

TCGAGCTTGT  CTGTGATTGC  GTTTTTTCTA  ACACTTGTTG  TTGCATCCGA  TCCGTCGCTA    240

CCAATTATTG  GTCATTGACA  GAC ATG ACT CAA CTG AAG CCA CCG AAC GGA           290
                           Met Thr Gln Leu Lys Pro Pro Asn Gly
                             1               5

ACC ACG CCG ATA GGC TTC TCG GCC ACT ACA TCC CTG AAC GCC AGT GGG           338
Thr Thr Pro Ile Gly Phe Ser Ala Thr Thr Ser Leu Asn Ala Ser Gly
 10              15                  20                  25

AGC TCG AGT GTG AAA AAT GGG ACC ATC AAA CCC AGC AAT GGC ATC TTC           386
Ser Ser Ser Val Lys Asn Gly Thr Ile Lys Pro Ser Asn Gly Ile Phe
                 30                  35                  40

AAG CCC AGC ACT AGG GAC ACC ATG GAC CCT TGC AGT GGG AAT GCG GCC           434
Lys Pro Ser Thr Arg Asp Thr Met Asp Pro Cys Ser Gly Asn Ala Ala
             45                  50                  55

GAT GGC AGT ATC CGC GTC CGT TTC CGT GGA GGA ATC GAA CGG TGG AAG           482
Asp Gly Ser Ile Arg Val Arg Phe Arg Gly Gly Ile Glu Arg Trp Lys
         60                  65                  70

GAG TGC GTC AAC CAG GTC CCC GAG CGC TGC GAC CTG AGT GGT CTG ACA           530
Glu Cys Val Asn Gln Val Pro Glu Arg Cys Asp Leu Ser Gly Leu Thr
     75                  80                  85

ACC GAC TCC ACG CGA TAT CAG CTC GCA TCG ACT GGG TTC GGT GAC GCG           578
Thr Asp Ser Thr Arg Tyr Gln Leu Ala Ser Thr Gly Phe Gly Asp Ala
 90                  95                 100                 105

AGC GCT GCG TAC CAG GAG CGC TTG ATG ACG GTC CCT GTT GAC GTA CAT           626
Ser Ala Ala Tyr Gln Glu Arg Leu Met Thr Val Pro Val Asp Val His
                110                 115                 120

GCC GCG CTC CAA GAG CTG TGC CTA GAA CGC CGT GTG AGC GTG GGA TCC           674
Ala Ala Leu Gln Glu Leu Cys Leu Glu Arg Arg Val Ser Val Gly Ser
            125                 130                 135

GTC ATT AAT TTC TCC GTG CAC CAG ATG CTG AAA GGG TTT GGA AAT GGC           722
Val Ile Asn Phe Ser Val His Gln Met Leu Lys Gly Phe Gly Asn Gly
        140                 145                 150

ACA CAC ACT ATC ACC GCC TCT CTG CAC CGT GAG CAG AAT TTG CAG AAT           770
Thr His Thr Ile Thr Ala Ser Leu His Arg Glu Gln Asn Leu Gln Asn
    155                 160                 165

TCT TCG CCA TCC TGG GTA GTC TCC CCC ACA ATC GTC ACC CAT GAG AAC           818
Ser Ser Pro Ser Trp Val Val Ser Pro Thr Ile Val Thr His Glu Asn
170                 175                 180                 185

AGA GAC GGA TGG TCC GTC GCG CAG GCG GTC GAG AGT ATC GAA GCG GCG           866
Arg Asp Gly Trp Ser Val Ala Gln Ala Val Glu Ser Ile Glu Ala Ala
                190                 195                 200
```

| | | | | | | | | | | | | | | | | |
|---|---|---|---|---|---|---|---|---|---|---|---|---|---|---|---|---|
| CGC | GGT | TCC | GAG | AAG | GAG | TCA | GTG | ACT | GCG | ATT | GAC | TCC | GCG | TCA | AGT | 914 |
| Arg | Gly | Ser | Glu | Lys | Glu | Ser | Val | Thr | Ala | Ile | Asp | Ser | Ala | Ser | Ser | |
| | | | 205 | | | | 210 | | | | | | 215 | | | |
| CTC | GTG | AAA | ATG | GGG | TTA | TTT | GAC | TTA | CTC | GTC | AGC | TTT | GTC | GAT | GCA | 962 |
| Leu | Val | Lys | Met | Gly | Leu | Phe | Asp | Leu | Leu | Val | Ser | Phe | Val | Asp | Ala | |
| | | 220 | | | | | 225 | | | | | 230 | | | | |
| GAC | GAT | GCT | CGT | ATT | CCA | TGT | TTC | GAC | TTT | CCC | CTC | GCA | GTG | ATA | GTG | 1010 |
| Asp | Asp | Ala | Arg | Ile | Pro | Cys | Phe | Asp | Phe | Pro | Leu | Ala | Val | Ile | Val | |
| | 235 | | | | | 240 | | | | | 245 | | | | | |
| CGT | GAG | TGT | GAT | GCC | AAC | CTC | TCG | CTG | ACT | CTG | CGT | TTC | TCC | GAC | TGT | 1058 |
| Arg | Glu | Cys | Asp | Ala | Asn | Leu | Ser | Leu | Thr | Leu | Arg | Phe | Ser | Asp | Cys | |
| 250 | | | | | 255 | | | | | 260 | | | | | 265 | |
| CTC | TTC | AAC | GAG | GAG | ACG | ATA | TGC | AAT | TTT | ACC | GAT | GCC | CTA | AAC | ATC | 1106 |
| Leu | Phe | Asn | Glu | Glu | Thr | Ile | Cys | Asn | Phe | Thr | Asp | Ala | Leu | Asn | Ile | |
| | | | | 270 | | | | | 275 | | | | | 280 | | |
| TTG | CTC | GCC | GAA | GCA | GTG | ATA | GGA | AGA | GTG | ACC | CCG | GTT | GCC | GAT | ATC | 1154 |
| Leu | Leu | Ala | Glu | Ala | Val | Ile | Gly | Arg | Val | Thr | Pro | Val | Ala | Asp | Ile | |
| | | | | 285 | | | | | 290 | | | | | 295 | | |
| GAA | CTA | CTA | TCC | GCG | GAG | CAG | AAG | CAG | CAG | CTG | GAA | GAG | TGG | AAC | AAC | 1202 |
| Glu | Leu | Leu | Ser | Ala | Glu | Gln | Lys | Gln | Gln | Leu | Glu | Glu | Trp | Asn | Asn | |
| | | 300 | | | | | 305 | | | | | 310 | | | | |
| ACG | GAT | GGC | GAG | TAC | CCT | TCA | TCA | AAG | CGA | CTG | CAC | CAT | CTC | ATT | GAA | 1250 |
| Thr | Asp | Gly | Glu | Tyr | Pro | Ser | Ser | Lys | Arg | Leu | His | His | Leu | Ile | Glu | |
| | 315 | | | | | 320 | | | | | 325 | | | | | |
| GAG | GTG | GTT | GAA | CGG | CAT | GAA | GAC | AAA | ATA | GCC | GTT | GTC | TGC | GAC | GAG | 1298 |
| Glu | Val | Val | Glu | Arg | His | Glu | Asp | Lys | Ile | Ala | Val | Val | Cys | Asp | Glu | |
| 330 | | | | | 335 | | | | | 340 | | | | | 345 | |
| CGA | GAG | CTC | ACT | TAC | GGC | GAG | CTC | AAT | GCC | CAA | GGC | AAC | AGC | CTC | GCA | 1346 |
| Arg | Glu | Leu | Thr | Tyr | Gly | Glu | Leu | Asn | Ala | Gln | Gly | Asn | Ser | Leu | Ala | |
| | | | | 350 | | | | | 355 | | | | | 360 | | |
| CGC | TAT | CTC | CGT | TCC | ATT | GGT | ATC | CTG | CCC | GAG | CAG | CTA | GTC | GCA | TTG | 1394 |
| Arg | Tyr | Leu | Arg | Ser | Ile | Gly | Ile | Leu | Pro | Glu | Gln | Leu | Val | Ala | Leu | |
| | | | 365 | | | | | 370 | | | | | 375 | | | |
| TTT | CTA | GAT | AAG | AGC | GAG | AAG | CTC | ATT | GTT | ACC | ATC | CTC | GGC | GTG | TGG | 1442 |
| Phe | Leu | Asp | Lys | Ser | Glu | Lys | Leu | Ile | Val | Thr | Ile | Leu | Gly | Val | Trp | |
| | | 380 | | | | | 385 | | | | | 390 | | | | |
| AAA | TCC | GGC | GCC | GCC | TAC | GTG | CCC | ATC | GAC | CCG | ACT | TAT | CCG | GAT | GAG | 1490 |
| Lys | Ser | Gly | Ala | Ala | Tyr | Val | Pro | Ile | Asp | Pro | Thr | Tyr | Pro | Asp | Glu | |
| | 395 | | | | | 400 | | | | | 405 | | | | | |
| CGA | GTG | CGC | TTC | GTG | CTG | GAT | GAC | ACC | AAG | GCA | CGG | GCC | ATC | ATC | GCC | 1538 |
| Arg | Val | Arg | Phe | Val | Leu | Asp | Asp | Thr | Lys | Ala | Arg | Ala | Ile | Ile | Ala | |
| 410 | | | | | 415 | | | | | 420 | | | | | 425 | |
| AGT | AAT | CAA | CAT | GTG | GAG | AGG | CTC | CAG | CGA | GAG | GTC | ATC | GGC | GAT | AGA | 1586 |
| Ser | Asn | Gln | His | Val | Glu | Arg | Leu | Gln | Arg | Glu | Val | Ile | Gly | Asp | Arg | |
| | | | | 430 | | | | | 435 | | | | | 440 | | |
| AAC | CTA | TGC | ATT | ATC | CGT | CTG | GAG | CCC | TTG | TTG | GCC | TCC | CTT | GCT | CAG | 1634 |
| Asn | Leu | Cys | Ile | Ile | Arg | Leu | Glu | Pro | Leu | Leu | Ala | Ser | Leu | Ala | Gln | |
| | | | 445 | | | | | 450 | | | | | 455 | | | |
| GAT | TCC | TCA | AAA | TTC | CCC | GCG | CAT | AAC | TTG | GAC | GAC | CTA | CCC | CTC | ACA | 1682 |
| Asp | Ser | Ser | Lys | Phe | Pro | Ala | His | Asn | Leu | Asp | Asp | Leu | Pro | Leu | Thr | |
| | | 460 | | | | | 465 | | | | | 470 | | | | |
| AGC | CAG | CAG | CTC | GCC | TAT | GTG | ACT | TAC | ACC | TCT | GGG | ACC | ACT | GGT | TTC | 1730 |
| Ser | Gln | Gln | Leu | Ala | Tyr | Val | Thr | Tyr | Thr | Ser | Gly | Thr | Thr | Gly | Phe | |
| | 475 | | | | | 480 | | | | | 485 | | | | | |
| CCA | AAG | GGC | ATA | TTT | AAA | CAA | CAC | ACC | AAT | GTG | GTG | AAC | AGT | ATT | ACC | 1778 |
| Pro | Lys | Gly | Ile | Phe | Lys | Gln | His | Thr | Asn | Val | Val | Asn | Ser | Ile | Thr | |
| 490 | | | | | 495 | | | | | 500 | | | | | 505 | |
| GAC | CTG | TCT | GCA | AGG | TAC | GGG | GTG | GCC | GGG | CAG | CAC | CAC | GAA | GCC | ATT | 1826 |
| Asp | Leu | Ser | Ala | Arg | Tyr | Gly | Val | Ala | Gly | Gln | His | His | Glu | Ala | Ile | |
| | | | | 510 | | | | | 515 | | | | | 520 | | |

```
CTG  CTT  TTC  TCG  GCC  TGC  GTG  TTC  GAG  CCG  TTC  GTT  CGA  CAG  ACG  CTC      1874
Leu  Leu  Phe  Ser  Ala  Cys  Val  Phe  Glu  Pro  Phe  Val  Arg  Gln  Thr  Leu
               525                      530                      535

ATG  GCA  CTC  GTG  AAT  GGC  CAT  CTC  CTC  GCA  GTT  ATC  AAT  GAC  GTG  GAA      1922
Met  Ala  Leu  Val  Asn  Gly  His  Leu  Leu  Ala  Val  Ile  Asn  Asp  Val  Glu
          540                      545                      550

AAA  TAT  GAT  GCC  GAT  ACG  CTC  CTG  CCG  TTC  ATA  CGC  AGA  CAC  AGC  ATC      1970
Lys  Tyr  Asp  Ala  Asp  Thr  Leu  Leu  Pro  Phe  Ile  Arg  Arg  His  Ser  Ile
     555                      560                      565

ACC  TAC  CTC  AAT  GGT  ACT  GCC  TCT  GTC  TTG  CAA  GAG  TAC  GAC  TTT  TCC      2018
Thr  Tyr  Leu  Asn  Gly  Thr  Ala  Ser  Val  Leu  Gln  Glu  Tyr  Asp  Phe  Ser
570                           575                      580                      585

GAC  TGC  CCA  TCA  CTG  AAT  CGG  ATA  ATC  CTG  GTG  GGT  GAG  AAC  CTG  ACA      2066
Asp  Cys  Pro  Ser  Leu  Asn  Arg  Ile  Ile  Leu  Val  Gly  Glu  Asn  Leu  Thr
                         590                      595                      600

GAA  GCC  CGG  TAT  CTG  GCG  CTG  CGC  CAG  CGG  TTC  AAG  AAT  CGC  ATC  CTC      2114
Glu  Ala  Arg  Tyr  Leu  Ala  Leu  Arg  Gln  Arg  Phe  Lys  Asn  Arg  Ile  Leu
               605                      610                      615

AAC  GAG  TAT  GGT  TTT  ACC  GAG  TCA  GCC  TTT  GTA  ACG  GCC  CTC  AAG  ATT      2162
Asn  Glu  Tyr  Gly  Phe  Thr  Glu  Ser  Ala  Phe  Val  Thr  Ala  Leu  Lys  Ile
          620                      625                      630

TTC  GAC  CCG  GAG  TCG  ACC  CGT  AAG  GAC  ACG  AGT  CTG  GGG  AGA  CCG  GTG      2210
Phe  Asp  Pro  Glu  Ser  Thr  Arg  Lys  Asp  Thr  Ser  Leu  Gly  Arg  Pro  Val
     635                      640                      645

CGC  AAC  GTC  AAG  TGC  TAC  ATC  CTC  AAT  CCA  TCC  CTT  AAA  CGT  GTC  CCG      2258
Arg  Asn  Val  Lys  Cys  Tyr  Ile  Leu  Asn  Pro  Ser  Leu  Lys  Arg  Val  Pro
650                           655                      660                      665

ATT  GGA  GCT  ACG  GGT  GAG  TTG  CAT  ATC  GGA  GGG  TTG  GGC  ATT  TCC  AAG      2306
Ile  Gly  Ala  Thr  Gly  Glu  Leu  His  Ile  Gly  Gly  Leu  Gly  Ile  Ser  Lys
                         670                      675                      680

GGA  TAC  CTC  AAC  CGC  CCC  GAA  CTC  ACG  CCG  CAC  CGC  TTC  ATT  CCC  AAC      2354
Gly  Tyr  Leu  Asn  Arg  Pro  Glu  Leu  Thr  Pro  His  Arg  Phe  Ile  Pro  Asn
               685                      690                      695

CCC  TTC  CAA  ACG  GAT  TGC  GAG  AAG  CAG  CTC  GGG  ATC  AAC  AGC  TTG  ATG      2402
Pro  Phe  Gln  Thr  Asp  Cys  Glu  Lys  Gln  Leu  Gly  Ile  Asn  Ser  Leu  Met
          700                      705                      710

TAC  AAG  ACC  GGT  GAC  CTG  GCC  CGC  TGG  CTT  CCG  AAC  GGC  GAG  GTT  GAG      2450
Tyr  Lys  Thr  Gly  Asp  Leu  Ala  Arg  Trp  Leu  Pro  Asn  Gly  Glu  Val  Glu
     715                      720                      725

TAT  CTC  GGA  CGC  GCA  GAT  TTC  CAG  ATC  AAA  CTG  CGA  GGT  ATT  CGA  ATT      2498
Tyr  Leu  Gly  Arg  Ala  Asp  Phe  Gln  Ile  Lys  Leu  Arg  Gly  Ile  Arg  Ile
730                           735                      740                      745

GAA  CCT  GGT  GAA  ATT  GAG  ACG  ATG  CTG  GCT  ATG  TAC  CCT  AGG  GTC  CGG      2546
Glu  Pro  Gly  Glu  Ile  Glu  Thr  Met  Leu  Ala  Met  Tyr  Pro  Arg  Val  Arg
                         750                      755                      760

ACC  AGT  TTA  GTG  GTG  TCC  AAA  AAG  CTC  CGC  AAC  GGT  CCA  GAG  GAA  ACT      2594
Thr  Ser  Leu  Val  Val  Ser  Lys  Lys  Leu  Arg  Asn  Gly  Pro  Glu  Glu  Thr
               765                      770                      775

ACC  AAC  GAG  CAC  CTC  GTG  GGT  TAT  TAT  GTT  TGT  GAT  AGC  GCC  TCA  GTG      2642
Thr  Asn  Glu  His  Leu  Val  Gly  Tyr  Tyr  Val  Cys  Asp  Ser  Ala  Ser  Val
          780                      785                      790

TCC  GAG  GCA  GAC  CTG  CTG  TCA  TTT  TTA  GAG  AAG  AAA  CTG  CCT  CGA  TAC      2690
Ser  Glu  Ala  Asp  Leu  Leu  Ser  Phe  Leu  Glu  Lys  Lys  Leu  Pro  Arg  Tyr
     795                      800                      805

ATG  ATT  CCC  ACG  CGG  TTG  GTA  CAG  CTG  TCG  CAG  ATC  CCA  GTG  AAT  GTG      2738
Met  Ile  Pro  Thr  Arg  Leu  Val  Gln  Leu  Ser  Gln  Ile  Pro  Val  Asn  Val
810                           815                      820                      825

AAC  GGG  AAG  GCG  GAC  CTA  CGC  GCC  TTG  CCG  GCC  GTC  GAT  ATC  TCC  AAT      2786
Asn  Gly  Lys  Ala  Asp  Leu  Arg  Ala  Leu  Pro  Ala  Val  Asp  Ile  Ser  Asn
                         830                      835                      840
```

| | | | | | | | | | | | | | | | | |
|---|---|---|---|---|---|---|---|---|---|---|---|---|---|---|---|---|
| TCC | ACG | GAG | GTG | CGT | TCC | GAC | CTT | CGA | GGC | GAT | ACG | GAA | ATC | GCC | CTC | 2834 |
| Ser | Thr | Glu | Val | Arg | Ser | Asp | Leu | Arg | Gly | Asp | Thr | Glu | Ile | Ala | Leu | |
| | | | 845 | | | | | 850 | | | | | 855 | | | |
| GGG | GAA | ATC | TGG | GCC | GAC | GTG | TTG | GGA | GCC | CGC | CAG | AGA | TCC | GTC | TCT | 2882 |
| Gly | Glu | Ile | Trp | Ala | Asp | Val | Leu | Gly | Ala | Arg | Gln | Arg | Ser | Val | Ser | |
| | | | 860 | | | | | 865 | | | | | 870 | | | |
| CGC | AAC | GAC | AAC | TTC | TTC | CGC | CTA | GGA | GGG | CAC | AGC | ATC | ACC | TGC | ATC | 2930 |
| Arg | Asn | Asp | Asn | Phe | Phe | Arg | Leu | Gly | Gly | His | Ser | Ile | Thr | Cys | Ile | |
| | 875 | | | | | 880 | | | | | 885 | | | | | |
| CAA | CTG | ATC | GCT | CGC | ATC | CGA | CAA | CGA | CAA | CGA | CTC | TCG | GTC | AGC | ATC | 2978 |
| Gln | Leu | Ile | Ala | Arg | Ile | Arg | Gln | Arg | Gln | Arg | Leu | Ser | Val | Ser | Ile | |
| 890 | | | | | 895 | | | | | 900 | | | | | 905 | |
| TCC | GTC | GAA | GAT | GTT | TTT | GCA | ACA | AGG | ACA | CTT | GAG | CGC | ATG | GCA | GAC | 3026 |
| Ser | Val | Glu | Asp | Val | Phe | Ala | Thr | Arg | Thr | Leu | Glu | Arg | Met | Ala | Asp | |
| | | | | 910 | | | | | 915 | | | | | 920 | | |
| CTT | CTA | CAG | AAC | AAG | CAG | CAG | GAG | AAA | TGC | GAC | AAA | CCC | CAT | GAG | GCG | 3074 |
| Leu | Leu | Gln | Asn | Lys | Gln | Gln | Glu | Lys | Cys | Asp | Lys | Pro | His | Glu | Ala | |
| | | | | 925 | | | | | 930 | | | | | 935 | | |
| CCG | ACA | GAG | CTG | CTT | GAG | GAG | AAT | GCA | GCA | ACG | GAC | AAT | ATC | TAT | CTG | 3122 |
| Pro | Thr | Glu | Leu | Leu | Glu | Glu | Asn | Ala | Ala | Thr | Asp | Asn | Ile | Tyr | Leu | |
| | | 940 | | | | | 945 | | | | | 950 | | | | |
| GCA | AAC | AGT | CTT | CAG | CAG | GGC | TTC | GTC | TAC | CAT | TAC | CTC | AAG | AGC | ATG | 3170 |
| Ala | Asn | Ser | Leu | Gln | Gln | Gly | Phe | Val | Tyr | His | Tyr | Leu | Lys | Ser | Met | |
| | 955 | | | | | 960 | | | | | 965 | | | | | |
| GAA | CAA | TCC | GAC | GCC | TAT | GTA | ATG | CAG | TCC | GTT | CTT | CGG | TAC | AAC | ACC | 3218 |
| Glu | Gln | Ser | Asp | Ala | Tyr | Val | Met | Gln | Ser | Val | Leu | Arg | Tyr | Asn | Thr | |
| 970 | | | | | 975 | | | | | 980 | | | | | 985 | |
| ACA | TTG | TCT | CCA | GAT | CTG | TTT | CAG | AGA | GCC | TGG | AAG | CAT | GCA | CAG | CAG | 3266 |
| Thr | Leu | Ser | Pro | Asp | Leu | Phe | Gln | Arg | Ala | Trp | Lys | His | Ala | Gln | Gln | |
| | | | | 990 | | | | | 995 | | | | | 1000 | | |
| TCC | TTT | CCA | GCG | CTG | CGG | CTG | CGG | TTC | TCA | TGG | GAA | AAG | GAG | GTT | TTC | 3314 |
| Ser | Phe | Pro | Ala | Leu | Arg | Leu | Arg | Phe | Ser | Trp | Glu | Lys | Glu | Val | Phe | |
| | | | | 1005 | | | | | 1010 | | | | | 1015 | | |
| CAA | CTG | CTC | GAT | CAG | GAT | CCA | CCA | TTG | GAC | TGG | CGT | TTC | CTC | TAC | TTC | 3362 |
| Gln | Leu | Leu | Asp | Gln | Asp | Pro | Pro | Leu | Asp | Trp | Arg | Phe | Leu | Tyr | Phe | |
| | | | 1020 | | | | | 1025 | | | | | 1030 | | | |
| ACC | GAC | GTT | GCC | GCG | GGT | GCT | GTC | GAG | GAC | CGG | AAA | TTG | GAA | GAC | TTG | 3410 |
| Thr | Asp | Val | Ala | Ala | Gly | Ala | Val | Glu | Asp | Arg | Lys | Leu | Glu | Asp | Leu | |
| | | | 1035 | | | | | 1040 | | | | | 1045 | | | |
| CGG | CGC | CAA | GAC | CTT | ACG | GAG | AGA | TTC | AAG | CTG | GAT | GTT | GGC | AGA | CTG | 3458 |
| Arg | Arg | Gln | Asp | Leu | Thr | Glu | Arg | Phe | Lys | Leu | Asp | Val | Gly | Arg | Leu | |
| 1050 | | | | | 1055 | | | | | 1060 | | | | | 1065 | |
| TTC | CGC | GTC | TAT | CTG | ATT | AAA | CAC | AGC | GAG | AAT | CGC | TTC | ACG | TGT | CTT | 3506 |
| Phe | Arg | Val | Tyr | Leu | Ile | Lys | His | Ser | Glu | Asn | Arg | Phe | Thr | Cys | Leu | |
| | | | | 1070 | | | | | 1075 | | | | | 1080 | | |
| TTC | AGC | TGC | CAT | CAT | GCA | ATC | CTC | GAT | GGT | TGG | AGT | CTG | CCA | CTC | TTG | 3554 |
| Phe | Ser | Cys | His | His | Ala | Ile | Leu | Asp | Gly | Trp | Ser | Leu | Pro | Leu | Leu | |
| | | | | 1085 | | | | | 1090 | | | | | 1095 | | |
| TTC | GAA | AAG | GTT | CAC | GAG | ACC | TAC | CTG | CAA | CTG | CTG | CAT | GGG | GAC | AAT | 3602 |
| Phe | Glu | Lys | Val | His | Glu | Thr | Tyr | Leu | Gln | Leu | Leu | His | Gly | Asp | Asn | |
| | | | 1100 | | | | | 1105 | | | | | 1110 | | | |
| CTC | ACT | TCG | TCC | ATG | GAT | GAC | CCT | TAC | ACT | CGC | ACC | CAG | CGG | TAT | CTC | 3650 |
| Leu | Thr | Ser | Ser | Met | Asp | Asp | Pro | Tyr | Thr | Arg | Thr | Gln | Arg | Tyr | Leu | |
| | | 1115 | | | | | 1120 | | | | | 1125 | | | | |
| CAC | GCT | CAC | CGT | GAG | GAT | CAC | CTC | GAC | TTT | TGG | GCC | GGT | GTG | GTT | CAA | 3698 |
| His | Ala | His | Arg | Glu | Asp | His | Leu | Asp | Phe | Trp | Ala | Gly | Val | Val | Gln | |
| | 1130 | | | | | 1135 | | | | | 1140 | | | | | 1145 |
| AAG | ATC | AAC | GAA | CGG | TGT | GAT | ATG | AAC | GCC | TTG | TTG | AAC | GAG | CGC | AGT | 3746 |
| Lys | Ile | Asn | Glu | Arg | Cys | Asp | Met | Asn | Ala | Leu | Leu | Asn | Glu | Arg | Ser | |
| | | | | 1150 | | | | | 1155 | | | | | 1160 | | |

```
CGT  TAC  AAA  GTC  CAG  CTG  GCA  GAC  TAT  GAC  CAG  GTG  CAG  GAG  CAG  CGA     3794
Arg  Tyr  Lys  Val  Gln  Leu  Ala  Asp  Tyr  Asp  Gln  Val  Gln  Glu  Gln  Arg
          1165                    1170                    1175

CAC  GTG  ACA  ATT  GCT  CTC  TCT  GGA  GAC  GCA  TGG  CTA  GCA  GAC  CTT  CGT     3842
His  Val  Thr  Ile  Ala  Leu  Ser  Gly  Asp  Ala  Trp  Leu  Ala  Asp  Leu  Arg
          1180                    1185                    1190

CAG  ACC  TGC  TCC  GCC  CAG  GGT  ATT  ACC  TTA  CAT  TCG  ATT  CTC  CAA  TTT     3890
Gln  Thr  Cys  Ser  Ala  Gln  Gly  Ile  Thr  Leu  His  Ser  Ile  Leu  Gln  Phe
          1195                    1200                    1205

GTT  TGG  CAC  GCC  GTG  CTG  CAC  GCT  TAT  GGC  GGT  GGC  ACC  CAC  ACC  ATA     3938
Val  Trp  His  Ala  Val  Leu  His  Ala  Tyr  Gly  Gly  Gly  Thr  His  Thr  Ile
1210                    1215                    1220                    1225

ACC  GGC  ACG  ACC  ATT  TCT  GGA  AGG  AAC  CTG  CCC  ATC  TTG  GGA  ATT  GAA     3986
Thr  Gly  Thr  Thr  Ile  Ser  Gly  Arg  Asn  Leu  Pro  Ile  Leu  Gly  Ile  Glu
                    1230                    1235                    1240

CGA  GCA  GTT  GGT  CCG  TAT  ATC  AAC  ACT  CTA  CCG  CTG  GTA  CTC  GAT  CAT     4034
Arg  Ala  Val  Gly  Pro  Tyr  Ile  Asn  Thr  Leu  Pro  Leu  Val  Leu  Asp  His
          1245                    1250                    1255

TCG  ACG  TTC  AAG  GAT  AAG  ACA  ATC  ATG  GAG  GCC  ATC  GAG  GAT  GTG  CAG     4082
Ser  Thr  Phe  Lys  Asp  Lys  Thr  Ile  Met  Glu  Ala  Ile  Glu  Asp  Val  Gln
          1260                    1265                    1270

GCC  AAG  GTA  AAC  GTC  ATG  AAC  AGC  CGG  GGC  AAT  GTG  GAA  CTG  GGC  CGT     4130
Ala  Lys  Val  Asn  Val  Met  Asn  Ser  Arg  Gly  Asn  Val  Glu  Leu  Gly  Arg
          1275                    1280                    1285

TTG  CAC  AAA  ACC  GAC  TTA  AAG  CAC  GGA  TTA  TTC  GAT  TCT  TTA  TTC  GTG     4178
Leu  His  Lys  Thr  Asp  Leu  Lys  His  Gly  Leu  Phe  Asp  Ser  Leu  Phe  Val
1290                    1295                    1300                    1305

CTT  GAA  AAC  TAC  CCG  AAT  TTG  GAC  AAA  TCG  CGA  ACA  CTT  GAG  CAC  CAG     4226
Leu  Glu  Asn  Tyr  Pro  Asn  Leu  Asp  Lys  Ser  Arg  Thr  Leu  Glu  His  Gln
                    1310                    1315                    1320

ACT  GAA  CTG  GGG  TAT  TCG  ATT  GAA  GGC  GGC  ACT  GAG  AAG  CTG  AAT  TAT     4274
Thr  Glu  Leu  Gly  Tyr  Ser  Ile  Glu  Gly  Gly  Thr  Glu  Lys  Leu  Asn  Tyr
          1325                    1330                    1335

CCA  CTG  GCT  GTC  ATC  GCG  CGC  GAA  GTC  GAG  ACG  ACT  GGC  GGA  TTC  ACA     4322
Pro  Leu  Ala  Val  Ile  Ala  Arg  Glu  Val  Glu  Thr  Thr  Gly  Gly  Phe  Thr
          1340                    1345                    1350

GTA  TCC  ATC  TGC  TAC  GCC  AGT  GAG  CTA  TTT  GAG  GAG  GTT  ATG  ATC  TCC     4370
Val  Ser  Ile  Cys  Tyr  Ala  Ser  Glu  Leu  Phe  Glu  Glu  Val  Met  Ile  Ser
          1355                    1360                    1365

GAG  CTT  CTT  CAT  ATG  GTC  CAG  GAC  ACA  CTG  ATG  CAG  GTT  GCC  CGA  GGT     4418
Glu  Leu  Leu  His  Met  Val  Gln  Asp  Thr  Leu  Met  Gln  Val  Ala  Arg  Gly
1370                    1375                    1380                    1385

TTG  AAT  GAA  CCC  GTC  GGC  AGC  CTG  GAG  TAT  CTC  TCA  TCT  ATC  CAA  TTG     4466
Leu  Asn  Glu  Pro  Val  Gly  Ser  Leu  Glu  Tyr  Leu  Ser  Ser  Ile  Gln  Leu
                    1390                    1395                    1400

GAG  CAA  CTC  GCC  GCG  TGG  AAT  GCC  ACG  GAA  GCT  GAG  TTT  CCC  GAT  ACC     4514
Glu  Gln  Leu  Ala  Ala  Trp  Asn  Ala  Thr  Glu  Ala  Glu  Phe  Pro  Asp  Thr
                    1405                    1410                    1415

ACG  CTT  CAT  GAG  ATG  TTT  GAA  AAC  GAA  GCG  AGC  CAG  AAG  CCG  GAC  AAG     4562
Thr  Leu  His  Glu  Met  Phe  Glu  Asn  Glu  Ala  Ser  Gln  Lys  Pro  Asp  Lys
          1420                    1425                    1430

ATA  GCA  GTG  GTC  TAT  GAG  GAG  ACG  TCC  TTG  ACT  TAC  CGC  GAG  TTG  AAT     4610
Ile  Ala  Val  Val  Tyr  Glu  Glu  Thr  Ser  Leu  Thr  Tyr  Arg  Glu  Leu  Asn
          1435                    1440                    1445

GAG  CGG  GCG  AAC  CGT  ATG  GCA  CAT  CAG  CTA  AGG  TCC  GAC  GTC  AGC  CCC     4658
Glu  Arg  Ala  Asn  Arg  Met  Ala  His  Gln  Leu  Arg  Ser  Asp  Val  Ser  Pro
1450                    1455                    1460                    1465

AAC  CCC  AAC  GAG  GTC  ATT  GCG  CTG  GTG  ATG  GAC  AAG  AGC  GAG  CAT  ATG     4706
Asn  Pro  Asn  Glu  Val  Ile  Ala  Leu  Val  Met  Asp  Lys  Ser  Glu  His  Met
                    1470                    1475                    1480
```

-continued

```
ATC GTC AAC ATT CTG GCC GTA TGG AAG AGC GGC GGT GCC TAT GTC CCC    4754
Ile Val Asn Ile Leu Ala Val Trp Lys Ser Gly Gly Ala Tyr Val Pro
        1485                1490                1495

ATT GAC CCT GGA TAT CCT AAC GAC CGC ATT CAA TAT ATC CTA GAG GAC    4802
Ile Asp Pro Gly Tyr Pro Asn Asp Arg Ile Gln Tyr Ile Leu Glu Asp
1500                1505                1510

ACA CAA GCC CTC GCA GTC ATC GCG GAC TCC TGC TAT CTG CCT CGC ATC    4850
Thr Gln Ala Leu Ala Val Ile Ala Asp Ser Cys Tyr Leu Pro Arg Ile
        1515                1520                1525

AAG GGA ATG GCT GCC TCC GGC ACG CTT CTT TAT CCC TCT GTC TTG CCT    4898
Lys Gly Met Ala Ala Ser Gly Thr Leu Leu Tyr Pro Ser Val Leu Pro
1530                1535                1540                1545

GCC AAT CCG GAT TCC AAG TGG AGC GTA TCG AAC CCT TCA CCG TTG AGT    4946
Ala Asn Pro Asp Ser Lys Trp Ser Val Ser Asn Pro Ser Pro Leu Ser
                1550                1555                1560

CGG AGC ACG GAC TTA GCT TAT ATC ATC TAT ACC TCT GGA ACG ACA GGT    4994
Arg Ser Thr Asp Leu Ala Tyr Ile Ile Tyr Thr Ser Gly Thr Thr Gly
        1565                1570                1575

CGG CCC AAG GGC GTC ACG GTA GAG CAT CAT GGA GTG GTC AAC CTG CAG    5042
Arg Pro Lys Gly Val Thr Val Glu His His Gly Val Val Asn Leu Gln
1580                1585                1590

GTG TCG CTA TCC AAA GTA TTC GGA CTA CGG GAT ACG GAC GAC GAG GTA    5090
Val Ser Leu Ser Lys Val Phe Gly Leu Arg Asp Thr Asp Asp Glu Val
        1595                1600                1605

ATT CTC TCC TTT TCC AAC TAT GTG TTC GAC CAT TTC GTG GAG CAG ATG    5138
Ile Leu Ser Phe Ser Asn Tyr Val Phe Asp His Phe Val Glu Gln Met
1610                1615                1620                1625

ACC GAC GCC ATT CTC AAT GGC CAA ACC CTC CTG GTC CTC AAC GAT GGA    5186
Thr Asp Ala Ile Leu Asn Gly Gln Thr Leu Leu Val Leu Asn Asp Gly
                1630                1635                1640

ATG CGC GGG GAC AAA GAG CGA CTC TAC AGA TAC ATT GAG AAG AAC CGA    5234
Met Arg Gly Asp Lys Glu Arg Leu Tyr Arg Tyr Ile Glu Lys Asn Arg
        1645                1650                1655

GTG ACC TAC TTG TCT GGC ACC CCA TCC GTG GTC TCC ATG TAC GAA TTT    5282
Val Thr Tyr Leu Ser Gly Thr Pro Ser Val Val Ser Met Tyr Glu Phe
1660                1665                1670

AGC CGG TTC AAG GAC CAT CTA CGC CGT GTG GAC TGC GTG GGG GAG GCG    5330
Ser Arg Phe Lys Asp His Leu Arg Arg Val Asp Cys Val Gly Glu Ala
        1675                1680                1685

TTC AGC GAA CCG GTC TTC GAC AAG ATC CGC GAA ACG TTC CAT GGC CTC    5378
Phe Ser Glu Pro Val Phe Asp Lys Ile Arg Glu Thr Phe His Gly Leu
1690                1695                1700                1705

GTT ATC AAC GGC TAC GGC CCA ACT GAA GTT TCC ATC ACC ACC CAC AAG    5426
Val Ile Asn Gly Tyr Gly Pro Thr Glu Val Ser Ile Thr Thr His Lys
                1710                1715                1720

CGG CTC TAT CCA TTC CCA GAG CGG CGA ATG GAC AAA AGT ATT GGC CAA    5474
Arg Leu Tyr Pro Phe Pro Glu Arg Arg Met Asp Lys Ser Ile Gly Gln
        1725                1730                1735

CAG GTC CAC AAT AGC ACG AGC TAT GTG CTG AAC GAG GAC ATG AAG CGC    5522
Gln Val His Asn Ser Thr Ser Tyr Val Leu Asn Glu Asp Met Lys Arg
1740                1745                1750

ACC CCC ATA GGG GCT GTC GGC GAG CTC TAC CTG GGT GGT GAA GGA GTG    5570
Thr Pro Ile Gly Ala Val Gly Glu Leu Tyr Leu Gly Gly Glu Gly Val
        1755                1760                1765

GTA CGG GGA TAT CAC AAT CGC GCA GAT GTG ACC GCG GAG CGT TTT ATT    5618
Val Arg Gly Tyr His Asn Arg Ala Asp Val Thr Ala Glu Arg Phe Ile
1770                1775                1780                1785

CCT AAT CCA TTC CAG TCG GAA GAA GAT AAG CGA GAA GGT CGT AAC TCC    5666
Pro Asn Pro Phe Gln Ser Glu Glu Asp Lys Arg Glu Gly Arg Asn Ser
                1790                1795                1800
```

| | | | | | | | | | | | | | | | | |
|---|---|---|---|---|---|---|---|---|---|---|---|---|---|---|---|---|
| CGT | TTG | TAC | AAG | ACC | GGT | GAC | CTG | GTA | CGC | TGG | ATT | CCT | GGA | AGC | AGC | 5714 |
| Arg | Leu | Tyr | Lys | Thr | Gly | Asp | Leu | Val | Arg | Trp | Ile | Pro | Gly | Ser | Ser | |
| | | | 1805 | | | | 1810 | | | | | 1815 | | | | |
| GGG | GAG | GTC | GAG | TAT | CTA | GGT | CGT | AAT | GAC | TTC | CAG | GTC | AAG | ATT | CGC | 5762 |
| Gly | Glu | Val | Glu | Tyr | Leu | Gly | Arg | Asn | Asp | Phe | Gln | Val | Lys | Ile | Arg | |
| | | | 1820 | | | | 1825 | | | | | 1830 | | | | |
| GGA | CTG | CGC | ATC | GAA | GTA | GGC | GAG | ATT | GAG | GCC | ATC | CTA | TCG | TCT | TAT | 5810 |
| Gly | Leu | Arg | Ile | Glu | Val | Gly | Glu | Ile | Glu | Ala | Ile | Leu | Ser | Ser | Tyr | |
| | | | 1835 | | | | 1840 | | | | | 1845 | | | | |
| CAC | GGA | ATC | AAA | CAG | TCT | GTG | GTG | ATT | GCC | AAG | GAT | TGC | AGA | GAA | GGG | 5858 |
| His | Gly | Ile | Lys | Gln | Ser | Val | Val | Ile | Ala | Lys | Asp | Cys | Arg | Glu | Gly | |
| 1850 | | | | 1855 | | | | | 1860 | | | | | | 1865 | |
| GCC | CAG | AAA | TTC | CTG | GTT | GGT | TAC | TAT | GTC | GCC | GAT | GCA | GCG | CTG | CCG | 5906 |
| Ala | Gln | Lys | Phe | Leu | Val | Gly | Tyr | Tyr | Val | Ala | Asp | Ala | Ala | Leu | Pro | |
| | | | 1870 | | | | 1875 | | | | | 1880 | | | | |
| TCC | GCT | GCC | ATT | CGG | CGC | TTC | ATG | CAG | TCT | CGG | CTC | CCT | GGC | TAC | ATG | 5954 |
| Ser | Ala | Ala | Ile | Arg | Arg | Phe | Met | Gln | Ser | Arg | Leu | Pro | Gly | Tyr | Met | |
| | | | 1885 | | | | 1890 | | | | | 1895 | | | | |
| GTG | CCC | TCT | CGT | CTC | ATT | CTC | GTC | AGC | AAG | TTC | CCC | GTC | ACT | CCT | AGT | 6002 |
| Val | Pro | Ser | Arg | Leu | Ile | Leu | Val | Ser | Lys | Phe | Pro | Val | Thr | Pro | Ser | |
| | | | 1900 | | | | 1905 | | | | | 1910 | | | | |
| GGA | AAA | TTA | GAC | ACC | AAG | GCT | TTG | CCC | CCA | GCC | GAG | GAA | GAG | AGC | GAG | 6050 |
| Gly | Lys | Leu | Asp | Thr | Lys | Ala | Leu | Pro | Pro | Ala | Glu | Glu | Glu | Ser | Glu | |
| | | | 1915 | | | | 1920 | | | | | 1925 | | | | |
| ATT | GAC | GTG | GTG | CCG | CCG | CGT | AGT | GAA | ATC | GAA | CGC | TCC | TTG | TGT | GAC | 6098 |
| Ile | Asp | Val | Val | Pro | Pro | Arg | Ser | Glu | Ile | Glu | Arg | Ser | Leu | Cys | Asp | |
| 1930 | | | | 1935 | | | | | 1940 | | | | | | 1945 | |
| ATC | TGG | GCG | GAA | CTA | CTC | GAG | ATG | CAC | CCA | GAG | GAG | ATC | GGC | ATT | TAC | 6146 |
| Ile | Trp | Ala | Glu | Leu | Leu | Glu | Met | His | Pro | Glu | Glu | Ile | Gly | Ile | Tyr | |
| | | | | 1950 | | | | 1955 | | | | | 1960 | | | |
| AGC | GAT | TTC | TTC | AGC | CTG | GGA | GGT | GAC | AGC | CTA | AAG | AGC | ACA | AAG | CTT | 6194 |
| Ser | Asp | Phe | Phe | Ser | Leu | Gly | Gly | Asp | Ser | Leu | Lys | Ser | Thr | Lys | Leu | |
| | | | 1965 | | | | 1970 | | | | | 1975 | | | | |
| TCC | TTC | ATG | ATT | CAC | GAG | TCC | TTT | AAC | CGC | GCC | GTC | TCA | GTC | AGC | GCC | 6242 |
| Ser | Phe | Met | Ile | His | Glu | Ser | Phe | Asn | Arg | Ala | Val | Ser | Val | Ser | Ala | |
| | | | 1980 | | | | 1985 | | | | | 1990 | | | | |
| CTT | TTC | TGT | CAC | CGG | ACA | GTT | GAA | GCC | CAG | ACG | CAC | TTG | ATC | CTG | AAC | 6290 |
| Leu | Phe | Cys | His | Arg | Thr | Val | Glu | Ala | Gln | Thr | His | Leu | Ile | Leu | Asn | |
| | | | 1995 | | | | 2000 | | | | | 2005 | | | | |
| GAT | GCT | GCA | GAT | GTG | CAC | GAA | ATT | ACT | CCC | ATA | GAT | TGC | AAT | GAT | ACG | 6338 |
| Asp | Ala | Ala | Asp | Val | His | Glu | Ile | Thr | Pro | Ile | Asp | Cys | Asn | Asp | Thr | |
| 2010 | | | | 2015 | | | | | 2020 | | | | | | 2025 | |
| CAG | ATG | ATT | CCC | GTG | TCC | CGT | GCC | CAG | GAG | CGA | CTC | CTC | TTC | ATC | CAC | 6386 |
| Gln | Met | Ile | Pro | Val | Ser | Arg | Ala | Gln | Glu | Arg | Leu | Leu | Phe | Ile | His | |
| | | | | 2030 | | | | 2035 | | | | | 2040 | | | |
| GAA | TTT | GAG | AAT | GGC | AGC | AAT | GCA | TAC | AAT | ATC | GAC | GCT | GCA | TTT | GAA | 6434 |
| Glu | Phe | Glu | Asn | Gly | Ser | Asn | Ala | Tyr | Asn | Ile | Asp | Ala | Ala | Phe | Glu | |
| | | | | 2045 | | | | 2050 | | | | | 2055 | | | |
| CTG | CCT | GGC | TCG | GTT | GAC | GCG | TCG | CTT | CTC | GAG | CAG | GCG | CTG | CGT | GGA | 6482 |
| Leu | Pro | Gly | Ser | Val | Asp | Ala | Ser | Leu | Leu | Glu | Gln | Ala | Leu | Arg | Gly | |
| | | | | 2060 | | | | 2065 | | | | | 2070 | | | |
| AAC | CTT | GCT | CGA | CAT | GAG | GCG | TTG | AGA | ACT | TTA | CTG | GTC | AAG | GAT | CAC | 6530 |
| Asn | Leu | Ala | Arg | His | Glu | Ala | Leu | Arg | Thr | Leu | Leu | Val | Lys | Asp | His | |
| | | | | 2075 | | | | 2080 | | | | | 2085 | | | |
| GCA | ACC | GGC | ATC | TAT | CTT | CAG | AAG | GTA | TTG | AGT | CCC | GAT | GAA | GCC | CAG | 6578 |
| Ala | Thr | Gly | Ile | Tyr | Leu | Gln | Lys | Val | Leu | Ser | Pro | Asp | Glu | Ala | Gln | |
| 2090 | | | | 2095 | | | | | 2100 | | | | | | 2105 | |
| GGC | ATG | TTC | TCC | GTC | AAC | GTG | GAC | ACA | GCC | AAG | CAG | GTG | GAG | CGG | CTG | 6626 |
| Gly | Met | Phe | Ser | Val | Asn | Val | Asp | Thr | Ala | Lys | Gln | Val | Glu | Arg | Leu | |
| | | | | 2110 | | | | 2115 | | | | | 2120 | | | |

```
GAC CAG GAG ATA GCC AGT CTA TCC CAG CAT GTT TTC CGC CTC GAT GAT      6674
Asp Gln Glu Ile Ala Ser Leu Ser Gln His Val Phe Arg Leu Asp Asp
         2125                    2130                    2135

GAA CTG CCT TGG GAG GCC CGC ATC CTT AAA CTC GAA TCC GGC GGC CTG      6722
Glu Leu Pro Trp Glu Ala Arg Ile Leu Lys Leu Glu Ser Gly Gly Leu
         2140                    2145                    2150

TAT CTC ATT CTG GCG TTC CAC CAT ACC TGC TTC GAT GCA TGG TCA TTG      6770
Tyr Leu Ile Leu Ala Phe His His Thr Cys Phe Asp Ala Trp Ser Leu
         2155                    2160                    2165

AAA GTC TTC GAG CAA GAG CTT CGG GCC TTG TAC GCA GCG CTC CAG AAA      6818
Lys Val Phe Glu Gln Glu Leu Arg Ala Leu Tyr Ala Ala Leu Gln Lys
2170                    2175                    2180                    2185

ACC AAA AGT GCA GCG AAC TTA CCA GCC CTC AAA GCG CAG TAC AAG GAA      6866
Thr Lys Ser Ala Ala Asn Leu Pro Ala Leu Lys Ala Gln Tyr Lys Glu
                2190                    2195                    2200

TAC GCG CTC TAC CAT CGC CGG CAG CTG TCT GGC GAT CGC ATG CGC AAC      6914
Tyr Ala Leu Tyr His Arg Arg Gln Leu Ser Gly Asp Arg Met Arg Asn
         2205                    2210                    2215

CTG TCA GAC TTT TGG CTG CGG AAA CTC ATT GGC TTG GAA CCA TTG CAG      6962
Leu Ser Asp Phe Trp Leu Arg Lys Leu Ile Gly Leu Glu Pro Leu Gln
         2220                    2225                    2230

CTG ATC ACG GAC CGC CCA CGT CCT GTG CAA TTC AAA TAC GAC GGT GAC      7010
Leu Ile Thr Asp Arg Pro Arg Pro Val Gln Phe Lys Tyr Asp Gly Asp
         2235                    2240                    2245

GAC CTC AGT ATC GAA CTG AGC AAG AAG GAA ACG GAG AAC CTG AGG GGG      7058
Asp Leu Ser Ile Glu Leu Ser Lys Lys Glu Thr Glu Asn Leu Arg Gly
2250                    2255                    2260                    2265

GTG GCC AAA CGT TGC AAG TCG AGT CTG TAC GTC GTG TTG GTT TCC GTT      7106
Val Ala Lys Arg Cys Lys Ser Ser Leu Tyr Val Val Leu Val Ser Val
                2270                    2275                    2280

TAT TGC GTT ATG CTA GCC TCG TAC GCG AAC CAG TCC GAT GTT TCC GTG      7154
Tyr Cys Val Met Leu Ala Ser Tyr Ala Asn Gln Ser Asp Val Ser Val
         2285                    2290                    2295

GGT ATC CCA GTC AGC CAC CGA ACG CAT CCT CAG TTC CAA TCG GTC ATT      7202
Gly Ile Pro Val Ser His Arg Thr His Pro Gln Phe Gln Ser Val Ile
         2300                    2305                    2310

GGA TTC TTC GTC AAC CTT GTG GTG CTA AGG GTG GAT ATT TCT CAG TCA      7250
Gly Phe Phe Val Asn Leu Val Val Leu Arg Val Asp Ile Ser Gln Ser
         2315                    2320                    2325

GCC ATT TGC GGG CTC ATC AGA AGG GTA ATG AAA GAG CTC GTG GAC GCC      7298
Ala Ile Cys Gly Leu Ile Arg Arg Val Met Lys Glu Leu Val Asp Ala
2330                    2335                    2340                    2345

CAA CTG CAC CAA GAC ATG CCG TTC CAG GAA GTG ACG AAG CTG CTG CAG      7346
Gln Leu His Gln Asp Met Pro Phe Gln Glu Val Thr Lys Leu Leu Gln
                2350                    2355                    2360

GTG GAT AAT GAC CCC AGC CGG CAT CCG CTG GTA CAG AAC GTG TTC AAC      7394
Val Asp Asn Asp Pro Ser Arg His Pro Leu Val Gln Asn Val Phe Asn
         2365                    2370                    2375

TTC GAA TCC CGT GCG AAC GGA GAA CAC GAT GCC AGG TCG GAG GAT GAA      7442
Phe Glu Ser Arg Ala Asn Gly Glu His Asp Ala Arg Ser Glu Asp Glu
         2380                    2385                    2390

GGA TCG CTT GCA TTC AAT CAA TAC CGG CCG GTT CAG CCC GTG GAT TCC      7490
Gly Ser Leu Ala Phe Asn Gln Tyr Arg Pro Val Gln Pro Val Asp Ser
         2395                    2400                    2405

GTT GCG AAG TTC GAT CTG AAC GCA ACG GTC ACG GAA TTG GAG TCG GGA      7538
Val Ala Lys Phe Asp Leu Asn Ala Thr Val Thr Glu Leu Glu Ser Gly
2410                    2415                    2420                    2425

TTG AGA GTC AAC TTC AAC TAT GCG ACC AGC CTA TTC AAC AAA AGC ACG      7586
Leu Arg Val Asn Phe Asn Tyr Ala Thr Ser Leu Phe Asn Lys Ser Thr
                2430                    2435                    2440
```

```
ATC CAG GGT TTT TTG CAT ACC TAT GAG TAT CTC CTG CGC CAG CTG TCC       7634
Ile Gln Gly Phe Leu His Thr Tyr Glu Tyr Leu Leu Arg Gln Leu Ser
            2445              2450                2455

GAA CTG AGT GCA GAA GGG ATC AAT GAG GAT ACG CAG CTG TCG TTA GTT       7682
Glu Leu Ser Ala Glu Gly Ile Asn Glu Asp Thr Gln Leu Ser Leu Val
            2460              2465                2470

CGC CCG ACA GAG AAT GGC GAT CTG CAC TTG CCA TTG GCA CAG TCC CCG       7730
Arg Pro Thr Glu Asn Gly Asp Leu His Leu Pro Leu Ala Gln Ser Pro
            2475              2480                2485

CTT GCG ACG ACT GCT GAG GAG CAG AAA GTA GCG TCG TTG AAC CAG GCC       7778
Leu Ala Thr Thr Ala Glu Glu Gln Lys Val Ala Ser Leu Asn Gln Ala
2490                2495              2500                2505

TTT GAG CGC GAA GCT TTC CTT GCC GCA GAG AAG ATT GCC GTC GTG CAG       7826
Phe Glu Arg Glu Ala Phe Leu Ala Ala Glu Lys Ile Ala Val Val Gln
            2510              2515                2520

GGA GAT AGA GCA CTT AGT TAT GCT GAT CTT AAC GGG CAG GCT AAC CAG       7874
Gly Asp Arg Ala Leu Ser Tyr Ala Asp Leu Asn Gly Gln Ala Asn Gln
            2525              2530                2535

CTC GCC CGG TAC ATA CAG TCC GTG TCC TGT ATT GGG GCA GAC GAC GGA       7922
Leu Ala Arg Tyr Ile Gln Ser Val Ser Cys Ile Gly Ala Asp Asp Gly
            2540              2545                2550

ATA GCT TTG ATG CTG GAA AAG AGT ATC GAC ACG ATT ATT TGC ATT CTC       7970
Ile Ala Leu Met Leu Glu Lys Ser Ile Asp Thr Ile Ile Cys Ile Leu
            2555              2560                2565

GCG ATT TGG AAG GCT GGT GCA GCA TAC GTG CCC TTG GAT CCG ACT TAC       8018
Ala Ile Trp Lys Ala Gly Ala Ala Tyr Val Pro Leu Asp Pro Thr Tyr
2570                2575              2580                2585

CCA CCC GGA CGC GTC CAG CTG ATT CTG GAG GAG ATT AAA GCG AAG GCT       8066
Pro Pro Gly Arg Val Gln Leu Ile Leu Glu Glu Ile Lys Ala Lys Ala
            2590              2595                2600

GTC CTT GTG CAC TCC AGT CAT GCT TCG AAA TGT GAA CGC CAT GGC GCG       8114
Val Leu Val His Ser Ser His Ala Ser Lys Cys Glu Arg His Gly Ala
            2605              2610                2615

AAG GTG ATT GCA GTC GAC TCG CCC GCC ATC GAG ACG GCG GTC AGC CAA       8162
Lys Val Ile Ala Val Asp Ser Pro Ala Ile Glu Thr Ala Val Ser Gln
            2620              2625                2630

CAG TCA GCT GCT GAC CTG CCC ACA ATT GCT AGC CTC GGC AAT CTA GCG       8210
Gln Ser Ala Ala Asp Leu Pro Thr Ile Ala Ser Leu Gly Asn Leu Ala
            2635              2640                2645

TAT ATA ATC TTT ACT TCA GGC ACT TCC GGT AAG CCA AAG GGA GTC CTA       8258
Tyr Ile Ile Phe Thr Ser Gly Thr Ser Gly Lys Pro Lys Gly Val Leu
2650                2655              2660                2665

GTT GAG CAA AAG GCA GTT CTT CTT CTA CGC GAT GCC CTC CGG GAG CGG       8306
Val Glu Gln Lys Ala Val Leu Leu Leu Arg Asp Ala Leu Arg Glu Arg
            2670              2675                2680

TAT TTC GGT CGA GAC TGT ACC AAG CAT CAT GGC GTC CTG TTC CTG TCC       8354
Tyr Phe Gly Arg Asp Cys Thr Lys His His Gly Val Leu Phe Leu Ser
            2685              2690                2695

AAC TAC GTC TTC GAC TTC TCC GTC GAA CAA CTT GTG TTG TCG GTG CTC       8402
Asn Tyr Val Phe Asp Phe Ser Val Glu Gln Leu Val Leu Ser Val Leu
            2700              2705                2710

AGC GGA CAC AAG CTG ATC GTT CCC CCA GCT GAG TTC GTC GCA GAT GAT       8450
Ser Gly His Lys Leu Ile Val Pro Pro Ala Glu Phe Val Ala Asp Asp
            2715              2720                2725

GAA TTT TAC AGA ATG GCC AGC ACG CAC GGT CTC TCC TAT CTC AGC GGC       8498
Glu Phe Tyr Arg Met Ala Ser Thr His Gly Leu Ser Tyr Leu Ser Gly
            2730              2735                2740                2745

ACA CCA TCC TTA CTG CAG AAG ATC GAT CTG GCA CGA CTG GAC CAT CTG       8546
Thr Pro Ser Leu Leu Gln Lys Ile Asp Leu Ala Arg Leu Asp His Leu
            2750              2755                2760
```

| | |
|---|---|
| CAG GTT GTT ACC GCC GCG GGC GAA GAG CTT CAC GCC ACC CAG TAC GAG<br>Gln Val Val Thr Ala Ala Gly Glu Glu Leu His Ala Thr Gln Tyr Glu<br>         2765                        2770                           2775 | 8594 |
| AAG ATG CGC CGC CGA TTC AAC GGT CCC ATC TAC AAT GCC TAT GGT GTC<br>Lys Met Arg Arg Arg Phe Asn Gly Pro Ile Tyr Asn Ala Tyr Gly Val<br>2780                            2785                        2790 | 8642 |
| ACC GAG ACC ACG GTG TAC AAC ATT ATC GCG GAA TTC ACA ACG AAT TCG<br>Thr Glu Thr Thr Val Tyr Asn Ile Ile Ala Glu Phe Thr Thr Asn Ser<br>2795                            2800                        2805 | 8690 |
| ATA TTT GAG AAT GCT CTT CGG GAA GTG CTC CCT GGT ACC CGA GCG TAT<br>Ile Phe Glu Asn Ala Leu Arg Glu Val Leu Pro Gly Thr Arg Ala Tyr<br>2810                            2815                        2820                        2825 | 8738 |
| GTG CTG ACC GCG GCA CTT CAG CCC GTC CCC TTC GAT GCT GTC GGA GAA<br>Val Leu Thr Ala Ala Leu Gln Pro Val Pro Phe Asp Ala Val Gly Glu<br>                        2830                        2835                        2840 | 8786 |
| CTC TAT CTT GCC GGC GAC ACG GTT ACG CGT GGT TAT CTC AAC CAA CCT<br>Leu Tyr Leu Ala Gly Asp Thr Val Thr Arg Gly Tyr Leu Asn Gln Pro<br>                        2845                        2850                        2855 | 8834 |
| CTT CTA ACG GAT CAG CGA TTC ATT CCC AAC CCT TTC TGC AAA GAG GAG<br>Leu Leu Thr Asp Gln Arg Phe Ile Pro Asn Pro Phe Cys Lys Glu Glu<br>                        2860                        2865                        2870 | 8882 |
| GAC ATC GCT ATG GGG CGC TTC GCG CGG CTC TAC AAG ACC GGC GAC CTG<br>Asp Ile Ala Met Gly Arg Phe Ala Arg Leu Tyr Lys Thr Gly Asp Leu<br>                        2875                        2880                        2885 | 8930 |
| GTT CGA TCG CGT TTC AAC CGT CAG CAG CAG CCG CAG CTG GAA TAC CTA<br>Val Arg Ser Arg Phe Asn Arg Gln Gln Gln Pro Gln Leu Glu Tyr Leu<br>2890                            2895                        2900                        2905 | 8978 |
| GGA AGA GGC GAT CTG CAG ATC AAG ATG AGG GGA TAC CGG ATC GAG ATT<br>Gly Arg Gly Asp Leu Gln Ile Lys Met Arg Gly Tyr Arg Ile Glu Ile<br>                        2910                        2915                        2920 | 9026 |
| TCT GAA GTT CAG AAC GTG CTC ACT TCA AGT CCC GGT GTC CGG GAG GGT<br>Ser Glu Val Gln Asn Val Leu Thr Ser Ser Pro Gly Val Arg Glu Gly<br>                        2925                        2930                        2935 | 9074 |
| GCA GTC GTT GCC AAG TAT GAG AAC AAC GAT ACC TAT TCC CGG ACC GCT<br>Ala Val Val Ala Lys Tyr Glu Asn Asn Asp Thr Tyr Ser Arg Thr Ala<br>                        2940                        2945                        2950 | 9122 |
| CAC TCT CTG GTC GGT TAC TAT ACC ACG GAC AAT GAA ACA GTA TCG GAA<br>His Ser Leu Val Gly Tyr Tyr Thr Thr Asp Asn Glu Thr Val Ser Glu<br>                        2955                        2960                        2965 | 9170 |
| GCC GAT ATT CTC ACT TTC ATG AAA GCA AGG CTT CCA ACG TAC ATG GTG<br>Ala Asp Ile Leu Thr Phe Met Lys Ala Arg Leu Pro Thr Tyr Met Val<br>2970                            2975                        2980                        2985 | 9218 |
| CCA AGC CAC CTC TGC TGT CTG GAA GGC GCA CTG CCT GTG ACG ATT AAC<br>Pro Ser His Leu Cys Cys Leu Glu Gly Ala Leu Pro Val Thr Ile Asn<br>                        2990                        2995                        3000 | 9266 |
| GGA AAG CTC GAC GTC CGG AGA TTG CCG GAG ATT ATC AAC GAC TCC GCG<br>Gly Lys Leu Asp Val Arg Arg Leu Pro Glu Ile Ile Asn Asp Ser Ala<br>                        3005                        3010                        3015 | 9314 |
| CAG TCC TCG TAC AGC CCA CCA AGG AAC ATA ATC GAG GCC AAG ATG TGC<br>Gln Ser Ser Tyr Ser Pro Pro Arg Asn Ile Ile Glu Ala Lys Met Cys<br>                        3020                        3025                        3030 | 9362 |
| AGA CTG TGG GAA TCC GCC TTG GGA ATG GAG CGA TGC GGT ATC GAC GAC<br>Arg Leu Trp Glu Ser Ala Leu Gly Met Glu Arg Cys Gly Ile Asp Asp<br>                        3035                        3040                        3045 | 9410 |
| GAC CTG TTC AAA CTG GGT GGC GAC AGC ATC ACA TCT TTG CAT CTC GTG<br>Asp Leu Phe Lys Leu Gly Gly Asp Ser Ile Thr Ser Leu His Leu Val<br>3050                            3055                        3060                        3065 | 9458 |
| GCC CAG ATT CAC AAC CAG GTG GGC TGC AAG ATC ACC GTT CGG GAT ATA<br>Ala Gln Ile His Asn Gln Val Gly Cys Lys Ile Thr Val Arg Asp Ile<br>                        3070                        3075                        3080 | 9506 |

```
TTT GAA CAT CGT ACC GCC CGA GCC CTC CAT GAT CAC GTC TTC ATG AAG      9554
Phe Glu His Arg Thr Ala Arg Ala Leu His Asp His Val Phe Met Lys
            3085                3090                3095

GAC TCC GAC CGG AGT AAT GTG ACT CAG TTC CGA ACC GAA CAA GGG CCG      9602
Asp Ser Asp Arg Ser Asn Val Thr Gln Phe Arg Thr Glu Gln Gly Pro
        3100                3105                3110

GTC ATC GGC GAG GCG CCC CTA CTG CCG ATT CAA GAC TGG TTT TTG TCA      9650
Val Ile Gly Glu Ala Pro Leu Leu Pro Ile Gln Asp Trp Phe Leu Ser
    3115                3120                3125

AAG GCT CTG CAG CAT CCG ATG TAT TGG AAT CAC ACT TTC TAC GTC CGA      9698
Lys Ala Leu Gln His Pro Met Tyr Trp Asn His Thr Phe Tyr Val Arg
3130                3135                3140                3145

ACG CCA GAG CTG GAT GTT GAT TCC TTA AGC GCT GCT GTC AGG GAC TTG      9746
Thr Pro Glu Leu Asp Val Asp Ser Leu Ser Ala Ala Val Arg Asp Leu
            3150                3155                3160

CAA CAG TAT CAC GAT GTT TTC CGC ATG CGA CTC AAG CGC GAG GAA GTC      9794
Gln Gln Tyr His Asp Val Phe Arg Met Arg Leu Lys Arg Glu Glu Val
        3165                3170                3175

GGA TTC GTG CAG TCC TTT GCT GAG GAC TTC TCT CCT GCC CAG CTT CGG      9842
Gly Phe Val Gln Ser Phe Ala Glu Asp Phe Ser Pro Ala Gln Leu Arg
    3180                3185                3190

GTG CTG AAC GTA AAA GAT GTT GAC GGG TCC GCG GCC GTC AAC GAG ATA      9890
Val Leu Asn Val Lys Asp Val Asp Gly Ser Ala Ala Val Asn Glu Ile
            3195                3200                3205

TTG GAT GGG TGG CAG TCT GGC TTC AAC CTT GAG AAC GGA CCC ATT GGT      9938
Leu Asp Gly Trp Gln Ser Gly Phe Asn Leu Glu Asn Gly Pro Ile Gly
3210                3215                3220                3225

TCC ATT GGC TAC CTA CAT GGG TAT GAA GAC CGA TCC GCG CGA GTC TGG      9986
Ser Ile Gly Tyr Leu His Gly Tyr Glu Asp Arg Ser Ala Arg Val Trp
            3230                3235                3240

TTC TCC GTT CAC CAT ATG GCC ATT GAC ACC GTC AGC TGG CAG ATC CTT     10034
Phe Ser Val His His Met Ala Ile Asp Thr Val Ser Trp Gln Ile Leu
        3245                3250                3255

GTC CGT GAC CTG CAG ACG CTG TAC CGA AAT GGA AGC CTC GGA AGC AAG     10082
Val Arg Asp Leu Gln Thr Leu Tyr Arg Asn Gly Ser Leu Gly Ser Lys
    3260                3265                3270

GGC AGC AGT TTC CGG CAG TGG GCT GAA GCC ATC CAA AAT TAC AAG GCG     10130
Gly Ser Ser Phe Arg Gln Trp Ala Glu Ala Ile Gln Asn Tyr Lys Ala
            3275                3280                3285

TCA GAC TCT GAG AGG AAC CAT TGG AAT AAG CTC GTC ATG GAA ACA GCT     10178
Ser Asp Ser Glu Arg Asn His Trp Asn Lys Leu Val Met Glu Thr Ala
3290                3295                3300                3305

TCC AGC ATA TCC GCA TTG CCT ACG TCA ACC GGT TCG CGC GTG CGC CTG     10226
Ser Ser Ile Ser Ala Leu Pro Thr Ser Thr Gly Ser Arg Val Arg Leu
            3310                3315                3320

AGC AGA AGT TTG AGC CCT GAG AAG ACA GCC TCA CTG ATC CAA GGA GGA     10274
Ser Arg Ser Leu Ser Pro Glu Lys Thr Ala Ser Leu Ile Gln Gly Gly
        3325                3330                3335

ATC GAT CGA CAG GAT GTC TCC GTG TAC GAC TCC CTC CTG ACT TCA GTT     10322
Ile Asp Arg Gln Asp Val Ser Val Tyr Asp Ser Leu Leu Thr Ser Val
    3340                3345                3350

GGA TTG GCG CTC CAA CAT ATC GCT CCA ACC GGC CCA AGT ATG GTT ACG     10370
Gly Leu Ala Leu Gln His Ile Ala Pro Thr Gly Pro Ser Met Val Thr
            3355                3360                3365

ATC GAG GGA CAT GGC CGT GAA GAA GTG GAT CAG ACA CTG GAT GTG AGC     10418
Ile Glu Gly His Gly Arg Glu Glu Val Asp Gln Thr Leu Asp Val Ser
3370                3375                3380                3385

CGC ACC ATG GGT TGG TTC ACC ACC ATG TAT CCA TTT GAA ATT CCC CGT     10466
Arg Thr Met Gly Trp Phe Thr Thr Met Tyr Pro Phe Glu Ile Pro Arg
            3390                3395                3400
```

```
CTC AGC ACC GAG AAC ATT GTT CAA GGA GTC GTC GCT GTG AGC GAA CGG    10514
Leu Ser Thr Glu Asn Ile Val Gln Gly Val Val Ala Val Ser Glu Arg
        3405                3410                3415

TTC AGA CAG GTG CCT GCC CGT GGC GTC GGG TAT GGA ACC TTG TAC GGC    10562
Phe Arg Gln Val Pro Ala Arg Gly Val Gly Tyr Gly Thr Leu Tyr Gly
        3420                3425                3430

TAT ACT CAA CAC CCG CTG CCC CAG GTG ACC GTC AAC TAC CTG GGC CAG    10610
Tyr Thr Gln His Pro Leu Pro Gln Val Thr Val Asn Tyr Leu Gly Gln
        3435                3440                3445

CTC GCC CGC AAG CAA TCG AAG CCA AAG GAA TGG GTC CTC GCG GTG GGC    10658
Leu Ala Arg Lys Gln Ser Lys Pro Lys Glu Trp Val Leu Ala Val Gly
3450                3455                3460                3465

GAC AAC GAA TTT GAA TAC GGA CTC ATG ACT AGC CCA GAG GAC AAA GAC    10706
Asp Asn Glu Phe Glu Tyr Gly Leu Met Thr Ser Pro Glu Asp Lys Asp
        3470                3475                3480

CGG AGC TCT TCT GCC GTC GAC GTC ACG GCC GTG TGT ATT GAC GGC ACT    10754
Arg Ser Ser Ser Ala Val Asp Val Thr Ala Val Cys Ile Asp Gly Thr
        3485                3490                3495

ATG ATC ATC GAT GTG GAC AGT GCT TGG AGC CTT GAG GAG AGC GAG CAA    10802
Met Ile Ile Asp Val Asp Ser Ala Trp Ser Leu Glu Glu Ser Glu Gln
        3500                3505                3510

TTC ATC TCG AGC ATC GAG GAA GGA CTG AAC AAG ATC CTC GAC GGC AGG    10850
Phe Ile Ser Ser Ile Glu Glu Gly Leu Asn Lys Ile Leu Asp Gly Arg
        3515                3520                3525

GCA AGT CAG CAA ACC TCG CGA TTC CCG GAT GTT CCT CAA CCG GCG GAG    10898
Ala Ser Gln Gln Thr Ser Arg Phe Pro Asp Val Pro Gln Pro Ala Glu
3530                3535                3540                3545

ACA TAT ACG CCG TAT TTC GAG TAT CTG GAA CCT CCA CGA CAG GGA CCG    10946
Thr Tyr Thr Pro Tyr Phe Glu Tyr Leu Glu Pro Pro Arg Gln Gly Pro
        3550                3555                3560

ACG CTG TTC CTG CTG CCG CCG GGC GAA GGA GGC GCC GAG AGT TAC TTC    10994
Thr Leu Phe Leu Leu Pro Pro Gly Glu Gly Gly Ala Glu Ser Tyr Phe
        3565                3570                3575

AAC AAC ATC GTC AAG CGC CTG CGT CAG ACA AAT ATG GTG GTC TTC AAC    11042
Asn Asn Ile Val Lys Arg Leu Arg Gln Thr Asn Met Val Val Phe Asn
        3580                3585                3590

AAC TAC TAC TTG CAC AGC AAA CGC CTG CGC ACG TTC GAG GAG CTG GCG    11090
Asn Tyr Tyr Leu His Ser Lys Arg Leu Arg Thr Phe Glu Glu Leu Ala
        3595                3600                3605

GAA ATG TAT CTC GAC CAA GTA CGC GGC ATC CAA CCA CAC GGA CCG TAC    11138
Glu Met Tyr Leu Asp Gln Val Arg Gly Ile Gln Pro His Gly Pro Tyr
3610                3615                3620                3625

CAC TTC ATC GGA TGG AGC TTC GGA GGA ATT CTC GCA ATG GAA ATG TCG    11186
His Phe Ile Gly Trp Ser Phe Gly Gly Ile Leu Ala Met Glu Met Ser
        3630                3635                3640

CGG CGA CTG GTA GCC TCG GAC GAG AAG ATT GGC TTC CTC GGT ATT ATC    11234
Arg Arg Leu Val Ala Ser Asp Glu Lys Ile Gly Phe Leu Gly Ile Ile
        3645                3650                3655

GAC ACC TAT TTC AAC GTG CGG GGA GCG ACA CGC ACC ATT GGC TTG GGG    11282
Asp Thr Tyr Phe Asn Val Arg Gly Ala Thr Arg Thr Ile Gly Leu Gly
        3660                3665                3670

GAC ACT GAG ATT CTG GAC CCG ATC CAT CAC ATC TAC AAT CCC GAT CCG    11330
Asp Thr Glu Ile Leu Asp Pro Ile His His Ile Tyr Asn Pro Asp Pro
        3675                3680                3685

GCC AAC TTC CAA CGC CTG CCC TCT GCA ACA GAT CGC ATT GTG CTG TTC    11378
Ala Asn Phe Gln Arg Leu Pro Ser Ala Thr Asp Arg Ile Val Leu Phe
        3690                3695                3700                3705

AAG GCC ATG AGG CCG AAC AAC AAG TAC GAA TCC GAG AAC CAG CGT CGC    11426
Lys Ala Met Arg Pro Asn Asn Lys Tyr Glu Ser Glu Asn Gln Arg Arg
        3710                3715                3720
```

| | | | | | | | | | | | | | | | | |
|---|---|---|---|---|---|---|---|---|---|---|---|---|---|---|---|---|
| CTG | TAC | GAG | TAC | TAT | GAC | CGC | ACT | CGA | CTC | AAC | GGA | CTG | GAC | AGC | TTG | 11474 |
| Leu | Tyr | Glu | Tyr | Tyr | Asp | Arg | Thr | Arg | Leu | Asn | Gly | Leu | Asp | Ser | Leu | |
| | | | 3725 | | | | 3730 | | | | | 3735 | | | | |
| TTA | CCA | AGC | GAT | TCC | GAC | GTC | CAG | CTG | GTC | CCG | CTT | ACG | GAC | GAT | ACA | 11522 |
| Leu | Pro | Ser | Asp | Ser | Asp | Val | Gln | Leu | Val | Pro | Leu | Thr | Asp | Asp | Thr | |
| | | 3740 | | | | | 3745 | | | | | 3750 | | | | |
| CAC | TTT | TCC | TGG | GTC | GGA | AAT | CCA | CAA | CAG | GTG | GAG | CAG | ATG | TGT | GCG | 11570 |
| His | Phe | Ser | Trp | Val | Gly | Asn | Pro | Gln | Gln | Val | Glu | Gln | Met | Cys | Ala | |
| | | 3755 | | | | | 3760 | | | | | 3765 | | | | |
| ACT | ATC | AAG | GAA | CAC | CTC | GCT | CGC | TAT | TGATCCGTCA | | CTAGCAGCAC | | | | | 11617 |
| Thr | Ile | Lys | Glu | His | Leu | Ala | Arg | Tyr | | | | | | | | |
| 3770 | | | | | 3775 | | | | | | | | | | | |

| | | | | | |
|---|---|---|---|---|---|
| AGTATATCGG | ACGATGGAAG | TGATGGAGTG | GGGGGGATAG | GATACGATCA | AACCAGAGTG | 11677 |
| CGGTTCTTTT | TCGGGGGAAC | TAGTCTCTGG | TTGAGGAAAG | CGAGGTAGCA | AATAAACTAC | 11737 |
| CAAGGTCTAG | ACCCACATAG | TCTGTCATTG | TTTTCGATCC | TAAATTGATA | TATAATAGGC | 11797 |
| GACACCTTTA | GTTAGCCAAA | TTTTCTATAT | AGAAACACCA | CGGTTTTTAG | GAGTTAGGAC | 11857 |
| CACGTCAGAC | CGTGGCCCTT | TCACTAACGC | TTCCGTTTAC | ATCCATACCG | GATGTCGTTG | 11917 |
| TAGCACATTT | ATATGATATC | ATTTAAGACT | ATATACGCCT | ATTCCCCCCT | ATCGAATAGG | 11977 |
| CCCCTACGTA | TTTCTTTTGT | TTTTTTCTTT | TTCTTTTTTT | TTTTTTTCTT | TTCGCTCTCT | 12037 |
| CCCCTTTTAT | ACCCAATATC | GGATCGAGTT | GATAATATCA | ATATCTAAAA | CTCCCAATTA | 12097 |
| AACCTACAAA | GCCTATCTTA | GTGTAAGTGA | ATTTGGGCTC | TGGACCAAAT | TCTCCGCCAA | 12157 |
| GGATAATCTT | TCCGATAAAC | GGTGGTTATC | CGGTCATCAT | AAAAAAGGAA | AAGGTACTCC | 12217 |
| GTCCTCGATA | ATAAAACGTA | ACATAAGCAT | GTCGTTCACC | ATAGACAAGA | GGAACCAACA | 12277 |
| TCATTAAGCA | GGGGATAGGT | TCATCCGGTC | TAGGGCGTCG | AGTGCCACCG | CCCGTAGGTT | 12337 |
| GTCAATCTTG | AGCTGGATTT | GGAGATC | | | | 12364 |

( 2 ) INFORMATION FOR SEQ ID NO:2:

( i ) SEQUENCE CHARACTERISTICS:
    ( A ) LENGTH: 3778 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

| Met | Thr | Gln | Leu | Lys | Pro | Pro | Asn | Gly | Thr | Thr | Pro | Ile | Gly | Phe | Ser |
|---|---|---|---|---|---|---|---|---|---|---|---|---|---|---|---|
| 1 | | | | 5 | | | | | 10 | | | | | 15 | |

| Ala | Thr | Thr | Ser | Leu | Asn | Ala | Ser | Gly | Ser | Ser | Val | Lys | Asn | Gly |
|---|---|---|---|---|---|---|---|---|---|---|---|---|---|---|
| | | | 20 | | | | | 25 | | | | | 30 | |

| Thr | Ile | Lys | Pro | Ser | Asn | Gly | Ile | Phe | Lys | Pro | Ser | Thr | Arg | Asp | Thr |
|---|---|---|---|---|---|---|---|---|---|---|---|---|---|---|---|
| | | | 35 | | | | | 40 | | | | | 45 | | |

| Met | Asp | Pro | Cys | Ser | Gly | Asn | Ala | Ala | Asp | Gly | Ser | Ile | Arg | Val | Arg |
|---|---|---|---|---|---|---|---|---|---|---|---|---|---|---|---|
| | 50 | | | | | 55 | | | | | 60 | | | | |

| Phe | Arg | Gly | Gly | Ile | Glu | Arg | Trp | Lys | Glu | Cys | Val | Asn | Gln | Val | Pro |
|---|---|---|---|---|---|---|---|---|---|---|---|---|---|---|---|
| 65 | | | | | 70 | | | | | 75 | | | | | 80 |

| Glu | Arg | Cys | Asp | Leu | Ser | Gly | Leu | Thr | Thr | Asp | Ser | Thr | Arg | Tyr | Gln |
|---|---|---|---|---|---|---|---|---|---|---|---|---|---|---|---|
| | | | | 85 | | | | | 90 | | | | | 95 | |

| Leu | Ala | Ser | Thr | Gly | Phe | Gly | Asp | Ala | Ser | Ala | Ala | Tyr | Gln | Glu | Arg |
|---|---|---|---|---|---|---|---|---|---|---|---|---|---|---|---|
| | | | 100 | | | | | 105 | | | | | 110 | | |

| Leu | Met | Thr | Val | Pro | Val | Asp | Val | His | Ala | Ala | Leu | Gln | Glu | Leu | Cys |
|---|---|---|---|---|---|---|---|---|---|---|---|---|---|---|---|
| | | | 115 | | | | | 120 | | | | | 125 | | |

| Leu | Glu | Arg | Arg | Val | Ser | Val | Gly | Ser | Val | Ile | Asn | Phe | Ser | Val | His |
|---|---|---|---|---|---|---|---|---|---|---|---|---|---|---|---|

|     |     |     | 130 |     |     |     | 135 |     |     |     | 140 |     |     |     |
| --- | --- | --- | --- | --- | --- | --- | --- | --- | --- | --- | --- | --- | --- | --- |

Gln Met Leu Lys Gly Phe Gly Asn Gly Thr His Thr Ile Thr Ala Ser
145                     150                     155                     160

Leu His Arg Glu Gln Asn Leu Gln Asn Ser Ser Pro Ser Trp Val Val
                        165                     170                     175

Ser Pro Thr Ile Val Thr His Glu Asn Arg Asp Gly Trp Ser Val Ala
                180                     185                     190

Gln Ala Val Glu Ser Ile Glu Ala Ala Arg Gly Ser Glu Lys Glu Ser
            195                     200                     205

Val Thr Ala Ile Asp Ser Ala Ser Ser Leu Val Lys Met Gly Leu Phe
        210                     215                     220

Asp Leu Leu Val Ser Phe Val Asp Ala Asp Ala Arg Ile Pro Cys
225                     230                     235                     240

Phe Asp Phe Pro Leu Ala Val Ile Val Arg Glu Cys Asp Ala Asn Leu
                    245                     250                     255

Ser Leu Thr Leu Arg Phe Ser Asp Cys Leu Phe Asn Glu Glu Thr Ile
            260                     265                     270

Cys Asn Phe Thr Asp Ala Leu Asn Ile Leu Leu Ala Glu Ala Val Ile
        275                     280                     285

Gly Arg Val Thr Pro Val Ala Asp Ile Glu Leu Leu Ser Ala Glu Gln
    290                     295                     300

Lys Gln Gln Leu Glu Glu Trp Asn Asn Thr Asp Gly Glu Tyr Pro Ser
305                     310                     315                     320

Ser Lys Arg Leu His His Leu Ile Glu Glu Val Val Glu Arg His Glu
                        325                     330                     335

Asp Lys Ile Ala Val Val Cys Asp Glu Arg Glu Leu Thr Tyr Gly Glu
                340                     345                     350

Leu Asn Ala Gln Gly Asn Ser Leu Ala Arg Tyr Leu Arg Ser Ile Gly
            355                     360                     365

Ile Leu Pro Glu Gln Leu Val Ala Leu Phe Leu Asp Lys Ser Glu Lys
        370                     375                     380

Leu Ile Val Thr Ile Leu Gly Val Trp Lys Ser Gly Ala Ala Tyr Val
385                     390                     395                     400

Pro Ile Asp Pro Thr Tyr Pro Asp Glu Arg Val Arg Phe Val Leu Asp
                    405                     410                     415

Asp Thr Lys Ala Arg Ala Ile Ile Ala Ser Asn Gln His Val Glu Arg
            420                     425                     430

Leu Gln Arg Glu Val Ile Gly Asp Arg Asn Leu Cys Ile Ile Arg Leu
        435                     440                     445

Glu Pro Leu Leu Ala Ser Leu Ala Gln Asp Ser Ser Lys Phe Pro Ala
    450                     455                     460

His Asn Leu Asp Asp Leu Pro Leu Thr Ser Gln Gln Leu Ala Tyr Val
465                     470                     475                     480

Thr Tyr Thr Ser Gly Thr Thr Gly Phe Pro Lys Gly Ile Phe Lys Gln
                485                     490                     495

His Thr Asn Val Val Asn Ser Ile Thr Asp Leu Ser Ala Arg Tyr Gly
            500                     505                     510

Val Ala Gly Gln His His Glu Ala Ile Leu Leu Phe Ser Ala Cys Val
        515                     520                     525

Phe Glu Pro Phe Val Arg Gln Thr Leu Met Ala Leu Val Asn Gly His
    530                     535                     540

Leu Leu Ala Val Ile Asn Asp Val Glu Lys Tyr Asp Ala Asp Thr Leu
545                     550                     555                     560

-continued

| | | | | | | | | | | | | | | |
|---|---|---|---|---|---|---|---|---|---|---|---|---|---|---|
| Leu | Pro | Phe | Ile | Arg<br>565 | Arg | His | Ser | Ile | Thr<br>570 | Tyr | Leu | Asn | Gly | Thr | Ala<br>575 |
| Ser | Val | Leu | Gln | Glu<br>580 | Tyr | Asp | Phe | Ser | Asp<br>585 | Cys | Pro | Ser | Leu<br>590 | Asn | Arg |
| Ile | Ile | Leu<br>595 | Val | Gly | Glu | Asn | Leu<br>600 | Thr | Glu | Ala | Arg | Tyr<br>605 | Leu | Ala | Leu |
| Arg | Gln<br>610 | Arg | Phe | Lys | Asn | Arg<br>615 | Ile | Leu | Asn | Glu | Tyr<br>620 | Gly | Phe | Thr | Glu |
| Ser<br>625 | Ala | Phe | Val | Thr | Ala<br>630 | Leu | Lys | Ile | Phe | Asp<br>635 | Pro | Glu | Ser | Thr | Arg<br>640 |
| Lys | Asp | Thr | Ser | Leu<br>645 | Gly | Arg | Pro | Val | Arg<br>650 | Asn | Val | Lys | Cys | Tyr<br>655 | Ile |
| Leu | Asn | Pro | Ser<br>660 | Leu | Lys | Arg | Val | Pro<br>665 | Ile | Gly | Ala | Thr | Gly<br>670 | Glu | Leu |
| His | Ile | Gly<br>675 | Gly | Leu | Gly | Ile | Ser<br>680 | Lys | Gly | Tyr | Leu | Asn<br>685 | Arg | Pro | Glu |
| Leu | Thr<br>690 | Pro | His | Arg | Phe | Ile<br>695 | Pro | Asn | Pro | Phe | Gln<br>700 | Thr | Asp | Cys | Glu |
| Lys<br>705 | Gln | Leu | Gly | Ile | Asn<br>710 | Ser | Leu | Met | Tyr | Lys<br>715 | Thr | Gly | Asp | Leu | Ala<br>720 |
| Arg | Trp | Leu | Pro | Asn<br>725 | Gly | Glu | Val | Glu | Tyr<br>730 | Leu | Gly | Arg | Ala | Asp<br>735 | Phe |
| Gln | Ile | Lys | Leu<br>740 | Arg | Gly | Ile | Arg | Ile<br>745 | Glu | Pro | Gly | Glu | Ile<br>750 | Glu | Thr |
| Met | Leu | Ala<br>755 | Met | Tyr | Pro | Arg | Val<br>760 | Arg | Thr | Ser | Leu | Val<br>765 | Val | Ser | Lys |
| Lys | Leu<br>770 | Arg | Asn | Gly | Pro | Glu<br>775 | Glu | Thr | Thr | Asn | Glu<br>780 | His | Leu | Val | Gly |
| Tyr<br>785 | Tyr | Val | Cys | Asp | Ser<br>790 | Ala | Ser | Val | Ser | Glu<br>795 | Ala | Asp | Leu | Leu | Ser<br>800 |
| Phe | Leu | Glu | Lys | Lys<br>805 | Leu | Pro | Arg | Tyr | Met<br>810 | Ile | Pro | Thr | Arg | Leu<br>815 | Val |
| Gln | Leu | Ser | Gln<br>820 | Ile | Pro | Val | Asn | Val<br>825 | Asn | Gly | Lys | Ala | Asp<br>830 | Leu | Arg |
| Ala | Leu | Pro<br>835 | Ala | Val | Asp | Ile | Ser<br>840 | Asn | Ser | Thr | Glu | Val<br>845 | Arg | Ser | Asp |
| Leu | Arg<br>850 | Gly | Asp | Thr | Glu | Ile<br>855 | Ala | Leu | Gly | Glu | Ile<br>860 | Trp | Ala | Asp | Val |
| Leu<br>865 | Gly | Ala | Arg | Gln | Arg<br>870 | Ser | Val | Ser | Arg | Asn<br>875 | Asp | Asn | Phe | Phe | Arg<br>880 |
| Leu | Gly | Gly | His | Ser<br>885 | Ile | Thr | Cys | Ile | Gln<br>890 | Leu | Ile | Ala | Arg | Ile<br>895 | Arg |
| Gln | Arg | Gln | Arg<br>900 | Leu | Ser | Val | Ser | Ile<br>905 | Ser | Val | Glu | Asp | Val<br>910 | Phe | Ala |
| Thr | Arg | Thr<br>915 | Leu | Glu | Arg | Met | Ala<br>920 | Asp | Leu | Leu | Gln | Asn<br>925 | Lys | Gln | Gln |
| Glu | Lys<br>930 | Cys | Asp | Lys | Pro | His<br>935 | Glu | Ala | Pro | Thr | Glu<br>940 | Leu | Leu | Glu |
| Asn<br>945 | Ala | Ala | Thr | Asp | Asn<br>950 | Ile | Tyr | Leu | Ala | Asn<br>955 | Ser | Leu | Gln | Gln | Gly<br>960 |
| Phe | Val | Tyr | His | Tyr<br>965 | Leu | Lys | Ser | Met | Glu<br>970 | Gln | Ser | Asp | Ala | Tyr<br>975 | Val |
| Met | Gln | Ser | Val<br>980 | Leu | Arg | Tyr | Asn | Thr<br>985 | Thr | Leu | Ser | Pro | Asp<br>990 | Leu | Phe |

```
Gln Arg Ala Trp Lys His Ala Gln Gln Ser Phe Pro Ala Leu Arg Leu
            995                1000                1005

Arg Phe Ser Trp Glu Lys Glu Val Phe Gln Leu Leu Asp Gln Asp Pro
        1010                1015                1020

Pro Leu Asp Trp Arg Phe Leu Tyr Phe Thr Asp Val Ala Ala Gly Ala
1025                1030                1035                1040

Val Glu Asp Arg Lys Leu Glu Asp Leu Arg Arg Gln Asp Leu Thr Glu
            1045                1050                1055

Arg Phe Lys Leu Asp Val Gly Arg Leu Phe Arg Val Tyr Leu Ile Lys
            1060                1065                1070

His Ser Glu Asn Arg Phe Thr Cys Leu Phe Ser Cys His Ala Ile
            1075                1080                1085

Leu Asp Gly Trp Ser Leu Pro Leu Leu Phe Glu Lys Val His Glu Thr
            1090                1095                1100

Tyr Leu Gln Leu Leu His Gly Asp Asn Leu Thr Ser Ser Met Asp Asp
1105                1110                1115                1120

Pro Tyr Thr Arg Thr Gln Arg Tyr Leu His Ala His Arg Glu Asp His
            1125                1130                1135

Leu Asp Phe Trp Ala Gly Val Val Gln Lys Ile Asn Glu Arg Cys Asp
            1140                1145                1150

Met Asn Ala Leu Leu Asn Glu Arg Ser Arg Tyr Lys Val Gln Leu Ala
            1155                1160                1165

Asp Tyr Asp Gln Val Gln Glu Gln Arg His Val Thr Ile Ala Leu Ser
    1170                1175                1180

Gly Asp Ala Trp Leu Ala Asp Leu Arg Gln Thr Cys Ser Ala Gln Gly
1185                1190                1195                1200

Ile Thr Leu His Ser Ile Leu Gln Phe Val Trp His Ala Val Leu His
            1205                1210                1215

Ala Tyr Gly Gly Gly Thr His Thr Ile Thr Gly Thr Thr Ile Ser Gly
            1220                1225                1230

Arg Asn Leu Pro Ile Leu Gly Ile Glu Arg Ala Val Gly Pro Tyr Ile
            1235                1240                1245

Asn Thr Leu Pro Leu Val Leu Asp His Ser Thr Phe Lys Asp Lys Thr
            1250                1255                1260

Ile Met Glu Ala Ile Glu Asp Val Gln Ala Lys Val Asn Val Met Asn
1265                1270                1275                1280

Ser Arg Gly Asn Val Glu Leu Gly Arg Leu His Lys Thr Asp Leu Lys
            1285                1290                1295

His Gly Leu Phe Asp Ser Leu Phe Val Leu Glu Asn Tyr Pro Asn Leu
            1300                1305                1310

Asp Lys Ser Arg Thr Leu Glu His Gln Thr Glu Leu Gly Tyr Ser Ile
            1315                1320                1325

Glu Gly Gly Thr Glu Lys Leu Asn Tyr Pro Leu Ala Val Ile Ala Arg
            1330                1335                1340

Glu Val Glu Thr Thr Gly Gly Phe Thr Val Ser Ile Cys Tyr Ala Ser
1345                1350                1355                1360

Glu Leu Phe Glu Glu Val Met Ile Ser Glu Leu Leu His Met Val Gln
            1365                1370                1375

Asp Thr Leu Met Gln Val Ala Arg Gly Leu Asn Glu Pro Val Gly Ser
            1380                1385                1390

Leu Glu Tyr Leu Ser Ser Ile Gln Leu Glu Gln Leu Ala Ala Trp Asn
            1395                1400                1405

Ala Thr Glu Ala Glu Phe Pro Asp Thr Thr Leu His Glu Met Phe Glu
```

```
                    1410                  1415                  1420
Asn  Glu  Ala  Ser  Gln  Lys  Pro  Asp  Lys  Ile  Ala  Val  Val  Tyr  Glu  Glu
1425                1430                      1435                      1440

Thr  Ser  Leu  Thr  Tyr  Arg  Glu  Leu  Asn  Glu  Arg  Ala  Asn  Arg  Met  Ala
               1445                      1450                      1455

His  Gln  Leu  Arg  Ser  Asp  Val  Ser  Pro  Asn  Pro  Asn  Glu  Val  Ile  Ala
               1460                      1465                      1470

Leu  Val  Met  Asp  Lys  Ser  Glu  His  Met  Ile  Val  Asn  Ile  Leu  Ala  Val
               1475                      1480                      1485

Trp  Lys  Ser  Gly  Gly  Ala  Tyr  Val  Pro  Ile  Asp  Pro  Gly  Tyr  Pro  Asn
               1490                      1495                      1500

Asp  Arg  Ile  Gln  Tyr  Ile  Leu  Glu  Asp  Thr  Gln  Ala  Leu  Ala  Val  Ile
1505                1510                      1515                      1520

Ala  Asp  Ser  Cys  Tyr  Leu  Pro  Arg  Ile  Lys  Gly  Met  Ala  Ala  Ser  Gly
               1525                      1530                      1535

Thr  Leu  Leu  Tyr  Pro  Ser  Val  Leu  Pro  Ala  Asn  Pro  Asp  Ser  Lys  Trp
               1540                      1545                      1550

Ser  Val  Ser  Asn  Pro  Ser  Pro  Leu  Ser  Arg  Ser  Thr  Asp  Leu  Ala  Tyr
               1555                      1560                      1565

Ile  Ile  Tyr  Thr  Ser  Gly  Thr  Thr  Gly  Arg  Pro  Lys  Gly  Val  Thr  Val
               1570                      1575                      1580

Glu  His  His  Gly  Val  Val  Asn  Leu  Gln  Val  Ser  Leu  Ser  Lys  Val  Phe
1585                1590                      1595                      1600

Gly  Leu  Arg  Asp  Thr  Asp  Asp  Glu  Val  Ile  Leu  Ser  Phe  Ser  Asn  Tyr
               1605                      1610                      1615

Val  Phe  Asp  His  Phe  Val  Glu  Gln  Met  Thr  Asp  Ala  Ile  Leu  Asn  Gly
               1620                      1625                      1630

Gln  Thr  Leu  Leu  Val  Leu  Asn  Asp  Gly  Met  Arg  Gly  Asp  Lys  Glu  Arg
               1635                      1640                      1645

Leu  Tyr  Arg  Tyr  Ile  Glu  Lys  Asn  Arg  Val  Thr  Tyr  Leu  Ser  Gly  Thr
               1650                      1655                      1660

Pro  Ser  Val  Val  Ser  Met  Tyr  Glu  Phe  Ser  Arg  Phe  Lys  Asp  His  Leu
1665                1670                      1675                      1680

Arg  Arg  Val  Asp  Cys  Val  Gly  Glu  Ala  Phe  Ser  Glu  Pro  Val  Phe  Asp
               1685                      1690                      1695

Lys  Ile  Arg  Glu  Thr  Phe  His  Gly  Leu  Val  Ile  Asn  Gly  Tyr  Gly  Pro
               1700                      1705                      1710

Thr  Glu  Val  Ser  Ile  Thr  Thr  His  Lys  Arg  Leu  Tyr  Pro  Phe  Pro  Glu
               1715                      1720                      1725

Arg  Arg  Met  Asp  Lys  Ser  Ile  Gly  Gln  Gln  Val  His  Asn  Ser  Thr  Ser
1730                1735                      1740

Tyr  Val  Leu  Asn  Glu  Asp  Met  Lys  Arg  Thr  Pro  Ile  Gly  Ala  Val  Gly
1745                1750                      1755                      1760

Glu  Leu  Tyr  Leu  Gly  Gly  Glu  Gly  Val  Val  Arg  Gly  Tyr  His  Asn  Arg
               1765                      1770                      1775

Ala  Asp  Val  Thr  Ala  Glu  Arg  Phe  Ile  Pro  Asn  Pro  Phe  Gln  Ser  Glu
               1780                      1785                      1790

Glu  Asp  Lys  Arg  Glu  Gly  Arg  Asn  Ser  Arg  Leu  Tyr  Lys  Thr  Gly  Asp
               1795                      1800                      1805

Leu  Val  Arg  Trp  Ile  Pro  Gly  Ser  Ser  Gly  Glu  Val  Glu  Tyr  Leu  Gly
               1810                      1815                      1820

Arg  Asn  Asp  Phe  Gln  Val  Lys  Ile  Arg  Gly  Leu  Arg  Ile  Glu  Val  Gly
1825                1830                      1835                      1840
```

```
Glu  Ile  Glu  Ala  Ile  Leu  Ser  Ser  Tyr  His  Gly  Ile  Lys  Gln  Ser  Val
                    1845                     1850                     1855

Val  Ile  Ala  Lys  Asp  Cys  Arg  Glu  Gly  Ala  Gln  Lys  Phe  Leu  Val  Gly
                    1860                     1865                     1870

Tyr  Tyr  Val  Ala  Asp  Ala  Ala  Leu  Pro  Ser  Ala  Ala  Ile  Arg  Arg  Phe
               1875                     1880                     1885

Met  Gln  Ser  Arg  Leu  Pro  Gly  Tyr  Met  Val  Pro  Ser  Arg  Leu  Ile  Leu
               1890                     1895                     1900

Val  Ser  Lys  Phe  Pro  Val  Thr  Pro  Ser  Gly  Lys  Leu  Asp  Thr  Lys  Ala
1905                     1910                     1915                     1920

Leu  Pro  Pro  Ala  Glu  Glu  Glu  Ser  Glu  Ile  Asp  Val  Val  Pro  Pro  Arg
                    1925                     1930                     1935

Ser  Glu  Ile  Glu  Arg  Ser  Leu  Cys  Asp  Ile  Trp  Ala  Glu  Leu  Leu  Glu
               1940                     1945                     1950

Met  His  Pro  Glu  Glu  Ile  Gly  Ile  Tyr  Ser  Asp  Phe  Phe  Ser  Leu  Gly
               1955                     1960                     1965

Gly  Asp  Ser  Leu  Lys  Ser  Thr  Lys  Leu  Ser  Phe  Met  Ile  His  Glu  Ser
               1970                     1975                     1980

Phe  Asn  Arg  Ala  Val  Ser  Val  Ser  Ala  Leu  Phe  Cys  His  Arg  Thr  Val
1985                     1990                     1995                     2000

Glu  Ala  Gln  Thr  His  Leu  Ile  Leu  Asn  Asp  Ala  Ala  Asp  Val  His  Glu
                    2005                     2010                     2015

Ile  Thr  Pro  Ile  Asp  Cys  Asn  Asp  Thr  Gln  Met  Ile  Pro  Val  Ser  Arg
               2020                     2025                     2030

Ala  Gln  Glu  Arg  Leu  Leu  Phe  Ile  His  Glu  Phe  Glu  Asn  Gly  Ser  Asn
               2035                     2040                     2045

Ala  Tyr  Asn  Ile  Asp  Ala  Ala  Phe  Glu  Leu  Pro  Gly  Ser  Val  Asp  Ala
               2050                     2055                     2060

Ser  Leu  Leu  Glu  Gln  Ala  Leu  Arg  Gly  Asn  Leu  Ala  Arg  His  Glu  Ala
2065                     2070                     2075                     2080

Leu  Arg  Thr  Leu  Leu  Val  Lys  Asp  His  Ala  Thr  Gly  Ile  Tyr  Leu  Gln
                    2085                     2090                     2095

Lys  Val  Leu  Ser  Pro  Asp  Glu  Ala  Gln  Gly  Met  Phe  Ser  Val  Asn  Val
                    2100                     2105                     2110

Asp  Thr  Ala  Lys  Gln  Val  Glu  Arg  Leu  Asp  Gln  Glu  Ile  Ala  Ser  Leu
               2115                     2120                     2125

Ser  Gln  His  Val  Phe  Arg  Leu  Asp  Asp  Glu  Leu  Pro  Trp  Glu  Ala  Arg
               2130                     2135                     2140

Ile  Leu  Lys  Leu  Glu  Ser  Gly  Gly  Leu  Tyr  Leu  Ile  Leu  Ala  Phe  His
2145                     2150                     2155                     2160

His  Thr  Cys  Phe  Asp  Ala  Trp  Ser  Leu  Lys  Val  Phe  Glu  Gln  Glu  Leu
                    2165                     2170                     2175

Arg  Ala  Leu  Tyr  Ala  Ala  Leu  Gln  Lys  Thr  Lys  Ser  Ala  Ala  Asn  Leu
               2180                     2185                     2190

Pro  Ala  Leu  Lys  Ala  Gln  Tyr  Lys  Glu  Tyr  Ala  Leu  Tyr  His  Arg  Arg
               2195                     2200                     2205

Gln  Leu  Ser  Gly  Asp  Arg  Met  Arg  Asn  Leu  Ser  Asp  Phe  Trp  Leu  Arg
               2210                     2215                     2220

Lys  Leu  Ile  Gly  Leu  Glu  Pro  Leu  Gln  Leu  Ile  Thr  Asp  Arg  Pro  Arg
2225                     2230                     2235                     2240

Pro  Val  Gln  Phe  Lys  Tyr  Asp  Gly  Asp  Asp  Leu  Ser  Ile  Glu  Leu  Ser
                    2245                     2250                     2255

Lys  Lys  Glu  Thr  Glu  Asn  Leu  Arg  Gly  Val  Ala  Lys  Arg  Cys  Lys  Ser
                    2260                     2265                     2270
```

```
Ser  Leu  Tyr  Val  Val  Leu  Val  Ser  Val  Tyr  Cys  Val  Met  Leu  Ala  Ser
          2275                    2280                    2285

Tyr  Ala  Asn  Gln  Ser  Asp  Val  Ser  Val  Gly  Ile  Pro  Val  Ser  His  Arg
          2290                    2295                    2300

Thr  His  Pro  Gln  Phe  Gln  Ser  Val  Ile  Gly  Phe  Phe  Val  Asn  Leu  Val
2305                     2310                    2315                    2320

Val  Leu  Arg  Val  Asp  Ile  Ser  Gln  Ser  Ala  Ile  Cys  Gly  Leu  Ile  Arg
          2325                    2330                    2335

Arg  Val  Met  Lys  Glu  Leu  Val  Asp  Ala  Gln  Leu  His  Gln  Asp  Met  Pro
          2340                    2345                    2350

Phe  Gln  Glu  Val  Thr  Lys  Leu  Leu  Gln  Val  Asp  Asn  Asp  Pro  Ser  Arg
          2355                    2360                    2365

His  Pro  Leu  Val  Gln  Asn  Val  Phe  Asn  Phe  Glu  Ser  Arg  Ala  Asn  Gly
          2370                    2375                    2380

Glu  His  Asp  Ala  Arg  Ser  Glu  Asp  Glu  Gly  Ser  Leu  Ala  Phe  Asn  Gln
2385                     2390                    2395                    2400

Tyr  Arg  Pro  Val  Gln  Pro  Val  Asp  Ser  Val  Ala  Lys  Phe  Asp  Leu  Asn
          2405                    2410                    2415

Ala  Thr  Val  Thr  Glu  Leu  Glu  Ser  Gly  Leu  Arg  Val  Asn  Phe  Asn  Tyr
          2420                    2425                    2430

Ala  Thr  Ser  Leu  Phe  Asn  Lys  Ser  Thr  Ile  Gln  Gly  Phe  Leu  His  Thr
          2435                    2440                    2445

Tyr  Glu  Tyr  Leu  Leu  Arg  Gln  Leu  Ser  Glu  Leu  Ser  Ala  Glu  Gly  Ile
          2450                    2455                    2460

Asn  Glu  Asp  Thr  Gln  Leu  Ser  Leu  Val  Arg  Pro  Thr  Glu  Asn  Gly  Asp
2465                     2470                    2475                    2480

Leu  His  Leu  Pro  Leu  Ala  Gln  Ser  Pro  Leu  Ala  Thr  Thr  Ala  Glu  Glu
          2485                    2490                    2495

Gln  Lys  Val  Ala  Ser  Leu  Asn  Gln  Ala  Phe  Glu  Arg  Glu  Ala  Phe  Leu
          2500                    2505                    2510

Ala  Ala  Glu  Lys  Ile  Ala  Val  Val  Gln  Gly  Asp  Arg  Ala  Leu  Ser  Tyr
          2515                    2520                    2525

Ala  Asp  Leu  Asn  Gly  Gln  Ala  Asn  Gln  Leu  Ala  Arg  Tyr  Ile  Gln  Ser
          2530                    2535                    2540

Val  Ser  Cys  Ile  Gly  Ala  Asp  Asp  Gly  Ile  Ala  Leu  Met  Leu  Glu  Lys
2545                     2550                    2555                    2560

Ser  Ile  Asp  Thr  Ile  Ile  Cys  Ile  Leu  Ala  Ile  Trp  Lys  Ala  Gly  Ala
          2565                    2570                    2575

Ala  Tyr  Val  Pro  Leu  Asp  Pro  Thr  Tyr  Pro  Pro  Gly  Arg  Val  Gln  Leu
          2580                    2585                    2590

Ile  Leu  Glu  Glu  Ile  Lys  Ala  Lys  Ala  Val  Leu  Val  His  Ser  Ser  His
          2595                    2600                    2605

Ala  Ser  Lys  Cys  Glu  Arg  His  Gly  Ala  Lys  Val  Ile  Ala  Val  Asp  Ser
          2610                    2615                    2620

Pro  Ala  Ile  Glu  Thr  Ala  Val  Ser  Gln  Gln  Ser  Ala  Ala  Asp  Leu  Pro
2625                     2630                    2635                    2640

Thr  Ile  Ala  Ser  Leu  Gly  Asn  Leu  Ala  Tyr  Ile  Ile  Phe  Thr  Ser  Gly
          2645                    2650                    2655

Thr  Ser  Gly  Lys  Pro  Lys  Gly  Val  Leu  Val  Glu  Gln  Lys  Ala  Val  Leu
          2660                    2665                    2670

Leu  Leu  Arg  Asp  Ala  Leu  Arg  Glu  Arg  Tyr  Phe  Gly  Arg  Asp  Cys  Thr
          2675                    2680                    2685

Lys  His  His  Gly  Val  Leu  Phe  Leu  Ser  Asn  Tyr  Val  Phe  Asp  Phe  Ser
```

|       |       |       |       |       | 2690  |       |       |       |       | 2695  |       |       |       |       | 2700  |
|-------|-------|-------|-------|-------|-------|-------|-------|-------|-------|-------|-------|-------|-------|-------|-------|

Val Glu Gln Leu Val Leu Ser Val Leu Ser Gly His Lys Leu Ile Val
2705                     2710                    2715                    2720

Pro Pro Ala Glu Phe Val Ala Asp Asp Glu Phe Tyr Arg Met Ala Ser
                        2725                    2730                    2735

Thr His Gly Leu Ser Tyr Leu Ser Gly Thr Pro Ser Leu Leu Gln Lys
                        2740                    2745                    2750

Ile Asp Leu Ala Arg Leu Asp His Leu Gln Val Val Thr Ala Ala Gly
                        2755                    2760                    2765

Glu Glu Leu His Ala Thr Gln Tyr Glu Lys Met Arg Arg Arg Phe Asn
                        2770                    2775                    2780

Gly Pro Ile Tyr Asn Ala Tyr Gly Val Thr Glu Thr Thr Val Tyr Asn
2785                    2790                    2795                    2800

Ile Ile Ala Glu Phe Thr Thr Asn Ser Ile Phe Glu Asn Ala Leu Arg
                        2805                    2810                    2815

Glu Val Leu Pro Gly Thr Arg Ala Tyr Val Leu Thr Ala Ala Leu Gln
                        2820                    2825                    2830

Pro Val Pro Phe Asp Ala Val Gly Glu Leu Tyr Leu Ala Gly Asp Thr
                        2835                    2840                    2845

Val Thr Arg Gly Tyr Leu Asn Gln Pro Leu Leu Thr Asp Gln Arg Phe
                        2850                    2855                    2860

Ile Pro Asn Pro Phe Cys Lys Glu Glu Asp Ile Ala Met Gly Arg Phe
2865                    2870                    2875                    2880

Ala Arg Leu Tyr Lys Thr Gly Asp Leu Val Arg Ser Arg Phe Asn Arg
                        2885                    2890                    2895

Gln Gln Gln Pro Gln Leu Glu Tyr Leu Gly Arg Gly Asp Leu Gln Ile
                        2900                    2905                    2910

Lys Met Arg Gly Tyr Arg Ile Glu Ile Ser Glu Val Gln Asn Val Leu
                        2915                    2920                    2925

Thr Ser Ser Pro Gly Val Arg Glu Gly Ala Val Val Ala Lys Tyr Glu
                        2930                    2935                    2940

Asn Asn Asp Thr Tyr Ser Arg Thr Ala His Ser Leu Val Gly Tyr Tyr
2945                    2950                    2955                    2960

Thr Thr Asp Asn Glu Thr Val Ser Glu Ala Asp Ile Leu Thr Phe Met
                        2965                    2970                    2975

Lys Ala Arg Leu Pro Thr Tyr Met Val Pro Ser His Leu Cys Cys Leu
                        2980                    2985                    2990

Glu Gly Ala Leu Pro Val Thr Ile Asn Gly Lys Leu Asp Val Arg Arg
                        2995                    3000                    3005

Leu Pro Glu Ile Ile Asn Asp Ser Ala Gln Ser Ser Tyr Ser Pro Pro
3010                    3015                    3020

Arg Asn Ile Ile Glu Ala Lys Met Cys Arg Leu Trp Glu Ser Ala Leu
3025                    3030                    3035                    3040

Gly Met Glu Arg Cys Gly Ile Asp Asp Asp Leu Phe Lys Leu Gly Gly
                        3045                    3050                    3055

Asp Ser Ile Thr Ser Leu His Leu Val Ala Gln Ile His Asn Gln Val
                        3060                    3065                    3070

Gly Cys Lys Ile Thr Val Arg Asp Ile Phe Glu His Arg Thr Ala Arg
                        3075                    3080                    3085

Ala Leu His Asp His Val Phe Met Lys Asp Ser Asp Arg Ser Asn Val
                        3090                    3095                    3100

Thr Gln Phe Arg Thr Glu Gln Gly Pro Val Ile Gly Glu Ala Pro Leu
3105                    3110                    3115                    3120

```
Leu  Pro  Ile  Gln  Asp  Trp  Phe  Leu  Ser  Lys  Ala  Leu  Gln  His  Pro  Met
          3125                     3130                     3135

Tyr  Trp  Asn  His  Thr  Phe  Tyr  Val  Arg  Thr  Pro  Glu  Leu  Asp  Val  Asp
          3140                     3145                     3150

Ser  Leu  Ser  Ala  Ala  Val  Arg  Asp  Leu  Gln  Gln  Tyr  His  Asp  Val  Phe
          3155                     3160                     3165

Arg  Met  Arg  Leu  Lys  Arg  Glu  Glu  Val  Gly  Phe  Val  Gln  Ser  Phe  Ala
          3170                     3175                     3180

Glu  Asp  Phe  Ser  Pro  Ala  Gln  Leu  Arg  Val  Leu  Asn  Val  Lys  Asp  Val
3185                     3190                     3195                     3200

Asp  Gly  Ser  Ala  Ala  Val  Asn  Glu  Ile  Leu  Asp  Gly  Trp  Gln  Ser  Gly
               3205                     3210                     3215

Phe  Asn  Leu  Glu  Asn  Gly  Pro  Ile  Gly  Ser  Ile  Gly  Tyr  Leu  His  Gly
          3220                     3225                     3230

Tyr  Glu  Asp  Arg  Ser  Ala  Arg  Val  Trp  Phe  Ser  Val  His  His  Met  Ala
          3235                     3240                     3245

Ile  Asp  Thr  Val  Ser  Trp  Gln  Ile  Leu  Val  Arg  Asp  Leu  Gln  Thr  Leu
          3250                     3255                     3260

Tyr  Arg  Asn  Gly  Ser  Leu  Gly  Ser  Lys  Gly  Ser  Ser  Phe  Arg  Gln  Trp
3265                     3270                     3275                     3280

Ala  Glu  Ala  Ile  Gln  Asn  Tyr  Lys  Ala  Ser  Asp  Ser  Glu  Arg  Asn  His
          3285                     3290                     3295

Trp  Asn  Lys  Leu  Val  Met  Glu  Thr  Ala  Ser  Ser  Ile  Ser  Ala  Leu  Pro
          3300                     3305                     3310

Thr  Ser  Thr  Gly  Ser  Arg  Val  Arg  Leu  Ser  Arg  Ser  Leu  Ser  Pro  Glu
          3315                     3320                     3325

Lys  Thr  Ala  Ser  Leu  Ile  Gln  Gly  Gly  Ile  Asp  Arg  Gln  Asp  Val  Ser
          3330                     3335                     3340

Val  Tyr  Asp  Ser  Leu  Leu  Thr  Ser  Val  Gly  Leu  Ala  Leu  Gln  His  Ile
3345                     3350                     3355                     3360

Ala  Pro  Thr  Gly  Pro  Ser  Met  Val  Thr  Ile  Glu  Gly  His  Gly  Arg  Glu
               3365                     3370                     3375

Glu  Val  Asp  Gln  Thr  Leu  Asp  Val  Ser  Arg  Thr  Met  Gly  Trp  Phe  Thr
               3380                     3385                     3390

Thr  Met  Tyr  Pro  Phe  Glu  Ile  Pro  Arg  Leu  Ser  Thr  Glu  Asn  Ile  Val
          3395                     3400                     3405

Gln  Gly  Val  Val  Ala  Val  Ser  Glu  Arg  Phe  Arg  Gln  Val  Pro  Ala  Arg
          3410                     3415                     3420

Gly  Val  Gly  Tyr  Gly  Thr  Leu  Tyr  Gly  Tyr  Thr  Gln  His  Pro  Leu  Pro
3425                     3430                     3435                     3440

Gln  Val  Thr  Val  Asn  Tyr  Leu  Gly  Gln  Leu  Ala  Arg  Lys  Gln  Ser  Lys
               3445                     3450                     3455

Pro  Lys  Glu  Trp  Val  Leu  Ala  Val  Gly  Asp  Asn  Glu  Phe  Glu  Tyr  Gly
               3460                     3465                     3470

Leu  Met  Thr  Ser  Pro  Glu  Asp  Lys  Asp  Arg  Ser  Ser  Ser  Ala  Val  Asp
          3475                     3480                     3485

Val  Thr  Ala  Val  Cys  Ile  Asp  Gly  Thr  Met  Ile  Ile  Asp  Val  Asp  Ser
          3490                     3495                     3500

Ala  Trp  Ser  Leu  Glu  Glu  Ser  Glu  Gln  Phe  Ile  Ser  Ser  Ile  Glu  Glu
3505                     3510                     3515                     3520

Gly  Leu  Asn  Lys  Ile  Leu  Asp  Gly  Arg  Ala  Ser  Gln  Gln  Thr  Ser  Arg
               3525                     3530                     3535

Phe  Pro  Asp  Val  Pro  Gln  Pro  Ala  Glu  Thr  Tyr  Thr  Pro  Tyr  Phe  Glu
               3540                     3545                     3550
```

| | | | | | | | | | | | | | |
|---|---|---|---|---|---|---|---|---|---|---|---|---|---|
| Tyr | Leu | Glu | Pro<br>3555 | Pro | Arg | Gln | Gly<br>3560 | Pro | Thr | Leu | Phe<br>3565 | Leu | Leu | Pro | Pro |
| Gly | Glu | Gly<br>3570 | Gly | Ala | Glu | Ser<br>3575 | Tyr | Phe | Asn | Asn<br>3580 | Ile | Val | Lys | Arg | Leu |
| Arg<br>3585 | Gln | Thr | Asn | Met | Val<br>3590 | Val | Phe | Asn | Asn | Tyr<br>3595 | Tyr | Leu | His | Ser | Lys<br>3600 |
| Arg | Leu | Arg | Thr | Phe<br>3605 | Glu | Glu | Leu | Ala | Glu<br>3610 | Met | Tyr | Leu | Asp | Gln<br>3615 | Val |
| Arg | Gly | Ile | Gln<br>3620 | Pro | His | Gly | Pro | Tyr<br>3625 | His | Phe | Ile | Gly | Trp<br>3630 | Ser | Phe |
| Gly | Gly | Ile<br>3635 | Leu | Ala | Met | Glu | Met<br>3640 | Ser | Arg | Arg | Leu | Val<br>3645 | Ala | Ser | Asp |
| Glu | Lys<br>3650 | Ile | Gly | Phe | Leu | Gly<br>3655 | Ile | Ile | Asp | Thr | Tyr<br>3660 | Phe | Asn | Val | Arg |
| Gly | Ala | Thr | Arg | Thr | Ile | Gly | Leu | Gly | Asp | Thr | Glu | Ile | Leu | Asp | Pro |
| 3665 | | | | | 3670 | | | | | 3675 | | | | | 3680 |
| Ile | His | His | Ile | Tyr<br>3685 | Asn | Pro | Asp | Pro | Ala<br>3690 | Asn | Phe | Gln | Arg | Leu<br>3695 | Pro |
| Ser | Ala | Thr | Asp<br>3700 | Arg | Ile | Val | Leu | Phe<br>3705 | Lys | Ala | Met | Arg | Pro<br>3710 | Asn | Asn |
| Lys | Tyr | Glu<br>3715 | Ser | Glu | Asn | Gln | Arg<br>3720 | Arg | Leu | Tyr | Glu | Tyr<br>3725 | Tyr | Asp | Arg |
| Thr | Arg<br>3730 | Leu | Asn | Gly | Leu | Asp<br>3735 | Ser | Leu | Leu | Pro | Ser<br>3740 | Asp | Ser | Asp | Val |
| Gln | Leu | Val | Pro | Leu | Thr | Asp | Asp | Thr | His | Phe | Ser | Trp | Val | Gly | Asn |
| 3745 | | | | | 3750 | | | | | 3755 | | | | | 3760 |
| Pro | Gln | Gln | Val | Glu<br>3765 | Gln | Met | Cys | Ala | Thr<br>3770 | Ile | Lys | Glu | His | Leu<br>3775 | Ala |
| Arg | Tyr | | | | | | | | | | | | | | |

( 2 ) INFORMATION FOR SEQ ID NO:3:

( i ) SEQUENCE CHARACTERISTICS:
        ( A ) LENGTH: 11601 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Acremonium chrysogenum ( i x ) FEATURE:
        ( A ) NAME/KEY: CDS
        ( B ) LOCATION: 388..11526
        ( D ) OTHER INFORMATION: /function="Enzyme"
            / product= "ACV Synthetase"

( i x ) FEATURE:
        ( A ) NAME/KEY: CDS
        ( B ) LOCATION: 8050..8052
        ( D ) OTHER INFORMATION:
            / note= "NNN=GCC, AGU, AGC, UCU, UCC, UCA, or UCG;
            Xaa=Ala or Ser "

( x i ) SEQUENCE DESCRIPTION: SEQ ID NO:3:

| | | | | | |
|---|---|---|---|---|---|
| GGATGCATGC | ATTGGCCTGT | ATCAAAGGTC | CGGGATTCCC | CAGGAGTATA | AGACGTTCGT | 60 |
| GCTGGGAGAT | CTAGCGACGT | GTTGGGAAAT | ATCGGCCGTA | GAGTGCGAAA | AAGAACTGGC | 120 |
| GGAAATATTT | CTCCTTGGAC | TCGGTCACAC | TCAGTCAGTA | GTGGACTGCC | AGTCTATCAT | 180 |

-continued

| | | | | |
|---|---|---|---|---|
| ACACCTTTGA | TATCAACATG | ACTATCCTTA | CAGGTGCCGA | CGACGCCTCG  TCATACCACA | 240 |
| GGTATGTCTT | CACAGCCTCT | GGAAAGCGCA | GTTGGGAGCT | ATCTCTAACA  TTACCACATC | 300 |
| AGGCGCAATG | GAAGCTCTGA | TATCCCAAAA | GGTGCCATCC | ACCGCAACGG  CTTCGCAGCC | 360 |

```
GCAGCCCCTG ACTGCTGGAT CCGGTCC GTG GCC CTG GAA CAG TGG AAG ACT      411
                             Val Ala Leu Glu Gln Trp Lys Thr
                              1                5

ACG GTC CAG TCC GTC TCG GAG CGG TGC GAT CTG AGC GGG CTG AGC CAG    459
Thr Val Gln Ser Val Ser Glu Arg Cys Asp Leu Ser Gly Leu Ser Gln
        10              15                  20

CAT CCC ACC GAC TAC CAG CTG GCC TCT ACG GGC GTG AAG GGC GCA GGC    507
His Pro Thr Asp Tyr Gln Leu Ala Ser Thr Gly Val Lys Gly Ala Gly
 25              30                  35                      40

GGT AGC AGC ATC GAG GAG CGC AGT GCC ATC GTC TCA GAC GAG TTG TTC    555
Gly Ser Ser Ile Glu Glu Arg Ser Ala Ile Val Ser Asp Glu Leu Phe
                 45                  50                  55

TCG AGT CTG CGA GAC GTG TGC TCA CAG AGA CAG CTG GAC CCT CGG TCA    603
Ser Ser Leu Arg Asp Val Cys Ser Gln Arg Gln Leu Asp Pro Arg Ser
             60                  65                  70

CTC ATG CTG TTT TCC GTG CAC CAG ATG CTC AAG AGG TTC GGA AAC GGA    651
Leu Met Leu Phe Ser Val His Gln Met Leu Lys Arg Phe Gly Asn Gly
         75                  80                  85

TCT CAC ACC GTC GTG GCG TCA CTC GTA ACT TCA TCA GAG GGA TGC CCT    699
Ser His Thr Val Val Ala Ser Leu Val Thr Ser Ser Glu Gly Cys Pro
     90                  95                 100

TCA ACT TCG GCC TGG AGG GCC ATC CCC TCC GTC ATC CAT CAT ATA GAG    747
Ser Thr Ser Ala Trp Arg Ala Ile Pro Ser Val Ile His His Ile Glu
105                 110                 115                 120

GGC GGA GAC AAC AAC AAC ACA GTC GCC TCT GCC GTG GAA CAG GCG GCG    795
Gly Gly Asp Asn Asn Asn Thr Val Ala Ser Ala Val Glu Gln Ala Ala
                125                 130                 135

AAT CTC CTG AAC TCA GAA GGA TCG GGA CAG GAC CTT CTG ATT CCC ATC    843
Asn Leu Leu Asn Ser Glu Gly Ser Gly Gln Asp Leu Leu Ile Pro Ile
            140                 145                 150

GGA CTC ACT GAG CTC GTC AAG TCG GAG CTG ATT GAC CTC CTG GTC ATC    891
Gly Leu Thr Glu Leu Val Lys Ser Glu Leu Ile Asp Leu Leu Val Ile
        155                 160                 165

TTC GAC GAC GAG ACA AAT AAC ATA CGA CTG CCG CAG GAC TTC CCA CTT    939
Phe Asp Asp Glu Thr Asn Asn Ile Arg Leu Pro Gln Asp Phe Pro Leu
170                 175                 180

ATC CTG CGG ATA CAT CAG CGG CAA GAC CAC TGG CAG CTG TCA GTC CGG   987
Ile Leu Arg Ile His Gln Arg Gln Asp His Trp Gln Leu Ser Val Arg
185                 190                 195                 200

TAT CCC TCG CCC CTT TTC GAC ACC ATG GTC ATC GAC AGC TTT CTG AGC   1035
Tyr Pro Ser Pro Leu Phe Asp Thr Met Val Ile Asp Ser Phe Leu Ser
                205                 210                 215

GCA CTT CAC AAC CTG TTG TCC GCG GTG ACA AAA CCC TCC CAG CTC GTG   1083
Ala Leu His Asn Leu Leu Ser Ala Val Thr Lys Pro Ser Gln Leu Val
            220                 225                 230

CGC GAC ATC GAG CTG CTC CCA GAA TAC CAG GTC GCT CAG CTG GAG AAG   1131
Arg Asp Ile Glu Leu Leu Pro Glu Tyr Gln Val Ala Gln Leu Glu Lys
        235                 240                 245

TGG AAC AAC ACA GAC GGC GAC TAC CCC ACC GAG AAG CGG CTA CAT CAT   1179
Trp Asn Asn Thr Asp Gly Asp Tyr Pro Thr Glu Lys Arg Leu His His
250                 255                 260

CTG TTC GAG GAG GCA GCA GTG CGT CGT CCC CAA CAC GTT GCC CTC ATC   1227
Leu Phe Glu Glu Ala Ala Val Arg Arg Pro Gln His Val Ala Leu Ile
265                 270                 275                 280

TGC GGC GAC AAG CGC ATC ACC TAT GAG GAG TTG AAT GCT ATG GCG AAT   1275
Cys Gly Asp Lys Arg Ile Thr Tyr Glu Glu Leu Asn Ala Met Ala Asn
```

|     |     |     |     |     | 285 |     |     |     | 290 |     |     |     | 295 |     |      |
|-----|-----|-----|-----|-----|-----|-----|-----|-----|-----|-----|-----|-----|-----|-----|------|

| CGC | CTG | GCC | CAC | CAT | CTG | GTA | TCC | TCG | GGT | ATC | CAG | ACT | GAG | CAG | CTC | 1323 |
|-----|-----|-----|-----|-----|-----|-----|-----|-----|-----|-----|-----|-----|-----|-----|-----|------|
| Arg | Leu | Ala | His | His | Leu | Val | Ser | Ser | Gly | Ile | Gln | Thr | Glu | Gln | Leu |      |
|     |     |     | 300 |     |     |     |     | 305 |     |     |     | 310 |     |     |     |      |

| GTC | GGT | CTC | TTC | CTC | GAC | AAG | ACC | GAG | CTC | ATG | ATC | GCT | ACT | ATT | CTG | 1371 |
| Val | Gly | Leu | Phe | Leu | Asp | Lys | Thr | Glu | Leu | Met | Ile | Ala | Thr | Ile | Leu |      |
|     |     | 315 |     |     |     |     | 320 |     |     |     | 325 |     |     |     |     |      |

| GGC | ATC | TGG | AAA | TCT | GGT | GCC | GCG | CAT | GTA | CCT | ATC | GAC | CCT | GGG | TAC | 1419 |
| Gly | Ile | Trp | Lys | Ser | Gly | Ala | Ala | His | Val | Pro | Ile | Asp | Pro | Gly | Tyr |      |
|     | 330 |     |     |     |     | 335 |     |     |     |     | 340 |     |     |     |     |      |

| CCG | GAC | GAG | CGT | GTC | AAG | TTC | GTC | CTG | AAT | GAT | ACG | AAG | GCG | CAA | GTG | 1467 |
| Pro | Asp | Glu | Arg | Val | Lys | Phe | Val | Leu | Asn | Asp | Thr | Lys | Ala | Gln | Val |      |
| 345 |     |     |     |     | 350 |     |     |     |     | 355 |     |     |     |     | 360 |      |

| GTC | ATT | GCT | AGT | CAG | AGG | CAC | GTC | GAT | CGA | CTG | CGG | GCT | GAG | GCT | GTT | 1515 |
| Val | Ile | Ala | Ser | Gln | Arg | His | Val | Asp | Arg | Leu | Arg | Ala | Glu | Ala | Val |      |
|     |     |     |     | 365 |     |     |     |     | 370 |     |     |     |     | 375 |     |      |

| GGC | GGC | CAG | CAT | CTT | CGC | ATC | ATC | GGT | CTC | GAA | TCT | CTG | TTC | GAC | AAC | 1563 |
| Gly | Gly | Gln | His | Leu | Arg | Ile | Ile | Gly | Leu | Glu | Ser | Leu | Phe | Asp | Asn |      |
|     |     |     | 380 |     |     |     |     | 385 |     |     |     |     | 390 |     |     |      |

| CTT | GCT | CAA | CAG | ACA | CAA | CAC | TCA | CCA | GAG | ACG | TCG | GGC | AAT | TTG | ACC | 1611 |
| Leu | Ala | Gln | Gln | Thr | Gln | His | Ser | Pro | Glu | Thr | Ser | Gly | Asn | Leu | Thr |      |
|     |     |     | 395 |     |     |     |     | 400 |     |     |     |     | 405 |     |     |      |

| CAT | CTG | CCC | CTG | AAC | AGC | AAA | CAG | CTT | GCG | TAC | GTG | ACA | TAC | ACC | TCG | 1659 |
| His | Leu | Pro | Leu | Asn | Ser | Lys | Gln | Leu | Ala | Tyr | Val | Thr | Tyr | Thr | Ser |      |
|     | 410 |     |     |     |     | 415 |     |     |     |     | 420 |     |     |     |     |      |

| GGC | ACC | ACG | GGC | TTC | CCG | AAA | GGC | ATC | TAC | AAG | GAG | CAC | ACA | AGC | GTC | 1707 |
| Gly | Thr | Thr | Gly | Phe | Pro | Lys | Gly | Ile | Tyr | Lys | Glu | His | Thr | Ser | Val |      |
| 425 |     |     |     |     | 430 |     |     |     |     | 435 |     |     |     |     | 440 |      |

| GTT | AAC | AGC | ATC | ACC | GAT | CTG | TCT | GCT | CGG | TAC | GGT | GTG | GCC | GGG | GAG | 1755 |
| Val | Asn | Ser | Ile | Thr | Asp | Leu | Ser | Ala | Arg | Tyr | Gly | Val | Ala | Gly | Glu |      |
|     |     |     |     | 445 |     |     |     |     | 450 |     |     |     |     | 455 |     |      |

| GAC | GAC | GAG | GTG | ATA | CTC | GTC | TTC | TCC | GCC | TAC | GTC | TTC | GAG | CCA | TTC | 1803 |
| Asp | Asp | Glu | Val | Ile | Leu | Val | Phe | Ser | Ala | Tyr | Val | Phe | Glu | Pro | Phe |      |
|     |     |     | 460 |     |     |     |     | 465 |     |     |     |     | 470 |     |     |      |

| GTG | CGC | CAG | ATG | CTC | ATG | GCC | CTG | ACC | ACG | GGC | AAC | TCT | CTC | GCC | ATC | 1851 |
| Val | Arg | Gln | Met | Leu | Met | Ala | Leu | Thr | Thr | Gly | Asn | Ser | Leu | Ala | Ile |      |
|     |     | 475 |     |     |     |     | 480 |     |     |     |     | 485 |     |     |     |      |

| ATC | AGC | GAC | GAG | GAC | AAG | TTC | GAC | CCT | GAC | ACC | CTT | ATT | CCC | TTC | ATC | 1899 |
| Ile | Ser | Asp | Glu | Asp | Lys | Phe | Asp | Pro | Asp | Thr | Leu | Ile | Pro | Phe | Ile |      |
|     | 490 |     |     |     |     | 495 |     |     |     |     | 500 |     |     |     |     |      |

| CAA | AAA | CAC | AAA | GTC | ACT | TAC | ATC | CAC | GCC | ACC | TCG | TCA | GTG | TTG | CAG | 1947 |
| Gln | Lys | His | Lys | Val | Thr | Tyr | Ile | His | Ala | Thr | Ser | Ser | Val | Leu | Gln |      |
| 505 |     |     |     |     | 510 |     |     |     |     | 515 |     |     |     |     | 520 |      |

| GAG | TAC | GAC | TTC | GGG | TCC | TGC | CCC | TCG | TTG | AAA | CGC | ATG | ATT | CTG | GTG | 1995 |
| Glu | Tyr | Asp | Phe | Gly | Ser | Cys | Pro | Ser | Leu | Lys | Arg | Met | Ile | Leu | Val |      |
|     |     |     |     | 525 |     |     |     |     | 530 |     |     |     |     | 535 |     |      |

| GGA | GAG | AAC | TTG | ACA | GAG | CCG | CGC | TAC | GAG | GCC | CTG | AGG | CAG | CGC | TTC | 2043 |
| Gly | Glu | Asn | Leu | Thr | Glu | Pro | Arg | Tyr | Glu | Ala | Leu | Arg | Gln | Arg | Phe |      |
|     |     |     |     | 540 |     |     |     |     | 545 |     |     |     |     | 550 |     |      |

| AAG | TCG | CGC | ATC | CTG | AAT | GAA | TAT | GGC | TTC | ACC | GAG | TCT | GCG | TTT | GTG | 2091 |
| Lys | Ser | Arg | Ile | Leu | Asn | Glu | Tyr | Gly | Phe | Thr | Glu | Ser | Ala | Phe | Val |      |
|     |     | 555 |     |     |     |     | 560 |     |     |     |     | 565 |     |     |     |      |

| ACG | GCG | CTC | AAC | ATA | TTC | GAG | CCT | ACC | TCA | CAG | AGG | AAG | GAC | ATG | AGT | 2139 |
| Thr | Ala | Leu | Asn | Ile | Phe | Glu | Pro | Thr | Ser | Gln | Arg | Lys | Asp | Met | Ser |      |
|     | 570 |     |     |     |     | 575 |     |     |     |     | 580 |     |     |     |     |      |

| CTG | GGA | AGG | CCG | GTG | CGC | AAC | GTC | AAG | TGC | TAT | ATC | TTG | GAT | GCC | AAC | 2187 |
| Leu | Gly | Arg | Pro | Val | Arg | Asn | Val | Lys | Cys | Tyr | Ile | Leu | Asp | Ala | Asn |      |
| 585 |     |     |     |     | 590 |     |     |     |     | 595 |     |     |     |     | 600 |      |

| CTC | AAG | AGA | GTC | CCC | ATC | GGT | GTT | ACA | GGG | GAG | CTG | CAC | ATC | GGT | GGC | 2235 |
| Leu | Lys | Arg | Val | Pro | Ile | Gly | Val | Thr | Gly | Glu | Leu | His | Ile | Gly | Gly |      |

-continued

```
                      605                              610                              615
TTG  GGT  ATA  TCC  CGG  GGG  TAC  ATG  AAT  AGG  GAG  GAG  CTC  ACA  AGG  CAG       2283
Leu  Gly  Ile  Ser  Arg  Gly  Tyr  Met  Asn  Arg  Glu  Glu  Leu  Thr  Arg  Gln
               620                      625                      630

AAG  TTC  CTC  CCG  AAC  CCC  TAC  CAG  ACC  GAT  AAG  GAG  CGC  CAA  CGG  GGT       2331
Lys  Phe  Leu  Pro  Asn  Pro  Tyr  Gln  Thr  Asp  Lys  Glu  Arg  Gln  Arg  Gly
635                           640                                645

GTC  AAC  TCA  ACC  ATG  TAC  AAG  ACA  GGA  GAT  CTG  GCC  CGC  TGG  CTA  CCC       2379
Val  Asn  Ser  Thr  Met  Tyr  Lys  Thr  Gly  Asp  Leu  Ala  Arg  Trp  Leu  Pro
     650                           655                           660

AGT  GGC  GAA  GTC  GAG  TAT  CTC  GGC  CGT  GCC  GAC  TTC  CAG  ATC  AAG  CTG       2427
Ser  Gly  Glu  Val  Glu  Tyr  Leu  Gly  Arg  Ala  Asp  Phe  Gln  Ile  Lys  Leu
665                      670                      675                      680

CGC  GGC  ATT  CGA  ATT  GAG  CCC  GGC  GAG  ATC  GAG  TCC  ACT  CTC  GCC  ATG       2475
Arg  Gly  Ile  Arg  Ile  Glu  Pro  Gly  Glu  Ile  Glu  Ser  Thr  Leu  Ala  Met
                              685                      690                      695

TAT  CCC  GGA  ATC  AGG  GCC  AGC  ATC  GTC  GTG  TCA  AAG  AAG  CTT  CTC  AGT       2523
Tyr  Pro  Gly  Ile  Arg  Ala  Ser  Ile  Val  Val  Ser  Lys  Lys  Leu  Leu  Ser
               700                      705                      710

CAG  GGG  CAG  GAG  ACG  ATC  CAA  GAC  CAC  CTT  GTG  GGG  TAC  TAT  GTT  TGC       2571
Gln  Gly  Gln  Glu  Thr  Ile  Gln  Asp  His  Leu  Val  Gly  Tyr  Tyr  Val  Cys
          715                      720                      725

GAT  GAG  GGC  CAC  ATC  CCC  GAG  GGT  GAC  CTG  CTG  AGC  TTC  CTG  GAG  AAG       2619
Asp  Glu  Gly  His  Ile  Pro  Glu  Gly  Asp  Leu  Leu  Ser  Phe  Leu  Glu  Lys
730                      735                      740

AAG  CTA  CCT  CGG  TAC  ATG  GTC  CCG  ACG  CGC  TTG  TCA  CAA  CTG  GCT  CAG       2667
Lys  Leu  Pro  Arg  Tyr  Met  Val  Pro  Thr  Arg  Leu  Val  Gln  Leu  Ala  Gln
745                      750                      755                      760

ATT  CCA  ACC  AAT  ATC  AAC  GGC  AAG  GCG  GAT  CTG  CGT  GCT  CTT  CCT  GCC       2715
Ile  Pro  Thr  Asn  Ile  Asn  Gly  Lys  Ala  Asp  Leu  Arg  Ala  Leu  Pro  Ala
                              765                      770                      775

GTC  GAA  GTC  GCC  GTA  GCT  CCC  ACC  CAC  AAG  CAG  GAT  GGC  GAG  CGA  GGA       2763
Val  Glu  Val  Ala  Val  Ala  Pro  Thr  His  Lys  Gln  Asp  Gly  Glu  Arg  Gly
               780                      785                      790

AAC  CAG  CTG  GAG  AGC  GAC  CTG  GCT  GCC  ATA  TGG  GGC  AAC  ATT  TTG  AGT       2811
Asn  Gln  Leu  Glu  Ser  Asp  Leu  Ala  Ala  Ile  Trp  Gly  Asn  Ile  Leu  Ser
          795                      800                      805

GTT  CCC  GCT  CAA  GAC  ATT  GGG  TCT  GAA  TCC  AAC  TTC  TTC  CGC  CTG  GGT       2859
Val  Pro  Ala  Gln  Asp  Ile  Gly  Ser  Glu  Ser  Asn  Phe  Phe  Arg  Leu  Gly
810                      815                      820

GGC  CAC  AGT  ATT  GCA  TGC  ATC  CAG  CTC  ATT  GCT  CGT  GTG  CGA  CAG  CAG       2907
Gly  His  Ser  Ile  Ala  Cys  Ile  Gln  Leu  Ile  Ala  Arg  Val  Arg  Gln  Gln
825                      830                      835                      840

CTA  GGC  CAG  GGG  ATT  ACC  CTC  GAG  GAG  GTC  TTC  CAG  ACC  AAG  ACG  TTG       2955
Leu  Gly  Gln  Gly  Ile  Thr  Leu  Glu  Glu  Val  Phe  Gln  Thr  Lys  Thr  Leu
                    845                      850                      855

CGA  GCT  ATG  GCT  GCC  CTC  TTG  TCG  GAA  AAG  TAC  ACG  AAG  GCG  TCG  AAT       3003
Arg  Ala  Met  Ala  Ala  Leu  Leu  Ser  Glu  Lys  Tyr  Thr  Lys  Ala  Ser  Asn
               860                      865                      870

GGG  ACG  AAC  GGA  GTG  ACC  AAC  GGC  ACT  GCT  CAC  GTC  AAC  GGC  CAC  GCA       3051
Gly  Thr  Asn  Gly  Val  Thr  Asn  Gly  Thr  Ala  His  Val  Asn  Gly  His  Ala
          875                      880                      885

GCG  AAC  GGC  CAT  GTC  AGC  GAC  AGC  TAC  GTG  GCC  AGC  AGT  TTG  CAG  CAA       3099
Ala  Asn  Gly  His  Val  Ser  Asp  Ser  Tyr  Val  Ala  Ser  Ser  Leu  Gln  Gln
     890                      895                      900

GGC  TTT  GTT  TAC  CAT  TCA  CTC  AAG  AAC  GAA  CTG  TCC  GAG  GCG  TAC  ACC       3147
Gly  Phe  Val  Tyr  His  Ser  Leu  Lys  Asn  Glu  Leu  Ser  Glu  Ala  Tyr  Thr
905                      910                      915                      920

ATG  CAA  TCC  ATG  ATC  CAC  TAT  GGT  GTG  CCC  CTG  AAA  CGG  GAT  ATT  TAC       3195
Met  Gln  Ser  Met  Ile  His  Tyr  Gly  Val  Pro  Leu  Lys  Arg  Asp  Ile  Tyr
```

-continued

```
                        925                             930                              935
CAA  GCG  GCA  TGG  CAG  AGG  GTA  CAG  GGG  GAG  CAC  CCT  GCA  CTG  CGG  CTT      3243
Gln  Ala  Ala  Trp  Gln  Arg  Val  Gln  Gly  Glu  His  Pro  Ala  Leu  Arg  Leu
               940                       945                      950

CGG  TTC  ACA  TGG  GAG  GCC  GAA  GTG  ATG  CAG  ATC  GTG  GAC  CCG  AAA  TCT      3291
Arg  Phe  Thr  Trp  Glu  Ala  Glu  Val  Met  Gln  Ile  Val  Asp  Pro  Lys  Ser
               955                       960                      965

GAA  CTC  GAC  TGG  CGT  GTT  GTT  GAC  TGG  ACC  GAT  GTT  TCG  AGC  CGG  GAG      3339
Glu  Leu  Asp  Trp  Arg  Val  Val  Asp  Trp  Thr  Asp  Val  Ser  Ser  Arg  Glu
               970                       975                      980

AAG  CAG  CTG  GTT  GCG  CTG  GAG  CAA  CTC  CAA  ACG  GAG  GAC  CTT  GCT  AAG      3387
Lys  Gln  Leu  Val  Ala  Leu  Glu  Gln  Leu  Gln  Thr  Glu  Asp  Leu  Ala  Lys
985                       990                      995                     1000

GTC  TAC  CAT  CTC  GAT  AAG  GGG  CCC  CTT  ATG  CGA  CTA  TAC  CTC  ATC  CTG      3435
Val  Tyr  His  Leu  Asp  Lys  Gly  Pro  Leu  Met  Arg  Leu  Tyr  Leu  Ile  Leu
              1005                      1010                     1015

CTT  CCG  GAC  TCA  AAG  TAC  TCC  TGT  CTG  TTC  AGC  TGC  CAC  CAT  GCC  ATT      3483
Leu  Pro  Asp  Ser  Lys  Tyr  Ser  Cys  Leu  Phe  Ser  Cys  His  His  Ala  Ile
              1020                      1025                     1030

CTC  GAT  GGG  TGG  AGT  CTG  CCC  CTG  CTC  TTC  AAC  AAT  GTC  CAC  CAG  GCC      3531
Leu  Asp  Gly  Trp  Ser  Leu  Pro  Leu  Leu  Phe  Asn  Asn  Val  His  Gln  Ala
              1035                      1040                     1045

TAC  CTC  GAT  CTC  GTC  GAA  GGC  ACT  GCT  TCG  CCC  GTC  GAG  CAG  GAC  GCT      3579
Tyr  Leu  Asp  Leu  Val  Glu  Gly  Thr  Ala  Ser  Pro  Val  Glu  Gln  Asp  Ala
              1050                      1055                     1060

ACC  TAC  CTA  CTC  GGC  CAG  CAG  TAC  CTG  CAG  AGC  CAC  AGG  GAC  GAC  CAT      3627
Thr  Tyr  Leu  Leu  Gly  Gln  Gln  Tyr  Leu  Gln  Ser  His  Arg  Asp  Asp  His
1065                      1070                     1075                    1080

CTC  GAC  TTC  TGG  GCC  GAG  CAG  ATC  GGC  AGG  ATC  GAA  GAG  CGC  TGC  GAC      3675
Leu  Asp  Phe  Trp  Ala  Glu  Gln  Ile  Gly  Arg  Ile  Glu  Glu  Arg  Cys  Asp
              1085                      1090                     1095

ATG  AAT  GCG  CTG  CTG  AAT  GAG  GCC  AGC  CGA  TAC  AAG  GTG  CCC  CTG  GCC      3723
Met  Asn  Ala  Leu  Leu  Asn  Glu  Ala  Ser  Arg  Tyr  Lys  Val  Pro  Leu  Ala
              1100                      1105                     1110

GAC  TAT  GAC  CAA  GTC  CGC  GAG  CAG  AGG  CAG  CAG  ACC  ATC  AGT  CTG  CCC      3771
Asp  Tyr  Asp  Gln  Val  Arg  Glu  Gln  Arg  Gln  Gln  Thr  Ile  Ser  Leu  Pro
              1115                      1120                     1125

TGG  AAC  AAC  TCC  ATG  GAC  GCT  GGT  GTG  CGG  GAA  GAA  CTC  TCC  AGT  CGT      3819
Trp  Asn  Asn  Ser  Met  Asp  Ala  Gly  Val  Arg  Glu  Glu  Leu  Ser  Ser  Arg
              1130                      1135                     1140

GGC  ATC  ACC  CTT  CAT  TCC  ATT  CTA  CAG  ACG  GTC  TGG  CAC  CTG  GTC  CTC      3867
Gly  Ile  Thr  Leu  His  Ser  Ile  Leu  Gln  Thr  Val  Trp  His  Leu  Val  Leu
1145                      1150                     1155                    1160

CAC  TCT  TAT  GGA  GGA  GGC  ACC  CAC  ACG  ATC  ACC  GGC  ACC  ACC  ATC  TCC      3915
His  Ser  Tyr  Gly  Gly  Gly  Thr  His  Thr  Ile  Thr  Gly  Thr  Thr  Ile  Ser
              1165                      1170                     1175

GGC  CGT  CAC  CTG  CCC  GTC  CCC  GGA  ATT  GAG  CGC  TCT  GTT  GGT  CTC  TTC      3963
Gly  Arg  His  Leu  Pro  Val  Pro  Gly  Ile  Glu  Arg  Ser  Val  Gly  Leu  Phe
              1180                      1185                     1190

ATC  AAC  ACA  CTC  CCT  ATG  ATC  TTT  GAT  CAC  ACC  GTC  TGC  CAG  GAT  ATG      4011
Ile  Asn  Thr  Leu  Pro  Met  Ile  Phe  Asp  His  Thr  Val  Cys  Gln  Asp  Met
              1195                      1200                     1205

ACA  GCG  CTC  GAG  GCC  ATT  GAG  CAT  GTC  CAA  GGC  CAA  GTC  AAC  GCC  ATG      4059
Thr  Ala  Leu  Glu  Ala  Ile  Glu  His  Val  Gln  Gly  Gln  Val  Asn  Ala  Met
              1210                      1215                     1220

AAC  TCC  CGG  GGC  AAC  GTC  GAG  CTC  GGA  CGC  ATG  AGC  AAG  AAC  GAC  CTC      4107
Asn  Ser  Arg  Gly  Asn  Val  Glu  Leu  Gly  Arg  Met  Ser  Lys  Asn  Asp  Leu
1225                      1230                     1235                    1240

AAG  CAC  GGG  CTC  TTC  GAC  ACC  CTC  TTC  GTC  CTC  GAG  AAC  TAC  CCA  AAC      4155
Lys  His  Gly  Leu  Phe  Asp  Thr  Leu  Phe  Val  Leu  Glu  Asn  Tyr  Pro  Asn
```

```
                          1245                          1250                         1255
CTC  GAC  ACG  GAG  CAG  CGG  GAG  AAG  CAC  GAG  GAG  AAG  CTC  AAG  TTC  ACC       4203
Leu  Asp  Thr  Glu  Gln  Arg  Glu  Lys  His  Glu  Glu  Lys  Leu  Lys  Phe  Thr
               1260                     1265                     1270

ATC  AAG  GGT  GGC  ACG  GAG  AAG  CTC  AGT  TAC  CCG  CTG  GCC  GTG  ATT  GCC       4251
Ile  Lys  Gly  Gly  Thr  Glu  Lys  Leu  Ser  Tyr  Pro  Leu  Ala  Val  Ile  Ala
               1275                     1280                     1285

CAA  GAG  GAC  GGC  GAC  AGC  GGA  TGC  TCG  TTT  ACG  CTC  TGC  TAT  GCG  GGC       4299
Gln  Glu  Asp  Gly  Asp  Ser  Gly  Cys  Ser  Phe  Thr  Leu  Cys  Tyr  Ala  Gly
               1290                     1295                     1300

GAG  CTC  TTC  ACG  GAT  GAG  TCC  ATC  CAG  GCG  CTC  CTG  GAC  ACT  GTC  CGG       4347
Glu  Leu  Phe  Thr  Asp  Glu  Ser  Ile  Gln  Ala  Leu  Leu  Asp  Thr  Val  Arg
1305                     1310                     1315                     1320

GAC  ACC  CTG  AGT  GAT  ATT  CTC  GGG  AAC  ATC  CAT  GCC  CCT  ATC  CGC  AAC       4395
Asp  Thr  Leu  Ser  Asp  Ile  Leu  Gly  Asn  Ile  His  Ala  Pro  Ile  Arg  Asn
               1325                     1330                     1335

ATG  GAG  TAC  CTC  TCC  TCG  AAC  CAG  ACG  GCG  CAG  CTC  GAC  AAG  TGG  AAT       4443
Met  Glu  Tyr  Leu  Ser  Ser  Asn  Gln  Thr  Ala  Gln  Leu  Asp  Lys  Trp  Asn
               1340                     1345                     1350

GCC  ACC  GCC  TTC  GAG  TAC  CCC  AAC  ACC  ACA  CTG  CAC  GCC  ATG  TTC  GAG       4491
Ala  Thr  Ala  Phe  Glu  Tyr  Pro  Asn  Thr  Thr  Leu  His  Ala  Met  Phe  Glu
               1355                     1360                     1365

TCC  GAG  GCG  CAG  CAG  AAG  CCG  GAC  AAG  GTG  GCC  GTG  GTG  TAC  GAG  GAT       4539
Ser  Glu  Ala  Gln  Gln  Lys  Pro  Asp  Lys  Val  Ala  Val  Val  Tyr  Glu  Asp
               1370                     1375                     1380

ATC  AGG  CTG  ACC  TAC  CGC  GAG  CTC  AAC  AGC  CGT  GCC  AAT  GCC  CTG  GCG       4587
Ile  Arg  Leu  Thr  Tyr  Arg  Glu  Leu  Asn  Ser  Arg  Ala  Asn  Ala  Leu  Ala
1385                     1390                     1395                     1400

TTC  TAC  CTC  CTC  TCC  CAG  GCG  GCT  ATC  CAA  CCG  AAC  AAG  CTG  GTC  GGG       4635
Phe  Tyr  Leu  Leu  Ser  Gln  Ala  Ala  Ile  Gln  Pro  Asn  Lys  Leu  Val  Gly
               1405                     1410                     1415

CTG  ATC  ATG  GAC  AAG  AGC  GAG  CAC  ATG  ATC  ACG  AGC  ATC  CTC  GCG  GTC       4683
Leu  Ile  Met  Asp  Lys  Ser  Glu  His  Met  Ile  Thr  Ser  Ile  Leu  Ala  Val
               1420                     1425                     1430

TGG  AAA  ACG  GGT  GGA  GCC  TAC  GTC  CCG  ATC  GAC  CCT  CGA  TAC  CCT  GAC       4731
Trp  Lys  Thr  Gly  Gly  Ala  Tyr  Val  Pro  Ile  Asp  Pro  Arg  Tyr  Pro  Asp
               1435                     1440                     1445

CAG  CGT  ATC  CAG  TAT  ATC  CTG  GAG  GAT  ACG  GCG  GCT  CTC  GCA  GTC  ATC       4779
Gln  Arg  Ile  Gln  Tyr  Ile  Leu  Glu  Asp  Thr  Ala  Ala  Leu  Ala  Val  Ile
               1450                     1455                     1460

ACG  GAC  AGT  CCT  CAT  ATT  GAC  CGT  CTG  CGC  AGC  ATC  ACC  AAC  AAC  CGC       4827
Thr  Asp  Ser  Pro  His  Ile  Asp  Arg  Leu  Arg  Ser  Ile  Thr  Asn  Asn  Arg
1465                     1470                     1475                     1480

CTT  CCT  GTT  ATC  CAG  TCG  GAC  TTT  GCT  CTC  CAA  CTC  CCG  CCC  AGC  CCA       4875
Leu  Pro  Val  Ile  Gln  Ser  Asp  Phe  Ala  Leu  Gln  Leu  Pro  Pro  Ser  Pro
               1485                     1490                     1495

GTT  CAT  CCC  GTC  TCA  AAC  TGC  AAG  CCA  AGC  GAC  CTC  GCC  TAC  ATC  ATG       4923
Val  His  Pro  Val  Ser  Asn  Cys  Lys  Pro  Ser  Asp  Leu  Ala  Tyr  Ile  Met
               1500                     1505                     1510

TAC  ACA  TCC  GGC  ACC  ACT  GGC  AAC  CCC  AAG  GGT  GTC  ATG  GTG  GAG  CAC       4971
Tyr  Thr  Ser  Gly  Thr  Thr  Gly  Asn  Pro  Lys  Gly  Val  Met  Val  Glu  His
               1515                     1520                     1525

CAC  GGT  GTA  GTG  AAT  CTG  TGC  GTT  TCA  CTC  TGC  CGG  CTC  TTC  GGC  CTT       5019
His  Gly  Val  Val  Asn  Leu  Cys  Val  Ser  Leu  Cys  Arg  Leu  Phe  Gly  Leu
               1530                     1535                     1540

CGG  AAC  ACA  GAT  GAC  GAG  GTC  ATC  CTC  TCG  TTC  TCG  AAC  TAC  GTC  TTC       5067
Arg  Asn  Thr  Asp  Asp  Glu  Val  Ile  Leu  Ser  Phe  Ser  Asn  Tyr  Val  Phe
1545                     1550                     1555                     1560

GAC  CAC  TTT  GTC  GAG  CAG  ATG  ACG  GAT  GCC  CTT  CTC  AAC  GGT  CAG  ACT       5115
Asp  His  Phe  Val  Glu  Gln  Met  Thr  Asp  Ala  Leu  Leu  Asn  Gly  Gln  Thr
```

|     |     |     |     |     |     |     |     |     |     |     |     |     |     |     |     |     |
|---|---|---|---|---|---|---|---|---|---|---|---|---|---|---|---|---|
| | | | | 1565 | | | | | 1570 | | | | | 1575 | | |
| CTT | GTG | GTC | CTC | AAC | GAC | GAG | ATG | CGT | GGC | GAC | AAG | GAG | AGG | CTT | TAC | 5163 |
| Leu | Val | Val | Leu | Asn | Asp | Glu | Met | Arg | Gly | Asp | Lys | Glu | Arg | Leu | Tyr | |
| | | | 1580 | | | | 1585 | | | | | 1590 | | | | |
| AGA | TAC | ATC | GAG | ACC | AAC | CGC | GTC | ACG | TAC | CTC | TCG | GGG | ACA | CCT | TCC | 5211 |
| Arg | Tyr | Ile | Glu | Thr | Asn | Arg | Val | Thr | Tyr | Leu | Ser | Gly | Thr | Pro | Ser | |
| | | 1595 | | | | | 1600 | | | | | 1605 | | | | |
| GTC | ATC | TCC | ATG | TAC | GAG | TTC | GAC | CGG | TTC | CGC | GAC | CAC | CTG | CGG | CGC | 5259 |
| Val | Ile | Ser | Met | Tyr | Glu | Phe | Asp | Arg | Phe | Arg | Asp | His | Leu | Arg | Arg | |
| | | 1610 | | | | | 1615 | | | | | 1620 | | | | |
| GTG | GAT | TGC | GTC | GGC | GAG | GCC | TTC | AGC | GAG | CCG | GTA | TTC | GAC | AAG | ATC | 5307 |
| Val | Asp | Cys | Val | Gly | Glu | Ala | Phe | Ser | Glu | Pro | Val | Phe | Asp | Lys | Ile | |
| 1625 | | | | | 1630 | | | | | 1635 | | | | | 1640 | |
| CGC | GAG | ACG | TTC | CCG | GGT | CTC | ATC | ATC | AAC | GGT | TAT | GGC | CCG | ACT | GAG | 5355 |
| Arg | Glu | Thr | Phe | Pro | Gly | Leu | Ile | Ile | Asn | Gly | Tyr | Gly | Pro | Thr | Glu | |
| | | | | 1645 | | | | | 1650 | | | | | 1655 | | |
| GTG | TCT | ATC | ACT | ACC | CAC | AAG | CGG | CCC | TAC | CCG | TTC | CCG | GAG | CGC | CGC | 5403 |
| Val | Ser | Ile | Thr | Thr | His | Lys | Arg | Pro | Tyr | Pro | Phe | Pro | Glu | Arg | Arg | |
| | | | 1660 | | | | | 1665 | | | | | 1670 | | | |
| ACA | GAC | AAG | AGC | ATC | GGT | TGC | CAG | CTG | GAC | AAC | AGC | ACG | AGC | TAC | GTC | 5451 |
| Thr | Asp | Lys | Ser | Ile | Gly | Cys | Gln | Leu | Asp | Asn | Ser | Thr | Ser | Tyr | Val | |
| | | 1675 | | | | | 1680 | | | | | 1685 | | | | |
| CTC | AAC | GAT | GAC | ATG | AAG | CGC | GTG | CCC | ATC | GGG | GCC | GTG | GGA | GAG | CTG | 5499 |
| Leu | Asn | Asp | Asp | Met | Lys | Arg | Val | Pro | Ile | Gly | Ala | Val | Gly | Glu | Leu | |
| | 1690 | | | | | 1695 | | | | | 1700 | | | | | |
| TAC | CTT | GGT | GGC | GAT | GGC | GTC | GCT | CGC | GGA | TAC | CAC | AAC | CGG | CCA | GAC | 5547 |
| Tyr | Leu | Gly | Gly | Asp | Gly | Val | Ala | Arg | Gly | Tyr | His | Asn | Arg | Pro | Asp | |
| 1705 | | | | | 1710 | | | | | 1715 | | | | | 1720 | |
| CTG | ACG | GCT | GAC | CGG | TTC | CCT | GCC | AAC | CCC | TTC | CAG | ACG | GAG | CAG | GAG | 5595 |
| Leu | Thr | Ala | Asp | Arg | Phe | Pro | Ala | Asn | Pro | Phe | Gln | Thr | Glu | Gln | Glu | |
| | | | | 1725 | | | | | 1730 | | | | | 1735 | | |
| AGA | CTT | GAG | GGC | CGA | AAT | GCG | CGT | CTG | TAT | AAG | ACT | GGT | GAC | TTG | GTT | 5643 |
| Arg | Leu | Glu | Gly | Arg | Asn | Ala | Arg | Leu | Tyr | Lys | Thr | Gly | Asp | Leu | Val | |
| | | | 1740 | | | | | 1745 | | | | | 1750 | | | |
| CGC | TGG | ATC | CAC | AAT | GCA | AAC | GGC | GAT | GGT | GAG | ATC | GAG | TAC | CTC | GGC | 5691 |
| Arg | Trp | Ile | His | Asn | Ala | Asn | Gly | Asp | Gly | Glu | Ile | Glu | Tyr | Leu | Gly | |
| | | | 1755 | | | | | 1760 | | | | | 1765 | | | |
| CGC | AAC | GAC | TTC | CAG | GTC | AAG | ATT | CGA | GGC | CAG | AGA | ATC | GAG | CTG | GGA | 5739 |
| Arg | Asn | Asp | Phe | Gln | Val | Lys | Ile | Arg | Gly | Gln | Arg | Ile | Glu | Leu | Gly | |
| | 1770 | | | | | 1775 | | | | | 1780 | | | | | |
| GAG | ATC | GAG | GCC | GTG | CTT | TCA | TCC | TAT | CCG | GGC | ATC | AAA | CAA | TCC | GTC | 5787 |
| Glu | Ile | Glu | Ala | Val | Leu | Ser | Ser | Tyr | Pro | Gly | Ile | Lys | Gln | Ser | Val | |
| 1785 | | | | | 1790 | | | | | 1795 | | | | | 1800 | |
| GTC | CTG | GCC | AAG | GAC | CGC | AAG | AAT | GAC | GGG | CAG | AAG | TAC | CTC | GTC | GGC | 5835 |
| Val | Leu | Ala | Lys | Asp | Arg | Lys | Asn | Asp | Gly | Gln | Lys | Tyr | Leu | Val | Gly | |
| | | | | 1805 | | | | | 1810 | | | | | 1815 | | |
| TAC | TTC | GTC | TCC | TCA | GCA | GGG | TCC | CTG | TCC | GCC | CAG | GCC | ATC | CGC | CGC | 5883 |
| Tyr | Phe | Val | Ser | Ser | Ala | Gly | Ser | Leu | Ser | Ala | Gln | Ala | Ile | Arg | Arg | |
| | | | 1820 | | | | | 1825 | | | | | 1830 | | | |
| TTC | ATG | CTC | ACG | AGC | CTG | CCC | GAT | TAC | ATG | GTT | CCT | GCG | CAG | CTG | GTG | 5931 |
| Phe | Met | Leu | Thr | Ser | Leu | Pro | Asp | Tyr | Met | Val | Pro | Ala | Gln | Leu | Val | |
| | | | 1835 | | | | | 1840 | | | | | 1845 | | | |
| CCC | ATC | GCC | AAG | TTC | CCC | GTC | ACC | GTG | AGC | GGG | AAG | CTC | GAT | GCC | AAG | 5979 |
| Pro | Ile | Ala | Lys | Phe | Pro | Val | Thr | Val | Ser | Gly | Lys | Leu | Asp | Ala | Lys | |
| | 1850 | | | | | 1855 | | | | | 1860 | | | | | |
| GCC | TTG | CCC | GTG | CCA | GAC | GAT | ACA | GTC | GAG | GAT | GAC | ATT | GTG | CCA | CCG | 6027 |
| Ala | Leu | Pro | Val | Pro | Asp | Asp | Thr | Val | Glu | Asp | Asp | Ile | Val | Pro | Pro | |
| 1865 | | | | | 1870 | | | | | 1875 | | | | | 1880 | |
| CGT | ACC | GAG | GTT | GAG | CGC | ATC | CTA | GCT | GGG | ATC | TGG | TCT | GAG | CTG | TTG | 6075 |
| Arg | Thr | Glu | Val | Glu | Arg | Ile | Leu | Ala | Gly | Ile | Trp | Ser | Glu | Leu | Leu | |

```
                        1885                         1890                          1895

GAG  ATA  CCG  GTC  GAC  AGG  ATC  AGC  ATC  TAC  AGT  GAC  TTC  TTC  AGT  CTG       6123
Glu  Ile  Pro  Val  Asp  Arg  Ile  Ser  Ile  Tyr  Ser  Asp  Phe  Phe  Ser  Leu
          1900                    1905                    1910

GGC  GGC  GAC  AGT  CTC  AAG  AGT  ACC  AAG  CTG  TCC  TTT  GCT  GCC  ACT  CGG       6171
Gly  Gly  Asp  Ser  Leu  Lys  Ser  Thr  Lys  Leu  Ser  Phe  Ala  Ala  Thr  Arg
          1915                    1920                    1925

GCT  CTC  GGT  GTG  GCC  GTC  AGT  GTC  CGC  AAC  TTG  TTC  AGC  CAT  CCG  ACT       6219
Ala  Leu  Gly  Val  Ala  Val  Ser  Val  Arg  Asn  Leu  Phe  Ser  His  Pro  Thr
          1930                    1935                    1940

ATC  GAA  GCC  TTG  TCT  CAG  TGG  ATT  ATC  AGG  GGT  TCG  AAC  GAG  GTC  AAG       6267
Ile  Glu  Ala  Leu  Ser  Gln  Trp  Ile  Ile  Arg  Gly  Ser  Asn  Glu  Val  Lys
1945                    1950                    1955                    1960

GAT  GTG  GCT  GTG  GTG  AAG  GGC  GGT  GCC  AGT  CTT  GAT  ATC  CCC  CTA  TCC       6315
Asp  Val  Ala  Val  Val  Lys  Gly  Gly  Ala  Ser  Leu  Asp  Ile  Pro  Leu  Ser
               1965                    1970                    1975

CCT  GCC  CAG  GAA  AGA  CTC  ATG  TTC  ATC  CAC  GAG  TTC  GGC  CAT  AGC  GGC       6363
Pro  Ala  Gln  Glu  Arg  Leu  Met  Phe  Ile  His  Glu  Phe  Gly  His  Ser  Gly
               1980                    1985                    1990

GAG  GAT  ACT  GGT  GCT  TAC  AAT  GTG  CCT  TTG  CAG  CTG  CAG  CTT  CAC  CAT       6411
Glu  Asp  Thr  Gly  Ala  Tyr  Asn  Val  Pro  Leu  Gln  Leu  Gln  Leu  His  His
          1995                    2000                    2005

GAT  GTC  TGT  CTC  GAG  TCG  CTT  GAG  AAG  GCT  CTG  CGG  GAT  GTC  GTC  TCG       6459
Asp  Val  Cys  Leu  Glu  Ser  Leu  Glu  Lys  Ala  Leu  Arg  Asp  Val  Val  Ser
     2010                    2015                    2020

AGA  CAC  GAG  GCT  CTC  CGG  ACC  TTG  ATC  ACC  AGG  ACC  CAG  AAG  TCC  TCC       6507
Arg  His  Glu  Ala  Leu  Arg  Thr  Leu  Ile  Thr  Arg  Thr  Gln  Lys  Ser  Ser
2025                    2030                    2035                    2040

GTG  CAC  TGC  CAG  AAG  ATC  CTC  GAC  GCC  GAA  GAA  GCG  CAA  AAG  CTC  TTC       6555
Val  His  Cys  Gln  Lys  Ile  Leu  Asp  Ala  Glu  Glu  Ala  Gln  Lys  Leu  Phe
                    2045                    2050                    2055

TCT  GTT  GAT  GTT  CTG  CGC  CTG  ACC  TCG  GAG  ACG  GAG  ATG  CAG  GGC  AGG       6603
Ser  Val  Asp  Val  Leu  Arg  Leu  Thr  Ser  Glu  Thr  Glu  Met  Gln  Gly  Arg
               2060                    2065                    2070

ATG  GCC  GAG  AGT  ACC  GCC  CAC  GCC  TTC  AAG  CTC  GAC  GAG  GAA  CTC  CCG       6651
Met  Ala  Glu  Ser  Thr  Ala  His  Ala  Phe  Lys  Leu  Asp  Glu  Glu  Leu  Pro
          2075                    2080                    2085

ATT  CAT  GTA  CGC  CTG  TAC  CAG  GTT  GTA  CGT  GAT  GGC  CGC  ACG  CTC  AGC       6699
Ile  His  Val  Arg  Leu  Tyr  Gln  Val  Val  Arg  Asp  Gly  Arg  Thr  Leu  Ser
2090                    2095                    2100

TTT  GCC  AGC  ATC  GTC  TGC  CAC  CAT  CTG  GCG  TTT  GAC  GCG  TGG  TCA  TGG       6747
Phe  Ala  Ser  Ile  Val  Cys  His  His  Leu  Ala  Phe  Asp  Ala  Trp  Ser  Trp
2105                    2110                    2115                    2120

GAT  GTG  TTC  CAG  AGG  GAC  TTG  GAC  GCC  TTC  TAT  GCC  GTC  CAT  ACG  AAG       6795
Asp  Val  Phe  Gln  Arg  Asp  Leu  Asp  Ala  Phe  Tyr  Ala  Val  His  Thr  Lys
               2125                    2130                    2135

CAC  AAG  GCT  GCC  GCC  AAC  CTG  CCA  ACC  CTC  CGC  GTG  CAA  TAT  AAG  GAG       6843
His  Lys  Ala  Ala  Ala  Asn  Leu  Pro  Thr  Leu  Arg  Val  Gln  Tyr  Lys  Glu
               2140                    2145                    2150

TAT  GCG  ATA  GAG  CAC  CGC  CGG  GCT  CTC  CGC  GCT  GAG  CAA  CAC  CGT  GTT       6891
Tyr  Ala  Ile  Glu  His  Arg  Arg  Ala  Leu  Arg  Ala  Glu  Gln  His  Arg  Val
          2155                    2160                    2165

CTC  GCG  GAC  TAC  TGG  CTG  CGC  AAG  CTC  AGT  GAC  ATG  GAG  GCG  TCT  TAT       6939
Leu  Ala  Asp  Tyr  Trp  Leu  Arg  Lys  Leu  Ser  Asp  Met  Glu  Ala  Ser  Tyr
2170                    2175                    2180

CTG  GTC  CCC  GAT  CGC  CCT  CGA  CCG  GCG  CAG  TTT  GAC  TAT  ACC  GGG  AAC       6987
Leu  Val  Pro  Asp  Arg  Pro  Arg  Pro  Ala  Gln  Phe  Asp  Tyr  Thr  Gly  Asn
          2185                    2190                    2195                2200

GAT  CTC  CAG  TTC  TCA  ACT  ACT  CCC  GAG  ACC  ACC  GCG  CAG  TTG  AAG  GAG       7035
Asp  Leu  Gln  Phe  Ser  Thr  Thr  Pro  Glu  Thr  Thr  Ala  Gln  Leu  Lys  Glu
```

-continued

|  |  |  |  |  |  |  |  |  |  |  |  |  |  |  |  |
|--|--|--|--|--|--|--|--|--|--|--|--|--|--|--|--|
|  |  |  |  | 2205 |  |  |  |  | 2210 |  |  |  |  | 2215 |  |

```
CTG  GCC  AAG  CGC  GAG  GGT  TCA  AGC  CTC  TAC  ACC  GTT  GTG  GCG  GCG  GCG       7083
Leu  Ala  Lys  Arg  Glu  Gly  Ser  Ser  Leu  Tyr  Thr  Val  Val  Ala  Ala  Ala
               2220                    2225                    2230

TAC  TTT  CTG  CTT  CTC  TAC  GTG  TAC  ACC  AAC  CAG  CGG  GAT  ATC  ACG  ATT       7131
Tyr  Phe  Leu  Leu  Leu  Tyr  Val  Tyr  Thr  Asn  Gln  Arg  Asp  Ile  Thr  Ile
          2235                    2240                    2245

GGT  ATT  CCC  GTT  GCG  CAC  CGT  AAC  CAT  CCG  GAC  TTT  GAG  TCG  GTT  GTC       7179
Gly  Ile  Pro  Val  Ala  His  Arg  Asn  His  Pro  Asp  Phe  Glu  Ser  Val  Val
2250                    2255                    2260

GGC  TTC  TTT  GTC  AAC  TTG  CTC  CCT  CTG  CGG  GTC  AAC  GTG  TCT  CAG  TCG       7227
Gly  Phe  Phe  Val  Asn  Leu  Leu  Pro  Leu  Arg  Val  Asn  Val  Ser  Gln  Ser
2265                    2270                    2275                    2280

GAC  ATT  CAT  GGA  CTT  ATC  CAG  GCA  GTG  CAG  AAA  GAG  CTT  GTC  GAT  GCC       7275
Asp  Ile  His  Gly  Leu  Ile  Gln  Ala  Val  Gln  Lys  Glu  Leu  Val  Asp  Ala
               2285                    2290                    2295

CAG  ATC  CAT  CAG  GAC  TTG  CCA  TTC  CAG  GAG  ATC  ACC  AAG  CTT  CTT  CAT       7323
Gln  Ile  His  Gln  Asp  Leu  Pro  Phe  Gln  Glu  Ile  Thr  Lys  Leu  Leu  His
          2300                    2305                    2310

GTG  CAG  CAC  GAT  CCA  AGC  CGC  CAT  CCC  CTT  CTC  CAG  GCC  GTG  TTC  AAC       7371
Val  Gln  His  Asp  Pro  Ser  Arg  His  Pro  Leu  Leu  Gln  Ala  Val  Phe  Asn
     2315                    2320                    2325

TGG  GAA  AAC  GTA  CCC  GCC  AAT  GTC  CAC  GAG  GAG  CAG  CTG  CTT  CAG  GAG       7419
Trp  Glu  Asn  Val  Pro  Ala  Asn  Val  His  Glu  Glu  Gln  Leu  Leu  Gln  Glu
2330                    2335                    2340

TAC  AAG  CCG  CCC  TCG  CCT  CTG  CCT  TCG  GCG  GCC  AAG  TTT  GAT  CTC  AAC       7467
Tyr  Lys  Pro  Pro  Ser  Pro  Leu  Pro  Ser  Ala  Ala  Lys  Phe  Asp  Leu  Asn
2345                    2350                    2355                    2360

GTC  ACG  GTG  AAA  GAG  AGC  GTC  AAT  TCG  CTC  AAC  GTC  AAC  TTC  AAC  TAT       7515
Val  Thr  Val  Lys  Glu  Ser  Val  Asn  Ser  Leu  Asn  Val  Asn  Phe  Asn  Tyr
               2365                    2370                    2375

CCT  ACC  AGC  CTC  TTC  GAG  GAG  GAG  ACC  GTT  CAG  GGG  TTC  ATG  GAA  ACC       7563
Pro  Thr  Ser  Leu  Phe  Glu  Glu  Glu  Thr  Val  Gln  Gly  Phe  Met  Glu  Thr
          2380                    2385                    2390

TTC  CAT  CTC  CTT  CTT  CGA  CAA  CTG  GCC  CAC  AAC  AAG  GCT  AGC  ACA  AGC       7611
Phe  His  Leu  Leu  Leu  Arg  Gln  Leu  Ala  His  Asn  Lys  Ala  Ser  Thr  Ser
     2395                    2400                    2405

CTC  TCG  AAG  CTG  TCG  GTT  GAA  GAT  GGA  GTG  TTG  AAT  CCA  GAG  CCG  ACT       7659
Leu  Ser  Lys  Leu  Ser  Val  Glu  Asp  Gly  Val  Leu  Asn  Pro  Glu  Pro  Thr
2410                    2415                    2420

AAC  CTT  CAG  CCC  TCA  AGC  CGG  GAC  AGC  GGA  AAT  TCA  CTC  CAT  GGG  CTC       7707
Asn  Leu  Gln  Pro  Ser  Ser  Arg  Asp  Ser  Gly  Asn  Ser  Leu  His  Gly  Leu
2425                    2430                    2435                    2440

TTC  GAG  GAC  ATC  GTG  GCC  TCG  ACC  CCG  GAC  CGC  ATC  GCA  ATT  GCT  GAC       7755
Phe  Glu  Asp  Ile  Val  Ala  Ser  Thr  Pro  Asp  Arg  Ile  Ala  Ile  Ala  Asp
               2445                    2450                    2455

GGC  ACC  AGG  AGT  CTC  TCG  TAC  TCC  GAA  CTC  AAC  GAG  CGG  GCA  AAC  CAG       7803
Gly  Thr  Arg  Ser  Leu  Ser  Tyr  Ser  Glu  Leu  Asn  Glu  Arg  Ala  Asn  Gln
          2460                    2465                    2470

CTC  GTA  CAT  TTG  ATC  ATC  TCT  TCT  GCC  AGT  ATT  GTA  GCA  GAC  GAC  CGC       7851
Leu  Val  His  Leu  Ile  Ile  Ser  Ser  Ala  Ser  Ile  Val  Ala  Asp  Asp  Arg
     2475                    2480                    2485

ATC  GCT  CTT  CTT  TTG  GAC  AAG  AGC  ATC  GAT  ATG  GTG  ATT  GCT  CTC  CTG       7899
Ile  Ala  Leu  Leu  Leu  Asp  Lys  Ser  Ile  Asp  Met  Val  Ile  Ala  Leu  Leu
2490                    2495                    2500

GCA  GTT  TGG  AAG  GCC  GGT  GCC  GCA  TAT  GTG  CCC  CTT  GAC  CCG  ACA  TAT       7947
Ala  Val  Trp  Lys  Ala  Gly  Ala  Ala  Tyr  Val  Pro  Leu  Asp  Pro  Thr  Tyr
2505                    2510                    2515                    2520

CCG  TCG  CAG  AGG  ACT  GAG  CTC  ATC  TTG  GAG  GAA  TCT  AGT  GCC  AGG  ACG       7995
Pro  Ser  Gln  Arg  Thr  Glu  Leu  Ile  Leu  Glu  Glu  Ser  Ser  Ala  Arg  Thr
```

```
                         2525                         2530                         2535
CTC  ATC  ACC  ACT  AGA  AAG  CAC  ACG  CCG  AGG  GGA  GGA  ACA  GTC  GCA  AAT           8043
Leu  Ile  Thr  Thr  Arg  Lys  His  Thr  Pro  Arg  Gly  Gly  Thr  Val  Ala  Asn
               2540                    2545                         2550

GTT  CCA  NNN  GTG  GTC  CTT  GAC  AGC  CCC  GAG  ACC  CTA  GCC  TGC  CTC  AAC           8091
Val  Pro  Xaa  Val  Val  Leu  Asp  Ser  Pro  Glu  Thr  Leu  Ala  Cys  Leu  Asn
          2555                         2560                         2565

CAG  CAG  TCA  AAG  GAA  AAC  CCG  ACA  ACG  TCA  ACG  CAG  AAA  CCG  TCC  GAC           8139
Gln  Gln  Ser  Lys  Glu  Asn  Pro  Thr  Thr  Ser  Thr  Gln  Lys  Pro  Ser  Asp
          2570                         2575                    2580

CTC  GCA  TAT  GTC  ATC  TTC  ACC  TCG  GGA  ACC  ACA  GGC  AAG  CCC  AAG  GGG           8187
Leu  Ala  Tyr  Val  Ile  Phe  Thr  Ser  Gly  Thr  Thr  Gly  Lys  Pro  Lys  Gly
2585                         2590                    2595                    2600

GTT  CTG  GTG  GAG  CAC  CAG  AGC  GTA  GTC  CAG  CTG  CGC  AAT  TCC  CTC  ATC           8235
Val  Leu  Val  Glu  His  Gln  Ser  Val  Val  Gln  Leu  Arg  Asn  Ser  Leu  Ile
                         2605                         2610                    2615

GAG  CGA  TAC  TTC  GGC  GAG  ACC  AAC  GGG  TCT  CAC  GCC  GTG  CTC  TTC  CTG           8283
Glu  Arg  Tyr  Phe  Gly  Glu  Thr  Asn  Gly  Ser  His  Ala  Val  Leu  Phe  Leu
               2620                         2625                    2630

TCC  AAC  TAC  GTC  TTC  GAC  TTC  TCT  CTT  GAA  CAG  CTC  TGT  CTC  TCA  GTC           8331
Ser  Asn  Tyr  Val  Phe  Asp  Phe  Ser  Leu  Glu  Gln  Leu  Cys  Leu  Ser  Val
               2635                    2640                         2645

TTG  GGT  GGA  AAC  AAG  CTC  ATC  ATT  CCA  CCA  GAG  GAG  GGT  CTC  ACG  CAC           8379
Leu  Gly  Gly  Asn  Lys  Leu  Ile  Ile  Pro  Pro  Glu  Glu  Gly  Leu  Thr  His
     2650                         2655                         2660

GAG  GCA  TTC  TAC  GAC  ATC  GGC  CGC  AGG  GAG  AAG  CTA  TCC  TAT  CTC  AGC           8427
Glu  Ala  Phe  Tyr  Asp  Ile  Gly  Arg  Arg  Glu  Lys  Leu  Ser  Tyr  Leu  Ser
2665                         2670                    2675                    2680

GGG  ACG  CCC  TCG  GTG  CTG  CAG  CAG  ATT  GAG  CTC  TCC  CGT  CTG  CCG  CAT           8475
Gly  Thr  Pro  Ser  Val  Leu  Gln  Gln  Ile  Glu  Leu  Ser  Arg  Leu  Pro  His
                    2685                         2690                    2695

CTT  CAC  ATG  GTC  ACC  GCT  GCG  GGC  GAG  GAG  TTC  CAC  GCT  AGT  CAG  TTT           8523
Leu  His  Met  Val  Thr  Ala  Ala  Gly  Glu  Glu  Phe  His  Ala  Ser  Gln  Phe
               2700                         2705                    2710

GAG  AAG  ATG  CGC  TCC  CAG  TTC  GCG  GGC  CAG  ATC  AAC  AAC  GCC  TAT  GGT           8571
Glu  Lys  Met  Arg  Ser  Gln  Phe  Ala  Gly  Gln  Ile  Asn  Asn  Ala  Tyr  Gly
               2715                    2720                    2725

ATC  ACT  GAG  ACG  ACC  GTG  TAC  AAC  ATC  ATC  ACC  ACG  TTC  AAG  GGC  GAT           8619
Ile  Thr  Glu  Thr  Thr  Val  Tyr  Asn  Ile  Ile  Thr  Thr  Phe  Lys  Gly  Asp
     2730                    2735                         2740

GCC  CCC  TTT  ACC  AAG  GCA  CTC  TGC  CAC  GGG  ATC  CCC  GGA  AGT  CAC  GTC           8667
Ala  Pro  Phe  Thr  Lys  Ala  Leu  Cys  His  Gly  Ile  Pro  Gly  Ser  His  Val
2745                         2750                    2755                    2760

TAC  GTC  CTG  AAC  GAC  CGA  CTT  CAG  CGT  GTT  CCT  TTC  AAC  GCT  GTT  GGC           8715
Tyr  Val  Leu  Asn  Asp  Arg  Leu  Gln  Arg  Val  Pro  Phe  Asn  Ala  Val  Gly
                    2765                         2770                    2775

GAG  CTC  TAC  TTG  GGC  GGT  GAC  TGC  CTT  GCT  CGC  GGG  TAC  CTC  AAC  CAG           8763
Glu  Leu  Tyr  Leu  Gly  Gly  Asp  Cys  Leu  Ala  Arg  Gly  Tyr  Leu  Asn  Gln
               2780                    2785                         2790

GAT  GCC  CTG  ACC  AAC  GAG  CGA  TTC  ATC  CCC  AAC  CCT  TTC  TAC  GAG  CCG           8811
Asp  Ala  Leu  Thr  Asn  Glu  Arg  Phe  Ile  Pro  Asn  Pro  Phe  Tyr  Glu  Pro
               2795                    2800                         2805

AAA  CAG  GCA  AGT  GAC  AGT  CGT  CCC  CAG  AGA  CTC  TAC  AAG  ACT  GGA  GAT           8859
Lys  Gln  Ala  Ser  Asp  Ser  Arg  Pro  Gln  Arg  Leu  Tyr  Lys  Thr  Gly  Asp
     2810                         2815                         2820

CTG  GTG  CGC  TTC  CGT  GGA  CCC  CAC  CAT  CTC  GAG  TAT  CTC  GGC  CGC  AAG           8907
Leu  Val  Arg  Phe  Arg  Gly  Pro  His  His  Leu  Glu  Tyr  Leu  Gly  Arg  Lys
2825                         2830                         2835                    2840

GAC  CAG  CAG  GTC  AAG  CTG  AGG  GGC  TTC  CGC  ATC  GAG  CTC  TCC  GAG  GTG           8955
Asp  Gln  Gln  Val  Lys  Leu  Arg  Gly  Phe  Arg  Ile  Glu  Leu  Ser  Glu  Val
```

|  |  |
|---|---|
| 2845 2850 2855 | |
| CGG GAT GCC GTC CTA GCC ATC TCT GCT GTT AAG GAG GCT GCC GTC ATC<br>Arg Asp Ala Val Leu Ala Ile Ser Ala Val Lys Glu Ala Ala Val Ile<br>2860 2865 2870 | 9003 |
| CCC AAG TAT GAC GAG GAT GGC TCC GAT TCA CGA AGG GTC AGC GCC ATC<br>Pro Lys Tyr Asp Glu Asp Gly Ser Asp Ser Arg Arg Val Ser Ala Ile<br>2875 2880 2885 | 9051 |
| GTC TGC TAC TAC ACG CTC AAC GCC GGA ACT GTG TGC GAA GCA TCG AGT<br>Val Cys Tyr Tyr Thr Leu Asn Ala Gly Thr Val Cys Glu Ala Ser Ser<br>2890 2895 2900 | 9099 |
| ATC CGT GAC CAC CTG CAC GCC AAC CTT CCC CCG TAC ATG GTC CCA AGT<br>Ile Arg Asp His Leu His Ala Asn Leu Pro Pro Tyr Met Val Pro Ser<br>2905 2910 2915 2920 | 9147 |
| CAG ATC CAC CAG TTG GAG GGA TCT CTC CCC GTG ACC GTC AAT GGG AAG<br>Gln Ile His Gln Leu Glu Gly Ser Leu Pro Val Thr Val Asn Gly Lys<br>2925 2930 2935 | 9195 |
| CTC GAC CTG AAC AGG CTC TCC ACA ACT CAA GTC TCG CAG CCA GAG CTT<br>Leu Asp Leu Asn Arg Leu Ser Thr Thr Gln Val Ser Gln Pro Glu Leu<br>2940 2945 2950 | 9243 |
| TAC ACC GCT CCA CGA AAT TCG ACA GAG GAA ACC TTG TGC CAG CTT TGG<br>Tyr Thr Ala Pro Arg Asn Ser Thr Glu Glu Thr Leu Cys Gln Leu Trp<br>2955 2960 2965 | 9291 |
| GCA TCT CTC CTA GGC GTC GAC CAC TGC GGC ATT GAC GAC GAC CTG TTT<br>Ala Ser Leu Leu Gly Val Asp His Cys Gly Ile Asp Asp Asp Leu Phe<br>2970 2975 2980 | 9339 |
| GCC CGA GGC GGC GAC AGC ATC TCC TCT CTC CGA CTA GTG GGT GAC ATC<br>Ala Arg Gly Gly Asp Ser Ile Ser Ser Leu Arg Leu Val Gly Asp Ile<br>2985 2990 2995 3000 | 9387 |
| TAC CGC GCG CTA GGA CGC AAG GTC ACC GTC AAG GAC ATC TAC CTC CAC<br>Tyr Arg Ala Leu Gly Arg Lys Val Thr Val Lys Asp Ile Tyr Leu His<br>3005 3010 3015 | 9435 |
| CGC AGC GTC CGA GCC CTA AGC GAA AAT GTC CTG ACC GAC CAG AAG GAT<br>Arg Ser Val Arg Ala Leu Ser Glu Asn Val Leu Thr Asp Gln Lys Asp<br>3020 3025 3030 | 9483 |
| AAG GGT ACT CTG CCA GCG TCT CCT CCC CTC CAG CGA GCG GAG CAG GGC<br>Lys Gly Thr Leu Pro Ala Ser Pro Pro Leu Gln Arg Ala Glu Gln Gly<br>3035 3040 3045 | 9531 |
| CAG GTT GAG GGC GAC GCA CCG CTT CTC CCC ATC CAG GAC TGG TTC CTT<br>Gln Val Glu Gly Asp Ala Pro Leu Leu Pro Ile Gln Asp Trp Phe Leu<br>3050 3055 3060 | 9579 |
| TCC AAG CCC CTG GAT AAC CCC GCT TAC TGG AAC CAC TGC TTC ACC ATT<br>Ser Lys Pro Leu Asp Asn Pro Ala Tyr Trp Asn His Cys Phe Thr Ile<br>3065 3070 3075 3080 | 9627 |
| CGA ACC GGG GCA CTC TCC GTC GAA GGG CTC CGG GGT GCT CTG AAG CTG<br>Arg Thr Gly Ala Leu Ser Val Glu Gly Leu Arg Gly Ala Leu Lys Leu<br>3085 3090 3095 | 9675 |
| CTG CAG GAG CGC CAC GAC GTG CTG CGT CTG AGA CTG CAA CGC CGG GAC<br>Leu Gln Glu Arg His Asp Val Leu Arg Leu Arg Leu Gln Arg Arg Asp<br>3100 3105 3110 | 9723 |
| GAA GGT CGC CAT GTT CAG ACC TTT GCG CGT GAC TGC GCG CAA CCT CGC<br>Glu Gly Arg His Val Gln Thr Phe Ala Arg Asp Cys Ala Gln Pro Arg<br>3115 3120 3125 | 9771 |
| TTG ACT GTG CTA GAC CGA CGA AGC TTC GAG GAC GCA GAG GAT GTA CAG<br>Leu Thr Val Leu Asp Arg Arg Ser Phe Glu Asp Ala Glu Asp Val Gln<br>3130 3135 3140 | 9819 |
| GAG GCT CTC TGC GAG ATC CAA TCT CAT TTC GAC CTC GAG AAT GGA CCC<br>Glu Ala Leu Cys Glu Ile Gln Ser His Phe Asp Leu Glu Asn Gly Pro<br>3145 3150 3155 3160 | 9867 |
| CTC TAC ACA GTG GCG TAC ATC CAC GGT TAC GAG GAC GGC TCC GCC CGA<br>Leu Tyr Thr Val Ala Tyr Ile His Gly Tyr Glu Asp Gly Ser Ala Arg | 9915 |

```
                          3165                          3170                         3175
GTG  TGG  TTT  GCC  TGC  CAT  CAC  GTC  ATG  GTC  GAC  ACT  GTG  AGC  TGG  AAC        9963
Val  Trp  Phe  Ala  Cys  His  His  Val  Met  Val  Asp  Thr  Val  Ser  Trp  Asn
               3180                         3185                         3190

ATT  ATA  CTG  CAA  GAC  CTG  CAG  GCT  CTC  TAT  CAT  GGA  GAC  AGC  CTT  GGT       10011
Ile  Ile  Leu  Gln  Asp  Leu  Gln  Ala  Leu  Tyr  His  Gly  Asp  Ser  Leu  Gly
               3195                         3200                         3205

CCC  AAG  AGC  AGC  AGC  GTG  CAG  CAG  TGG  TCG  CTA  GCT  GTC  AGC  GAC  TAC       10059
Pro  Lys  Ser  Ser  Ser  Val  Gln  Gln  Trp  Ser  Leu  Ala  Val  Ser  Asp  Tyr
               3210                         3215                         3220

AAA  ATG  CCA  CTG  TCG  GAG  AGG  GCG  CAT  TGG  AAT  GTG  CTC  AGG  AAG  ACA       10107
Lys  Met  Pro  Leu  Ser  Glu  Arg  Ala  His  Trp  Asn  Val  Leu  Arg  Lys  Thr
3225                         3230                         3235                3240

GTC  GCC  CAG  AGC  TTC  GAG  ACC  CTG  CCT  ATC  TGC  ATG  GGC  GGC  GTG  CTC       10155
Val  Ala  Gln  Ser  Phe  Glu  Thr  Leu  Pro  Ile  Cys  Met  Gly  Gly  Val  Leu
               3245                         3250                         3255

CAG  TGC  CAG  GAG  AAG  TTC  TCG  AGG  GAA  ACG  ACA  ACA  GCT  CTG  CTC  TCC       10203
Gln  Cys  Gln  Glu  Lys  Phe  Ser  Arg  Glu  Thr  Thr  Thr  Ala  Leu  Leu  Ser
               3260                         3265                         3270

AAG  GCC  TGC  CCT  GCC  TTG  GAC  TCC  GGT  ATG  CAT  GAG  ATC  CTT  CTC  ATG       10251
Lys  Ala  Cys  Pro  Ala  Leu  Asp  Ser  Gly  Met  His  Glu  Ile  Leu  Leu  Met
               3275                         3280                         3285

GCC  GTG  GGC  TCC  GCG  CTG  CAG  AAG  GCG  GCA  GGG  GAT  GTC  CCT  CAG  GTC       10299
Ala  Val  Gly  Ser  Ala  Leu  Gln  Lys  Ala  Ala  Gly  Asp  Val  Pro  Gln  Val
               3290                         3295                         3300

GTC  ACG  ATA  GAG  GGT  CAC  GGG  CGC  GAA  GAT  ACT  ATC  GAC  GCA  ACT  CTG       10347
Val  Thr  Ile  Glu  Gly  His  Gly  Arg  Glu  Asp  Thr  Ile  Asp  Ala  Thr  Leu
3305                         3310                         3315                3320

GAC  GTC  AGC  CGG  ACA  GTC  GGC  TGG  TTC  ACG  AGC  ATG  TAC  CCC  TTC  GAG       10395
Asp  Val  Ser  Arg  Thr  Val  Gly  Trp  Phe  Thr  Ser  Met  Tyr  Pro  Phe  Glu
               3325                         3330                         3335

ATC  CCC  AAA  GTG  ACC  GAC  CCC  GCT  CAG  GGC  GTC  GTC  GAT  GTC  AAG  GAG       10443
Ile  Pro  Lys  Val  Thr  Asp  Pro  Ala  Gln  Gly  Val  Val  Asp  Val  Lys  Glu
               3340                         3345                         3350

GCG  ATG  CGT  CGC  GTG  CCG  AAT  AGG  GGT  GTC  GGT  TAC  GGT  CCA  GCC  TAC       10491
Ala  Met  Arg  Arg  Val  Pro  Asn  Arg  Gly  Val  Gly  Tyr  Gly  Pro  Ala  Tyr
               3355                         3360                         3365

GGA  TAC  GGC  GGA  TCG  TGC  CTG  CCC  GCG  GTG  AGC  TTC  AAC  TAC  CTT  GGT       10539
Gly  Tyr  Gly  Gly  Ser  Cys  Leu  Pro  Ala  Val  Ser  Phe  Asn  Tyr  Leu  Gly
               3370                         3375                         3380

CGC  CTG  GAC  CAG  GCT  TCC  TCG  GGG  GCT  CAA  AGG  GAC  TGG  ACG  CTG  GTC       10587
Arg  Leu  Asp  Gln  Ala  Ser  Ser  Gly  Ala  Gln  Arg  Asp  Trp  Thr  Leu  Val
3385                         3390                         3395                3400

ATG  GAT  GAA  GAC  GAG  TAT  CCG  GTC  GGA  CTG  TGC  ACC  AGC  GCT  GAG  GAC       10635
Met  Asp  Glu  Asp  Glu  Tyr  Pro  Val  Gly  Leu  Cys  Thr  Ser  Ala  Glu  Asp
               3405                         3410                         3415

TCG  GGA  CGA  AGC  TCC  TCC  ATG  GTG  GAT  TTC  ACC  TTC  TCT  ATC  TCT  GGC       10683
Ser  Gly  Arg  Ser  Ser  Ser  Met  Val  Asp  Phe  Thr  Phe  Ser  Ile  Ser  Gly
               3420                         3425                         3430

GGC  CAG  CTT  GTC  ATG  GAT  ATG  AGT  AGC  AGC  TGG  GGC  CAC  GGC  GCA  CGA       10731
Gly  Gln  Leu  Val  Met  Asp  Met  Ser  Ser  Ser  Trp  Gly  His  Gly  Ala  Arg
               3435                         3440                         3445

AAT  GAA  TTC  GTT  CGC  ACA  GTT  CGT  AAC  ACA  CTA  GAT  GAC  TTG  ATC  AAA       10779
Asn  Glu  Phe  Val  Arg  Thr  Val  Arg  Asn  Thr  Leu  Asp  Asp  Leu  Ile  Lys
               3450                         3455                         3460

ACA  ACG  AGC  AGC  AGG  GAC  TTC  AGC  GCA  CCT  CTG  CCT  CCG  TCG  GAT  CAG       10827
Thr  Thr  Ser  Ser  Arg  Asp  Phe  Ser  Ala  Pro  Leu  Pro  Pro  Ser  Asp  Gln
3465                         3470                         3475                3480

GAG  TCC  AGC  TTC  ACC  CCT  TAT  TTT  GTC  TTC  GAA  GAG  GGC  GAG  CGA  CAC       10875
Glu  Ser  Ser  Phe  Thr  Pro  Tyr  Phe  Val  Phe  Glu  Glu  Gly  Glu  Arg  His
```

-continued

```
                  3485                         3490                         3495
GGC  GCT  CCG  CTC  TTC  CTG  CTC  CCA  CCT  GGC  GAA  GGC  GGA  GCG  GAG  AGC        10923
Gly  Ala  Pro  Leu  Phe  Leu  Leu  Pro  Pro  Gly  Glu  Gly  Gly  Ala  Glu  Ser
               3500                         3505                         3510

TAC  TTC  CAC  AAC  ATT  GTC  AAG  GGT  CTC  CCG  AAC  CGC  AAT  CTT  GTC  GTG        10971
Tyr  Phe  His  Asn  Ile  Val  Lys  Gly  Leu  Pro  Asn  Arg  Asn  Leu  Val  Val
               3515                         3520                         3525

TTC  AAC  AAT  CAT  TAC  CGC  GAG  GAG  AAG  ACG  CTC  CGG  ACC  ATC  GAG  GCG        11019
Phe  Asn  Asn  His  Tyr  Arg  Glu  Glu  Lys  Thr  Leu  Arg  Thr  Ile  Glu  Ala
               3530                         3535                         3540

CTG  GCC  GAG  TAC  TAC  CTG  TCG  CAC  ATC  CGA  TCC  ATC  CAG  CCG  GAG  GGG        11067
Leu  Ala  Glu  Tyr  Tyr  Leu  Ser  His  Ile  Arg  Ser  Ile  Gln  Pro  Glu  Gly
3545                         3550                         3555                    3560

CCA  TAC  CAC  ATC  CTC  GGC  TGG  AGT  TTC  GGA  GGC  ATC  CTC  GGT  CTC  GAG        11115
Pro  Tyr  His  Ile  Leu  Gly  Trp  Ser  Phe  Gly  Gly  Ile  Leu  Gly  Leu  Glu
               3565                         3570                         3575

GCG  GCA  AAG  CGA  TTG  ACT  GGC  GAG  GGT  CAC  AAG  ATT  GCC  ACG  CTG  GCA        11163
Ala  Ala  Lys  Arg  Leu  Thr  Gly  Glu  Gly  His  Lys  Ile  Ala  Thr  Leu  Ala
               3580                         3585                         3590

CTT  ATC  GAT  CCG  TAC  TTT  GAC  ATC  CCG  TCC  GCG  TCC  AAG  GCC  ATC  GGC        11211
Leu  Ile  Asp  Pro  Tyr  Phe  Asp  Ile  Pro  Ser  Ala  Ser  Lys  Ala  Ile  Gly
               3595                         3600                         3605

CAA  CCT  GAC  GAT  GCC  TGC  GTC  TTG  GAC  CCC  ATA  TAC  CAC  GTC  TAC  CAC        11259
Gln  Pro  Asp  Asp  Ala  Cys  Val  Leu  Asp  Pro  Ile  Tyr  His  Val  Tyr  His
               3610                         3615                         3620

CCG  TCG  CCG  GAG  AGC  TTC  AGG  ACG  GTG  TCA  TCT  CTC  ACT  AAT  CAC  ATA        11307
Pro  Ser  Pro  Glu  Ser  Phe  Arg  Thr  Val  Ser  Ser  Leu  Thr  Asn  His  Ile
3625                         3630                         3635                    3640

GCC  CTG  TTC  AAG  GCT  ACC  GAG  ACG  AAT  GAC  CAG  CAT  GGC  AAT  GCC  ACG        11355
Ala  Leu  Phe  Lys  Ala  Thr  Glu  Thr  Asn  Asp  Gln  His  Gly  Asn  Ala  Thr
               3645                         3650                         3655

CAG  CAG  GCC  CTG  TAT  GAG  TGG  TTT  GCC  ACG  TGC  CCT  TTG  AAC  AAC  CTG        11403
Gln  Gln  Ala  Leu  Tyr  Glu  Trp  Phe  Ala  Thr  Cys  Pro  Leu  Asn  Asn  Leu
               3660                         3665                         3670

GAC  AAG  TTT  TTG  GCG  GCC  GAC  ACG  ATC  AAG  GTG  GTT  CCT  CTG  GAG  GGT        11451
Asp  Lys  Phe  Leu  Ala  Ala  Asp  Thr  Ile  Lys  Val  Val  Pro  Leu  Glu  Gly
               3675                         3680                         3685

ACA  CAT  TTT  ACC  TGG  GTG  CAC  CAC  CCG  GAG  CAG  GTG  CGC  TCA  ATG  TGC        11499
Thr  His  Phe  Thr  Trp  Val  His  His  Pro  Glu  Gln  Val  Arg  Ser  Met  Cys
               3690                         3695                         3700

ACT  ATG  CTG  GAT  GAA  TGG  CTT  GGG  TGAACGAGGC  AGTTGCTGTG  AGAGAATGAG           11553
Thr  Met  Leu  Asp  Glu  Trp  Leu  Gly
3705                         3710

AATGAGACAC  AAAACGCGGG  CGGAAGAGAG  ACTTCCTCGG  ACGGCGGG                            11601
```

( 2 ) INFORMATION FOR SEQ ID NO:4:

( i ) SEQUENCE CHARACTERISTICS:
        ( A ) LENGTH: 3712 amino acids
        ( B ) TYPE: amino acid
        ( D ) TOPOLOGY: linear ( i i ) MOLECULE TYPE: protein ( i x ) FEATURE:
        ( A ) NAME/KEY: Modified-site
        ( B ) LOCATION: 2555
        ( D ) OTHER INFORMATION:
            / note= "Xaa=Ala or Ser"

( x i ) SEQUENCE DESCRIPTION: SEQ ID NO:4:

```
Val  Ala  Leu  Glu  Gln  Trp  Lys  Thr  Thr  Val  Gln  Ser  Val  Ser  Glu  Arg
 1                   5                        10                        15
```

Cys Asp Leu Ser Gly Leu Ser Gln His Pro Thr Asp Tyr Gln Leu Ala
                    20                  25                  30

Ser Thr Gly Val Lys Gly Ala Gly Ser Ser Ile Glu Glu Arg Ser
            35                  40                  45

Ala Ile Val Ser Asp Glu Leu Phe Ser Ser Leu Arg Asp Val Cys Ser
        50                  55                  60

Gln Arg Gln Leu Asp Pro Arg Ser Leu Met Leu Phe Ser Val His Gln
65                      70                  75                  80

Met Leu Lys Arg Phe Gly Asn Gly Ser His Thr Val Val Ala Ser Leu
                85                  90                  95

Val Thr Ser Ser Glu Gly Cys Pro Ser Thr Ser Ala Trp Arg Ala Ile
            100                 105                 110

Pro Ser Val Ile His His Ile Glu Gly Gly Asp Asn Asn Thr Val
        115                 120                 125

Ala Ser Ala Val Glu Gln Ala Ala Asn Leu Leu Asn Ser Glu Gly Ser
    130                 135                 140

Gly Gln Asp Leu Leu Ile Pro Ile Gly Leu Thr Glu Leu Val Lys Ser
145                 150                 155                 160

Glu Leu Ile Asp Leu Leu Val Ile Phe Asp Asp Glu Thr Asn Asn Ile
                165                 170                 175

Arg Leu Pro Gln Asp Phe Pro Leu Ile Leu Arg Ile His Gln Arg Gln
            180                 185                 190

Asp His Trp Gln Leu Ser Val Arg Tyr Pro Ser Pro Leu Phe Asp Thr
        195                 200                 205

Met Val Ile Asp Ser Phe Leu Ser Ala Leu His Asn Leu Leu Ser Ala
    210                 215                 220

Val Thr Lys Pro Ser Gln Leu Val Arg Asp Ile Glu Leu Leu Pro Glu
225                 230                 235                 240

Tyr Gln Val Ala Gln Leu Glu Lys Trp Asn Asn Thr Asp Gly Asp Tyr
                245                 250                 255

Pro Thr Glu Lys Arg Leu His His Leu Phe Glu Glu Ala Ala Val Arg
            260                 265                 270

Arg Pro Gln His Val Ala Leu Ile Cys Gly Asp Lys Arg Ile Thr Tyr
        275                 280                 285

Glu Glu Leu Asn Ala Met Ala Asn Arg Leu Ala His Leu Val Ser
    290                 295                 300

Ser Gly Ile Gln Thr Glu Gln Leu Val Gly Leu Phe Leu Asp Lys Thr
305                 310                 315                 320

Glu Leu Met Ile Ala Thr Ile Leu Gly Ile Trp Lys Ser Gly Ala Ala
                325                 330                 335

His Val Pro Ile Asp Pro Gly Tyr Pro Asp Glu Arg Val Lys Phe Val
            340                 345                 350

Leu Asn Asp Thr Lys Ala Gln Val Val Ile Ala Ser Gln Arg His Val
        355                 360                 365

Asp Arg Leu Arg Ala Glu Ala Val Gly Gly Gln His Leu Arg Ile Ile
    370                 375                 380

Gly Leu Glu Ser Leu Phe Asp Asn Leu Ala Gln Gln Thr Gln His Ser
385                 390                 395                 400

Pro Glu Thr Ser Gly Asn Leu Thr His Leu Pro Leu Asn Ser Lys Gln
                405                 410                 415

Leu Ala Tyr Val Thr Tyr Thr Ser Gly Thr Thr Gly Phe Pro Lys Gly
            420                 425                 430

Ile Tyr Lys Glu His Thr Ser Val Val Asn Ser Ile Thr Asp Leu Ser

```
                     435                          440                          445
Ala  Arg  Tyr  Gly  Val  Ala  Gly  Glu  Asp  Asp  Glu  Val  Ile  Leu  Val  Phe
     450                       455                      460

Ser  Ala  Tyr  Val  Phe  Glu  Pro  Phe  Val  Arg  Gln  Met  Leu  Met  Ala  Leu
465                           470                      475                    480

Thr  Thr  Gly  Asn  Ser  Leu  Ala  Ile  Ile  Ser  Asp  Glu  Asp  Lys  Phe  Asp
                    485                       490                      495

Pro  Asp  Thr  Leu  Ile  Pro  Phe  Ile  Gln  Lys  His  Lys  Val  Thr  Tyr  Ile
               500                       505                      510

His  Ala  Thr  Ser  Ser  Val  Leu  Gln  Glu  Tyr  Asp  Phe  Gly  Ser  Cys  Pro
          515                       520                      525

Ser  Leu  Lys  Arg  Met  Ile  Leu  Val  Gly  Glu  Asn  Leu  Thr  Glu  Pro  Arg
530                           535                      540

Tyr  Glu  Ala  Leu  Arg  Gln  Arg  Phe  Lys  Ser  Arg  Ile  Leu  Asn  Glu  Tyr
545                      550                      555                      560

Gly  Phe  Thr  Glu  Ser  Ala  Phe  Val  Thr  Ala  Leu  Asn  Ile  Phe  Glu  Pro
                         565                      570                      575

Thr  Ser  Gln  Arg  Lys  Asp  Met  Ser  Leu  Gly  Arg  Pro  Val  Arg  Asn  Val
               580                       585                      590

Lys  Cys  Tyr  Ile  Leu  Asp  Ala  Asn  Leu  Lys  Arg  Val  Pro  Ile  Gly  Val
          595                       600                      605

Thr  Gly  Glu  Leu  His  Ile  Gly  Gly  Leu  Gly  Ile  Ser  Arg  Gly  Tyr  Met
     610                       615                      620

Asn  Arg  Glu  Glu  Leu  Thr  Arg  Gln  Lys  Phe  Leu  Pro  Asn  Pro  Tyr  Gln
625                           630                      635                    640

Thr  Asp  Lys  Glu  Arg  Gln  Arg  Gly  Val  Asn  Ser  Thr  Met  Tyr  Lys  Thr
                    645                       650                      655

Gly  Asp  Leu  Ala  Arg  Trp  Leu  Pro  Ser  Gly  Glu  Val  Glu  Tyr  Leu  Gly
               660                       665                      670

Arg  Ala  Asp  Phe  Gln  Ile  Lys  Leu  Arg  Gly  Ile  Arg  Ile  Glu  Pro  Gly
          675                       680                      685

Glu  Ile  Glu  Ser  Thr  Leu  Ala  Met  Tyr  Pro  Gly  Ile  Arg  Ala  Ser  Ile
     690                       695                      700

Val  Val  Ser  Lys  Lys  Leu  Leu  Ser  Gln  Gly  Gln  Glu  Thr  Ile  Gln  Asp
705                           710                      715                    720

His  Leu  Val  Gly  Tyr  Tyr  Val  Cys  Asp  Glu  Gly  His  Ile  Pro  Glu  Gly
                    725                       730                      735

Asp  Leu  Leu  Ser  Phe  Leu  Glu  Lys  Lys  Leu  Pro  Arg  Tyr  Met  Val  Pro
               740                       745                      750

Thr  Arg  Leu  Val  Gln  Leu  Ala  Gln  Ile  Pro  Thr  Asn  Ile  Asn  Gly  Lys
          755                       760                      765

Ala  Asp  Leu  Arg  Ala  Leu  Pro  Ala  Val  Glu  Val  Ala  Val  Ala  Pro  Thr
     770                       775                      780

His  Lys  Gln  Asp  Gly  Glu  Arg  Gly  Asn  Gln  Leu  Glu  Ser  Asp  Leu  Ala
785                           790                      795                    800

Ala  Ile  Trp  Gly  Asn  Ile  Leu  Ser  Val  Pro  Ala  Gln  Asp  Ile  Gly  Ser
                    805                       810                      815

Glu  Ser  Asn  Phe  Phe  Arg  Leu  Gly  Gly  His  Ser  Ile  Ala  Cys  Ile  Gln
               820                       825                      830

Leu  Ile  Ala  Arg  Val  Arg  Gln  Gln  Leu  Gly  Gln  Gly  Ile  Thr  Leu  Glu
          835                       840                      845

Glu  Val  Phe  Gln  Thr  Lys  Thr  Leu  Arg  Ala  Met  Ala  Ala  Leu  Leu  Ser
850                           855                      860
```

```
Glu  Lys  Tyr  Thr  Lys  Ala  Ser  Asn  Gly  Thr  Asn  Gly  Val  Thr  Asn  Gly
865                 870                 875                           880

Thr  Ala  His  Val  Asn  Gly  His  Ala  Ala  Asn  Gly  His  Val  Ser  Asp  Ser
                    885                 890                      895

Tyr  Val  Ala  Ser  Ser  Leu  Gln  Gln  Gly  Phe  Val  Tyr  His  Ser  Leu  Lys
               900                 905                           910

Asn  Glu  Leu  Ser  Glu  Ala  Tyr  Thr  Met  Gln  Ser  Met  Ile  His  Tyr  Gly
          915                      920                 925

Val  Pro  Leu  Lys  Arg  Asp  Ile  Tyr  Gln  Ala  Ala  Trp  Gln  Arg  Val  Gln
930                      935                           940

Gly  Glu  His  Pro  Ala  Leu  Arg  Leu  Arg  Phe  Thr  Trp  Glu  Ala  Glu  Val
945                      950                 955                           960

Met  Gln  Ile  Val  Asp  Pro  Lys  Ser  Glu  Leu  Asp  Trp  Arg  Val  Val  Asp
                    965                 970                           975

Trp  Thr  Asp  Val  Ser  Ser  Arg  Glu  Lys  Gln  Leu  Val  Ala  Leu  Glu  Gln
               980                 985                           990

Leu  Gln  Thr  Glu  Asp  Leu  Ala  Lys  Val  Tyr  His  Leu  Asp  Lys  Gly  Pro
          995                 1000                     1005

Leu  Met  Arg  Leu  Tyr  Leu  Ile  Leu  Leu  Pro  Asp  Ser  Lys  Tyr  Ser  Cys
     1010                     1015                     1020

Leu  Phe  Ser  Cys  His  His  Ala  Ile  Leu  Asp  Gly  Trp  Ser  Leu  Pro  Leu
1025                1030                     1035                          1040

Leu  Phe  Asn  Asn  Val  His  Gln  Ala  Tyr  Leu  Asp  Leu  Val  Glu  Gly  Thr
               1045                     1050                          1055

Ala  Ser  Pro  Val  Glu  Gln  Asp  Ala  Thr  Tyr  Leu  Leu  Gly  Gln  Gln  Tyr
               1060                1065                          1070

Leu  Gln  Ser  His  Arg  Asp  Asp  His  Leu  Asp  Phe  Trp  Ala  Glu  Gln  Ile
          1075                1080                     1085

Gly  Arg  Ile  Glu  Glu  Arg  Cys  Asp  Met  Asn  Ala  Leu  Leu  Asn  Glu  Ala
          1090                1095                          1100

Ser  Arg  Tyr  Lys  Val  Pro  Leu  Ala  Asp  Tyr  Asp  Gln  Val  Arg  Glu  Gln
1105                     1110                1115                          1120

Arg  Gln  Gln  Thr  Ile  Ser  Leu  Pro  Trp  Asn  Asn  Ser  Met  Asp  Ala  Gly
               1125                1130                          1135

Val  Arg  Glu  Glu  Leu  Ser  Ser  Arg  Gly  Ile  Thr  Leu  His  Ser  Ile  Leu
               1140                1145                          1150

Gln  Thr  Val  Trp  His  Leu  Val  Leu  His  Ser  Tyr  Gly  Gly  Gly  Thr  His
               1155                1160                          1165

Thr  Ile  Thr  Gly  Thr  Thr  Ile  Ser  Gly  Arg  His  Leu  Pro  Val  Pro  Gly
          1170                1175                     1180

Ile  Glu  Arg  Ser  Val  Gly  Leu  Phe  Ile  Asn  Thr  Leu  Pro  Met  Ile  Phe
1185                     1190                1195                          1200

Asp  His  Thr  Val  Cys  Gln  Asp  Met  Thr  Ala  Leu  Glu  Ala  Ile  Glu  His
               1205                1210                          1215

Val  Gln  Gly  Gln  Val  Asn  Ala  Met  Asn  Ser  Arg  Gly  Asn  Val  Glu  Leu
          1220                     1225                          1230

Gly  Arg  Met  Ser  Lys  Asn  Asp  Leu  Lys  His  Gly  Leu  Phe  Asp  Thr  Leu
          1235                     1240                          1245

Phe  Val  Leu  Glu  Asn  Tyr  Pro  Asn  Leu  Asp  Thr  Glu  Gln  Arg  Glu  Lys
     1250                     1255                     1260

His  Glu  Glu  Lys  Leu  Lys  Phe  Thr  Ile  Lys  Gly  Gly  Thr  Glu  Lys  Leu
1265                     1270                     1275                     1280

Ser  Tyr  Pro  Leu  Ala  Val  Ile  Ala  Gln  Glu  Asp  Gly  Asp  Ser  Gly  Cys
               1285                     1290                          1295
```

```
Ser Phe Thr Leu Cys Tyr Ala Gly Glu Leu Phe Thr Asp Glu Ser Ile
            1300                1305                1310
Gln Ala Leu Leu Asp Thr Val Arg Asp Thr Leu Ser Asp Ile Leu Gly
        1315                1320                1325
Asn Ile His Ala Pro Ile Arg Asn Met Glu Tyr Leu Ser Ser Asn Gln
        1330                1335                1340
Thr Ala Gln Leu Asp Lys Trp Asn Ala Thr Ala Phe Glu Tyr Pro Asn
1345                1350                1355                1360
Thr Thr Leu His Ala Met Phe Glu Ser Glu Ala Gln Gln Lys Pro Asp
            1365                1370                1375
Lys Val Ala Val Val Tyr Glu Asp Ile Arg Leu Thr Tyr Arg Glu Leu
                1380                1385                1390
Asn Ser Arg Ala Asn Ala Leu Ala Phe Tyr Leu Leu Ser Gln Ala Ala
            1395                1400                1405
Ile Gln Pro Asn Lys Leu Val Gly Leu Ile Met Asp Lys Ser Glu His
        1410                1415                1420
Met Ile Thr Ser Ile Leu Ala Val Trp Lys Thr Gly Gly Ala Tyr Val
1425                1430                1435                1440
Pro Ile Asp Pro Arg Tyr Pro Asp Gln Arg Ile Gln Tyr Ile Leu Glu
                1445                1450                1455
Asp Thr Ala Ala Leu Ala Val Ile Thr Asp Ser Pro His Ile Asp Arg
            1460                1465                1470
Leu Arg Ser Ile Thr Asn Asn Arg Leu Pro Val Ile Gln Ser Asp Phe
            1475                1480                1485
Ala Leu Gln Leu Pro Pro Ser Pro Val His Pro Val Ser Asn Cys Lys
            1490                1495                1500
Pro Ser Asp Leu Ala Tyr Ile Met Tyr Thr Ser Gly Thr Thr Gly Asn
1505                1510                1515                1520
Pro Lys Gly Val Met Val Glu His His Gly Val Val Asn Leu Cys Val
                1525                1530                1535
Ser Leu Cys Arg Leu Phe Gly Leu Arg Asn Thr Asp Asp Glu Val Ile
            1540                1545                1550
Leu Ser Phe Ser Asn Tyr Val Phe Asp His Phe Val Glu Gln Met Thr
            1555                1560                1565
Asp Ala Leu Leu Asn Gly Gln Thr Leu Val Val Leu Asn Asp Glu Met
        1570                1575                1580
Arg Gly Asp Lys Glu Arg Leu Tyr Arg Tyr Ile Glu Thr Asn Arg Val
1585                1590                1595                1600
Thr Tyr Leu Ser Gly Thr Pro Ser Val Ile Ser Met Tyr Glu Phe Asp
                1605                1610                1615
Arg Phe Arg Asp His Leu Arg Arg Val Asp Cys Val Gly Glu Ala Phe
            1620                1625                1630
Ser Glu Pro Val Phe Asp Lys Ile Arg Glu Thr Phe Pro Gly Leu Ile
        1635                1640                1645
Ile Asn Gly Tyr Gly Pro Thr Glu Val Ser Ile Thr Thr His Lys Arg
        1650                1655                1660
Pro Tyr Pro Phe Pro Glu Arg Arg Thr Asp Lys Ser Ile Gly Cys Gln
1665                1670                1675                1680
Leu Asp Asn Ser Thr Ser Tyr Val Leu Asn Asp Asp Met Lys Arg Val
            1685                1690                1695
Pro Ile Gly Ala Val Gly Glu Leu Tyr Leu Gly Gly Asp Gly Val Ala
            1700                1705                1710
Arg Gly Tyr His Asn Arg Pro Asp Leu Thr Ala Asp Arg Phe Pro Ala
```

```
                    1715                        1720                        1725
Asn  Pro  Phe  Gln  Thr  Glu  Gln  Glu  Arg  Leu  Glu  Gly  Arg  Asn  Ala  Arg
     1730                         1735                      1740

Leu  Tyr  Lys  Thr  Gly  Asp  Leu  Val  Arg  Trp  Ile  His  Asn  Ala  Asn  Gly
1745                     1750                    1755                        1760

Asp  Gly  Glu  Ile  Glu  Tyr  Leu  Gly  Arg  Asn  Asp  Phe  Gln  Val  Lys  Ile
               1765                    1770                         1775

Arg  Gly  Gln  Arg  Ile  Glu  Leu  Gly  Glu  Ile  Glu  Ala  Val  Leu  Ser  Ser
          1780                         1785                         1790

Tyr  Pro  Gly  Ile  Lys  Gln  Ser  Val  Val  Leu  Ala  Lys  Asp  Arg  Lys  Asn
          1795                    1800                    1805

Asp  Gly  Gln  Lys  Tyr  Leu  Val  Gly  Tyr  Phe  Val  Ser  Ser  Ala  Gly  Ser
     1810                    1815                    1820

Leu  Ser  Ala  Gln  Ala  Ile  Arg  Arg  Phe  Met  Leu  Thr  Ser  Leu  Pro  Asp
1825                     1830                    1835                        1840

Tyr  Met  Val  Pro  Ala  Gln  Leu  Val  Pro  Ile  Ala  Lys  Phe  Pro  Val  Thr
                    1845                    1850                        1855

Val  Ser  Gly  Lys  Leu  Asp  Ala  Lys  Ala  Leu  Pro  Val  Pro  Asp  Asp  Thr
               1860                    1865                    1870

Val  Glu  Asp  Asp  Ile  Val  Pro  Pro  Arg  Thr  Glu  Val  Glu  Arg  Ile  Leu
          1875                    1880                    1885

Ala  Gly  Ile  Trp  Ser  Glu  Leu  Leu  Glu  Ile  Pro  Val  Asp  Arg  Ile  Ser
          1890                         1895                    1900

Ile  Tyr  Ser  Asp  Phe  Phe  Ser  Leu  Gly  Gly  Asp  Ser  Leu  Lys  Ser  Thr
1905                     1910                    1915                        1920

Lys  Leu  Ser  Phe  Ala  Ala  Thr  Arg  Ala  Leu  Gly  Val  Ala  Val  Ser  Val
                    1925                    1930                        1935

Arg  Asn  Leu  Phe  Ser  His  Pro  Thr  Ile  Glu  Ala  Leu  Ser  Gln  Trp  Ile
               1940                    1945                    1950

Ile  Arg  Gly  Ser  Asn  Glu  Val  Lys  Asp  Val  Ala  Val  Val  Lys  Gly  Gly
          1955                    1960                         1965

Ala  Ser  Leu  Asp  Ile  Pro  Leu  Ser  Pro  Ala  Gln  Glu  Arg  Leu  Met  Phe
1970                     1975                    1980

Ile  His  Glu  Phe  Gly  His  Ser  Gly  Glu  Asp  Thr  Gly  Ala  Tyr  Asn  Val
1985                     1990                    1995                        2000

Pro  Leu  Gln  Leu  Gln  Leu  His  His  Asp  Val  Cys  Leu  Glu  Ser  Leu  Glu
                    2005                    2010                        2015

Lys  Ala  Leu  Arg  Asp  Val  Val  Ser  Arg  His  Glu  Ala  Leu  Arg  Thr  Leu
               2020                    2025                    2030

Ile  Thr  Arg  Thr  Gln  Lys  Ser  Ser  Val  His  Cys  Gln  Lys  Ile  Leu  Asp
          2035                    2040                    2045

Ala  Glu  Glu  Ala  Gln  Lys  Leu  Phe  Ser  Val  Asp  Val  Leu  Arg  Leu  Thr
     2050                    2055                    2060

Ser  Glu  Thr  Glu  Met  Gln  Gly  Arg  Met  Ala  Glu  Ser  Thr  Ala  His  Ala
2065                     2070                    2075                        2080

Phe  Lys  Leu  Asp  Glu  Glu  Leu  Pro  Ile  His  Val  Arg  Leu  Tyr  Gln  Val
                    2085                    2090                        2095

Val  Arg  Asp  Gly  Arg  Thr  Leu  Ser  Phe  Ala  Ser  Ile  Val  Cys  His  His
               2100                    2105                    2110

Leu  Ala  Phe  Asp  Ala  Trp  Ser  Trp  Asp  Val  Phe  Gln  Arg  Asp  Leu  Asp
          2115                    2120                    2125

Ala  Phe  Tyr  Ala  Val  His  Thr  Lys  His  Lys  Ala  Ala  Ala  Asn  Leu  Pro
     2130                    2135                         2140
```

```
Thr  Leu  Arg  Val  Gln  Tyr  Lys  Glu  Tyr  Ala  Ile  Glu  His  Arg  Arg  Ala
2145                2150                2155                          2160

Leu  Arg  Ala  Glu  Gln  His  Arg  Val  Leu  Ala  Asp  Tyr  Trp  Leu  Arg  Lys
                2165                2170                     2175

Leu  Ser  Asp  Met  Glu  Ala  Ser  Tyr  Leu  Val  Pro  Asp  Arg  Pro  Arg  Pro
               2180                2185                          2190

Ala  Gln  Phe  Asp  Tyr  Thr  Gly  Asn  Asp  Leu  Gln  Phe  Ser  Thr  Thr  Pro
               2195                2200                     2205

Glu  Thr  Thr  Ala  Gln  Leu  Lys  Glu  Leu  Ala  Lys  Arg  Glu  Gly  Ser  Ser
2210                2215                2220

Leu  Tyr  Thr  Val  Val  Ala  Ala  Ala  Tyr  Phe  Leu  Leu  Leu  Tyr  Val  Tyr
2225                2230                2235                          2240

Thr  Asn  Gln  Arg  Asp  Ile  Thr  Ile  Gly  Ile  Pro  Val  Ala  His  Arg  Asn
                2245                2250                          2255

His  Pro  Asp  Phe  Glu  Ser  Val  Val  Gly  Phe  Phe  Val  Asn  Leu  Leu  Pro
                2260                2265                          2270

Leu  Arg  Val  Asn  Val  Ser  Gln  Ser  Asp  Ile  His  Gly  Leu  Ile  Gln  Ala
                2275                2280                     2285

Val  Gln  Lys  Glu  Leu  Val  Asp  Ala  Gln  Ile  His  Gln  Asp  Leu  Pro  Phe
     2290                2295                     2300

Gln  Glu  Ile  Thr  Lys  Leu  Leu  His  Val  Gln  His  Asp  Pro  Ser  Arg  His
2305                2310                2315                          2320

Pro  Leu  Leu  Gln  Ala  Val  Phe  Asn  Trp  Glu  Asn  Val  Pro  Ala  Asn  Val
                2325                2330                     2335

His  Glu  Glu  Gln  Leu  Leu  Gln  Glu  Tyr  Lys  Pro  Pro  Ser  Pro  Leu  Pro
           2340                2345                     2350

Ser  Ala  Ala  Lys  Phe  Asp  Leu  Asn  Val  Thr  Val  Lys  Glu  Ser  Val  Asn
          2355                2360                     2365

Ser  Leu  Asn  Val  Asn  Phe  Asn  Tyr  Pro  Thr  Ser  Leu  Phe  Glu  Glu  Glu
     2370                2375                     2380

Thr  Val  Gln  Gly  Phe  Met  Glu  Thr  Phe  His  Leu  Leu  Leu  Arg  Gln  Leu
2385                2390                2395                          2400

Ala  His  Asn  Lys  Ala  Ser  Thr  Ser  Leu  Ser  Lys  Leu  Ser  Val  Glu  Asp
                2405                2410                          2415

Gly  Val  Leu  Asn  Pro  Glu  Pro  Thr  Asn  Leu  Gln  Pro  Ser  Ser  Arg  Asp
                2420                2425                          2430

Ser  Gly  Asn  Ser  Leu  His  Gly  Leu  Phe  Glu  Asp  Ile  Val  Ala  Ser  Thr
           2435                2440                     2445

Pro  Asp  Arg  Ile  Ala  Ile  Ala  Asp  Gly  Thr  Arg  Ser  Leu  Ser  Tyr  Ser
           2450                2455                     2460

Glu  Leu  Asn  Glu  Arg  Ala  Asn  Gln  Leu  Val  His  Leu  Ile  Ile  Ser  Ser
2465                2470                2475                          2480

Ala  Ser  Ile  Val  Ala  Asp  Asp  Arg  Ile  Ala  Leu  Leu  Leu  Asp  Lys  Ser
                2485                2490                          2495

Ile  Asp  Met  Val  Ile  Ala  Leu  Leu  Ala  Val  Trp  Lys  Ala  Gly  Ala  Ala
                2500                2505                          2510

Tyr  Val  Pro  Leu  Asp  Pro  Thr  Tyr  Pro  Ser  Gln  Arg  Thr  Glu  Leu  Ile
               2515                2520                     2525

Leu  Glu  Glu  Ser  Ser  Ala  Arg  Thr  Leu  Ile  Thr  Thr  Arg  Lys  His  Thr
          2530                2535                     2540

Pro  Arg  Gly  Gly  Thr  Val  Ala  Asn  Val  Pro  Xaa  Val  Val  Leu  Asp  Ser
2545                2550                2555                          2560

Pro  Glu  Thr  Leu  Ala  Cys  Leu  Asn  Gln  Gln  Ser  Lys  Glu  Asn  Pro  Thr
                2565                2570                     2575
```

```
Thr  Ser  Thr  Gln  Lys  Pro  Ser  Asp  Leu  Ala  Tyr  Val  Ile  Phe  Thr  Ser
              2580                2585                     2590

Gly  Thr  Thr  Gly  Lys  Pro  Lys  Gly  Val  Leu  Val  Glu  His  Gln  Ser  Val
              2595                2600                     2605

Val  Gln  Leu  Arg  Asn  Ser  Leu  Ile  Glu  Arg  Tyr  Phe  Gly  Glu  Thr  Asn
         2610                2615                     2620

Gly  Ser  His  Ala  Val  Leu  Phe  Leu  Ser  Asn  Tyr  Val  Phe  Asp  Phe  Ser
2625                     2630                2635                          2640

Leu  Glu  Gln  Leu  Cys  Leu  Ser  Val  Leu  Gly  Gly  Asn  Lys  Leu  Ile  Ile
              2645                2650                     2655

Pro  Pro  Glu  Glu  Gly  Leu  Thr  His  Glu  Ala  Phe  Tyr  Asp  Ile  Gly  Arg
              2660                2665                     2670

Arg  Glu  Lys  Leu  Ser  Tyr  Leu  Ser  Gly  Thr  Pro  Ser  Val  Leu  Gln  Gln
              2675                2680                     2685

Ile  Glu  Leu  Ser  Arg  Leu  Pro  His  Leu  His  Met  Val  Thr  Ala  Ala  Gly
              2690                2695                     2700

Glu  Glu  Phe  His  Ala  Ser  Gln  Phe  Glu  Lys  Met  Arg  Ser  Gln  Phe  Ala
2705                     2710                2715                          2720

Gly  Gln  Ile  Asn  Asn  Ala  Tyr  Gly  Ile  Thr  Glu  Thr  Val  Tyr  Asn
              2725                2730                     2735

Ile  Ile  Thr  Thr  Phe  Lys  Gly  Asp  Ala  Pro  Phe  Thr  Lys  Ala  Leu  Cys
              2740                2745                     2750

His  Gly  Ile  Pro  Gly  Ser  His  Val  Tyr  Val  Leu  Asn  Asp  Arg  Leu  Gln
              2755                2760                     2765

Arg  Val  Pro  Phe  Asn  Ala  Val  Gly  Glu  Leu  Tyr  Leu  Gly  Gly  Asp  Cys
              2770                2775                     2780

Leu  Ala  Arg  Gly  Tyr  Leu  Asn  Gln  Asp  Ala  Leu  Thr  Asn  Glu  Arg  Phe
2785                     2790                2795                          2800

Ile  Pro  Asn  Pro  Phe  Tyr  Glu  Pro  Lys  Gln  Ala  Ser  Asp  Ser  Arg  Pro
              2805                2810                     2815

Gln  Arg  Leu  Tyr  Lys  Thr  Gly  Asp  Leu  Val  Arg  Phe  Arg  Gly  Pro  His
              2820                2825                     2830

His  Leu  Glu  Tyr  Leu  Gly  Arg  Lys  Asp  Gln  Gln  Val  Lys  Leu  Arg  Gly
              2835                2840                     2845

Phe  Arg  Ile  Glu  Leu  Ser  Glu  Val  Arg  Asp  Ala  Val  Leu  Ala  Ile  Ser
2850                     2855                2860

Ala  Val  Lys  Glu  Ala  Ala  Val  Ile  Pro  Lys  Tyr  Asp  Glu  Asp  Gly  Ser
2865                     2870                2875                          2880

Asp  Ser  Arg  Arg  Val  Ser  Ala  Ile  Val  Cys  Tyr  Tyr  Thr  Leu  Asn  Ala
              2885                2890                     2895

Gly  Thr  Val  Cys  Glu  Ala  Ser  Ser  Ile  Arg  Asp  His  Leu  His  Ala  Asn
              2900                2905                     2910

Leu  Pro  Pro  Tyr  Met  Val  Pro  Ser  Gln  Ile  His  Gln  Leu  Glu  Gly  Ser
              2915                2920                     2925

Leu  Pro  Val  Thr  Val  Asn  Gly  Lys  Leu  Asp  Leu  Asn  Arg  Leu  Ser  Thr
              2930                2935                     2940

Thr  Gln  Val  Ser  Gln  Pro  Glu  Leu  Tyr  Thr  Ala  Pro  Arg  Asn  Ser  Thr
2945                     2950                2955                          2960

Glu  Glu  Thr  Leu  Cys  Gln  Leu  Trp  Ala  Ser  Leu  Leu  Gly  Val  Asp  His
              2965                2970                     2975

Cys  Gly  Ile  Asp  Asp  Asp  Leu  Phe  Ala  Arg  Gly  Gly  Asp  Ser  Ile  Ser
              2980                2985                     2990

Ser  Leu  Arg  Leu  Val  Gly  Asp  Ile  Tyr  Arg  Ala  Leu  Gly  Arg  Lys  Val
```

|   |   |   | 2995 |   |   |   |   | 3000 |   |   |   |   | 3005 |   |
|---|---|---|---|---|---|---|---|---|---|---|---|---|---|---|

Thr Val Lys Asp Ile Tyr Leu His Arg Ser Val Arg Ala Leu Ser Glu
                3010                3015                3020

Asn Val Leu Thr Asp Gln Lys Asp Lys Gly Thr Leu Pro Ala Ser Pro
3025                3030                3035                3040

Pro Leu Gln Arg Ala Glu Gln Gly Gln Val Glu Gly Asp Ala Pro Leu
                3045                3050                3055

Leu Pro Ile Gln Asp Trp Phe Leu Ser Lys Pro Leu Asp Asn Pro Ala
                3060                3065                3070

Tyr Trp Asn His Cys Phe Thr Ile Arg Thr Gly Ala Leu Ser Val Glu
                3075                3080                3085

Gly Leu Arg Gly Ala Leu Lys Leu Leu Gln Glu Arg His Asp Val Leu
                3090                3095                3100

Arg Leu Arg Leu Gln Arg Arg Asp Glu Gly Arg His Val Gln Thr Phe
3105                3110                3115                3120

Ala Arg Asp Cys Ala Gln Pro Arg Leu Thr Val Leu Asp Arg Arg Ser
                3125                3130                3135

Phe Glu Asp Ala Glu Asp Val Gln Glu Ala Leu Cys Glu Ile Gln Ser
                3140                3145                3150

His Phe Asp Leu Glu Asn Gly Pro Leu Tyr Thr Val Ala Tyr Ile His
                3155                3160                3165

Gly Tyr Glu Asp Gly Ser Ala Arg Val Trp Phe Ala Cys His His Val
                3170                3175                3180

Met Val Asp Thr Val Ser Trp Asn Ile Ile Leu Gln Asp Leu Gln Ala
3185                3190                3195                3200

Leu Tyr His Gly Asp Ser Leu Gly Pro Lys Ser Ser Val Gln Gln
                3205                3210                3215

Trp Ser Leu Ala Val Ser Asp Tyr Lys Met Pro Leu Ser Glu Arg Ala
                3220                3225                3230

His Trp Asn Val Leu Arg Lys Thr Val Ala Gln Ser Phe Glu Thr Leu
                3235                3240                3245

Pro Ile Cys Met Gly Gly Val Leu Gln Cys Gln Glu Lys Phe Ser Arg
                3250                3255                3260

Glu Thr Thr Thr Ala Leu Leu Ser Lys Ala Cys Pro Ala Leu Asp Ser
3265                3270                3275                3280

Gly Met His Glu Ile Leu Leu Met Ala Val Gly Ser Ala Leu Gln Lys
                3285                3290                3295

Ala Ala Gly Asp Val Pro Gln Val Val Thr Ile Glu Gly His Gly Arg
                3300                3305                3310

Glu Asp Thr Ile Asp Ala Thr Leu Asp Val Ser Arg Thr Val Gly Trp
                3315                3320                3325

Phe Thr Ser Met Tyr Pro Phe Glu Ile Pro Lys Val Thr Asp Pro Ala
3330                3335                3340

Gln Gly Val Val Asp Val Lys Glu Ala Met Arg Arg Val Pro Asn Arg
3345                3350                3355                3360

Gly Val Gly Tyr Gly Pro Ala Tyr Gly Tyr Gly Gly Ser Cys Leu Pro
                3365                3370                3375

Ala Val Ser Phe Asn Tyr Leu Gly Arg Leu Asp Gln Ala Ser Ser Gly
                3380                3385                3390

Ala Gln Arg Asp Trp Thr Leu Val Met Asp Glu Asp Glu Tyr Pro Val
                3395                3400                3405

Gly Leu Cys Thr Ser Ala Glu Asp Ser Gly Arg Ser Ser Ser Met Val
                3410                3415                3420

```
Asp  Phe  Thr  Phe  Ser  Ile  Ser  Gly  Gly  Gln  Leu  Val  Met  Asp  Met  Ser
3425                3430                3435                          3440

Ser  Ser  Trp  Gly  His  Gly  Ala  Arg  Asn  Glu  Phe  Val  Arg  Thr  Val  Arg
                    3445                3450                     3455

Asn  Thr  Leu  Asp  Asp  Leu  Ile  Lys  Thr  Ser  Ser  Arg  Asp  Phe  Ser
               3460                3465                3470

Ala  Pro  Leu  Pro  Pro  Ser  Asp  Gln  Glu  Ser  Ser  Phe  Thr  Pro  Tyr  Phe
               3475                3480                     3485

Val  Phe  Glu  Glu  Gly  Glu  Arg  His  Gly  Ala  Pro  Leu  Phe  Leu  Leu  Pro
          3490                3495                     3500

Pro  Gly  Glu  Gly  Gly  Ala  Glu  Ser  Tyr  Phe  His  Asn  Ile  Val  Lys  Gly
3505                3510                     3515                          3520

Leu  Pro  Asn  Arg  Asn  Leu  Val  Val  Phe  Asn  Asn  His  Tyr  Arg  Glu  Glu
               3525                3530                          3535

Lys  Thr  Leu  Arg  Thr  Ile  Glu  Ala  Leu  Ala  Glu  Tyr  Tyr  Leu  Ser  His
               3540                3545                     3550

Ile  Arg  Ser  Ile  Gln  Pro  Glu  Gly  Pro  Tyr  His  Ile  Leu  Gly  Trp  Ser
               3555                3560                     3565

Phe  Gly  Gly  Ile  Leu  Gly  Leu  Glu  Ala  Ala  Lys  Arg  Leu  Thr  Gly  Glu
     3570                3575                     3580

Gly  His  Lys  Ile  Ala  Thr  Leu  Ala  Leu  Ile  Asp  Pro  Tyr  Phe  Asp  Ile
3585                3590                     3595                          3600

Pro  Ser  Ala  Ser  Lys  Ala  Ile  Gly  Gln  Pro  Asp  Asp  Ala  Cys  Val  Leu
               3605                3610                          3615

Asp  Pro  Ile  Tyr  His  Val  Tyr  His  Pro  Ser  Pro  Glu  Ser  Phe  Arg  Thr
               3620                3625                     3630

Val  Ser  Ser  Leu  Thr  Asn  His  Ile  Ala  Leu  Phe  Lys  Ala  Thr  Glu  Thr
          3635                3640                     3645

Asn  Asp  Gln  His  Gly  Asn  Ala  Thr  Gln  Gln  Ala  Leu  Tyr  Glu  Trp  Phe
3650                3655                     3660

Ala  Thr  Cys  Pro  Leu  Asn  Asn  Leu  Asp  Lys  Phe  Leu  Ala  Ala  Asp  Thr
3665                3670                     3675                          3680

Ile  Lys  Val  Val  Pro  Leu  Glu  Gly  Thr  His  Phe  Thr  Trp  Val  His  His
                    3685                3690                          3695

Pro  Glu  Gln  Val  Arg  Ser  Met  Cys  Thr  Met  Leu  Asp  Glu  Trp  Leu  Gly
               3700                3705                     3710
```

( 2 ) INFORMATION FOR SEQ ID NO:5:

( i ) SEQUENCE CHARACTERISTICS:
        ( A ) LENGTH: 768 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Penicillium chrysogenum ( i x ) FEATURE:
        ( A ) NAME/KEY: Domain
        ( B ) LOCATION: 1..768
        ( D ) OTHER INFORMATION: /label=Domain I
            / note= "Domain I of ACV Synthetase from
            Penicillium chrysogenum; aa 301-1068"

( x i ) SEQUENCE DESCRIPTION: SEQ ID NO:5:

```
Ser Ala Glu Gln Lys Gln Gln Leu Glu Glu Trp Asn Asn Thr Asp Gly
 1               5                  10                  15
Glu Tyr Pro Ser Ser Lys Arg Leu His His Leu Ile Glu Val Val
            20                  25                  30
Glu Arg His Glu Asp Lys Ile Ala Val Val Cys Asp Glu Arg Glu Leu
            35                  40                  45
Thr Tyr Gly Glu Leu Asn Ala Gln Gly Asn Ser Leu Ala Arg Tyr Leu
         50                  55                  60
Arg Ser Ile Gly Ile Leu Pro Glu Gln Leu Val Ala Leu Phe Leu Asp
 65                  70                  75                  80
Lys Ser Glu Lys Leu Ile Val Thr Ile Leu Gly Val Trp Lys Ser Gly
                 85                  90                  95
Ala Ala Tyr Val Pro Ile Asp Pro Thr Tyr Pro Asp Glu Arg Val Arg
                100                 105                 110
Phe Val Leu Asp Asp Thr Lys Ala Arg Ala Ile Ile Ala Ser Asn Gln
            115                 120                 125
His Val Glu Arg Leu Gln Arg Glu Val Ile Gly Asp Arg Asn Leu Cys
        130                 135                 140
Ile Ile Arg Leu Glu Pro Leu Leu Ala Ser Leu Ala Gln Asp Ser Ser
145                 150                 155                 160
Lys Phe Pro Ala His Asn Leu Asp Asp Leu Pro Leu Thr Ser Gln Gln
                165                 170                 175
Leu Ala Tyr Val Thr Tyr Thr Ser Gly Thr Thr Gly Phe Pro Lys Gly
                180                 185                 190
Ile Phe Lys Gln His Thr Asn Val Val Asn Ser Ile Thr Asp Leu Ser
            195                 200                 205
Ala Arg Tyr Gly Val Ala Gly Gln His His Glu Ala Ile Leu Leu Phe
        210                 215                 220
Ser Ala Cys Val Phe Glu Pro Phe Val Arg Gln Thr Leu Met Ala Leu
225                 230                 235                 240
Val Asn Gly His Leu Leu Ala Val Ile Asn Asp Val Glu Lys Tyr Asp
                245                 250                 255
Ala Asp Thr Leu Leu Pro Phe Ile Arg Arg His Ser Ile Thr Tyr Leu
            260                 265                 270
Asn Gly Thr Ala Ser Val Leu Gln Glu Tyr Asp Phe Ser Asp Cys Pro
        275                 280                 285
Ser Leu Asn Arg Ile Ile Leu Val Gly Glu Asn Leu Thr Glu Ala Arg
    290                 295                 300
Tyr Leu Ala Leu Arg Gln Arg Phe Lys Asn Arg Ile Leu Asn Glu Tyr
305                 310                 315                 320
Gly Phe Thr Glu Ser Ala Phe Val Thr Ala Leu Lys Ile Phe Asp Pro
                325                 330                 335
Glu Ser Thr Arg Lys Asp Thr Ser Leu Gly Arg Pro Val Arg Asn Val
            340                 345                 350
Lys Cys Tyr Ile Leu Asn Pro Ser Leu Lys Arg Val Pro Ile Gly Ala
        355                 360                 365
Thr Gly Glu Leu His Ile Gly Gly Leu Gly Ile Ser Lys Gly Tyr Leu
    370                 375                 380
Asn Arg Pro Glu Leu Thr Pro His Arg Phe Ile Pro Asn Pro Phe Gln
385                 390                 395                 400
Thr Asp Cys Glu Lys Gln Leu Gly Ile Asn Ser Leu Met Tyr Lys Thr
                405                 410                 415
```

| | | | | | | | | | | | | | | |
|---|---|---|---|---|---|---|---|---|---|---|---|---|---|---|
| Gly | Asp | Leu | Ala | Arg | Trp | Leu | Pro | Asn | Gly | Glu | Val | Glu | Tyr | Leu | Gly |
| | | | 420 | | | | 425 | | | | | | 430 | | |
| Arg | Ala | Asp | Phe | Gln | Ile | Lys | Leu | Arg | Gly | Ile | Arg | Ile | Glu | Pro | Gly |
| | | 435 | | | | | 440 | | | | | 445 | | | |
| Glu | Ile | Glu | Thr | Met | Leu | Ala | Met | Tyr | Pro | Arg | Val | Arg | Thr | Ser | Leu |
| | 450 | | | | | 455 | | | | | 460 | | | | |
| Val | Val | Ser | Lys | Lys | Leu | Arg | Asn | Gly | Pro | Glu | Thr | Thr | Asn | Glu |
| 465 | | | | | 470 | | | | | 475 | | | | 480 |
| His | Leu | Val | Gly | Tyr | Tyr | Val | Cys | Asp | Ser | Ala | Ser | Val | Ser | Glu | Ala |
| | | | | 485 | | | | | 490 | | | | | 495 | |
| Asp | Leu | Leu | Ser | Phe | Leu | Glu | Lys | Lys | Leu | Pro | Arg | Tyr | Met | Ile | Pro |
| | | | 500 | | | | | 505 | | | | | 510 | | |
| Thr | Arg | Leu | Val | Gln | Leu | Ser | Gln | Ile | Pro | Val | Asn | Val | Asn | Gly | Lys |
| | | 515 | | | | | 520 | | | | | 525 | | | |
| Ala | Asp | Leu | Arg | Ala | Leu | Pro | Ala | Val | Asp | Ile | Ser | Asn | Ser | Thr | Glu |
| | 530 | | | | | 535 | | | | | 540 | | | | |
| Val | Arg | Ser | Asp | Leu | Arg | Gly | Asp | Thr | Glu | Ile | Ala | Leu | Gly | Glu | Ile |
| 545 | | | | | 550 | | | | | 555 | | | | | 560 |
| Trp | Ala | Asp | Val | Leu | Gly | Ala | Arg | Gln | Arg | Ser | Val | Ser | Arg | Asn | Asp |
| | | | | 565 | | | | | 570 | | | | | 575 | |
| Asn | Phe | Phe | Arg | Leu | Gly | Gly | His | Ser | Ile | Thr | Cys | Ile | Gln | Leu | Ile |
| | | | 580 | | | | | 585 | | | | | 590 | | |
| Ala | Arg | Ile | Arg | Gln | Arg | Gln | Arg | Leu | Ser | Val | Ser | Ile | Ser | Val | Glu |
| | | | 595 | | | | | 600 | | | | | 605 | | |
| Asp | Val | Phe | Ala | Thr | Arg | Thr | Leu | Glu | Arg | Met | Ala | Asp | Leu | Leu | Gln |
| | | 610 | | | | | 615 | | | | | 620 | | | |
| Asn | Lys | Gln | Gln | Glu | Lys | Cys | Asp | Lys | Pro | His | Glu | Ala | Pro | Thr | Glu |
| 625 | | | | | 630 | | | | | 635 | | | | | 640 |
| Leu | Leu | Glu | Glu | Asn | Ala | Ala | Thr | Asp | Asn | Ile | Tyr | Leu | Ala | Asn | Ser |
| | | | | 645 | | | | | 650 | | | | | 655 | |
| Leu | Gln | Gln | Gly | Phe | Val | Tyr | His | Tyr | Leu | Lys | Ser | Met | Glu | Gln | Ser |
| | | | | 660 | | | | | 665 | | | | | 670 | |
| Asp | Ala | Tyr | Val | Met | Gln | Ser | Val | Leu | Arg | Tyr | Asn | Thr | Thr | Leu | Ser |
| | | 675 | | | | | 680 | | | | | 685 | | | |
| Pro | Asp | Leu | Phe | Gln | Arg | Ala | Trp | Lys | His | Ala | Gln | Ser | Phe | Pro |
| | 690 | | | | | 695 | | | | | 700 | | | | |
| Ala | Leu | Arg | Leu | Arg | Phe | Ser | Trp | Glu | Lys | Glu | Val | Phe | Gln | Leu | Leu |
| 705 | | | | | 710 | | | | | 715 | | | | | 720 |
| Asp | Gln | Asp | Pro | Pro | Leu | Asp | Trp | Arg | Phe | Leu | Tyr | Phe | Thr | Asp | Val |
| | | | | 725 | | | | | 730 | | | | | 735 | |
| Ala | Ala | Gly | Ala | Val | Glu | Asp | Arg | Lys | Leu | Glu | Asp | Leu | Arg | Arg | Gln |
| | | | 740 | | | | | 745 | | | | | 750 | | |
| Asp | Leu | Thr | Glu | Arg | Phe | Lys | Leu | Asp | Val | Gly | Arg | Leu | Phe | Arg | Val |
| | | 755 | | | | | 760 | | | | | 765 | | | |

( 2 ) INFORMATION FOR SEQ ID NO:6:

( i ) SEQUENCE CHARACTERISTICS:
        ( A ) LENGTH: 758 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal (vi) ORIGINAL SOURCE:
   (A) ORGANISM: Penicillium chrysogenum (ix) FEATURE:
   (A) NAME/KEY: Domain
   (B) LOCATION: 1..758
   (D) OTHER INFORMATION: /label=Domain II
        / note= "Domain II of ACV Synthetase from
        Penicillium chrysogenum; aa 1397-2154"

(xi) SEQUENCE DESCRIPTION: SEQ ID NO:6:

| | | | | | | | | | | | | | | |
|---|---|---|---|---|---|---|---|---|---|---|---|---|---|---|
| Ser | Ser | Ile | Gln | Leu | Glu | Gln | Leu | Ala | Ala | Trp | Asn | Ala | Thr | Glu | Ala |
| 1 | | | | 5 | | | | | 10 | | | | | 15 | |
| Glu | Phe | Pro | Asp | Thr | Thr | Leu | His | Glu | Met | Phe | Glu | Asn | Glu | Ala | Ser |
| | | | 20 | | | | | 25 | | | | | 30 | | |
| Gln | Lys | Pro | Asp | Lys | Ile | Ala | Val | Val | Tyr | Glu | Glu | Thr | Ser | Leu | Thr |
| | | | 35 | | | | 40 | | | | | 45 | | | |
| Tyr | Arg | Glu | Leu | Asn | Glu | Arg | Ala | Asn | Arg | Met | Ala | His | Gln | Leu | Arg |
| | | 50 | | | | | 55 | | | | | 60 | | | |
| Ser | Asp | Val | Ser | Pro | Asn | Pro | Asn | Glu | Val | Ile | Ala | Leu | Val | Met | Asp |
| 65 | | | | | 70 | | | | | 75 | | | | | 80 |
| Lys | Ser | Glu | His | Met | Ile | Val | Asn | Ile | Leu | Ala | Val | Trp | Lys | Ser | Gly |
| | | | | 85 | | | | | 90 | | | | | 95 | |
| Gly | Ala | Tyr | Val | Pro | Ile | Asp | Pro | Gly | Tyr | Pro | Asn | Asp | Arg | Ile | Gln |
| | | | | 100 | | | | | 105 | | | | | 110 | |
| Tyr | Ile | Leu | Glu | Asp | Thr | Gln | Ala | Leu | Ala | Val | Ile | Ala | Asp | Ser | Cys |
| | | | | 115 | | | | | 120 | | | | | 125 | |
| Tyr | Leu | Pro | Arg | Ile | Lys | Gly | Met | Ala | Ala | Ser | Gly | Thr | Leu | Leu | Tyr |
| | | | 130 | | | | | 135 | | | | | 140 | | |
| Pro | Ser | Val | Leu | Pro | Ala | Asn | Pro | Asp | Ser | Lys | Trp | Ser | Val | Ser | Asn |
| 145 | | | | | 150 | | | | | 155 | | | | | 160 |
| Pro | Ser | Pro | Leu | Ser | Arg | Ser | Thr | Asp | Leu | Ala | Tyr | Ile | Ile | Tyr | Thr |
| | | | | 165 | | | | | 170 | | | | | 175 | |
| Ser | Gly | Thr | Thr | Gly | Arg | Pro | Lys | Gly | Val | Thr | Val | Glu | His | His | Gly |
| | | | 180 | | | | | 185 | | | | | 190 | | |
| Val | Val | Asn | Leu | Gln | Val | Ser | Leu | Ser | Lys | Val | Phe | Gly | Leu | Arg | Asp |
| | | 195 | | | | | 200 | | | | | 205 | | | |
| Thr | Asp | Asp | Glu | Val | Ile | Leu | Ser | Phe | Ser | Asn | Tyr | Val | Phe | Asp | His |
| | 210 | | | | | 215 | | | | | 220 | | | | |
| Phe | Val | Glu | Gln | Met | Thr | Asp | Ala | Ile | Leu | Asn | Gly | Gln | Thr | Leu | Leu |
| 225 | | | | | 230 | | | | | 235 | | | | | 240 |
| Val | Leu | Asn | Asp | Gly | Met | Arg | Gly | Asp | Lys | Glu | Arg | Leu | Tyr | Arg | Tyr |
| | | | | 245 | | | | | 250 | | | | | 255 | |
| Ile | Glu | Lys | Asn | Arg | Val | Thr | Tyr | Leu | Ser | Gly | Thr | Pro | Ser | Val | Val |
| | | | 260 | | | | | 265 | | | | | 270 | | |
| Ser | Met | Tyr | Glu | Phe | Ser | Arg | Phe | Lys | Asp | His | Leu | Arg | Arg | Val | Asp |
| | | 275 | | | | | 280 | | | | | 285 | | | |
| Cys | Val | Gly | Glu | Ala | Phe | Ser | Glu | Pro | Val | Phe | Asp | Lys | Ile | Arg | Glu |
| | 290 | | | | | 295 | | | | | 300 | | | | |
| Thr | Phe | His | Gly | Leu | Val | Ile | Asn | Gly | Tyr | Gly | Pro | Thr | Glu | Val | Ser |
| 305 | | | | | 310 | | | | | 315 | | | | | 320 |
| Ile | Thr | Thr | His | Lys | Arg | Leu | Tyr | Pro | Phe | Pro | Glu | Arg | Arg | Met | Asp |
| | | | | 325 | | | | | 330 | | | | | 335 | |
| Lys | Ser | Ile | Gly | Gln | Gln | Val | His | Asn | Ser | Thr | Ser | Tyr | Val | Leu | Asn |
| | | | 340 | | | | | 345 | | | | | 350 | | |
| Glu | Asp | Met | Lys | Arg | Thr | Pro | Ile | Gly | Ala | Val | Gly | Glu | Leu | Tyr | Leu |
| | | 355 | | | | | 360 | | | | | 365 | | | |

```
Gly  Gly  Glu  Gly  Val  Val  Arg  Gly  Tyr  His  Asn  Arg  Ala  Asp  Val  Thr
370                      375                 380

Ala  Glu  Arg  Phe  Ile  Pro  Asn  Pro  Phe  Gln  Ser  Glu  Glu  Asp  Lys  Arg
385                      390                 395                          400

Glu  Gly  Arg  Asn  Ser  Arg  Leu  Tyr  Lys  Thr  Gly  Asp  Leu  Val  Arg  Trp
                    405                 410                          415

Ile  Pro  Gly  Ser  Ser  Gly  Glu  Val  Glu  Tyr  Leu  Gly  Arg  Asn  Asp  Phe
               420                 425                          430

Gln  Val  Lys  Ile  Arg  Gly  Leu  Arg  Ile  Glu  Leu  Gly  Glu  Ile  Glu  Ala
               435                 440                 445

Ile  Leu  Ser  Ser  Tyr  His  Gly  Ile  Lys  Gln  Ser  Val  Val  Ile  Ala  Lys
450                      455                 460

Asp  Cys  Arg  Glu  Gly  Ala  Gln  Lys  Phe  Leu  Val  Gly  Tyr  Tyr  Val  Ala
465                      470                 475                          480

Asp  Ala  Ala  Leu  Pro  Ser  Ala  Ala  Ile  Arg  Arg  Phe  Met  Gln  Ser  Arg
                    485                 490                          495

Leu  Pro  Gly  Tyr  Met  Val  Pro  Ser  Arg  Leu  Ile  Leu  Val  Ser  Lys  Phe
               500                 505                          510

Pro  Val  Thr  Pro  Ser  Gly  Lys  Leu  Asp  Thr  Lys  Ala  Leu  Pro  Pro  Ala
               515                 520                 525

Glu  Glu  Ser  Glu  Ile  Asp  Val  Val  Pro  Pro  Arg  Ser  Glu  Ile  Glu
530                      535                 540

Arg  Ser  Leu  Cys  Asp  Ile  Trp  Ala  Glu  Leu  Leu  Glu  Met  His  Pro  Glu
545                 550                 555                               560

Glu  Ile  Gly  Ile  Tyr  Ser  Asp  Phe  Phe  Ser  Leu  Gly  Gly  Asp  Ser  Leu
               565                 570                          575

Lys  Ser  Thr  Lys  Leu  Ser  Phe  Met  Ile  His  Glu  Ser  Phe  Asn  Arg  Ala
               580                 585                          590

Val  Ser  Val  Ser  Ala  Leu  Phe  Cys  His  Arg  Thr  Val  Glu  Ala  Gln  Thr
               595                 600                 605

His  Leu  Ile  Leu  Asn  Asp  Ala  Ala  Asp  Val  His  Glu  Ile  Thr  Pro  Ile
     610                      615                 620

Asp  Cys  Asn  Asp  Thr  Gln  Met  Ile  Pro  Val  Ser  Arg  Ala  Gln  Glu  Arg
625                      630                 635                          640

Leu  Leu  Phe  Ile  His  Glu  Phe  Glu  Asn  Gly  Ser  Asn  Ala  Tyr  Asn  Ile
               645                 650                          655

Asp  Ala  Ala  Phe  Glu  Leu  Pro  Gly  Ser  Val  Asp  Ala  Ser  Leu  Leu  Glu
               660                 665                          670

Gln  Ala  Leu  Arg  Gly  Asn  Leu  Ala  Arg  His  Glu  Ala  Leu  Arg  Thr  Leu
          675                 680                 685

Leu  Val  Lys  Asp  His  Ala  Thr  Gly  Ile  Tyr  Leu  Gln  Lys  Val  Leu  Ser
690                      695                 700

Pro  Asp  Glu  Ala  Gln  Gly  Met  Phe  Ser  Val  Asn  Val  Asp  Thr  Ala  Lys
705                      710                 715                          720

Gln  Val  Glu  Arg  Leu  Asp  Gln  Glu  Ile  Ala  Ser  Leu  Ser  Gln  His  Val
                    725                 730                 735

Phe  Arg  Leu  Asp  Asp  Glu  Leu  Pro  Trp  Glu  Ala  Arg  Ile  Leu  Lys  Leu
                    740                 745                 750

Glu  Ser  Gly  Gly  Leu  Tyr
               755
```

( 2 ) INFORMATION FOR SEQ ID NO:7:

( i ) SEQUENCE CHARACTERISTICS:

(A) LENGTH: 822 amino acids
(B) TYPE: amino acid
(C) STRANDEDNESS: single
(D) TOPOLOGY: linear (ii) MOLECULE TYPE: peptide (v) FRAGMENT TYPE: internal (vi) ORIGINAL SOURCE:
(A) ORGANISM: Penicillium chrysogenum (ix) FEATURE:
(A) NAME/KEY: Domain
(B) LOCATION: 1..822
(D) OTHER INFORMATION: /label=Domain III
/ note= "Domain III of ACV Synthetase from Penicillium chrysogenum; aa 2474-3295"

(xi) SEQUENCE DESCRIPTION: SEQ ID NO:7:

```
Arg Pro Thr Glu Asn Gly Asp Leu His Leu Pro Leu Ala Gln Ser Pro
1               5                   10                  15
Leu Ala Thr Thr Ala Glu Glu Gln Lys Val Ala Ser Leu Asn Gln Ala
            20                  25                  30
Phe Glu Arg Glu Ala Phe Leu Ala Glu Lys Ile Ala Val Val Gln
        35                  40                  45
Gly Asp Arg Ala Leu Ser Tyr Ala Asp Leu Asn Gly Gln Ala Asn Gln
    50                  55                  60
Leu Ala Arg Tyr Ile Gln Ser Val Ser Cys Ile Gly Ala Asp Asp Gly
65                  70                  75                  80
Ile Ala Leu Met Leu Glu Lys Ser Ile Asp Thr Ile Ile Cys Ile Leu
                85                  90                  95
Ala Ile Trp Lys Ala Gly Ala Ala Tyr Val Pro Leu Asp Pro Thr Tyr
            100                 105                 110
Pro Pro Gly Arg Val Gln Leu Ile Leu Glu Glu Ile Lys Ala Lys Ala
        115                 120                 125
Val Leu Val His Ser Ser His Ala Ser Lys Cys Glu Arg His Gly Ala
    130                 135                 140
Lys Val Ile Ala Val Asp Ser Pro Ala Ile Glu Thr Ala Val Ser Gln
145                 150                 155                 160
Gln Ser Ala Ala Asp Leu Pro Thr Ile Ala Ser Leu Gly Asn Leu Ala
                165                 170                 175
Tyr Ile Ile Phe Thr Ser Gly Thr Ser Gly Lys Pro Lys Gly Val Leu
            180                 185                 190
Val Glu Gln Lys Ala Val Leu Leu Leu Arg Asp Ala Leu Arg Glu Arg
        195                 200                 205
Tyr Phe Gly Arg Asp Cys Thr Lys His His Gly Val Leu Phe Leu Ser
    210                 215                 220
Asn Tyr Val Phe Asp Phe Ser Val Glu Gln Leu Val Leu Ser Val Leu
225                 230                 235                 240
Ser Gly His Lys Leu Ile Val Pro Pro Ala Glu Phe Val Ala Asp Asp
                245                 250                 255
Glu Phe Tyr Arg Met Ala Ser Thr His Gly Leu Ser Tyr Leu Ser Gly
            260                 265                 270
Thr Pro Ser Leu Leu Gln Lys Ile Asp Leu Ala Arg Leu Asp His Leu
        275                 280                 285
Gln Val Val Thr Ala Ala Gly Glu Glu Leu His Ala Thr Gln Tyr Glu
    290                 295                 300
Lys Met Arg Arg Arg Phe Asn Gly Pro Ile Tyr Asn Ala Tyr Gly Val
305                 310                 315                 320
```

-continued

```
Thr  Glu  Thr  Thr  Val  Tyr  Asn  Ile  Ile  Ala  Glu  Phe  Thr  Thr  Asn  Ser
               325                      330                     335

Ile  Phe  Glu  Asn  Ala  Leu  Arg  Glu  Val  Leu  Pro  Gly  Thr  Arg  Ala  Tyr
               340                      345                     350

Val  Leu  Asn  Ala  Ala  Leu  Gln  Pro  Val  Pro  Phe  Asp  Ala  Val  Gly  Glu
               355                      360                     365

Leu  Tyr  Leu  Ala  Gly  Asp  Thr  Val  Thr  Arg  Gly  Tyr  Leu  Asn  Gln  Pro
          370                      375                     380

Leu  Leu  Thr  Asp  Gln  Arg  Phe  Ile  Pro  Asn  Pro  Phe  Cys  Lys  Glu  Glu
385                      390                     395                     400

Asp  Ile  Ala  Met  Gly  Arg  Phe  Ala  Arg  Leu  Tyr  Lys  Thr  Gly  Asp  Leu
                    405                     410                     415

Val  Arg  Ser  Arg  Phe  Asn  Arg  Gln  Gln  Gln  Pro  Gln  Leu  Glu  Tyr  Leu
               420                      425                     430

Gly  Arg  Gly  Asp  Leu  Gln  Ile  Lys  Met  Arg  Gly  Tyr  Arg  Ile  Glu  Ile
               435                      440                     445

Ser  Glu  Val  Gln  Asn  Val  Leu  Thr  Ser  Ser  Pro  Gly  Val  Arg  Glu  Gly
          450                      455                     460

Ala  Val  Val  Ala  Lys  Tyr  Glu  Asn  Asn  Asp  Thr  Tyr  Ser  Arg  Thr  Ala
465                      470                     475                     480

His  Ser  Leu  Val  Gly  Tyr  Tyr  Thr  Thr  Asp  Asn  Glu  Thr  Val  Ser  Glu
                    485                     490                     495

Ala  Asp  Ile  Leu  Thr  Phe  Met  Lys  Ala  Arg  Leu  Pro  Thr  Tyr  Met  Val
                    500                     505                     510

Pro  Ser  His  Leu  Cys  Cys  Leu  Glu  Gly  Ala  Leu  Pro  Val  Thr  Ile  Asn
               515                      520                     525

Gly  Lys  Leu  Asp  Val  Arg  Arg  Leu  Pro  Glu  Ile  Ile  Asn  Asp  Ser  Ala
          530                      535                     540

Gln  Ser  Ser  Tyr  Ser  Pro  Pro  Arg  Asn  Ile  Ile  Glu  Ala  Lys  Met  Cys
545                      550                     555                     560

Arg  Leu  Trp  Glu  Ser  Ala  Leu  Gly  Met  Glu  Arg  Cys  Gly  Ile  Asp  Asp
                    565                     570                     575

Asp  Leu  Phe  Lys  Leu  Gly  Gly  Asp  Ser  Ile  Thr  Ser  Leu  His  Leu  Val
               580                      585                     590

Ala  Gln  Ile  His  Asn  Gln  Val  Gly  Cys  Lys  Ile  Thr  Val  Arg  Asp  Ile
               595                      600                     605

Phe  Glu  His  Arg  Thr  Ala  Arg  Ala  Leu  His  Asp  His  Val  Phe  Met  Lys
          610                      615                     620

Asp  Ser  Asp  Arg  Ser  Asn  Val  Thr  Gln  Phe  Arg  Thr  Glu  Gln  Gly  Pro
625                      630                     635                     640

Val  Ile  Gly  Glu  Ala  Pro  Leu  Leu  Pro  Ile  Gln  Asp  Trp  Phe  Leu  Ser
                    645                     650                     655

Lys  Ala  Leu  Gln  His  Pro  Met  Tyr  Trp  Asn  His  Thr  Phe  Tyr  Val  Arg
               660                      665                     670

Thr  Pro  Glu  Leu  Asp  Val  Asp  Ser  Leu  Ser  Ala  Ala  Val  Arg  Asp  Leu
          675                      680                     685

Gln  Gln  Tyr  His  Asp  Val  Phe  Arg  Met  Arg  Leu  Lys  Arg  Glu  Glu  Val
          690                      695                     700

Gly  Phe  Val  Gln  Ser  Phe  Ala  Glu  Asp  Phe  Ser  Pro  Ala  Gln  Leu  Arg
705                      710                     715                     720

Val  Leu  Asn  Val  Lys  Asp  Val  Asp  Gly  Ser  Ala  Ala  Val  Asn  Glu  Ile
               725                      730                     735

Leu  Asp  Gly  Trp  Gln  Ser  Gly  Phe  Asn  Leu  Glu  Asn  Gly  Pro  Ile  Gly
```

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 740 |     |     |     | 745 |     |     |     | 750 |     |     |
| Ser | Ile | Gly | Tyr | Leu | His | Gly | Tyr | Glu | Asp | Arg | Ser | Ala | Arg | Val | Trp |
|     |     | 755 |     |     |     |     |     | 760 |     |     |     | 765 |     |     |     |
| Phe | Ser | Val | His | His | Met | Ala | Ile | Asp | Thr | Val | Ser | Trp | Gln | Ile | Leu |
|     | 770 |     |     |     |     | 775 |     |     |     |     | 780 |     |     |     |     |
| Val | Arg | Asp | Leu | Gln | Thr | Leu | Tyr | Arg | Asn | Gly | Ser | Leu | Gly | Ser | Lys |
| 785 |     |     |     |     | 790 |     |     |     |     | 795 |     |     |     |     | 800 |
| Gly | Ser | Ser | Phe | Arg | Gln | Trp | Ala | Glu | Ala | Ile | Gln | Asn | Tyr | Lys | Ala |
|     |     |     |     | 805 |     |     |     | 810 |     |     |     |     |     | 815 |     |
| Ser | Asp | Ser | Glu | Arg | Asn |     |     |     |     |     |     |     |     |     |     |
|     |     |     | 820 |     |     |     |     |     |     |     |     |     |     |     |     |

(2) INFORMATION FOR SEQ ID NO:8:

(i) SEQUENCE CHARACTERISTICS:
        (A) LENGTH: 798 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) ORIGINAL SOURCE:
        (A) ORGANISM: Bacillus brevis (xi) SEQUENCE DESCRIPTION: SEQ ID NO:8:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Leu | Ala | Asn | Gln | Ala | Asn | Leu | Ile | Asp | Asn | Lys | Arg | Glu | Leu | Glu |
| 1   |     |     |     | 5   |     |     |     |     | 10  |     |     |     |     | 15  |     |
| Gln | His | Ala | Leu | Val | Pro | Tyr | Ala | Gln | Gly | Lys | Ser | Ile | His | Gln | Leu |
|     |     |     | 20  |     |     |     |     | 25  |     |     |     |     | 30  |     |     |
| Phe | Glu | Glu | Gln | Ala | Glu | Ala | Phe | Pro | Asp | Arg | Val | Ala | Ile | Val | Phe |
|     |     | 35  |     |     |     |     | 40  |     |     |     |     | 45  |     |     |     |
| Glu | Asn | Arg | Arg | Leu | Ser | Tyr | Gln | Glu | Leu | Asn | Arg | Lys | Ala | Asn | Gln |
|     | 50  |     |     |     |     | 55  |     |     |     |     | 60  |     |     |     |     |
| Leu | Ala | Arg | Ala | Leu | Leu | Glu | Lys | Gly | Val | Gln | Thr | Asp | Ser | Ile | Val |
| 65  |     |     |     |     | 70  |     |     |     |     | 75  |     |     |     |     | 80  |
| Gly | Val | Met | Met | Glu | Lys | Ser | Ile | Glu | Asn | Val | Ile | Ala | Ile | Leu | Ala |
|     |     |     |     | 85  |     |     |     |     | 90  |     |     |     |     | 95  |     |
| Val | Leu | Lys | Ala | Gly | Gly | Ala | Tyr | Val | Pro | Ile | Asp | Ile | Glu | Tyr | Pro |
|     |     |     | 100 |     |     |     |     | 105 |     |     |     |     | 110 |     |     |
| Arg | Asp | Arg | Ile | Gln | Tyr | Ile | Leu | Gln | Asp | Ser | Gln | Thr | Lys | Ile | Val |
|     |     |     | 115 |     |     |     |     | 120 |     |     |     |     | 125 |     |     |
| Leu | Thr | Gln | Lys | Ser | Val | Ser | Gln | Leu | Val | His | Asp | Val | Gly | Tyr | Ser |
|     | 130 |     |     |     |     | 135 |     |     |     |     | 140 |     |     |     |     |
| Gly | Glu | Val | Val | Val | Leu | Asp | Glu | Glu | Gln | Leu | Asp | Ala | Arg | Glu | Thr |
| 145 |     |     |     |     | 150 |     |     |     |     | 155 |     |     |     |     | 160 |
| Ala | Asn | Leu | His | Gln | Pro | Ser | Lys | Pro | Thr | Asp | Leu | Ala | Tyr | Val | Ile |
|     |     |     |     | 165 |     |     |     |     | 170 |     |     |     |     | 175 |     |
| Tyr | Thr | Ser | Gly | Thr | Thr | Gly | Lys | Pro | Lys | Gly | Thr | Met | Leu | Glu | His |
|     |     |     |     | 180 |     |     |     |     | 185 |     |     |     |     | 190 |     |
| Lys | Gly | Ile | Ala | Ile | Cys | Asn | Pro | Phe | Ser | Lys | Ile | Arg | Leu | Ala | Ser |
|     |     |     | 195 |     |     |     |     | 200 |     |     |     |     | 205 |     |     |
| Pro | Ser | Lys | Thr | Gly | Ser | Gly | Phe | Leu | Pro | Ala | Cys | Arg | Ser | Thr | His |
|     |     |     | 210 |     |     |     |     | 215 |     |     |     |     | 220 |     |     |
| Pro | Phe | Gly | Lys | Cys | Ser | Trp | Leu | Cys | Cys | Leu | Ala | Pro | Arg | Val | His |

```
                225                      230                     235                       240
Pro  Ser  Lys  Gln  Thr  Ile  His  Asp  Phe  Ala  Phe  Glu  His  Tyr  Leu
                    245                      250                     255
Ser  Glu  Asn  Glu  Leu  Thr  Ile  Ile  Thr  Leu  Pro  Pro  Thr  Tyr  Leu  Thr
                    260                      265                     270
His  Leu  Thr  Pro  Glu  Arg  Ile  Thr  Ser  Leu  Arg  Ile  Met  Ile  Thr  Ala
                    275                      280                     285
Gly  Ser  Ala  Ser  Ser  Ala  Pro  Leu  Val  Asn  Lys  Trp  Lys  Asp  Lys  Leu
          290                      295                     300
Arg  Tyr  Ile  Asn  Ala  Tyr  Gly  Pro  Thr  Glu  Thr  Ser  Ile  Cys  Ala  Thr
305                      310                     315                      320
Ile  Trp  Glu  Ala  Pro  Ser  Asn  Gln  Leu  Ser  Val  Gln  Ser  Val  Pro  Ile
                    325                      330                     335
Gly  Lys  Pro  Ile  Gln  Asn  Thr  His  Ile  Tyr  Ile  Val  Asn  Glu  Asp  Leu
                    340                      345                     350
Gln  Leu  Leu  Pro  Thr  Ala  Asp  Glu  Gly  Glu  Leu  Cys  Ile  Gly  Gly  Val
                    355                      360                     365
Gly  Leu  Ala  Arg  Gly  Tyr  Trp  Asn  Arg  Pro  Asp  Leu  Thr  Ala  Glu  Lys
          370                      375                     380
Phe  Val  Asp  Asn  Pro  Phe  Val  Pro  Gly  Glu  Lys  Met  Tyr  Arg  Thr  Gly
385                      390                     395                      400
Asp  Leu  Ala  Lys  Trp  Leu  Thr  Asp  Gly  Thr  Ile  Glu  Phe  Leu  Gly  Arg
                    405                      410                     415
Ile  Asp  His  Gln  Val  Lys  Ile  Arg  Gly  His  Arg  Ile  Glu  Leu  Gly  Glu
                    420                      425                     430
Ile  Glu  Ser  Val  Leu  Leu  Ala  His  Glu  His  Ile  Thr  Glu  Ala  Val  Val
          435                      440                     445
Ile  Ala  Arg  Glu  Asp  Gln  His  Ala  Gly  Gln  Tyr  Leu  Cys  Ala  Tyr  Tyr
450                      455                     460
Ile  Ser  Gln  Gln  Glu  Ala  Thr  Pro  Ala  Gln  Leu  Arg  Asp  Tyr  Ala  Ala
465                      470                     475                      480
Gln  Lys  Leu  Pro  Ala  Tyr  Met  Leu  Pro  Ser  Tyr  Phe  Val  Lys  Leu  Asp
                    485                      490                     495
Lys  Met  Pro  Leu  Thr  Pro  Asn  Asp  Lys  Ile  Asp  Arg  Lys  Ala  Leu  Pro
                    500                      505                     510
Glu  Pro  Asp  Leu  Thr  Ala  Asn  Gln  Ser  Gln  Ala  Ala  Tyr  His  Pro  Pro
                    515                      520                     525
Arg  Thr  Glu  Thr  Glu  Ser  Ile  Leu  Val  Ser  Ile  Trp  Gln  Asn  Val  Leu
          530                      535                     540
Gly  Ile  Glu  Lys  Ile  Gly  Ile  Arg  Asp  Asn  Phe  Tyr  Ser  Leu  Gly  Gly
545                      550                     555                      560
Asp  Ser  Ile  Gln  Ala  Ile  Gln  Val  Val  Ala  Arg  Leu  His  Ser  Tyr  Gln
                    565                      570                     575
Leu  Lys  Leu  Glu  Thr  Lys  Asp  Leu  Leu  Asn  Tyr  Pro  Thr  Ile  Glu  Gln
                    580                      585                     590
Val  Ala  Leu  Phe  Val  Lys  Ser  Thr  Thr  Arg  Lys  Ser  Asp  Gln  Gly  Ile
                    595                      600                     605
Ile  Ala  Gly  Asn  Val  Pro  Leu  Thr  Pro  Ile  Gln  Lys  Trp  Phe  Phe  Gly
          610                      615                     620
Lys  Asn  Phe  Thr  Asn  Thr  Gly  His  Trp  Asn  Gln  Ser  Ser  Val  Leu  Tyr
625                      630                     635                      640
Arg  Pro  Glu  Gly  Phe  Asp  Pro  Lys  Val  Ile  Gln  Ser  Val  Met  Asp  Lys
                    645                      650                     655
```

| | | | | | | | | | | | | | | | |
|---|---|---|---|---|---|---|---|---|---|---|---|---|---|---|---|
| Ile | Ile | Glu | His 660 | His | Asp | Ala | Val | Arg 665 | Met | Val | Tyr | Gln | His 670 | Glu | Asn |
| Gly | Asn | Val 675 | Val | Gln | His | Asn | Arg 680 | Gly | Leu | Gly | Gly | Gln 685 | Leu | Tyr | Asp |
| Phe | Phe 690 | Ser | Tyr | Asn | Leu | Thr 695 | Ala | Gln | Pro | Asp | Val 700 | Gln | Gln | Ala | Ile |
| Glu 705 | Ala | Glu | Thr | Gln | Arg 710 | Leu | His | Ser | Ser | Met 715 | Asn | Leu | Gln | Glu | Gly 720 |
| Pro | Leu | Val | Lys | Val 725 | Ala | Leu | Phe | Gln | Thr 730 | Leu | His | Gly | Asp | His 735 | Phe |
| Phe | Leu | Ala | Ile 740 | His | His | Leu | Val | Val 745 | Asp | Gly | Ile | Ser | Trp 750 | Arg | Ile |
| Leu | Phe | Lys 755 | Ile | Trp | Gln | Pro | Asp 760 | Thr | Arg | Arg | His | Leu 765 | Gln | Gly | Lys |
| Arg | Ser 770 | Val | Cys | Pro | Lys | Lys 775 | Arg | Ile | Leu | Phe | Lys 780 | Ala | Gly | His | Asn |
| Gly 785 | Cys | Lys | Asn | Asn | Ala 790 | Asn | Glu | Ala | Asp | Leu 795 | Leu | Ser | Glu | | |

( 2 ) INFORMATION FOR SEQ ID NO:9:

( i ) SEQUENCE CHARACTERISTICS:
        ( A ) LENGTH: 797 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Bacillus brevis ( i x ) FEATURE:
        ( A ) NAME/KEY: Region
        ( B ) LOCATION: 1..797
        ( D ) OTHER INFORMATION: /label=Homology
            / note= "Homologous region from Gramicidine
            Synthetase of Bacillus brevis; aa 13-809 "

( x i ) SEQUENCE DESCRIPTION: SEQ ID NO:9:

| | | | | | | | | | | | | | | | |
|---|---|---|---|---|---|---|---|---|---|---|---|---|---|---|---|
| Gln 1 | Asn | Lys | Asn | Gly 5 | Thr | His | Glu | Glu | Glu 10 | Gln | Tyr | Leu | Phe | Ala 15 | Val |
| Asn | Asn | Thr | Lys 20 | Ala | Glu | Tyr | Pro | Arg 25 | Asp | Lys | Thr | Ile | His 30 | Gln | Leu |
| Phe | Glu | Glu 35 | Gln | Val | Ser | Lys | Arg 40 | Pro | Asn | Asn | Val | Ala 45 | Ile | Val | Cys |
| Glu | Asn 50 | Glu | Gln | Leu | Thr | Tyr 55 | His | Glu | Leu | Asn | Val 60 | Lys | Ala | Asn | Gln |
| Leu 65 | Ala | Arg | Ile | Phe | Ile 70 | Glu | Lys | Gly | Ile | Gly 75 | Lys | Asp | Thr | Leu | Val 80 |
| Gly | Ile | Met | Met | Glu 85 | Lys | Ser | Ile | Asp | Leu 90 | Phe | Ile | Gly | Ile | Leu 95 | Ala |
| Val | Leu | Lys | Ala 100 | Gly | Gly | Ala | Tyr | Val 105 | Pro | Ile | Asp | Ile | Glu 110 | Tyr | Pro |
| Lys | Glu | Arg 115 | Ile | Gln | Tyr | Ile | Leu 120 | Asp | Asp | Ser | Gln | Ala 125 | Arg | Met | Leu |
| Leu | Thr 130 | Gln | Lys | His | Leu | Val 135 | His | Leu | Ile | His | Asn 140 | Ile | Gln | Phe | Asn |

```
Gly  Gln  Val  Glu  Ile  Phe  Glu  Glu  Asp  Thr  Ile  Lys  Ile  Arg  Glu  Gly
145                 150                      155                           160

Thr  Asn  Leu  His  Val  Pro  Ser  Lys  Ser  Thr  Asp  Leu  Ala  Tyr  Val  Ile
                    165                      170                      175

Tyr  Thr  Ser  Gly  Thr  Thr  Gly  Asn  Pro  Lys  Gly  Thr  Met  Leu  Glu  His
               180                      185                      190

Lys  Gly  Ile  Ser  Asn  Leu  Lys  Val  Phe  Phe  Glu  Asn  Ser  Leu  Asn  Val
               195                 200                      205

Thr  Glu  Lys  Asp  Arg  Ile  Gly  Gln  Phe  Ala  Ser  Ile  Ser  Phe  Asp  Ala
          210                 215                      220

Ser  Val  Trp  Glu  Met  Phe  Met  Ala  Leu  Leu  Thr  Gly  Ala  Ser  Leu  Tyr
225                      230                 235                           240

Ile  Ile  Leu  Lys  Asp  Thr  Ile  Asn  Asp  Phe  Val  Lys  Phe  Glu  Gln  Tyr
               245                      250                           255

Ile  Asn  Gln  Lys  Glu  Ile  Thr  Val  Ile  Thr  Leu  Pro  Pro  Thr  Ile  Val
               260                 265                      270

Val  His  Leu  Asp  Pro  Glu  Arg  Ile  Leu  Ser  Ile  Gln  Thr  Leu  Ile  Thr
          275                      280                      285

Ala  Gly  Ser  Ala  Thr  Ser  Pro  Ser  Leu  Val  Asn  Lys  Trp  Lys  Glu  Lys
     290                      295                 300

Val  Thr  Tyr  Ile  Asn  Ala  Tyr  Gly  Pro  Thr  Glu  Thr  Thr  Ile  Cys  Ala
305                      310                 315                           320

Thr  Thr  Trp  Val  Ala  Thr  Lys  Glu  Thr  Ile  Gly  His  Ser  Val  Pro  Ile
               325                      330                           335

Gly  Ala  Pro  Ile  Gln  Asn  Thr  Gln  Ile  Tyr  Ile  Val  Asp  Glu  Asn  Leu
               340                      345                      350

Gln  Leu  Lys  Ser  Val  Gly  Glu  Ala  Gly  Glu  Leu  Cys  Ile  Gly  Gly  Glu
               355                      360                 365

Gly  Leu  Ala  Arg  Gly  Tyr  Trp  Lys  Arg  Pro  Glu  Leu  Thr  Ser  Gln  Lys
               370                      375                 380

Phe  Val  Asp  Asn  Pro  Phe  Val  Pro  Gly  Glu  Lys  Leu  Tyr  Lys  Thr  Gly
385                      390                      395                      400

Asp  Gln  Ala  Arg  Trp  Leu  Ser  Asp  Gly  Asn  Ile  Glu  Tyr  Leu  Gly  Arg
                    405                      410                           415

Ile  Asp  Asn  Gln  Val  Lys  Ile  Arg  Gly  His  Arg  Val  Glu  Leu  Glu  Glu
               420                      425                      430

Val  Glu  Ser  Ile  Leu  Leu  Lys  His  Met  Tyr  Ile  Ser  Glu  Thr  Ala  Val
          435                      440                 445

Ser  Val  His  Lys  Asp  His  Gln  Glu  Gln  Pro  Tyr  Leu  Cys  Ala  Tyr  Phe
     450                      455                      460

Val  Ser  Glu  Lys  His  Ile  Pro  Leu  Glu  Gln  Leu  Arg  Gln  Phe  Ser  Ser
465                      470                      475                      480

Glu  Glu  Leu  Pro  Thr  Tyr  Met  Ile  Pro  Ser  Tyr  Phe  Ile  Gln  Leu  Asp
               485                      490                           495

Lys  Met  Pro  Leu  Thr  Ser  Asn  Gly  Lys  Ile  Asp  Arg  Lys  Gln  Leu  Pro
               500                      505                      510

Glu  Pro  Asp  Leu  Thr  Phe  Gly  Met  Arg  Val  Asp  Tyr  Glu  Ala  Pro  Arg
               515                      520                      525

Asn  Glu  Ile  Glu  Glu  Thr  Leu  Val  Thr  Ile  Trp  Gln  Asp  Val  Leu  Gly
          530                      535                 540

Ile  Glu  Lys  Ile  Gly  Ile  Lys  Asp  Asn  Phe  Tyr  Ala  Leu  Gly  Gly  Asp
545                      550                      555                      560

Ser  Ile  Lys  Ala  Ile  Gln  Val  Ala  Ala  Arg  Leu  His  Ser  Tyr  Gln  Leu
```

|     |     |     |     | 565 |     |     |     | 570 |     |     |     | 575 |     |     |
| --- | --- | --- | --- | --- | --- | --- | --- | --- | --- | --- | --- | --- | --- | --- |
| Lys | Leu | Glu | Thr<br>580 | Lys | Asp | Leu | Leu | Lys<br>585 | Tyr | Pro | Thr | Ile | Asp<br>590 | Gln | Leu |
| Val | His | Tyr<br>595 | Ile | Lys | Asp | Ser | Lys<br>600 | Arg | Arg | Ser | Glu | Gln<br>605 | Gly | Ile | Val |
| Glu | Gly<br>610 | Glu | Ile | Gly | Leu | Thr<br>615 | Pro | Ile | Gln | His | Trp<br>620 | Phe | Phe | Glu | Gln |
| Gln<br>625 | Phe | Thr | Asn | Met | His<br>630 | His | Trp | Asn | Gln | Ser<br>635 | Tyr | Met | Leu | Tyr | Arg<br>640 |
| Pro | Asn | Gly | Phe | Asp<br>645 | Lys | Glu | Ile | Leu | Leu<br>650 | Arg | Val | Phe | Asn | Lys<br>655 | Ile |
| Val | Glu | His | His<br>660 | Asp | Ala | Leu | Arg | Met<br>665 | Ile | Tyr | Lys | His | His<br>670 | Asn | Gly |
| Lys | Ile | Val<br>675 | Gln | Ile | Asn | Arg | Gly<br>680 | Leu | Glu | Gly | Thr | Leu<br>685 | Phe | Asp | Phe |
| Tyr | Thr<br>690 | Phe | Asp | Leu | Thr | Ala<br>695 | Asn | Asp | Asn | Glu | Gln<br>700 | Gln | Val | Ile | Cys |
| Glu<br>705 | Glu | Ser | Ala | Arg | Leu<br>710 | Gln | Asn | Ser | Ile | Asn<br>715 | Leu | Glu | Val | Gly | Pro<br>720 |
| Leu | Val | Lys | Ile | Ala<br>725 | Leu | Phe | His | Thr | Gln<br>730 | Asn | Gly | Asp | His | Leu<br>735 | Phe |
| Met | Ala | Ile | His<br>740 | His | Leu | Val | Val | Asp<br>745 | Gly | Ile | Ser | Trp | Arg<br>750 | Ile | Leu |
| Phe | Glu | Asp<br>755 | Leu | Ala | Thr | Ala | Tyr<br>760 | Glu | Gln | Ala | Met | His<br>765 | Gln | Gln | Thr |
| Ile | Ala | Leu<br>770 | Pro | Glu | Lys | Thr<br>775 | Asp | Ser | Phe | Lys | Asp<br>780 | Trp | Ser | Ile | Glu |
| Leu<br>785 | Glu | Lys | Tyr | Ala | Asn<br>790 | Ser | Glu | Leu | Phe | Leu<br>795 | Glu | Glu |     |     |     |

( 2 ) INFORMATION FOR SEQ ID NO:10:

( i ) SEQUENCE CHARACTERISTICS:
        ( A ) LENGTH: 85 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Penicillium chrysogenum ( i x ) FEATURE:
        ( A ) NAME/KEY: Domain
        ( B ) LOCATION: 1..85
        ( D ) OTHER INFORMATION: /label=DomainIV
            / note= "Domain IV of ACV Synthetase from
            Penicillium chrysogenum; aa 3563-3647"

( x i ) SEQUENCE DESCRIPTION: SEQ ID NO:10:

| Leu<br>1 | Phe | Leu | Leu | Pro<br>5 | Pro | Gly | Glu | Gly | Gly<br>10 | Ala | Glu | Ser | Tyr | Phe<br>15 | Asn |
| --- | --- | --- | --- | --- | --- | --- | --- | --- | --- | --- | --- | --- | --- | --- | --- |
| Asn | Ile | Val | Lys<br>20 | Arg | Leu | Arg | Gln | Thr<br>25 | Asn | Met | Val | Val | Phe<br>30 | Asn | Asn |
| Tyr | Tyr | Leu | His | Ser | Lys | Arg | Leu | Arg | Thr | Phe | Glu | Glu | Leu | Ala | Glu |

|   | 35 | | | | 40 | | | | | 45 | | | |
|---|---|---|---|---|---|---|---|---|---|---|---|---|---|

Met Tyr Leu Asp Gln Val Arg Gly Ile Gln Pro His Gly Pro Tyr His
    50                        55                            60

Phe Ile Gly Trp Ser Phe Gly Gly Ile Leu Ala Met Glu Met Ser Arg
65                        70                        75                      80

Arg Leu Val Ala Ser
              85

( 2 ) INFORMATION FOR SEQ ID NO:11:

( i ) SEQUENCE CHARACTERISTICS:
        ( A ) LENGTH: 86 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: rat ( i x ) FEATURE:
        ( A ) NAME/KEY: Domain
        ( B ) LOCATION: 1..86
        ( D ) OTHER INFORMATION: /label=Homology
            / note= "Homologous region from fatty acid
            synthetase of rat; aa 2161-2246"

( x i ) SEQUENCE DESCRIPTION: SEQ ID NO:11:

Glu Arg Pro Leu Phe Leu Val His Pro Ile Glu Gly Ser Ile Thr Val
1                      5                    10                    15

His Phe His Ser Leu Ala Ala Lys Leu Ser Val Pro Thr Tyr Gly Leu
              20                    25                        30

Gln Cys Thr Gln Ala Ala Pro Leu Asp Ser Ile Pro Asn Leu Ala Ala
        35                        40                        45

Tyr Tyr Ile Asp Cys Ile Lys Gln Val Gln Pro Glu Gly Pro Tyr Arg
    50                        55                        60

Val Ala Gly Tyr Ser Phe Gly Ala Cys Val Ala Phe Glu Met Cys Ser
65                      70                        75                      80

Gln Leu Gln Ala Gln Gln
              85

( 2 ) INFORMATION FOR SEQ ID NO:12:

( i ) SEQUENCE CHARACTERISTICS:
        ( A ) LENGTH: 3666 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Penicillium chrysogenum ( i x ) FEATURE:
        ( A ) NAME/KEY: Protein
        ( B ) LOCATION: 1..3666
        ( D ) OTHER INFORMATION: /label=region / note= "Region of ACV Synthetase; aa 62-3727"

(xi) SEQUENCE DESCRIPTION: SEQ ID NO:12:

| Arg | Val | Arg | Phe | Arg | Gly | Gly | Ile | Glu | Arg | Trp | Lys | Glu | Cys | Val | Asn |
|---|---|---|---|---|---|---|---|---|---|---|---|---|---|---|---|
| 1 | | | | 5 | | | | | 10 | | | | | 15 | |
| Gln | Val | Pro | Glu | Arg | Cys | Asp | Leu | Ser | Gly | Leu | Thr | Thr | Asp | Ser | Thr |
| | | | 20 | | | | | 25 | | | | | 30 | | |
| Arg | Tyr | Gln | Leu | Ala | Ser | Thr | Gly | Phe | Gly | Asp | Ala | Ser | Ala | Ala | Tyr |
| | | 35 | | | | | 40 | | | | | 45 | | | |
| Gln | Glu | Arg | Leu | Met | Thr | Val | Pro | Val | Asp | Val | His | Ala | Ala | Leu | Gln |
| | 50 | | | | | 55 | | | | | 60 | | | | |
| Glu | Leu | Cys | Leu | Glu | Arg | Val | Ser | Val | Gly | Ser | Val | Ile | Asn | Phe | |
| 65 | | | | | 70 | | | | 75 | | | | | 80 | |
| Ser | Val | His | Gln | Met | Leu | Lys | Gly | Phe | Gly | Asn | Gly | Thr | His | Thr | Ile |
| | | | | 85 | | | | | 90 | | | | | 95 | |
| Thr | Ala | Ser | Leu | His | Arg | Glu | Gln | Asn | Leu | Gln | Asn | Ser | Ser | Pro | Ser |
| | | | 100 | | | | | 105 | | | | | 110 | | |
| Trp | Val | Val | Ser | Pro | Thr | Ile | Val | Thr | His | Glu | Asn | Arg | Asp | Gly | Trp |
| | | 115 | | | | | 120 | | | | | 125 | | | |
| Ser | Val | Ala | Gln | Ala | Val | Glu | Ser | Ile | Glu | Ala | Ala | Arg | Gly | Ser | Glu |
| | 130 | | | | | 135 | | | | | 140 | | | | |
| Lys | Glu | Ser | Val | Thr | Ala | Ile | Asp | Ser | Ala | Ser | Ser | Leu | Val | Lys | Met |
| 145 | | | | | 150 | | | | | 155 | | | | | 160 |
| Gly | Leu | Phe | Asp | Leu | Leu | Val | Ser | Phe | Val | Asp | Ala | Asp | Asp | Ala | Arg |
| | | | | 165 | | | | | 170 | | | | | 175 | |
| Ile | Pro | Cys | Phe | Asp | Phe | Pro | Leu | Ala | Val | Ile | Val | Arg | Glu | Cys | Asp |
| | | | 180 | | | | | 185 | | | | | 190 | | |
| Ala | Asn | Leu | Ser | Leu | Thr | Leu | Arg | Phe | Ser | Asp | Cys | Leu | Phe | Asn | Glu |
| | | 195 | | | | | 200 | | | | | 205 | | | |
| Glu | Thr | Ile | Cys | Asn | Phe | Thr | Asp | Ala | Leu | Asn | Ile | Leu | Leu | Ala | Glu |
| | 210 | | | | | 215 | | | | | 220 | | | | |
| Ala | Val | Ile | Gly | Arg | Val | Thr | Pro | Val | Ala | Asp | Ile | Glu | Leu | Leu | Ser |
| 225 | | | | | 230 | | | | | 235 | | | | | 240 |
| Ala | Glu | Gln | Lys | Gln | Gln | Leu | Glu | Glu | Trp | Asn | Asn | Thr | Asp | Gly | Glu |
| | | | | 245 | | | | | 250 | | | | | 255 | |
| Tyr | Pro | Ser | Ser | Lys | Arg | Leu | His | His | Leu | Ile | Glu | Glu | Val | Val | Glu |
| | | | 260 | | | | | 265 | | | | | 270 | | |
| Arg | His | Glu | Asp | Lys | Ile | Ala | Val | Val | Cys | Asp | Glu | Arg | Glu | Leu | Thr |
| | | | 275 | | | | | 280 | | | | | 285 | | |
| Tyr | Gly | Glu | Leu | Asn | Ala | Gln | Gly | Asn | Ser | Leu | Ala | Arg | Tyr | Leu | Arg |
| | | 290 | | | | | 295 | | | | | 300 | | | |
| Ser | Ile | Gly | Ile | Leu | Pro | Glu | Gln | Leu | Val | Ala | Leu | Phe | Leu | Asp | Lys |
| 305 | | | | | 310 | | | | | 315 | | | | | 320 |
| Ser | Glu | Lys | Leu | Ile | Val | Thr | Ile | Leu | Gly | Val | Trp | Lys | Ser | Gly | Ala |
| | | | | 325 | | | | | 330 | | | | | 335 | |
| Ala | Tyr | Val | Pro | Ile | Asp | Pro | Thr | Tyr | Pro | Asp | Glu | Arg | Val | Arg | Phe |
| | | | 340 | | | | | 345 | | | | | 350 | | |
| Val | Leu | Asp | Asp | Thr | Lys | Ala | Arg | Ala | Ile | Ile | Ala | Ser | Asn | Gln | His |
| | | 355 | | | | | 360 | | | | | 365 | | | |
| Val | Glu | Arg | Leu | Gln | Arg | Glu | Val | Ile | Gly | Asp | Arg | Asn | Leu | Cys | Ile |
| | 370 | | | | | 375 | | | | | 380 | | | | |
| Ile | Arg | Leu | Glu | Pro | Leu | Leu | Ala | Ser | Leu | Ala | Gln | Asp | Ser | Ser | Lys |
| 385 | | | | | 390 | | | | | 395 | | | | | 400 |
| Phe | Pro | Ala | His | Asn | Leu | Asp | Asp | Leu | Pro | Leu | Thr | Ser | Gln | Gln | Leu |

-continued

```
                              405                      410                       415
    Ala  Tyr  Val  Thr  Tyr  Thr  Ser  Gly  Thr  Gly  Phe  Pro  Lys  Gly  Ile
                   420                      425                      430

Phe  Lys  Gln  His  Thr  Asn  Val  Val  Asn  Ser  Ile  Thr  Asp  Leu  Ser  Ala
              435                      440                      445

Arg  Tyr  Gly  Val  Ala  Gly  Gln  His  His  Glu  Ala  Ile  Leu  Leu  Phe  Ser
         450                      455                      460

Ala  Cys  Val  Phe  Glu  Pro  Phe  Val  Arg  Gln  Thr  Leu  Met  Ala  Leu  Val
    465                      470                      475                      480

Asn  Gly  His  Leu  Leu  Ala  Val  Ile  Asn  Asp  Val  Glu  Lys  Tyr  Asp  Ala
                        485                      490                      495

Asp  Thr  Leu  Leu  Pro  Phe  Ile  Arg  Arg  His  Ser  Ile  Thr  Tyr  Leu  Asn
                   500                      505                      510

Gly  Thr  Ala  Ser  Val  Leu  Gln  Glu  Tyr  Asp  Phe  Ser  Asp  Cys  Pro  Ser
              515                      520                      525

Leu  Asn  Arg  Ile  Ile  Leu  Val  Gly  Glu  Asn  Leu  Thr  Glu  Ala  Arg  Tyr
         530                      535                      540

Leu  Ala  Leu  Arg  Gln  Arg  Phe  Lys  Asn  Arg  Ile  Leu  Asn  Glu  Tyr  Gly
    545                      550                      555                      560

Phe  Thr  Glu  Ser  Ala  Phe  Val  Thr  Ala  Leu  Lys  Ile  Phe  Asp  Pro  Glu
                        565                      570                      575

Ser  Thr  Arg  Lys  Asp  Thr  Ser  Leu  Gly  Arg  Pro  Val  Arg  Asn  Val  Lys
                   580                      585                      590

Cys  Tyr  Ile  Leu  Asn  Pro  Ser  Leu  Lys  Arg  Val  Pro  Ile  Gly  Ala  Thr
              595                      600                      605

Gly  Glu  Leu  His  Ile  Gly  Gly  Leu  Gly  Ile  Ser  Lys  Gly  Tyr  Leu  Asn
         610                      615                      620

Arg  Pro  Glu  Leu  Thr  Pro  His  Arg  Phe  Ile  Pro  Asn  Pro  Phe  Gln  Thr
    625                      630                      635                      640

Asp  Cys  Glu  Lys  Gln  Leu  Gly  Ile  Asn  Ser  Leu  Met  Tyr  Lys  Thr  Gly
                        645                      650                      655

Asp  Leu  Ala  Arg  Trp  Leu  Pro  Asn  Gly  Glu  Val  Glu  Tyr  Leu  Gly  Arg
                   660                      665                      670

Ala  Asp  Phe  Gln  Ile  Lys  Leu  Arg  Gly  Ile  Arg  Ile  Glu  Pro  Gly  Glu
              675                      680                      685

Ile  Glu  Thr  Met  Leu  Ala  Met  Tyr  Pro  Arg  Val  Arg  Thr  Ser  Leu  Val
         690                      695                      700

Val  Ser  Lys  Lys  Leu  Arg  Asn  Gly  Pro  Glu  Glu  Thr  Thr  Asn  Glu  His
    705                      710                      715                      720

Leu  Val  Gly  Tyr  Tyr  Val  Cys  Asp  Ser  Ala  Ser  Val  Ser  Glu  Ala  Asp
                        725                      730                      735

Leu  Leu  Ser  Phe  Leu  Glu  Lys  Lys  Leu  Pro  Arg  Tyr  Met  Ile  Pro  Thr
                   740                      745                      750

Arg  Leu  Val  Gln  Leu  Ser  Gln  Ile  Pro  Val  Asn  Val  Asn  Gly  Lys  Ala
              755                      760                      765

Asp  Leu  Arg  Ala  Leu  Pro  Ala  Val  Asp  Ile  Ser  Asn  Ser  Thr  Glu  Val
         770                      775                      780

Arg  Ser  Asp  Leu  Arg  Gly  Asp  Thr  Glu  Ile  Ala  Leu  Gly  Glu  Ile  Trp
    785                      790                      795                      800

Ala  Asp  Val  Leu  Gly  Ala  Arg  Gln  Arg  Ser  Val  Ser  Arg  Asn  Asp  Asn
                        805                      810                      815

Phe  Phe  Arg  Leu  Gly  Gly  His  Ser  Ile  Thr  Cys  Ile  Gln  Leu  Ile  Ala
                   820                      825                      830
```

```
Arg Ile Arg Gln Arg Gln Arg Leu Ser Val Ser Ile Ser Val Glu Asp
            835                 840                 845
Val Phe Ala Thr Arg Thr Leu Glu Arg Met Ala Asp Leu Leu Gln Asn
850                 855                 860
Lys Gln Gln Glu Lys Cys Asp Lys Pro His Glu Ala Pro Thr Glu Leu
865                 870                 875                 880
Leu Glu Glu Asn Ala Ala Thr Asp Asn Ile Tyr Leu Ala Asn Ser Leu
                885                 890                 895
Gln Gln Gly Phe Val Tyr His Tyr Leu Lys Ser Met Glu Gln Ser Asp
            900                 905                 910
Ala Tyr Val Met Gln Ser Val Leu Arg Tyr Asn Thr Thr Leu Ser Pro
            915                 920                 925
Asp Leu Phe Gln Arg Ala Trp Lys His Ala Gln Gln Ser Phe Pro Ala
930                 935                 940
Leu Arg Leu Arg Phe Ser Trp Glu Lys Glu Val Phe Gln Leu Leu Asp
945                 950                 955                 960
Gln Asp Pro Pro Leu Asp Trp Arg Phe Leu Tyr Phe Thr Asp Val Ala
                965                 970                 975
Ala Gly Ala Val Glu Asp Arg Lys Leu Glu Asp Leu Arg Arg Gln Asp
            980                 985                 990
Leu Thr Glu Arg Phe Lys Leu Asp Val Gly Arg Leu Phe Arg Val Tyr
            995                 1000                1005
Leu Ile Lys His Ser Glu Asn Arg Phe Thr Cys Leu Phe Ser Cys His
    1010                1015                1020
His Ala Ile Leu Asp Gly Trp Ser Leu Pro Leu Leu Phe Glu Lys Val
    1025                1030                1035                1040
His Glu Thr Tyr Leu Gln Leu Leu His Gly Asp Asn Leu Thr Ser Ser
                1045                1050                1055
Met Asp Asp Pro Tyr Thr Arg Thr Gln Arg Tyr Leu His Ala His Arg
            1060                1065                1070
Glu Asp His Leu Asp Phe Trp Ala Gly Val Val Gln Lys Ile Asn Glu
        1075                1080                1085
Arg Cys Asp Met Asn Ala Leu Leu Asn Glu Arg Ser Arg Tyr Lys Val
        1090                1095                1100
Gln Leu Ala Asp Tyr Asp Gln Val Gln Glu Gln Arg His Val Thr Ile
1105                1110                1115                1120
Ala Leu Ser Gly Asp Ala Trp Leu Ala Asp Leu Arg Gln Thr Cys Ser
                1125                1130                1135
Ala Gln Gly Ile Thr Leu His Ser Ile Leu Gln Phe Val Trp His Ala
            1140                1145                1150
Val Leu His Ala Tyr Gly Gly Gly Thr His Thr Ile Thr Gly Thr Thr
        1155                1160                1165
Ile Ser Gly Arg Asn Leu Pro Ile Leu Gly Ile Glu Arg Ala Val Gly
    1170                1175                1180
Pro Tyr Ile Asn Thr Leu Pro Leu Val Leu Asp His Ser Thr Phe Lys
1185                1190                1195                1200
Asp Lys Thr Ile Met Glu Ala Ile Glu Asp Val Gln Ala Lys Val Asn
                1205                1210                1215
Val Met Asn Ser Arg Gly Asn Val Glu Leu Gly Arg Leu His Lys Thr
            1220                1225                1230
Asp Leu Lys His Gly Leu Phe Asp Ser Leu Phe Val Leu Glu Asn Tyr
        1235                1240                1245
Pro Asn Leu Asp Lys Ser Arg Thr Leu Glu His Gln Thr Glu Leu Gly
        1250                1255                1260
```

```
Tyr  Ser  Ile  Glu  Gly  Gly  Thr  Glu  Lys  Leu  Asn  Tyr  Pro  Leu  Ala  Val
1265                1270                1275                     1280

Ile  Ala  Arg  Glu  Val  Glu  Thr  Thr  Gly  Gly  Phe  Thr  Val  Ser  Ile  Cys
                    1285                1290                     1295

Tyr  Ala  Ser  Glu  Leu  Phe  Glu  Glu  Val  Met  Ile  Ser  Glu  Leu  Leu  His
                    1300                1305                     1310

Met  Val  Gln  Asp  Thr  Leu  Met  Gln  Val  Ala  Arg  Gly  Leu  Asn  Glu  Pro
                    1315                1320                     1325

Val  Gly  Ser  Leu  Glu  Tyr  Leu  Ser  Ser  Ile  Gln  Leu  Glu  Gln  Leu  Ala
                    1330                1335                     1340

Ala  Trp  Asn  Ala  Thr  Glu  Ala  Glu  Phe  Pro  Asp  Thr  Thr  Leu  His  Glu
1345                1350                1355                     1360

Met  Phe  Glu  Asn  Glu  Ala  Ser  Gln  Lys  Pro  Asp  Lys  Ile  Ala  Val  Val
                    1365                1370                     1375

Tyr  Glu  Glu  Thr  Ser  Leu  Thr  Tyr  Arg  Glu  Leu  Asn  Glu  Arg  Ala  Asn
                    1380                1385                     1390

Arg  Met  Ala  His  Gln  Leu  Arg  Ser  Asp  Val  Ser  Pro  Asn  Pro  Asn  Glu
                    1395                1400                     1405

Val  Ile  Ala  Leu  Val  Met  Asp  Lys  Ser  Glu  His  Met  Ile  Val  Asn  Ile
                    1410                1415                     1420

Leu  Ala  Val  Trp  Lys  Ser  Gly  Gly  Ala  Tyr  Val  Pro  Ile  Asp  Pro  Gly
1425                1430                1435                     1440

Tyr  Pro  Asn  Asp  Arg  Ile  Gln  Tyr  Ile  Leu  Glu  Asp  Thr  Gln  Ala  Leu
                    1445                1450                     1455

Ala  Val  Ile  Ala  Asp  Ser  Cys  Tyr  Leu  Pro  Arg  Ile  Lys  Gly  Met  Ala
                    1460                1465                     1470

Ala  Ser  Gly  Thr  Leu  Leu  Tyr  Pro  Ser  Val  Leu  Pro  Ala  Asn  Pro  Asp
                    1475                1480                     1485

Ser  Lys  Trp  Ser  Val  Ser  Asn  Pro  Ser  Pro  Leu  Ser  Arg  Ser  Thr  Asp
                    1490                1495                     1500

Leu  Ala  Tyr  Ile  Ile  Tyr  Thr  Ser  Gly  Thr  Thr  Gly  Arg  Pro  Lys  Gly
1505                1510                1515                     1520

Val  Thr  Val  Glu  His  His  Gly  Val  Val  Asn  Leu  Gln  Val  Ser  Leu  Ser
                    1525                1530                     1535

Lys  Val  Phe  Gly  Leu  Arg  Asp  Thr  Asp  Asp  Glu  Val  Ile  Leu  Ser  Phe
                    1540                1545                     1550

Ser  Asn  Tyr  Val  Phe  Asp  His  Phe  Val  Glu  Gln  Met  Thr  Asp  Ala  Ile
                    1555                1560                     1565

Leu  Asn  Gly  Gln  Thr  Leu  Leu  Val  Leu  Asn  Asp  Gly  Met  Arg  Gly  Asp
                    1570                1575                     1580

Lys  Glu  Arg  Leu  Tyr  Arg  Tyr  Ile  Glu  Lys  Asn  Arg  Val  Thr  Tyr  Leu
1585                1590                1595                     1600

Ser  Gly  Thr  Pro  Ser  Val  Val  Ser  Met  Tyr  Glu  Phe  Ser  Arg  Phe  Lys
                    1605                1610                     1615

Asp  His  Leu  Arg  Arg  Val  Asp  Cys  Val  Gly  Glu  Ala  Phe  Ser  Glu  Pro
                    1620                1625                     1630

Val  Phe  Asp  Lys  Ile  Arg  Glu  Thr  Phe  His  Gly  Leu  Val  Ile  Asn  Gly
                    1635                1640                     1645

Tyr  Gly  Pro  Thr  Glu  Val  Ser  Ile  Thr  Thr  His  Lys  Arg  Leu  Tyr  Pro
                    1650                1655                     1660

Phe  Pro  Glu  Arg  Arg  Met  Asp  Lys  Ser  Ile  Gly  Gln  Gln  Val  His  Asn
1665                1670                1675                     1680

Ser  Thr  Ser  Tyr  Val  Leu  Asn  Glu  Asp  Met  Lys  Arg  Thr  Pro  Ile  Gly
```

-continued

```
                        1685                    1690                    1695
   Ala  Val  Gly  Glu  Leu  Tyr  Leu  Gly  Gly  Glu  Gly  Val  Val  Arg  Gly  Tyr
                       1700                    1705                    1710

His  Asn  Arg  Ala  Asp  Val  Thr  Ala  Glu  Arg  Phe  Ile  Pro  Asn  Pro  Phe
                       1715                    1720                    1725

Gln  Ser  Glu  Glu  Asp  Lys  Arg  Glu  Gly  Arg  Asn  Ser  Arg  Leu  Tyr  Lys
                       1730                    1735                    1740

Thr  Gly  Asp  Leu  Val  Arg  Trp  Ile  Pro  Gly  Ser  Ser  Gly  Glu  Val  Glu
   1745                    1750                    1755                    1760

Tyr  Leu  Gly  Arg  Asn  Asp  Phe  Gln  Val  Lys  Ile  Arg  Gly  Leu  Arg  Ile
                       1765                    1770                    1775

Glu  Leu  Gly  Glu  Ile  Glu  Ala  Ile  Leu  Ser  Ser  Tyr  His  Gly  Ile  Lys
                       1780                    1785                    1790

Gln  Ser  Val  Val  Ile  Ala  Lys  Asp  Cys  Arg  Glu  Gly  Ala  Gln  Lys  Phe
                       1795                    1800                    1805

Leu  Val  Gly  Tyr  Tyr  Val  Ala  Asp  Ala  Ala  Leu  Pro  Ser  Ala  Ala  Ile
                       1810                    1815                    1820

Arg  Arg  Phe  Met  Gln  Ser  Arg  Leu  Pro  Gly  Tyr  Met  Val  Pro  Ser  Arg
   1825                    1830                    1835                    1840

Leu  Ile  Leu  Val  Ser  Lys  Phe  Pro  Val  Thr  Pro  Ser  Gly  Lys  Leu  Asp
                       1845                    1850                    1855

Thr  Lys  Ala  Leu  Pro  Pro  Ala  Glu  Glu  Ser  Glu  Ile  Asp  Val  Val
                       1860                    1865                    1870

Pro  Pro  Arg  Ser  Glu  Ile  Glu  Arg  Ser  Leu  Cys  Asp  Ile  Trp  Ala  Glu
                       1875                    1880                    1885

Leu  Leu  Glu  Met  His  Pro  Glu  Glu  Ile  Gly  Ile  Tyr  Ser  Asp  Phe  Phe
                       1890                    1895                    1900

Ser  Leu  Gly  Gly  Asp  Ser  Leu  Lys  Ser  Thr  Lys  Leu  Ser  Phe  Met  Ile
   1905                    1910                    1915                    1920

His  Glu  Ser  Phe  Asn  Arg  Ala  Val  Ser  Val  Ser  Ala  Leu  Phe  Cys  His
                       1925                    1930                    1935

Arg  Thr  Val  Glu  Ala  Gln  Thr  His  Leu  Ile  Leu  Asn  Asp  Ala  Ala  Asp
                       1940                    1945                    1950

Val  His  Glu  Ile  Thr  Pro  Ile  Asp  Cys  Asn  Asp  Thr  Gln  Met  Ile  Pro
                       1955                    1960                    1965

Val  Ser  Arg  Ala  Gln  Glu  Arg  Leu  Leu  Phe  Ile  His  Glu  Phe  Glu  Asn
                       1970                    1975                    1980

Gly  Ser  Asn  Ala  Tyr  Asn  Ile  Asp  Ala  Ala  Phe  Glu  Leu  Pro  Gly  Ser
   1985                    1990                    1995                    2000

Val  Asp  Ala  Ser  Leu  Leu  Glu  Gln  Ala  Leu  Arg  Gly  Asn  Leu  Ala  Arg
                       2005                    2010                    2015

His  Glu  Ala  Leu  Arg  Thr  Leu  Leu  Val  Lys  Asp  His  Ala  Thr  Gly  Ile
                       2020                    2025                    2030

Tyr  Leu  Gln  Lys  Val  Leu  Ser  Pro  Asp  Glu  Ala  Gln  Gly  Met  Phe  Ser
                       2035                    2040                    2045

Val  Asn  Val  Asp  Thr  Ala  Lys  Gln  Val  Glu  Arg  Leu  Asp  Gln  Glu  Ile
                       2050                    2055                    2060

Ala  Ser  Leu  Ser  Gln  His  Val  Phe  Arg  Leu  Asp  Asp  Glu  Leu  Pro  Trp
   2065                    2070                    2075                    2080

Glu  Ala  Arg  Ile  Leu  Lys  Leu  Glu  Ser  Gly  Gly  Leu  Tyr  Leu  Ile  Leu
                       2085                    2090                    2095

Ala  Phe  His  His  Thr  Cys  Phe  Asp  Ala  Trp  Ser  Leu  Lys  Val  Phe  Glu
                       2100                    2105                    2110
```

```
Gln Glu Leu Arg Ala Leu Tyr Ala Ala Leu Gln Lys Thr Lys Ser Ala
         2115                2120                2125

Ala Asn Leu Pro Ala Leu Lys Ala Gln Tyr Lys Glu Tyr Ala Leu Tyr
         2130                2135                2140

His Arg Arg Gln Leu Ser Gly Asp Arg Met Arg Asn Leu Ser Asp Phe
2145                2150                2155                2160

Trp Leu Arg Lys Leu Ile Gly Leu Glu Pro Leu Gln Leu Ile Thr Asp
                 2165                2170                2175

Arg Pro Arg Pro Val Gln Phe Lys Tyr Asp Gly Asp Asp Leu Ser Ile
             2180                2185                2190

Glu Leu Ser Lys Lys Glu Thr Glu Asn Leu Arg Gly Val Ala Lys Arg
             2195                2200                2205

Cys Lys Ser Ser Leu Tyr Val Val Leu Val Ser Val Tyr Cys Val Met
         2210                2215                2220

Leu Ala Ser Tyr Ala Asn Gln Ser Asp Val Ser Val Gly Ile Pro Val
2225                2230                2235                2240

Ser His Arg Thr His Pro Gln Phe Gln Ser Val Ile Gly Phe Phe Val
                 2245                2250                2255

Asn Leu Val Val Leu Arg Val Asp Ile Ser Gln Ser Ala Ile Cys Gly
             2260                2265                2270

Leu Ile Arg Arg Val Met Lys Glu Leu Val Asp Ala Gln Leu His Gln
         2275                2280                2285

Asp Met Pro Phe Gln Glu Val Thr Lys Leu Leu Gln Val Asp Asn Asp
         2290                2295                2300

Pro Ser Arg His Pro Leu Val Gln Asn Val Phe Asn Phe Glu Ser Arg
2305                2310                2315                2320

Ala Asn Gly Glu His Asp Ala Arg Ser Glu Asp Glu Gly Ser Leu Ala
                 2325                2330                2335

Phe Asn Gln Tyr Arg Pro Val Gln Pro Val Asp Ser Val Ala Lys Phe
             2340                2345                2350

Asp Leu Asn Ala Thr Val Thr Glu Leu Glu Ser Gly Leu Arg Val Asn
             2355                2360                2365

Phe Asn Tyr Ala Thr Ser Leu Phe Asn Lys Ser Thr Ile Gln Gly Phe
         2370                2375                2380

Leu His Thr Tyr Glu Tyr Leu Leu Arg Gln Leu Ser Glu Leu Ser Ala
2385                2390                2395                2400

Glu Gly Ile Asn Glu Asp Thr Gln Leu Ser Leu Val Arg Pro Thr Glu
                 2405                2410                2415

Asn Gly Asp Leu His Leu Pro Leu Ala Gln Ser Pro Leu Ala Thr Thr
             2420                2425                2430

Ala Glu Glu Gln Lys Val Ala Ser Leu Asn Gln Ala Phe Glu Arg Glu
         2435                2440                2445

Ala Phe Leu Ala Ala Glu Lys Ile Ala Val Val Gln Gly Asp Arg Ala
         2450                2455                2460

Leu Ser Tyr Ala Asp Leu Asn Gly Gln Ala Asn Gln Leu Ala Arg Tyr
         2465                2470                2475                2480

Ile Gln Ser Val Ser Cys Ile Gly Ala Asp Asp Gly Ile Ala Leu Met
                 2485                2490                2495

Leu Glu Lys Ser Ile Asp Thr Ile Ile Cys Ile Leu Ala Ile Trp Lys
                 2500                2505                2510

Ala Gly Ala Ala Tyr Val Pro Leu Asp Pro Thr Tyr Pro Pro Gly Arg
             2515                2520                2525

Val Gln Leu Ile Leu Glu Glu Ile Lys Ala Lys Ala Val Leu Val His
         2530                2535                2540
```

```
Ser  Ser  His  Ala  Ser  Lys  Cys  Glu  Arg  His  Gly  Ala  Lys  Val  Ile  Ala
2545                 2550                 2555                      2560

Val  Asp  Ser  Pro  Ala  Ile  Glu  Thr  Ala  Val  Ser  Gln  Gln  Ser  Ala  Ala
                         2565                 2570                 2575

Asp  Leu  Pro  Thr  Ile  Ala  Ser  Leu  Gly  Asn  Leu  Ala  Tyr  Ile  Ile  Phe
                         2580                 2585                 2590

Thr  Ser  Gly  Thr  Ser  Gly  Lys  Pro  Lys  Gly  Val  Leu  Val  Glu  Gln  Lys
                2595                 2600                 2605

Ala  Val  Leu  Leu  Leu  Arg  Asp  Ala  Leu  Arg  Glu  Arg  Tyr  Phe  Gly  Arg
2610                      2615                 2620

Asp  Cys  Thr  Lys  His  His  Gly  Val  Leu  Phe  Leu  Ser  Asn  Tyr  Val  Phe
2625                 2630                 2635                      2640

Asp  Phe  Ser  Val  Glu  Gln  Leu  Val  Leu  Ser  Val  Leu  Ser  Gly  His  Lys
                         2645                 2650                 2655

Leu  Ile  Val  Pro  Pro  Ala  Glu  Phe  Val  Ala  Asp  Asp  Glu  Phe  Tyr  Arg
                    2660                 2665                 2670

Met  Ala  Ser  Thr  His  Gly  Leu  Ser  Tyr  Leu  Ser  Gly  Thr  Pro  Ser  Leu
                2675                 2680                 2685

Leu  Gln  Lys  Ile  Asp  Leu  Ala  Arg  Leu  Asp  His  Leu  Gln  Val  Val  Thr
                2690                 2695                 2700

Ala  Ala  Gly  Glu  Glu  Leu  His  Ala  Thr  Gln  Tyr  Glu  Lys  Met  Arg  Arg
2705                      2710                 2715                      2720

Arg  Phe  Asn  Gly  Pro  Ile  Tyr  Asn  Ala  Tyr  Gly  Val  Thr  Glu  Thr  Thr
                    2725                 2730                 2735

Val  Tyr  Asn  Ile  Ile  Ala  Glu  Phe  Thr  Thr  Asn  Ser  Ile  Phe  Glu  Asn
                    2740                 2745                 2750

Ala  Leu  Arg  Glu  Val  Leu  Pro  Gly  Thr  Arg  Ala  Tyr  Val  Leu  Asn  Ala
                    2755                 2760                 2765

Ala  Leu  Gln  Pro  Val  Pro  Phe  Asp  Ala  Val  Gly  Glu  Leu  Tyr  Leu  Ala
                    2770                 2775                 2780

Gly  Asp  Thr  Val  Thr  Arg  Gly  Tyr  Leu  Asn  Gln  Pro  Leu  Leu  Thr  Asp
2785                      2790                 2795                      2800

Gln  Arg  Phe  Ile  Pro  Asn  Pro  Phe  Cys  Lys  Glu  Glu  Asp  Ile  Ala  Met
                         2805                 2810                 2815

Gly  Arg  Phe  Ala  Arg  Leu  Tyr  Lys  Thr  Gly  Asp  Leu  Val  Arg  Ser  Arg
                    2820                 2825                 2830

Phe  Asn  Arg  Gln  Gln  Gln  Pro  Gln  Leu  Glu  Tyr  Leu  Gly  Arg  Gly  Asp
                2835                 2840                 2845

Leu  Gln  Ile  Lys  Met  Arg  Gly  Tyr  Arg  Ile  Glu  Ile  Ser  Glu  Val  Gln
2850                      2855                 2860

Asn  Val  Leu  Thr  Ser  Ser  Pro  Gly  Val  Arg  Glu  Gly  Ala  Val  Val  Ala
2865                 2870                 2875                      2880

Lys  Tyr  Glu  Asn  Asn  Asp  Thr  Tyr  Ser  Arg  Thr  Ala  His  Ser  Leu  Val
                    2885                 2890                 2895

Gly  Tyr  Tyr  Thr  Thr  Asp  Asn  Glu  Thr  Val  Ser  Glu  Ala  Asp  Ile  Leu
                2900                 2905                 2910

Thr  Phe  Met  Lys  Ala  Arg  Leu  Pro  Thr  Tyr  Met  Val  Pro  Ser  His  Leu
                2915                 2920                 2925

Cys  Cys  Leu  Glu  Gly  Ala  Leu  Pro  Val  Thr  Ile  Asn  Gly  Lys  Leu  Asp
                2930                 2935                 2940

Val  Arg  Arg  Leu  Pro  Glu  Ile  Ile  Asn  Asp  Ser  Ala  Gln  Ser  Ser  Tyr
2945                 2950                 2955                      2960

Ser  Pro  Pro  Arg  Asn  Ile  Ile  Glu  Ala  Lys  Met  Cys  Arg  Leu  Trp  Glu
```

```
                         2 9 6 5                          2 9 7 0                          2 9 7 5
    Ser  Ala  Leu  Gly  Met  Glu  Arg  Cys  Gly  Ile  Asp  Asp  Asp  Leu  Phe  Lys
                        2 9 8 0                          2 9 8 5                          2 9 9 0
    Leu  Gly  Gly  Asp  Ser  Ile  Thr  Ser  Leu  His  Leu  Val  Ala  Gln  Ile  His
                        2 9 9 5                          3 0 0 0                          3 0 0 5
    Asn  Gln  Val  Gly  Cys  Lys  Ile  Thr  Val  Arg  Asp  Ile  Phe  Glu  His  Arg
                        3 0 1 0                          3 0 1 5                          3 0 2 0
    Thr  Ala  Arg  Ala  Leu  His  Asp  His  Val  Phe  Met  Lys  Asp  Ser  Asp  Arg
3 0 2 5                  3 0 3 0                          3 0 3 5                          3 0 4 0
    Ser  Asn  Val  Thr  Gln  Phe  Arg  Thr  Glu  Gln  Gly  Pro  Val  Ile  Gly  Glu
                        3 0 4 5                          3 0 5 0                          3 0 5 5
    Ala  Pro  Leu  Leu  Pro  Ile  Gln  Asp  Trp  Phe  Leu  Ser  Lys  Ala  Leu  Gln
                        3 0 6 0                          3 0 6 5                          3 0 7 0
    His  Pro  Met  Tyr  Trp  Asn  His  Thr  Phe  Tyr  Val  Arg  Thr  Pro  Glu  Leu
                        3 0 7 5                          3 0 8 0                          3 0 8 5
    Asp  Val  Asp  Ser  Leu  Ser  Ala  Ala  Val  Arg  Asp  Leu  Gln  Gln  Tyr  His
                        3 0 9 0                          3 0 9 5                          3 1 0 0
    Asp  Val  Phe  Arg  Met  Arg  Leu  Lys  Arg  Glu  Glu  Val  Gly  Phe  Val  Gln
3 1 0 5                  3 1 1 0                          3 1 1 5                          3 1 2 0
    Ser  Phe  Ala  Glu  Asp  Phe  Ser  Pro  Ala  Gln  Leu  Arg  Val  Leu  Asn  Val
                        3 1 2 5                          3 1 3 0                          3 1 3 5
    Lys  Asp  Val  Asp  Gly  Ser  Ala  Ala  Val  Asn  Glu  Ile  Leu  Asp  Gly  Trp
                        3 1 4 0                          3 1 4 5                          3 1 5 0
    Gln  Ser  Gly  Phe  Asn  Leu  Glu  Asn  Gly  Pro  Ile  Gly  Ser  Ile  Gly  Tyr
                        3 1 5 5                          3 1 6 0                          3 1 6 5
    Leu  His  Gly  Tyr  Glu  Asp  Arg  Ser  Ala  Arg  Val  Trp  Phe  Ser  Val  His
                        3 1 7 0                          3 1 7 5                          3 1 8 0
    His  Met  Ala  Ile  Asp  Thr  Val  Ser  Trp  Gln  Ile  Leu  Val  Arg  Asp  Leu
3 1 8 5                  3 1 9 0                          3 1 9 5                          3 2 0 0
    Gln  Thr  Leu  Tyr  Arg  Asn  Gly  Ser  Leu  Gly  Ser  Lys  Gly  Ser  Ser  Phe
                        3 2 0 5                          3 2 1 0                          3 2 1 5
    Arg  Gln  Trp  Ala  Glu  Ala  Ile  Gln  Asn  Tyr  Lys  Ala  Ser  Asp  Ser  Glu
                        3 2 2 0                          3 2 2 5                          3 2 3 0
    Arg  Asn  His  Trp  Asn  Lys  Leu  Val  Met  Glu  Thr  Ala  Ser  Ser  Ile  Ser
                        3 2 3 5                          3 2 4 0                          3 2 4 5
    Ala  Leu  Pro  Thr  Ser  Thr  Gly  Ser  Arg  Val  Arg  Leu  Ser  Arg  Ser  Leu
                        3 2 5 0                          3 2 5 5                          3 2 6 0
    Ser  Pro  Glu  Lys  Thr  Ala  Ser  Leu  Ile  Gln  Gly  Gly  Ile  Asp  Arg  Gln
3 2 6 5                  3 2 7 0                          3 2 7 5                          3 2 8 0
    Asp  Val  Ser  Val  Tyr  Asp  Ser  Leu  Leu  Thr  Ser  Val  Gly  Leu  Ala  Leu
                        3 2 8 5                          3 2 9 0                          3 2 9 5
    Gln  His  Ile  Ala  Pro  Thr  Gly  Pro  Ser  Met  Val  Thr  Ile  Glu  Gly  His
                        3 3 0 0                          3 3 0 5                          3 3 1 0
    Gly  Arg  Glu  Glu  Val  Asp  Gln  Thr  Leu  Asp  Val  Ser  Arg  Thr  Met  Gly
                        3 3 1 5                          3 3 2 0                          3 3 2 5
    Trp  Phe  Thr  Thr  Met  Tyr  Pro  Phe  Glu  Ile  Pro  Arg  Leu  Ser  Thr  Glu
                        3 3 3 0                          3 3 3 5                          3 3 4 0
    Asn  Ile  Val  Gln  Gly  Val  Val  Ala  Val  Ser  Glu  Arg  Phe  Arg  Gln  Val
3 3 4 5                  3 3 5 0                          3 3 5 5                          3 3 6 0
    Pro  Ala  Arg  Gly  Val  Gly  Tyr  Gly  Thr  Leu  Tyr  Gly  Tyr  Thr  Gln  His
                        3 3 6 5                          3 3 7 0                          3 3 7 5
    Pro  Leu  Pro  Gln  Val  Thr  Val  Asn  Tyr  Leu  Gly  Gln  Leu  Ala  Arg  Lys
                        3 3 8 0                          3 3 8 5                          3 3 9 0
```

| | | | | | | | | | | | | | | |
|---|---|---|---|---|---|---|---|---|---|---|---|---|---|---|
| Gln | Ser | Lys | Pro | Lys | Glu | Trp | Val | Leu | Ala | Val | Gly | Asp | Asn | Glu | Phe |
| | | 3395 | | | | 3400 | | | | | 3405 | | | | |
| Glu | Tyr | Gly | Leu | Met | Thr | Ser | Pro | Glu | Asp | Lys | Asp | Arg | Ser | Ser | Ser |
| | 3410 | | | | | 3415 | | | | 3420 | | | | | |
| Ala | Val | Asp | Val | Thr | Ala | Val | Cys | Ile | Asp | Gly | Thr | Met | Ile | Ile | Asp |
| 3425 | | | | | 3430 | | | | 3435 | | | | | | 3440 |
| Val | Asp | Ser | Ala | Trp | Ser | Leu | Glu | Glu | Ser | Glu | Gln | Phe | Ile | Ser | Ser |
| | | | | 3445 | | | | | 3450 | | | | | 3455 | |
| Ile | Glu | Glu | Gly | Leu | Asn | Lys | Ile | Leu | Asp | Gly | Arg | Ala | Ser | Gln | Gln |
| | | | 3460 | | | | | 3465 | | | | | 3470 | | |
| Thr | Ser | Arg | Phe | Pro | Asp | Val | Pro | Gln | Pro | Ala | Glu | Thr | Tyr | Thr | Pro |
| | | | 3475 | | | | 3480 | | | | | 3485 | | | |
| Tyr | Phe | Glu | Tyr | Leu | Glu | Pro | Pro | Arg | Gln | Gly | Pro | Thr | Leu | Phe | Leu |
| | 3490 | | | | | 3495 | | | | | 3500 | | | | |
| Leu | Pro | Pro | Gly | Glu | Gly | Gly | Ala | Glu | Ser | Tyr | Phe | Asn | Asn | Ile | Val |
| 3505 | | | | | 3510 | | | | 3515 | | | | | | 3520 |
| Lys | Arg | Leu | Arg | Gln | Thr | Asn | Met | Val | Val | Phe | Asn | Asn | Tyr | Tyr | Leu |
| | | | | 3525 | | | | | 3530 | | | | | 3535 | |
| His | Ser | Lys | Arg | Leu | Arg | Thr | Phe | Glu | Glu | Leu | Ala | Glu | Met | Tyr | Leu |
| | | | | 3540 | | | | | 3545 | | | | | 3550 | |
| Asp | Gln | Val | Arg | Gly | Ile | Gln | Pro | His | Gly | Pro | Tyr | His | Phe | Ile | Gly |
| | | | 3555 | | | | | 3560 | | | | | 3565 | | |
| Trp | Ser | Phe | Gly | Gly | Ile | Leu | Ala | Met | Glu | Met | Ser | Arg | Arg | Leu | Val |
| | 3570 | | | | | 3575 | | | | | 3580 | | | | |
| Ala | Ser | Asp | Glu | Lys | Ile | Gly | Phe | Leu | Gly | Ile | Ile | Asp | Thr | Tyr | Phe |
| 3585 | | | | | 3590 | | | | | 3595 | | | | | 3600 |
| Asn | Val | Arg | Gly | Ala | Thr | Arg | Thr | Ile | Gly | Leu | Gly | Asp | Thr | Glu | Ile |
| | | | | 3605 | | | | | 3610 | | | | | | 3615 |
| Leu | Asp | Pro | Ile | His | His | Ile | Tyr | Asn | Pro | Asp | Pro | Ala | Asn | Phe | Gln |
| | | | | 3620 | | | | | 3625 | | | | | 3630 | |
| Arg | Leu | Pro | Ser | Ala | Thr | Asp | Arg | Ile | Val | Leu | Phe | Lys | Ala | Met | Arg |
| | | | | 3635 | | | | | 3640 | | | | | 3645 | |
| Pro | Asn | Asn | Lys | Tyr | Glu | Ser | Glu | Asn | Gln | Arg | Arg | Leu | Tyr | Glu | Tyr |
| | | | | 3650 | | | | | 3655 | | | | | 3660 | |
| Tyr | Asp | | | | | | | | | | | | | | |
| 3665 | | | | | | | | | | | | | | | |

( 2 ) INFORMATION FOR SEQ ID NO:13:

( i ) SEQUENCE CHARACTERISTICS:
        ( A ) LENGTH: 3665 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Acremonium chrysogenum ( i x ) FEATURE:
        ( A ) NAME/KEY: Protein
        ( B ) LOCATION: 1..3665
        ( D ) OTHER INFORMATION: /label=ACVS
          / note= "ACV Synthetase from Acremonium
          chrysogenum; aa 1-3665"

( x i ) SEQUENCE DESCRIPTION: SEQ ID NO:13:

```
Val  Ala  Leu  Glu  Gln  Trp  Lys  Thr  Thr  Val  Gln  Ser  Val  Ser  Glu  Arg
  1              5                         10                      15

Cys  Asp  Leu  Ser  Gly  Leu  Ser  Gln  His  Pro  Thr  Asp  Tyr  Gln  Leu  Ala
              20                    25                    30

Ser  Thr  Gly  Val  Lys  Gly  Ala  Gly  Gly  Ser  Ser  Ile  Glu  Glu  Arg  Ser
          35                        40                    45

Ala  Ile  Val  Ser  Asp  Glu  Leu  Phe  Ser  Ser  Leu  Arg  Asp  Val  Cys  Ser
     50                         55                    60

Gln  Arg  Gln  Leu  Asp  Pro  Arg  Ser  Leu  Met  Leu  Phe  Ser  Val  His  Gln
 65                        70                    75                         80

Met  Leu  Lys  Arg  Phe  Gly  Asn  Gly  Ser  His  Thr  Val  Val  Ala  Ser  Leu
                    85                    90                          95

Val  Thr  Ser  Ser  Glu  Gly  Cys  Pro  Ser  Thr  Ser  Ala  Trp  Arg  Ala  Ile
               100                       105                      110

Pro  Ser  Val  Ile  His  His  Ile  Glu  Gly  Gly  Asp  Asn  Asn  Asn  Thr  Val
          115                       120                      125

Ala  Ser  Ala  Val  Glu  Gln  Ala  Ala  Asn  Leu  Leu  Asn  Ser  Glu  Gly  Ser
     130                        135                      140

Gly  Gln  Asp  Leu  Leu  Ile  Pro  Ile  Gly  Leu  Thr  Glu  Leu  Val  Lys  Ser
145                      150                      155                         160

Glu  Leu  Ile  Asp  Leu  Leu  Val  Ile  Phe  Asp  Glu  Thr  Asn  Asn  Ile
                    165                       170                      175

Arg  Leu  Pro  Gln  Asp  Phe  Pro  Leu  Ile  Leu  Arg  Ile  His  Gln  Arg  Gln
               180                       185                      190

Asp  His  Trp  Gln  Leu  Ser  Val  Arg  Tyr  Pro  Ser  Pro  Leu  Phe  Asp  Thr
          195                       200                      205

Met  Val  Ile  Asp  Ser  Phe  Leu  Ser  Ala  Leu  His  Asn  Leu  Leu  Ser  Ala
     210                        215                      220

Val  Thr  Lys  Pro  Ser  Gln  Leu  Val  Arg  Asp  Ile  Glu  Leu  Leu  Pro  Glu
225                      230                      235                         240

Tyr  Gln  Val  Ala  Gln  Leu  Glu  Lys  Trp  Asn  Asn  Thr  Asp  Gly  Asp  Tyr
               245                       250                      255

Pro  Thr  Glu  Lys  Arg  Leu  His  His  Leu  Phe  Glu  Glu  Ala  Ala  Val  Arg
               260                       265                      270

Arg  Pro  Gln  His  Val  Ala  Leu  Ile  Cys  Gly  Asp  Lys  Arg  Ile  Thr  Tyr
               275                       280                      285

Glu  Glu  Leu  Asn  Ala  Met  Ala  Asn  Arg  Leu  Ala  His  His  Leu  Val  Ser
     290                        295                      300

Ser  Gly  Ile  Gln  Thr  Glu  Gln  Leu  Val  Gly  Leu  Phe  Leu  Asp  Lys  Thr
305                      310                      315                         320

Glu  Leu  Met  Ile  Ala  Thr  Ile  Leu  Gly  Ile  Trp  Lys  Ser  Gly  Ala  Ala
               325                       330                      335

His  Val  Pro  Ile  Asp  Pro  Gly  Tyr  Pro  Asp  Glu  Arg  Val  Lys  Phe  Val
               340                       345                      350

Leu  Asn  Asp  Thr  Lys  Ala  Gln  Val  Val  Ile  Ala  Ser  Gln  Arg  His  Val
               355                       360                      365

Asp  Arg  Leu  Arg  Ala  Glu  Ala  Val  Gly  Gly  Gln  His  Leu  Arg  Ile  Ile
     370                        375                      380

Gly  Leu  Glu  Ser  Leu  Phe  Asp  Asn  Leu  Ala  Gln  Gln  Thr  Gln  His  Ser
385                      390                      395                         400

Pro  Glu  Thr  Ser  Gly  Asn  Leu  Thr  His  Leu  Pro  Leu  Asn  Ser  Lys  Gln
               405                       410                      415

Leu  Ala  Tyr  Val  Thr  Tyr  Thr  Ser  Gly  Thr  Thr  Gly  Phe  Pro  Lys  Gly
```

-continued

|     |     |     | 420 |     |     |     | 425 |     |     |     | 430 |     |     |
|---|---|---|---|---|---|---|---|---|---|---|---|---|---|
| Ile | Tyr | Lys<br>435 | Glu | His | Thr | Ser | Val<br>440 | Val | Asn | Ser | Ile | Thr<br>445 | Asp | Leu | Ser |
| Ala | Arg<br>450 | Tyr | Gly | Val | Ala | Gly<br>455 | Glu | Asp | Asp | Glu<br>460 | Val | Ile | Leu | Val | Phe |
| Ser<br>465 | Ala | Tyr | Val | Phe | Glu<br>470 | Pro | Phe | Val | Arg | Gln<br>475 | Met | Leu | Met | Ala | Leu<br>480 |
| Thr | Thr | Gly | Asn | Ser<br>485 | Leu | Ala | Ile | Ile | Ser<br>490 | Asp | Glu | Asp | Lys | Phe<br>495 | Asp |
| Pro | Asp | Thr | Leu<br>500 | Ile | Pro | Phe | Ile | Gln<br>505 | Lys | His | Lys | Val | Thr<br>510 | Tyr | Ile |
| His | Ala | Thr<br>515 | Ser | Ser | Val | Leu | Gln<br>520 | Glu | Tyr | Asp | Phe | Gly<br>525 | Ser | Cys | Pro |
| Ser | Leu<br>530 | Lys | Arg | Met | Ile | Leu<br>535 | Val | Gly | Glu | Asn | Leu<br>540 | Thr | Glu | Pro | Arg |
| Tyr<br>545 | Glu | Ala | Leu | Arg | Gln<br>550 | Arg | Phe | Lys | Ser | Arg<br>555 | Ile | Leu | Asn | Glu | Tyr<br>560 |
| Gly | Phe | Thr | Glu | Ser<br>565 | Ala | Phe | Val | Thr | Ala<br>570 | Leu | Asn | Ile | Phe | Glu<br>575 | Pro |
| Thr | Ser | Gln | Arg<br>580 | Lys | Asp | Met | Ser | Leu<br>585 | Gly | Arg | Pro | Val | Arg<br>590 | Asn | Val |
| Lys | Cys | Tyr<br>595 | Ile | Leu | Asp | Ala | Asn<br>600 | Leu | Lys | Arg | Val | Pro<br>605 | Ile | Gly | Val |
| Thr | Gly<br>610 | Glu | Leu | His | Ile | Gly<br>615 | Gly | Leu | Gly | Ile | Ser<br>620 | Arg | Gly | Tyr | Met |
| Asn<br>625 | Arg | Glu | Glu | Leu | Thr<br>630 | Arg | Gln | Lys | Phe | Leu<br>635 | Pro | Asn | Pro | Tyr | Gln<br>640 |
| Thr | Asp | Lys | Glu | Arg<br>645 | Gln | Arg | Gly | Val | Asn<br>650 | Ser | Thr | Met | Tyr | Lys<br>655 | Thr |
| Gly | Asp | Leu | Ala<br>660 | Arg | Trp | Leu | Pro | Ser<br>665 | Gly | Glu | Val | Glu | Tyr<br>670 | Leu | Gly |
| Arg | Ala | Asp<br>675 | Phe | Gln | Ile | Lys | Leu<br>680 | Arg | Gly | Ile | Arg | Ile<br>685 | Glu | Pro | Gly |
| Glu | Ile<br>690 | Glu | Ser | Thr | Leu | Ala<br>695 | Met | Tyr | Pro | Gly | Ile<br>700 | Arg | Ala | Ser | Ile |
| Val<br>705 | Val | Ser | Lys | Lys | Leu<br>710 | Leu | Ser | Gln | Gly | Gln<br>715 | Glu | Thr | Ile | Gln | Asp<br>720 |
| His | Leu | Val | Gly | Tyr<br>725 | Val | Cys | Asp | Glu<br>730 | Gly | His | Ile | Pro | Glu<br>735 | Gly |
| Asp | Leu | Leu | Ser<br>740 | Phe | Leu | Glu | Lys | Lys<br>745 | Leu | Pro | Arg | Tyr | Met<br>750 | Val | Pro |
| Thr | Arg | Leu<br>755 | Val | Gln | Leu | Ala | Gln<br>760 | Ile | Pro | Thr | Asn | Ile<br>765 | Asn | Gly | Lys |
| Ala | Asp<br>770 | Leu | Arg | Ala | Leu | Pro<br>775 | Ala | Val | Glu | Val<br>780 | Ala | Val | Ala | Pro | Thr |
| His<br>785 | Lys | Gln | Asp | Gly | Glu<br>790 | Arg | Gly | Asn | Gln | Leu<br>795 | Glu | Ser | Asp | Leu | Ala<br>800 |
| Ala | Ile | Trp | Gly | Asn<br>805 | Ile | Leu | Ser | Val | Pro<br>810 | Ala | Gln | Asp | Ile | Gly<br>815 | Ser |
| Glu | Ser | Asn | Phe<br>820 | Phe | Arg | Leu | Gly | Gly<br>825 | His | Ser | Ile | Ala | Cys<br>830 | Ile | Gln |
| Leu | Ile | Ala<br>835 | Arg | Val | Arg | Gln | Gln<br>840 | Leu | Gly | Gln | Gly | Ile<br>845 | Thr | Leu | Glu |

-continued

```
Glu Val Phe Gln Thr Lys Thr Leu Arg Ala Met Ala Ala Leu Leu Ser
    850             855                 860

Glu Lys Tyr Thr Lys Ala Ser Asn Gly Thr Asn Gly Val Thr Asn Gly
    865             870                 875                 880

Thr Ala His Val Asn Gly His Ala Ala Asn Gly His Val Ser Asp Ser
                885                 890                 895

Tyr Val Ala Ser Ser Leu Gln Gln Gly Phe Val Tyr His Ser Leu Lys
            900                 905                 910

Asn Glu Leu Ser Glu Ala Tyr Thr Met Gln Ser Met Ile His Tyr Gly
        915                 920                 925

Val Pro Leu Lys Arg Asp Ile Tyr Gln Ala Ala Trp Gln Arg Val Gln
    930                 935                 940

Gly Glu His Pro Ala Leu Arg Leu Arg Phe Thr Trp Glu Ala Glu Val
945                 950                 955                 960

Met Gln Ile Val Asp Pro Lys Ser Glu Leu Asp Trp Arg Val Val Asp
                965                 970                 975

Trp Thr Asp Val Ser Ser Arg Glu Lys Gln Leu Val Ala Leu Glu Gln
            980                 985                 990

Leu Gln Thr Glu Asp Leu Ala Lys Val Tyr His Leu Asp Lys Gly Pro
        995                 1000                1005

Leu Met Arg Leu Tyr Leu Ile Leu Leu Pro Asp Ser Lys Tyr Ser Cys
    1010                1015                1020

Leu Phe Ser Cys His His Ala Ile Leu Asp Gly Trp Ser Leu Pro Leu
1025                1030                1035                1040

Leu Phe Asn Asn Val His Gln Ala Tyr Leu Asp Leu Val Glu Gly Thr
                1045                1050                1055

Ala Ser Pro Val Glu Gln Asp Ala Thr Tyr Leu Leu Gly Gln Gln Tyr
            1060                1065                1070

Leu Gln Ser His Arg Asp Asp His Leu Asp Phe Trp Ala Glu Gln Ile
        1075                1080                1085

Gly Arg Ile Glu Glu Arg Cys Asp Met Asn Ala Leu Leu Asn Glu Ala
    1090                1095                1100

Ser Arg Tyr Lys Val Pro Leu Ala Asp Tyr Asp Gln Val Arg Glu Gln
1105                1110                1115                1120

Arg Gln Gln Thr Ile Ser Leu Pro Trp Asn Asn Ser Met Asp Ala Gly
                1125                1130                1135

Val Arg Glu Glu Leu Ser Ser Arg Gly Ile Thr Leu His Ser Ile Leu
            1140                1145                1150

Gln Thr Val Trp His Leu Val Leu His Ser Tyr Gly Gly Gly Thr His
        1155                1160                1165

Thr Ile Thr Gly Thr Thr Ile Ser Gly Arg His Leu Pro Val Pro Gly
    1170                1175                1180

Ile Glu Arg Ser Val Gly Leu Phe Ile Asn Thr Leu Pro Met Ile Phe
1185                1190                1195                1200

Asp His Thr Val Cys Gln Asp Met Thr Ala Leu Glu Ala Ile Glu His
                1205                1210                1215

Val Gln Gly Gln Val Asn Ala Met Asn Ser Arg Gly Asn Val Glu Leu
            1220                1225                1230

Gly Arg Met Ser Lys Asn Asp Leu Lys His Gly Leu Phe Asp Thr Leu
        1235                1240                1245

Phe Val Leu Glu Asn Tyr Pro Asn Leu Asp Thr Glu Gln Arg Glu Lys
    1250                1255                1260

His Glu Glu Lys Leu Lys Phe Thr Ile Lys Gly Gly Thr Glu Lys Leu
1265                1270                1275                1280
```

```
Ser Tyr Pro Leu Ala Val Ile Ala Gln Glu Asp Gly Asp Ser Gly Cys
            1285                1290                1295
Ser Phe Thr Leu Cys Tyr Ala Gly Glu Leu Phe Thr Asp Glu Ser Ile
            1300                1305                1310
Gln Ala Leu Leu Asp Thr Val Arg Asp Thr Leu Ser Asp Ile Leu Gly
            1315                1320                1325
Asn Ile His Ala Pro Ile Arg Asn Met Glu Tyr Leu Ser Ser Asn Gln
            1330                1335                1340
Thr Ala Gln Leu Asp Lys Trp Asn Ala Thr Ala Phe Glu Tyr Pro Asn
1345                1350                1355                1360
Thr Thr Leu His Ala Met Phe Glu Ser Glu Ala Gln Gln Lys Pro Asp
            1365                1370                1375
Lys Val Ala Val Val Tyr Glu Asp Ile Arg Leu Thr Tyr Arg Glu Leu
            1380                1385                1390
Asn Ser Arg Ala Asn Ala Leu Ala Phe Tyr Leu Leu Ser Gln Ala Ala
            1395                1400                1405
Ile Gln Pro Asn Lys Leu Val Gly Leu Ile Met Asp Lys Ser Glu His
            1410                1415                1420
Met Ile Thr Ser Ile Leu Ala Val Trp Lys Thr Gly Gly Ala Tyr Val
1425                1430                1435                1440
Pro Ile Asp Pro Arg Tyr Pro Asp Gln Arg Ile Gln Tyr Ile Leu Glu
            1445                1450                1455
Asp Thr Ala Ala Leu Ala Val Ile Thr Asp Ser Pro His Ile Asp Arg
            1460                1465                1470
Leu Arg Ser Ile Thr Asn Asn Arg Leu Pro Val Ile Gln Ser Asp Phe
            1475                1480                1485
Ala Leu Gln Leu Pro Pro Ser Pro Val His Pro Val Ser Asn Cys Lys
            1490                1495                1500
Pro Ser Asp Leu Ala Tyr Ile Met Tyr Thr Ser Gly Thr Thr Gly Asn
1505                1510                1515                1520
Pro Lys Gly Val Met Val Glu His His Gly Val Val Asn Leu Cys Val
            1525                1530                1535
Ser Leu Cys Arg Leu Phe Gly Leu Arg Asn Thr Asp Asp Glu Val Ile
            1540                1545                1550
Leu Ser Phe Ser Asn Tyr Val Phe Asp His Phe Val Glu Gln Met Thr
            1555                1560                1565
Asp Ala Leu Leu Asn Gly Gln Thr Leu Val Val Leu Asn Asp Glu Met
            1570                1575                1580
Arg Gly Asp Lys Glu Arg Leu Tyr Arg Tyr Ile Glu Thr Asn Arg Val
1585                1590                1595                1600
Thr Tyr Leu Ser Gly Thr Pro Ser Val Ile Ser Met Tyr Glu Phe Asp
            1605                1610                1615
Arg Phe Arg Asp His Leu Arg Arg Val Asp Cys Val Gly Glu Ala Phe
            1620                1625                1630
Ser Glu Pro Val Phe Asp Lys Ile Arg Glu Thr Phe Pro Gly Leu Ile
            1635                1640                1645
Ile Asn Gly Tyr Gly Pro Thr Glu Val Ser Ile Thr Thr His Lys Arg
            1650                1655                1660
Pro Tyr Pro Phe Pro Glu Arg Arg Thr Asp Lys Ser Ile Gly Cys Gln
1665                1670                1675                1680
Leu Asp Asn Ser Thr Ser Tyr Val Leu Asn Asp Asp Met Lys Arg Val
            1685                1690                1695
Pro Ile Gly Ala Val Gly Glu Leu Tyr Leu Gly Gly Asp Gly Val Ala
```

-continued

```
                           1700                    1705                    1710
       Arg  Gly  Tyr  His  Asn  Arg  Pro  Asp  Leu  Thr  Ala  Asp  Arg  Phe  Pro  Ala
                 1715                    1720                    1725
       Asn  Pro  Phe  Gln  Thr  Glu  Gln  Glu  Arg  Leu  Glu  Gly  Arg  Asn  Ala  Arg
                 1730                    1735                    1740
       Leu  Tyr  Lys  Thr  Gly  Asp  Leu  Val  Arg  Trp  Ile  His  Asn  Ala  Asn  Gly
       1745                    1750                    1755                    1760
       Asp  Gly  Glu  Ile  Glu  Tyr  Leu  Gly  Arg  Asn  Asp  Phe  Gln  Val  Lys  Ile
                           1765                    1770                    1775
       Arg  Gly  Gln  Arg  Ile  Glu  Leu  Gly  Glu  Ile  Glu  Ala  Val  Leu  Ser  Ser
                 1780                    1785                    1790
       Tyr  Pro  Gly  Ile  Lys  Gln  Ser  Val  Val  Leu  Ala  Lys  Asp  Arg  Lys  Asn
                 1795                    1800                    1805
       Asp  Gly  Gln  Lys  Tyr  Leu  Val  Gly  Tyr  Phe  Val  Ser  Ser  Ala  Gly  Ser
                 1810                    1815                    1820
       Leu  Ser  Ala  Gln  Ala  Ile  Arg  Arg  Phe  Met  Leu  Thr  Ser  Leu  Pro  Asp
       1825                    1830                    1835                    1840
       Tyr  Met  Val  Pro  Ala  Gln  Leu  Val  Pro  Ile  Ala  Lys  Phe  Pro  Val  Thr
                           1845                    1850                    1855
       Val  Ser  Gly  Lys  Leu  Asp  Ala  Lys  Ala  Leu  Pro  Val  Pro  Asp  Asp  Thr
                           1860                    1865                    1870
       Val  Glu  Asp  Asp  Ile  Val  Pro  Pro  Arg  Thr  Glu  Val  Glu  Arg  Ile  Leu
                           1875                    1880                    1885
       Ala  Gly  Ile  Trp  Ser  Glu  Leu  Leu  Glu  Ile  Pro  Val  Asp  Arg  Ile  Ser
                 1890                    1895                    1900
       Ile  Tyr  Ser  Asp  Phe  Phe  Ser  Leu  Gly  Gly  Asp  Ser  Leu  Lys  Ser  Thr
       1905                    1910                    1915                    1920
       Lys  Leu  Ser  Phe  Ala  Ala  Thr  Arg  Ala  Leu  Gly  Val  Ala  Val  Ser  Val
                           1925                    1930                    1935
       Arg  Asn  Leu  Phe  Ser  His  Pro  Thr  Ile  Glu  Ala  Leu  Ser  Gln  Trp  Ile
                           1940                    1945                    1950
       Ile  Arg  Gly  Ser  Asn  Glu  Val  Lys  Asp  Val  Ala  Val  Val  Lys  Gly  Gly
                           1955                    1960                    1965
       Ala  Ser  Leu  Asp  Ile  Pro  Leu  Ser  Pro  Ala  Gln  Glu  Arg  Leu  Met  Phe
                 1970                    1975                    1980
       Ile  His  Glu  Phe  Gly  His  Ser  Gly  Glu  Asp  Thr  Gly  Ala  Tyr  Asn  Val
       1985                    1990                    1995                    2000
       Pro  Leu  Gln  Leu  Gln  Leu  His  His  Asp  Val  Cys  Leu  Glu  Ser  Leu  Glu
                           2005                    2010                    2015
       Lys  Ala  Leu  Arg  Asp  Val  Val  Ser  Arg  His  Glu  Ala  Leu  Arg  Thr  Leu
                 2020                    2025                    2030
       Ile  Thr  Arg  Thr  Gln  Lys  Ser  Ser  Val  His  Cys  Gln  Lys  Ile  Leu  Asp
                 2035                    2040                    2045
       Ala  Glu  Glu  Ala  Gln  Lys  Leu  Phe  Ser  Val  Asp  Val  Leu  Arg  Leu  Thr
                 2050                    2055                    2060
       Ser  Glu  Thr  Glu  Met  Gln  Gly  Arg  Met  Ala  Glu  Ser  Thr  Ala  His  Ala
       2065                    2070                    2075                    2080
       Phe  Lys  Leu  Asp  Glu  Glu  Leu  Pro  Ile  His  Val  Arg  Leu  Tyr  Gln  Val
                           2085                    2090                    2095
       Val  Arg  Asp  Gly  Arg  Thr  Leu  Ser  Phe  Ala  Ser  Ile  Val  Cys  His  His
                           2100                    2105                    2110
       Leu  Ala  Phe  Asp  Ala  Trp  Ser  Trp  Asp  Val  Phe  Gln  Arg  Asp  Leu  Asp
                           2115                    2120                    2125
```

```
Ala  Phe  Tyr  Ala  Val  His  Thr  Lys  His  Lys  Ala  Ala  Ala  Asn  Leu  Pro
     2130                2135                2140

Thr  Leu  Arg  Val  Gln  Tyr  Lys  Glu  Tyr  Ala  Ile  Glu  His  Arg  Arg  Ala
2145                2150                2155                          2160

Leu  Arg  Ala  Glu  Gln  His  Arg  Val  Leu  Ala  Asp  Tyr  Trp  Leu  Arg  Lys
               2165                2170                          2175

Leu  Ser  Asp  Met  Glu  Ala  Ser  Tyr  Leu  Val  Pro  Asp  Arg  Pro  Arg  Pro
               2180                2185                          2190

Ala  Gln  Phe  Asp  Tyr  Thr  Gly  Asn  Asp  Leu  Gln  Phe  Ser  Thr  Thr  Pro
               2195                2200                2205

Glu  Thr  Thr  Ala  Gln  Leu  Lys  Glu  Leu  Ala  Lys  Arg  Glu  Gly  Ser  Ser
               2210                2215                2220

Leu  Tyr  Thr  Val  Val  Ala  Ala  Ala  Tyr  Phe  Leu  Leu  Leu  Tyr  Val  Tyr
2225                2230                2235                          2240

Thr  Asn  Gln  Arg  Asp  Ile  Thr  Ile  Gly  Ile  Pro  Val  Ala  His  Arg  Asn
               2245                2250                          2255

His  Pro  Asp  Phe  Glu  Ser  Val  Val  Gly  Phe  Phe  Val  Asn  Leu  Leu  Pro
               2260                2265                          2270

Leu  Arg  Val  Asn  Val  Ser  Gln  Ser  Asp  Ile  His  Gly  Leu  Ile  Gln  Ala
               2275                2280                2285

Val  Gln  Lys  Glu  Leu  Val  Asp  Ala  Gln  Ile  His  Gln  Asp  Leu  Pro  Phe
     2290                2295                2300

Gln  Glu  Ile  Thr  Lys  Leu  Leu  His  Val  Gln  His  Asp  Pro  Ser  Arg  His
2305                2310                2315                          2320

Pro  Leu  Leu  Gln  Ala  Val  Phe  Asn  Trp  Glu  Asn  Val  Pro  Ala  Asn  Val
               2325                2330                          2335

His  Glu  Glu  Gln  Leu  Leu  Gln  Glu  Tyr  Lys  Pro  Pro  Ser  Pro  Leu  Pro
               2340                2345                2350

Ser  Ala  Ala  Lys  Phe  Asp  Leu  Asn  Val  Thr  Val  Lys  Glu  Ser  Val  Asn
               2355                2360                2365

Ser  Leu  Asn  Val  Asn  Phe  Asn  Tyr  Pro  Thr  Ser  Leu  Phe  Glu  Glu  Glu
               2370                2375                2380

Thr  Val  Gln  Gly  Phe  Met  Glu  Thr  Phe  His  Leu  Leu  Leu  Arg  Gln  Leu
2385                2390                2395                          2400

Ala  His  Asn  Lys  Ala  Ser  Thr  Ser  Leu  Ser  Lys  Leu  Ser  Val  Glu  Asp
               2405                2410                2415

Gly  Val  Leu  Asn  Pro  Glu  Pro  Thr  Asn  Leu  Gln  Pro  Ser  Ser  Arg  Asp
               2420                2425                2430

Ser  Gly  Asn  Ser  Leu  His  Gly  Leu  Phe  Glu  Asp  Ile  Val  Ala  Ser  Thr
               2435                2440                2445

Pro  Asp  Arg  Ile  Ala  Ile  Ala  Asp  Gly  Thr  Arg  Ser  Leu  Ser  Tyr  Ser
     2450                2455                2460

Glu  Leu  Asn  Glu  Arg  Ala  Asn  Gln  Leu  Val  His  Leu  Ile  Ile  Ser  Ser
2465                2470                2475                          2480

Ala  Ser  Ile  Val  Ala  Asp  Asp  Arg  Ile  Ala  Leu  Leu  Leu  Asp  Lys  Ser
               2485                2490                2495

Ile  Asp  Met  Val  Ile  Ala  Leu  Leu  Ala  Val  Trp  Lys  Ala  Gly  Ala  Ala
               2500                2505                2510

Tyr  Val  Pro  Leu  Asp  Pro  Thr  Tyr  Pro  Ser  Gln  Arg  Thr  Glu  Leu  Ile
               2515                2520                2525

Leu  Glu  Glu  Ser  Ser  Ala  Arg  Thr  Leu  Ile  Thr  Thr  Arg  Lys  His  Thr
               2530                2535                2540

Pro  Arg  Gly  Gly  Thr  Val  Ala  Asn  Val  Pro  Ser  Val  Val  Leu  Asp  Ser
2545                2550                2555                          2560
```

```
Pro Glu Thr Leu Ala Cys Leu Asn Gln Gln Ser Lys Glu Asn Pro Thr
                2565                2570                2575
Thr Ser Thr Gln Lys Pro Ser Asp Leu Ala Tyr Val Ile Phe Thr Ser
                2580                2585                2590
Gly Thr Thr Gly Lys Pro Lys Gly Val Leu Val Glu His Gln Ser Val
                2595                2600                2605
Val Gln Leu Arg Asn Ser Leu Ile Glu Arg Tyr Phe Gly Glu Thr Asn
    2610                2615                2620
Gly Ser His Ala Val Leu Phe Leu Ser Asn Tyr Val Phe Asp Phe Ser
2625                2630                2635                2640
Leu Glu Gln Leu Cys Leu Ser Val Leu Gly Gly Asn Lys Leu Ile Ile
                2645                2650                2655
Pro Pro Glu Glu Gly Leu Thr His Glu Ala Phe Tyr Asp Ile Gly Arg
                2660                2665                2670
Arg Glu Lys Leu Ser Tyr Leu Ser Gly Thr Pro Ser Val Leu Gln Gln
                2675                2680                2685
Ile Glu Leu Ser Arg Leu Pro His Leu His Met Val Thr Ala Ala Gly
                2690                2695                2700
Glu Glu Phe His Ala Ser Gln Phe Glu Lys Met Arg Ser Gln Phe Ala
2705                2710                2715                2720
Gly Gln Ile Asn Asn Ala Tyr Gly Ile Thr Glu Thr Thr Val Tyr Asn
                2725                2730                2735
Ile Ile Thr Thr Phe Lys Gly Asp Ala Pro Phe Thr Lys Ala Leu Cys
                2740                2745                2750
His Gly Ile Pro Gly Ser His Val Tyr Val Leu Asn Asp Arg Leu Gln
                2755                2760                2765
Arg Val Pro Phe Asn Ala Val Gly Glu Leu Tyr Leu Gly Gly Asp Cys
                2770                2775                2780
Leu Ala Arg Gly Tyr Leu Asn Gln Asp Ala Leu Thr Asn Glu Arg Phe
2785                2790                2795                2800
Ile Pro Asn Pro Phe Tyr Glu Pro Lys Gln Ala Ser Asp Ser Arg Pro
                2805                2810                2815
Gln Arg Leu Tyr Lys Thr Gly Asp Leu Val Arg Phe Arg Gly Pro His
                2820                2825                2830
His Leu Glu Tyr Leu Gly Arg Lys Asp Gln Gln Val Lys Leu Arg Gly
                2835                2840                2845
Phe Arg Ile Glu Leu Ser Glu Val Arg Asp Ala Val Leu Ala Ile Ser
                2850                2855                2860
Ala Val Lys Glu Ala Ala Val Ile Pro Lys Tyr Asp Glu Asp Gly Ser
2865                2870                2875                2880
Asp Ser Arg Arg Val Ser Ala Ile Val Cys Tyr Tyr Thr Leu Asn Ala
                2885                2890                2895
Gly Thr Val Cys Glu Ala Ser Ser Ile Arg Asp His Leu His Ala Asn
                2900                2905                2910
Leu Pro Pro Tyr Met Val Pro Ser Gln Ile His Gln Leu Glu Gly Ser
                2915                2920                2925
Leu Pro Val Thr Val Asn Gly Lys Leu Asp Leu Asn Arg Leu Ser Thr
                2930                2935                2940
Thr Gln Val Ser Gln Pro Glu Leu Tyr Thr Ala Pro Arg Asn Ser Thr
2945                2950                2955                2960
Glu Glu Thr Leu Cys Gln Leu Trp Ala Ser Leu Leu Gly Val Asp His
                2965                2970                2975
Cys Gly Ile Asp Asp Asp Leu Phe Ala Arg Gly Gly Asp Ser Ile Ser
```

```
                          2980                    2985                    2990
     Ser  Leu  Arg  Leu  Val  Gly  Asp  Ile  Tyr  Arg  Ala  Leu  Gly  Arg  Lys  Val
                    2995                    3000                    3005
     Thr  Val  Lys  Asp  Ile  Tyr  Leu  His  Arg  Ser  Val  Arg  Ala  Leu  Ser  Glu
                    3010                    3015                    3020
     Asn  Val  Leu  Thr  Asp  Gln  Lys  Asp  Lys  Gly  Thr  Leu  Pro  Ala  Ser  Pro
3025                    3030                    3035                    3040
     Pro  Leu  Gln  Arg  Ala  Glu  Gln  Gly  Gln  Val  Glu  Gly  Asp  Ala  Pro  Leu
                    3045                    3050                    3055
     Leu  Pro  Ile  Gln  Asp  Trp  Phe  Leu  Ser  Lys  Pro  Leu  Asp  Asn  Pro  Ala
                    3060                    3065                    3070
     Tyr  Trp  Asn  His  Cys  Phe  Thr  Ile  Arg  Thr  Gly  Ala  Leu  Ser  Val  Glu
                    3075                    3080                    3085
     Gly  Leu  Arg  Gly  Ala  Leu  Lys  Leu  Leu  Gln  Glu  Arg  His  Asp  Val  Leu
                    3090                    3095                    3100
     Arg  Leu  Arg  Leu  Gln  Arg  Arg  Asp  Glu  Gly  Arg  His  Val  Gln  Thr  Phe
3105                    3110                    3115                    3120
     Ala  Arg  Asp  Cys  Ala  Gln  Pro  Arg  Leu  Thr  Val  Leu  Asp  Arg  Arg  Ser
                    3125                    3130                    3135
     Phe  Glu  Asp  Ala  Glu  Asp  Val  Gln  Glu  Ala  Leu  Cys  Glu  Ile  Gln  Ser
                    3140                    3145                    3150
     His  Phe  Asp  Leu  Glu  Asn  Gly  Pro  Leu  Tyr  Thr  Val  Ala  Tyr  Ile  His
                    3155                    3160                    3165
     Gly  Tyr  Glu  Asp  Gly  Ser  Ala  Arg  Val  Trp  Phe  Ala  Cys  His  His  Val
                    3170                    3175                    3180
     Met  Val  Asp  Thr  Val  Ser  Trp  Asn  Ile  Ile  Leu  Gln  Asp  Leu  Gln  Ala
3185                    3190                    3195                    3200
     Leu  Tyr  His  Gly  Asp  Ser  Leu  Gly  Pro  Lys  Ser  Ser  Val  Gln  Gln
                    3205                    3210                    3215
     Trp  Ser  Leu  Ala  Val  Ser  Asp  Tyr  Lys  Met  Pro  Leu  Ser  Glu  Arg  Ala
                    3220                    3225                    3230
     His  Trp  Asn  Val  Leu  Arg  Lys  Thr  Val  Ala  Gln  Ser  Phe  Glu  Thr  Leu
                    3235                    3240                    3245
     Pro  Ile  Cys  Met  Gly  Gly  Val  Leu  Gln  Cys  Gln  Glu  Lys  Phe  Ser  Arg
                    3250                    3255                    3260
     Glu  Thr  Thr  Thr  Ala  Leu  Leu  Ser  Lys  Ala  Cys  Pro  Ala  Leu  Asp  Ser
3265                    3270                    3275                    3280
     Gly  Met  His  Glu  Ile  Leu  Leu  Met  Ala  Val  Gly  Ser  Ala  Leu  Gln  Lys
                    3285                    3290                    3295
     Ala  Ala  Gly  Asp  Val  Pro  Gln  Val  Val  Thr  Ile  Glu  Gly  His  Gly  Arg
                    3300                    3305                    3310
     Glu  Asp  Thr  Ile  Asp  Ala  Thr  Leu  Asp  Val  Ser  Arg  Thr  Val  Gly  Trp
                    3315                    3320                    3325
     Phe  Thr  Ser  Met  Tyr  Pro  Phe  Glu  Ile  Pro  Lys  Val  Thr  Asp  Pro  Ala
                    3330                    3335                    3340
     Gln  Gly  Val  Val  Asp  Val  Lys  Glu  Ala  Met  Arg  Arg  Val  Pro  Asn  Arg
3345                    3350                    3355                    3360
     Gly  Val  Gly  Tyr  Gly  Pro  Ala  Tyr  Gly  Tyr  Gly  Gly  Ser  Cys  Leu  Pro
                    3365                    3370                    3375
     Ala  Val  Ser  Phe  Asn  Tyr  Leu  Gly  Arg  Leu  Asp  Gln  Ala  Ser  Ser  Gly
                    3380                    3385                    3390
     Ala  Gln  Arg  Asp  Trp  Thr  Leu  Val  Met  Asp  Glu  Asp  Glu  Tyr  Pro  Val
                    3395                    3400                    3405
```

-continued

```
Gly Leu Cys Thr Ser Ala Glu Asp Ser Gly Arg Ser Ser Met Val
    3410                3415                3420

Asp Phe Thr Phe Ser Ile Ser Gly Gly Gln Leu Val Met Asp Met Ser
3425                3430                3435                3440

Ser Ser Trp Gly His Gly Ala Arg Asn Glu Phe Val Arg Thr Val Arg
                3445                3450                3455

Asn Thr Leu Asp Asp Leu Ile Lys Thr Thr Ser Ser Arg Asp Phe Ser
                3460            3465                3470

Ala Pro Leu Pro Pro Ser Asp Gln Glu Ser Ser Phe Thr Pro Tyr Phe
            3475            3480            3485

Val Phe Glu Glu Gly Glu Arg His Gly Ala Pro Leu Phe Leu Leu Pro
    3490                3495                3500

Pro Gly Glu Gly Gly Ala Glu Ser Tyr Phe His Asn Ile Val Lys Gly
3505                3510                3515                3520

Leu Pro Asn Arg Asn Leu Val Val Phe Asn Asn His Tyr Arg Glu Glu
                3525                3530                3535

Lys Thr Leu Arg Thr Ile Glu Ala Leu Ala Glu Tyr Tyr Leu Ser His
                3540            3545            3550

Ile Arg Ser Ile Gln Pro Glu Gly Pro Tyr His Ile Leu Gly Trp Ser
                3555            3560            3565

Phe Gly Gly Ile Leu Gly Leu Glu Ala Ala Lys Arg Leu Thr Gly Glu
    3570            3575            3580

Gly His Lys Ile Ala Thr Leu Ala Leu Ile Asp Pro Tyr Phe Asp Ile
3585            3590            3595            3600

Pro Ser Ala Ser Lys Ala Ile Gly Gln Pro Asp Asp Ala Cys Val Leu
            3605            3610            3615

Asp Pro Ile Tyr His Val Tyr His Pro Ser Pro Glu Ser Phe Arg Thr
            3620            3625            3630

Val Ser Ser Leu Thr Asn His Ile Ala Leu Phe Lys Ala Thr Glu Thr
            3635            3640            3645

Asn Asp Gln His Gly Asn Ala Thr Gln Gln Ala Leu Tyr Glu Trp Phe
            3650            3655            3660

Ala
3665
```

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other nucleic acid
        / synthetic DNA ( i i i ) HYPOTHETICAL: NO ( i v ) ANTI-SENSE: NO ( x i ) SEQUENCE DESCRIPTION: SEQ ID NO:14:

CCCAGACGCA CTTGATCCTG                                                        20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i  i  ) MOLECULE TYPE: Other nucleic acid
/   synthetic DNA (  i  i  i  ) HYPOTHETICAL: NO (  i  v  ) ANTI-SENSE: NO (  x  i  ) SEQUENCE DESCRIPTION: SEQ ID NO:15:

GTCCCCGCTT GCGACGACTG                                            20

( 2 ) INFORMATION FOR SEQ ID NO:16:

(  i  ) SEQUENCE CHARACTERISTICS:
( A ) LENGTH: 19 base pairs
( B ) TYPE: nucleic acid
( C ) STRANDEDNESS: single
( D ) TOPOLOGY: linear (  i  i  ) MOLECULE TYPE: Other nucleic acid
/   synthetic DNA (  i  i  i  ) HYPOTHETICAL: NO (  i  v  ) ANTI-SENSE: NO (  x  i  ) SEQUENCE DESCRIPTION: SEQ ID NO:16:

CGGGAATCAT CTGCGTATC                                             19

( 2 ) INFORMATION FOR SEQ ID NO:17:

(  i  ) SEQUENCE CHARACTERISTICS:
( A ) LENGTH: 20 base pairs
( B ) TYPE: nucleic acid
( C ) STRANDEDNESS: single
( D ) TOPOLOGY: linear (  i  i  ) MOLECULE TYPE: Other nucleic acid
/   synthetic DNA (  i  i  i  ) HYPOTHETICAL: NO (  i  v  ) ANTI-SENSE: NO (  x  i  ) SEQUENCE DESCRIPTION: SEQ ID NO:17:

CGCGCTCAAA GGCCTGGTTC                                            20

( 2 ) INFORMATION FOR SEQ ID NO:18:

(  i  ) SEQUENCE CHARACTERISTICS:
( A ) LENGTH: 36 amino acids
( B ) TYPE: amino acid
( D ) TOPOLOGY: linear (  i  i  ) MOLECULE TYPE: peptide (  i  i  i  ) HYPOTHETICAL: NO (  i  v  ) ANTI-SENSE: NO ( v ) FRAGMENT TYPE: internal (  i  x  ) FEATURE:
( A ) NAME/KEY: Modified-site
( B ) LOCATION: 24..35
( D ) OTHER INFORMATION: /label=alternativeaas
/ note= "aa24=Asp or Arg; aa26=Gly or Trp;
aa28=Asp or Tyr; aa29=Asp or Val; aa32=unknown;
aa35=Asp or Arg"

(  x  i  ) SEQUENCE DESCRIPTION: SEQ ID NO:18:

Asn  Ala  Asn  Val  Tyr  Leu  Ala  Asn  Ser  Leu  Gln  Gln  Gly  Phe  Val  Tyr
1                 5                                  10                                 15

```
          Gln Phe Leu Lys Asn Met Gly Xaa Ser Xaa Ala Xaa Xaa Met Gln Xaa
                      20                  25              30

Val Thr Xaa Tyr
                  35
```

(2) INFORMATION FOR SEQ ID NO:19:

(i) SEQUENCE CHARACTERISTICS:
        (A) LENGTH: 24 amino acids
        (B) TYPE: amino acid
        (D) TOPOLOGY: linear (i i) MOLECULE TYPE: peptide (i i i) HYPOTHETICAL: NO (v) FRAGMENT TYPE: internal (i x) FEATURE:
        (A) NAME/KEY: Modified-site
        (B) LOCATION: 5..22
        (D) OTHER INFORMATION: /label=alternativeaas
            / note= "aa5=unknown; aa19=unknown; aa21=Leu or Ser; aa22=Asp or Glu"

(x i) SEQUENCE DESCRIPTION: SEQ ID NO:19:

```
          Gln Ser Val Gln Xaa Ile Lys Ser Val Ala Lys Phe Asp Leu Asn Ala
          1               5                   10                  15

Thr Ala Xaa Glu Xaa Xaa Lys Ala
                      20
```

(2) INFORMATION FOR SEQ ID NO:20:

(i) SEQUENCE CHARACTERISTICS:
        (A) LENGTH: 17 amino acids
        (B) TYPE: amino acid
        (C) STRANDEDNESS: single
        (D) TOPOLOGY: linear (i i) MOLECULE TYPE: peptide (i i i) HYPOTHETICAL: NO (v) FRAGMENT TYPE: internal (i x) FEATURE:
        (A) NAME/KEY: Modified-site
        (B) LOCATION: 1..16
        (D) OTHER INFORMATION: /label=alternativeaas
            / note= "aa1=Gln or Ser or Cys; aa15=Thr or Gln; aa16=His or Gln"

(x i) SEQUENCE DESCRIPTION: SEQ ID NO:20:

```
          Xaa Gln Thr Val Leu Gly Asp Ala Pro Leu Leu Pro Ile Gln Xaa Xaa
          1               5                   10                  15

Phe
```

(2) INFORMATION FOR SEQ ID NO:21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (i i) MOLECULE TYPE: Other nucleic acid
        / synthetic DNA (i i i) HYPOTHETICAL: NO (i v) ANTI-SENSE: NO ( x i ) SEQUENCE DESCRIPTION: SEQ ID NO:21:

TGGCTTCAGT TGAGTCATAT GGGTAGTTAA TGGTAT 36

( 2 ) INFORMATION FOR SEQ ID NO: 22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid
        / synthetic DNA ( i i i ) HYPOTHETICAL: NO ( i v ) ANTI-SENSE: NO ( x i ) SEQUENCE DESCRIPTION: SEQ ID NO: 22:

TTCGGCGATA ACATGGAG 18

( 2 ) INFORMATION FOR SEQ ID NO: 23:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid
        / synthetic DNA ( i i i ) HYPOTHETICAL: NO ( i v ) ANTI-SENSE: NO ( x i ) SEQUENCE DESCRIPTION: SEQ ID NO: 23:

TTCGGCGATA ATATGGAG 18

( 2 ) INFORMATION FOR SEQ ID NO:24:

( i ) SEQUENCE CHARACTERISTICS:
        ( A ) LENGTH: 11601 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Acremonium chrysogenum ( i x ) FEATURE:
        ( A ) NAME/KEY: CDS
        ( B ) LOCATION: 388..11526
        ( D ) OTHER INFORMATION: /function="Enzyme"
            / product= "ACV Synthetase"

( i x ) FEATURE:
        ( A ) NAME/KEY: CDS
        ( B ) LOCATION: 8050..8052
        ( D ) OTHER INFORMATION:
            / note= "NNN=AGU, AGC, UCU, UCC, UCA, or UCG"

( x i ) SEQUENCE DESCRIPTION: SEQ ID NO:24:

GGATGCATGC ATTGGCCTGT ATCAAAGGTC CGGGATTCCC CAGGAGTATA AGACGTTCGT 60

GCTGGGAGAT CTAGCGACGT GTTGGGAAAT ATCGGCCGTA GAGTGCGAAA AAGAACTGGC 120

GGAAATATTT CTCCTTGGAC TCGGTCACAC TCAGTCAGTA GTGGACTGCC AGTCTATCAT 180

ACACCTTTGA TATCAACATG ACTATCCTTA CAGGTGCCGA CGACGCCTCG TCATACCACA 240

```
GGTATGTCTT CACAGCCTCT GGAAAGCGCA GTTGGGAGCT ATCTCTAACA TTACCACATC      300

AGGCGCAATG GAAGCTCTGA TATCCCAAAA GGTGCCATCC ACCGCAACGG CTTCGCAGCC      360

GCAGCCCCTG ACTGCTGGAT CCGGTCC GTG GCC CTG GAA CAG TGG AAG ACT          411
                             Val Ala Leu Glu Gln Trp Lys Thr
                              1                   5

ACG GTC CAG TCC GTC TCG GAG CGG TGC GAT CTG AGC GGG CTG AGC CAG        459
Thr Val Gln Ser Val Ser Glu Arg Cys Asp Leu Ser Gly Leu Ser Gln
         10              15                  20

CAT CCC ACC GAC TAC CAG CTG GCC TCT ACG GGC GTG AAG GGC GCA GGC        507
His Pro Thr Asp Tyr Gln Leu Ala Ser Thr Gly Val Lys Gly Ala Gly
 25              30                  35                      40

GGT AGC AGC ATC GAG GAG CGC AGT GCC ATC GTC TCA GAC GAG TTG TTC        555
Gly Ser Ser Ile Glu Glu Arg Ser Ala Ile Val Ser Asp Glu Leu Phe
                 45                  50                  55

TCG AGT CTG CGA GAC GTG TGC TCA CAG AGA CAG CTG GAC CCT CGG TCA        603
Ser Ser Leu Arg Asp Val Cys Ser Gln Arg Gln Leu Asp Pro Arg Ser
             60                  65                  70

CTC ATG CTG TTT TCC GTG CAC CAG ATG CTC AAG AGG TTC GGA AAC GGA        651
Leu Met Leu Phe Ser Val His Gln Met Leu Lys Arg Phe Gly Asn Gly
         75                  80                  85

TCT CAC ACC GTC GTG GCG TCA CTC GTA ACT TCA TCA GAG GGA TGC CCT        699
Ser His Thr Val Val Ala Ser Leu Val Thr Ser Ser Glu Gly Cys Pro
     90                  95                 100

TCA ACT TCG GCC TGG AGG GCC ATC CCC TCC GTC ATC CAT CAT ATA GAG        747
Ser Thr Ser Ala Trp Arg Ala Ile Pro Ser Val Ile His His Ile Glu
105              110                 115                 120

GGC GGA GAC AAC AAC AAC ACA GTC GCC TCT GCC GTG GAA CAG GCG GCG        795
Gly Gly Asp Asn Asn Asn Thr Val Ala Ser Ala Val Glu Gln Ala Ala
                 125                 130                 135

AAT CTC CTG AAC TCA GAA GGA TCG GGA CAG GAC CTT CTG ATT CCC ATC        843
Asn Leu Leu Asn Ser Glu Gly Ser Gly Gln Asp Leu Leu Ile Pro Ile
             140                 145                 150

GGA CTC ACT GAG CTC GTC AAG TCG GAG CTG ATT GAC CTC CTG GTC ATC        891
Gly Leu Thr Glu Leu Val Lys Ser Glu Leu Ile Asp Leu Leu Val Ile
         155                 160                 165

TTC GAC GAC GAG ACA AAT AAC ATA CGA CTG CCG CAG GAC TTC CCA CTT        939
Phe Asp Asp Glu Thr Asn Asn Ile Arg Leu Pro Gln Asp Phe Pro Leu
170                 175                 180

ATC CTG CGG ATA CAT CAG CGG CAA GAC CAC TGG CAG CTG TCA GTC CGG        987
Ile Leu Arg Ile His Gln Arg Gln Asp His Trp Gln Leu Ser Val Arg
185                 190                 195                 200

TAT CCC TCG CCC CTT TTC GAC ACC ATG GTC ATC GAC AGC TTT CTG AGC       1035
Tyr Pro Ser Pro Leu Phe Asp Thr Met Val Ile Asp Ser Phe Leu Ser
             205                 210                 215

GCA CTT CAC AAC CTG TTG TCC GCG GTG ACA AAA CCC TCC CAG CTC GTG       1083
Ala Leu His Asn Leu Leu Ser Ala Val Thr Lys Pro Ser Gln Leu Val
         220                 225                 230

CGC GAC ATC GAG CTG CTC CCA GAA TAC CAG GTC GCT CAG CTG GAG AAG       1131
Arg Asp Ile Glu Leu Leu Pro Glu Tyr Gln Val Ala Gln Leu Glu Lys
             235                 240                 245

TGG AAC AAC ACA GAC GGC GAC TAC CCC ACC GAG AAG CGG CTA CAT CAT       1179
Trp Asn Asn Thr Asp Gly Asp Tyr Pro Thr Glu Lys Arg Leu His His
250                 255                 260

CTG TTC GAG GAG GCA GCA GTG CGT CGT CCC CAA CAC GTT GCC CTC ATC       1227
Leu Phe Glu Glu Ala Ala Val Arg Arg Pro Gln His Val Ala Leu Ile
265                 270                 275                 280

TGC GGC GAC AAG CGC ATC ACC TAT GAG GAG TTG AAT GCT ATG GCG AAT       1275
Cys Gly Asp Lys Arg Ile Thr Tyr Glu Glu Leu Asn Ala Met Ala Asn
             285                 290                 295
```

| | | | | | | | | | | | | | | | | |
|---|---|---|---|---|---|---|---|---|---|---|---|---|---|---|---|---|
| CGC | CTG | GCC | CAC | CAT | CTG | GTA | TCC | TCG | GGT | ATC | CAG | ACT | GAG | CAG | CTC | 1323 |
| Arg | Leu | Ala | His 300 | His | Leu | Val | Ser | Ser 305 | Gly | Ile | Gln | Thr | Glu 310 | Gln | Leu | |
| GTC | GGT | CTC | TTC | CTC | GAC | AAG | ACC | GAG | CTC | ATG | ATC | GCT | ACT | ATT | CTG | 1371 |
| Val | Gly | Leu 315 | Phe | Leu | Asp | Lys | Thr 320 | Glu | Leu | Met | Ile | Ala 325 | Thr | Ile | Leu | |
| GGC | ATC | TGG | AAA | TCT | GGT | GCC | GCG | CAT | GTA | CCT | ATC | GAC | CCT | GGG | TAC | 1419 |
| Gly | Ile | Trp 330 | Lys | Ser | Gly | Ala | Ala 335 | His | Val | Pro | Ile | Asp 340 | Pro | Gly | Tyr | |
| CCG | GAC | GAG | CGT | GTC | AAG | TTC | GTC | CTG | AAT | GAT | ACG | AAG | GCG | CAA | GTG | 1467 |
| Pro | Asp | Glu | Arg | Val | Lys 350 | Phe | Val | Leu | Asn | Asp 355 | Thr | Lys | Ala | Gln | Val 360 | |
| Pro 345 | | | | | | | | | | | | | | | | |
| GTC | ATT | GCT | AGT | CAG | AGG | CAC | GTC | GAT | CGA | CTG | CGG | GCT | GAG | GCT | GTT | 1515 |
| Val | Ile | Ala | Ser | Gln 365 | Arg | His | Val | Asp | Arg 370 | Leu | Arg | Ala | Glu | Ala 375 | Val | |
| GGC | GGC | CAG | CAT | CTT | CGC | ATC | ATC | GGT | CTC | GAA | TCT | CTG | TTC | GAC | AAC | 1563 |
| Gly | Gly | Gln | His 380 | Leu | Arg | Ile | Ile | Gly 385 | Leu | Glu | Ser | Leu | Phe 390 | Asp | Asn | |
| CTT | GCT | CAA | CAG | ACA | CAA | CAC | TCA | CCA | GAG | ACG | TCG | GGC | AAT | TTG | ACC | 1611 |
| Leu | Ala | Gln | Gln 395 | Thr | Gln | His | Ser | Pro 400 | Glu | Thr | Ser | Gly | Asn 405 | Leu | Thr | |
| CAT | CTG | CCC | CTG | AAC | AGC | AAA | CAG | CTT | GCG | TAC | GTG | ACA | TAC | ACC | TCG | 1659 |
| His | Leu 410 | Pro | Leu | Asn | Ser | Lys 415 | Gln | Leu | Ala | Tyr | Val 420 | Thr | Tyr | Thr | Ser | |
| GGC | ACC | ACG | GGC | TTC | CCG | AAA | GGC | ATC | TAC | AAG | GAG | CAC | ACA | AGC | GTC | 1707 |
| Gly | Thr 425 | Thr | Gly | Phe | Pro 430 | Lys | Gly | Ile | Tyr | Lys 435 | Glu | His | Thr | Ser | Val 440 | |
| GTT | AAC | AGC | ATC | ACC | GAT | CTG | TCT | GCT | CGG | TAC | GGT | GTG | GCC | GGG | GAG | 1755 |
| Val | Asn | Ser | Ile | Thr 445 | Asp | Leu | Ser | Ala | Arg 450 | Tyr | Gly | Val | Ala | Gly 455 | Glu | |
| GAC | GAC | GAG | GTG | ATA | CTC | GTC | TTC | TCC | GCC | TAC | GTC | TTC | GAG | CCA | TTC | 1803 |
| Asp | Asp | Glu | Val 460 | Ile | Leu | Val | Phe | Ser 465 | Ala | Tyr | Val | Phe | Glu 470 | Pro | Phe | |
| GTG | CGC | CAG | ATG | CTC | ATG | GCC | CTG | ACC | ACG | GGC | AAC | TCT | CTC | GCC | ATC | 1851 |
| Val | Arg | Gln | Met 475 | Leu | Met | Ala | Leu | Thr 480 | Thr | Gly | Asn | Ser | Leu 485 | Ala | Ile | |
| ATC | AGC | GAC | GAG | GAC | AAG | TTC | GAC | CCT | GAC | ACC | CTT | ATT | CCC | TTC | ATC | 1899 |
| Ile | Ser | Asp 490 | Glu | Asp | Lys | Phe | Asp 495 | Pro | Asp | Thr | Leu | Ile 500 | Pro | Phe | Ile | |
| CAA | AAA | CAC | AAA | GTC | ACT | TAC | ATC | CAC | GCC | ACC | TCG | TCA | GTG | TTG | CAG | 1947 |
| Gln | Lys | His | Lys | Val 510 | Thr | Tyr | Ile | His | Ala 515 | Thr | Ser | Ser | Val | Leu | Gln 520 | |
| Gln 505 | | | | | | | | | | | | | | | | |
| GAG | TAC | GAC | TTC | GGG | TCC | TGC | CCC | TCG | TTG | AAA | CGC | ATG | ATT | CTG | GTG | 1995 |
| Glu | Tyr | Asp | Phe | Gly 525 | Ser | Cys | Pro | Ser | Leu 530 | Lys | Arg | Met | Ile | Leu 535 | Val | |
| GGA | GAG | AAC | TTG | ACA | GAG | CCG | CGC | TAC | GAG | GCC | CTG | AGG | CAG | CGC | TTC | 2043 |
| Gly | Glu | Asn | Leu | Thr 540 | Glu | Pro | Arg | Tyr | Glu 545 | Ala | Leu | Arg | Gln | Arg 550 | Phe | |
| AAG | TCG | CGC | ATC | CTG | AAT | GAA | TAT | GGC | TTC | ACC | GAG | TCT | GCG | TTT | GTG | 2091 |
| Lys | Ser | Arg 555 | Ile | Leu | Asn | Glu | Tyr 560 | Gly | Phe | Thr | Glu | Ser 565 | Ala | Phe | Val | |
| ACG | GCG | CTC | AAC | ATA | TTC | GAG | CCT | ACC | TCA | CAG | AGG | AAG | GAC | ATG | AGT | 2139 |
| Thr | Ala | Leu 570 | Asn | Ile | Phe | Glu | Pro 575 | Thr | Ser | Gln | Arg | Lys 580 | Asp | Met | Ser | |
| CTG | GGA | AGG | CCG | GTG | CGC | AAC | GTC | AAG | TGC | TAT | ATC | TTG | GAT | GCC | AAC | 2187 |
| Leu | Gly | Arg | Pro | Val 590 | Arg | Asn | Val | Lys | Cys 595 | Tyr | Ile | Leu | Asp | Ala | Asn 600 | |
| Leu 585 | | | | | | | | | | | | | | | | |
| CTC | AAG | AGA | GTC | CCC | ATC | GGT | GTT | ACA | GGG | GAG | CTG | CAC | ATC | GGT | GGC | 2235 |
| Leu | Lys | Arg | Val | Pro 605 | Ile | Gly | Val | Thr | Gly 610 | Glu | Leu | His | Ile | Gly 615 | Gly | |

| | | | | | | | | | | | | | | | | |
|---|---|---|---|---|---|---|---|---|---|---|---|---|---|---|---|---|
| TTG | GGT | ATA | TCC | CGG | GGG | TAC | ATG | AAT | AGG | GAG | GAG | CTC | ACA | AGG | CAG | 2283 |
| Leu | Gly | Ile | Ser | Arg | Gly | Tyr | Met | Asn | Arg | Glu | Glu | Leu | Thr | Arg | Gln | |
| | | | 620 | | | | 625 | | | | | 630 | | | | |
| AAG | TTC | CTC | CCG | AAC | CCC | TAC | CAG | ACC | GAT | AAG | GAG | CGC | AA | CGG | GGT | 2331 |
| Lys | Phe | Leu | Pro | Asn | Pro | Tyr | Gln | Thr | Asp | Lys | Glu | Arg | Gln | Arg | Gly | |
| | | 635 | | | | | 640 | | | | | 645 | | | | |
| GTC | AAC | TCA | ACC | ATG | TAC | AAG | ACA | GGA | GAT | CTG | GCC | CGC | TGG | CTA | CCC | 2379 |
| Val | Asn | Ser | Thr | Met | Tyr | Lys | Thr | Gly | Asp | Leu | Ala | Arg | Trp | Leu | Pro | |
| | | 650 | | | | | 655 | | | | | 660 | | | | |
| AGT | GGC | GAA | GTC | GAG | TAT | CTC | GGC | CGT | GCC | GAC | TTC | CAG | ATC | AAG | CTG | 2427 |
| Ser | Gly | Glu | Val | Glu | Tyr | Leu | Gly | Arg | Ala | Asp | Phe | Gln | Ile | Lys | Leu | |
| 665 | | | | | 670 | | | | | 675 | | | | | 680 | |
| CGC | GGC | ATT | CGA | ATT | GAG | CCC | GGC | GAG | ATC | GAG | TCC | ACT | CTC | GCC | ATG | 2475 |
| Arg | Gly | Ile | Arg | Ile | Glu | Pro | Gly | Glu | Ile | Glu | Ser | Thr | Leu | Ala | Met | |
| | | | | 685 | | | | | 690 | | | | | 695 | | |
| TAT | CCC | GGA | ATC | AGG | GCC | AGC | ATC | GTC | GTG | TCA | AAG | AAG | CTT | CTC | AGT | 2523 |
| Tyr | Pro | Gly | Ile | Arg | Ala | Ser | Ile | Val | Val | Ser | Lys | Lys | Leu | Leu | Ser | |
| | | | 700 | | | | | 705 | | | | | 710 | | | |
| CAG | GGG | CAG | GAG | ACG | ATC | CAA | GAC | CAC | CTT | GTG | GGG | TAC | TAT | GTT | TGC | 2571 |
| Gln | Gly | Gln | Glu | Thr | Ile | Gln | Asp | His | Leu | Val | Gly | Tyr | Tyr | Val | Cys | |
| | | | 715 | | | | | 720 | | | | | 725 | | | |
| GAT | GAG | GGC | CAC | ATC | CCC | GAG | GGT | GAC | CTG | CTG | AGC | TTC | CTG | GAG | AAG | 2619 |
| Asp | Glu | Gly | His | Ile | Pro | Glu | Gly | Asp | Leu | Leu | Ser | Phe | Leu | Glu | Lys | |
| | 730 | | | | | 735 | | | | | 740 | | | | | |
| AAG | CTA | CCT | CGG | TAC | ATG | GTC | CCG | ACG | CGC | CTT | GTC | CAA | CTG | GCT | CAG | 2667 |
| Lys | Leu | Pro | Arg | Tyr | Met | Val | Pro | Thr | Arg | Leu | Val | Gln | Leu | Ala | Gln | |
| 745 | | | | | 750 | | | | | 755 | | | | | 760 | |
| ATT | CCA | ACC | AAT | ATC | AAC | GGC | AAG | GCG | GAT | CTG | CGT | GCT | CTT | CCT | GCC | 2715 |
| Ile | Pro | Thr | Asn | Ile | Asn | Gly | Lys | Ala | Asp | Leu | Arg | Ala | Leu | Pro | Ala | |
| | | | | 765 | | | | | 770 | | | | | 775 | | |
| GTC | GAA | GTC | GCC | GTA | GCT | CCC | ACC | CAC | AAG | CAG | GAT | GGC | GAG | CGA | GGA | 2763 |
| Val | Glu | Val | Ala | Val | Ala | Pro | Thr | His | Lys | Gln | Asp | Gly | Glu | Arg | Gly | |
| | | | 780 | | | | | 785 | | | | | 790 | | | |
| AAC | CAG | CTG | GAG | AGC | GAC | CTG | GCT | GCC | ATA | TGG | GGC | AAC | ATT | TTG | AGT | 2811 |
| Asn | Gln | Leu | Glu | Ser | Asp | Leu | Ala | Ala | Ile | Trp | Gly | Asn | Ile | Leu | Ser | |
| | | 795 | | | | | 800 | | | | | 805 | | | | |
| GTT | CCC | GCT | CAA | GAC | ATT | GGG | TCT | GAA | TCC | AAC | TTC | TTC | CGC | CTG | GGT | 2859 |
| Val | Pro | Ala | Gln | Asp | Ile | Gly | Ser | Glu | Ser | Asn | Phe | Phe | Arg | Leu | Gly | |
| 810 | | | | | 815 | | | | | 820 | | | | | | |
| GGC | CAC | AGT | ATT | GCA | TGC | ATC | CAG | CTC | ATT | GCT | CGT | GTG | CGA | CAG | CAG | 2907 |
| Gly | His | Ser | Ile | Ala | Cys | Ile | Gln | Leu | Ile | Ala | Arg | Val | Arg | Gln | Gln | |
| 825 | | | | | 830 | | | | | 835 | | | | | 840 | |
| CTA | GGC | CAG | GGG | ATT | ACC | CTC | GAG | GAG | GTC | TTC | CAG | ACC | AAG | ACG | TTG | 2955 |
| Leu | Gly | Gln | Gly | Ile | Thr | Leu | Glu | Glu | Val | Phe | Gln | Thr | Lys | Thr | Leu | |
| | | | | 845 | | | | | 850 | | | | | 855 | | |
| CGA | GCT | ATG | GCT | GCC | CTC | TTG | TCG | GAA | AAG | TAC | ACG | AAG | GCG | TCG | AAT | 3003 |
| Arg | Ala | Met | Ala | Ala | Leu | Leu | Ser | Glu | Lys | Tyr | Thr | Lys | Ala | Ser | Asn | |
| | | | 860 | | | | | 865 | | | | | 870 | | | |
| GGG | ACG | AAC | GGA | GTG | ACC | AAC | GGC | ACT | GCT | CAC | GTC | AAC | GGC | CAC | GCA | 3051 |
| Gly | Thr | Asn | Gly | Val | Thr | Asn | Gly | Thr | Ala | His | Val | Asn | Gly | His | Ala | |
| | | 875 | | | | | 880 | | | | | 885 | | | | |
| GCG | AAC | GGC | CAT | GTC | AGC | GAC | AGC | TAC | GTG | GCC | AGC | AGT | TTG | CAG | CAA | 3099 |
| Ala | Asn | Gly | His | Val | Ser | Asp | Ser | Tyr | Val | Ala | Ser | Ser | Leu | Gln | Gln | |
| | | 890 | | | | | 895 | | | | | 900 | | | | |
| GGC | TTT | GTT | TAC | CAT | TCA | CTC | AAG | AAC | GAA | CTG | TCC | GAG | GCG | TAC | ACC | 3147 |
| Gly | Phe | Val | Tyr | His | Ser | Leu | Lys | Asn | Glu | Leu | Ser | Glu | Ala | Tyr | Thr | |
| 905 | | | | | 910 | | | | | 915 | | | | | 920 | |
| ATG | CAA | TCC | ATG | ATC | CAC | TAT | GGT | GTG | CCC | CTG | AAA | CGG | GAT | ATT | TAC | 3195 |
| Met | Gln | Ser | Met | Ile | His | Tyr | Gly | Val | Pro | Leu | Lys | Arg | Asp | Ile | Tyr | |
| | | | | 925 | | | | | 930 | | | | | 935 | | |

| | | | | | | | | | | | | | | | | |
|---|---|---|---|---|---|---|---|---|---|---|---|---|---|---|---|---|
| CAA | GCG | GCA | TGG | CAG | AGG | GTA | CAG | GGG | GAG | CAC | CCT | GCA | CTG | CGG | CTT | 3243 |
| Gln | Ala | Ala | Trp | Gln | Arg | Val | Gln | Gly | Glu | His | Pro | Ala | Leu | Arg | Leu | |
| | | | 940 | | | | 945 | | | | | 950 | | | | |
| CGG | TTC | ACA | TGG | GAG | GCC | GAA | GTG | ATG | CAG | ATC | GTG | GAC | CCG | AAA | TCT | 3291 |
| Arg | Phe | Thr | Trp | Glu | Ala | Glu | Val | Met | Gln | Ile | Val | Asp | Pro | Lys | Ser | |
| | | 955 | | | | | 960 | | | | | | 965 | | | |
| GAA | CTC | GAC | TGG | CGT | GTT | GTT | GAC | TGG | ACC | GAT | GTT | TCG | AGC | CGG | GAG | 3339 |
| Glu | Leu | Asp | Trp | Arg | Val | Val | Asp | Trp | Thr | Asp | Val | Ser | Ser | Arg | Glu | |
| 970 | | | | | 975 | | | | | | 980 | | | | | |
| AAG | CAG | CTG | GTT | GCG | CTG | GAG | CAA | CTC | CAA | ACG | GAG | GAC | CTT | GCT | AAG | 3387 |
| Lys | Gln | Leu | Val | Ala | Leu | Glu | Gln | Leu | Gln | Thr | Glu | Asp | Leu | Ala | Lys | |
| 985 | | | | | 990 | | | | | 995 | | | | | 1000 | |
| GTC | TAC | CAT | CTC | GAT | AAG | GGG | CCC | CTT | ATG | CGA | CTA | TAC | CTC | ATC | CTG | 3435 |
| Val | Tyr | His | Leu | Asp | Lys | Gly | Pro | Leu | Met | Arg | Leu | Tyr | Leu | Ile | Leu | |
| | | | | | | | | | 1005 | | | 1010 | | | 1015 | |
| CTT | CCG | GAC | TCA | AAG | TAC | TCC | TGT | CTG | TTC | AGC | TGC | CAC | CAT | GCC | ATT | 3483 |
| Leu | Pro | Asp | Ser | Lys | Tyr | Ser | Cys | Leu | Phe | Ser | Cys | His | His | Ala | Ile | |
| | | | 1020 | | | | | 1025 | | | | | 1030 | | | |
| CTC | GAT | GGG | TGG | AGT | CTG | CCC | CTG | CTC | TTC | AAC | AAT | GTC | CAC | CAG | GCC | 3531 |
| Leu | Asp | Gly | Trp | Ser | Leu | Pro | Leu | Leu | Phe | Asn | Asn | Val | His | Gln | Ala | |
| | | 1035 | | | | | 1040 | | | | | 1045 | | | | |
| TAC | CTC | GAT | CTC | GTC | GAA | GGC | ACT | GCT | TCG | CCC | GTC | GAG | CAG | GAC | GCT | 3579 |
| Tyr | Leu | Asp | Leu | Val | Glu | Gly | Thr | Ala | Ser | Pro | Val | Glu | Gln | Asp | Ala | |
| 1050 | | | | | 1055 | | | | | | 1060 | | | | | |
| ACC | TAC | CTA | CTC | GGC | CAG | CAG | TAC | CTG | CAG | AGC | CAC | AGG | GAC | GAC | CAT | 3627 |
| Thr | Tyr | Leu | Leu | Gly | Gln | Gln | Tyr | Leu | Gln | Ser | His | Arg | Asp | Asp | His | |
| 1065 | | | | | 1070 | | | | | 1075 | | | | | 1080 | |
| CTC | GAC | TTC | TGG | GCC | GAG | CAG | ATC | GGC | AGG | ATC | GAA | GAG | CGC | TGC | GAC | 3675 |
| Leu | Asp | Phe | Trp | Ala | Glu | Gln | Ile | Gly | Arg | Ile | Glu | Glu | Arg | Cys | Asp | |
| | | | | 1085 | | | | | 1090 | | | | | 1095 | | |
| ATG | AAT | GCG | CTG | CTG | AAT | GAG | GCC | AGC | CGA | TAC | AAG | GTG | CCC | CTG | GCC | 3723 |
| Met | Asn | Ala | Leu | Leu | Asn | Glu | Ala | Ser | Arg | Tyr | Lys | Val | Pro | Leu | Ala | |
| | | | 1100 | | | | | 1105 | | | | | 1110 | | | |
| GAC | TAT | GAC | CAA | GTC | CGC | GAG | CAG | AGG | CAG | CAG | ACC | ATC | AGT | CTG | CCC | 3771 |
| Asp | Tyr | Asp | Gln | Val | Arg | Glu | Gln | Arg | Gln | Gln | Thr | Ile | Ser | Leu | Pro | |
| | | | 1115 | | | | | 1120 | | | | | 1125 | | | |
| TGG | AAC | AAC | TCC | ATG | GAC | GCT | GGT | GTG | CGG | GAA | GAA | CTC | TCC | AGT | CGT | 3819 |
| Trp | Asn | Asn | Ser | Met | Asp | Ala | Gly | Val | Arg | Glu | Glu | Leu | Ser | Ser | Arg | |
| | 1130 | | | | | 1135 | | | | | 1140 | | | | | |
| GGC | ATC | ACC | CTT | CAT | TCC | ATT | CTA | CAG | ACG | GTC | TGG | CAC | CTG | GTC | CTC | 3867 |
| Gly | Ile | Thr | Leu | His | Ser | Ile | Leu | Gln | Thr | Val | Trp | His | Leu | Val | Leu | |
| 1145 | | | | | 1150 | | | | | 1155 | | | | | 1160 | |
| CAC | TCT | TAT | GGA | GGA | GGC | ACC | CAC | ACG | ATC | ACC | GGC | ACC | ACC | ATC | TCC | 3915 |
| His | Ser | Tyr | Gly | Gly | Gly | Thr | His | Thr | Ile | Thr | Gly | Thr | Thr | Ile | Ser | |
| | | | | 1165 | | | | | 1170 | | | | | 1175 | | |
| GGC | CGT | CAC | CTG | CCC | GTC | CCC | GGA | ATT | GAG | CGC | TCT | GTT | GGT | CTC | TTC | 3963 |
| Gly | Arg | His | Leu | Pro | Val | Pro | Gly | Ile | Glu | Arg | Ser | Val | Gly | Leu | Phe | |
| | | | 1180 | | | | | 1185 | | | | | 1190 | | | |
| ATC | AAC | ACA | CTC | CCT | ATG | ATC | TTT | GAT | CAC | ACC | GTC | TGC | CAG | GAT | ATG | 4011 |
| Ile | Asn | Thr | Leu | Pro | Met | Ile | Phe | Asp | His | Thr | Val | Cys | Gln | Asp | Met | |
| | | | 1195 | | | | | 1200 | | | | | 1205 | | | |
| ACA | GCG | CTC | GAG | GCC | ATT | GAG | CAT | GTC | CAA | GGC | CAA | GTC | AAC | GCC | ATG | 4059 |
| Thr | Ala | Leu | Glu | Ala | Ile | Glu | His | Val | Gln | Gly | Gln | Val | Asn | Ala | Met | |
| | 1210 | | | | | 1215 | | | | | 1220 | | | | | |
| AAC | TCC | CGG | GGC | AAC | GTC | GAG | CTC | GGA | CGC | ATG | AGC | AAG | AAC | GAC | CTC | 4107 |
| Asn | Ser | Arg | Gly | Asn | Val | Glu | Leu | Gly | Arg | Met | Ser | Lys | Asn | Asp | Leu | |
| 1225 | | | | | 1230 | | | | | 1235 | | | | | 1240 | |
| AAG | CAC | GGG | CTC | TTC | GAC | ACC | CTC | TTC | GTC | CTC | GAG | AAC | TAC | CCA | AAC | 4155 |
| Lys | His | Gly | Leu | Phe | Asp | Thr | Leu | Phe | Val | Leu | Glu | Asn | Tyr | Pro | Asn | |
| | | | | 1245 | | | | | 1250 | | | | | 1255 | | |

| | | | | | | | | | | | | | | | | |
|---|---|---|---|---|---|---|---|---|---|---|---|---|---|---|---|---|
| CTC | GAC | ACG | GAG | CAG | CGG | GAG | AAG | CAC | GAG | GAG | AAG | CTC | AAG | TTC | ACC | 4203 |
| Leu | Asp | Thr | Glu | Gln | Arg | Glu | Lys | His | Glu | Glu | Lys | Leu | Lys | Phe | Thr | |
| | | | 1260 | | | | 1265 | | | | | 1270 | | | | |
| ATC | AAG | GGT | GGC | ACG | GAG | AAG | CTC | AGT | TAC | CCG | CTG | GCC | GTG | ATT | GCC | 4251 |
| Ile | Lys | Gly | Gly | Thr | Glu | Lys | Leu | Ser | Tyr | Pro | Leu | Ala | Val | Ile | Ala | |
| | | 1275 | | | | | 1280 | | | | | 1285 | | | | |
| CAA | GAG | GAC | GGC | GAC | AGC | GGA | TGC | TCG | TTT | ACG | CTC | TGC | TAT | GCG | GGC | 4299 |
| Gln | Glu | Asp | Gly | Asp | Ser | Gly | Cys | Ser | Phe | Thr | Leu | Cys | Tyr | Ala | Gly | |
| | | | 1290 | | | | | 1295 | | | | | 1300 | | | |
| GAG | CTC | TTC | ACG | GAT | GAG | TCC | ATC | CAG | GCG | CTC | CTG | GAC | ACT | GTC | CGG | 4347 |
| Glu | Leu | Phe | Thr | Asp | Glu | Ser | Ile | Gln | Ala | Leu | Leu | Asp | Thr | Val | Arg | |
| 1305 | | | | | 1310 | | | | | 1315 | | | | | 1320 | |
| GAC | ACC | CTG | AGT | GAT | ATT | CTC | GGG | AAC | ATC | CAT | GCC | CCT | ATC | CGC | AAC | 4395 |
| Asp | Thr | Leu | Ser | Asp | Ile | Leu | Gly | Asn | Ile | His | Ala | Pro | Ile | Arg | Asn | |
| | | | | 1325 | | | | | 1330 | | | | | 1335 | | |
| ATG | GAG | TAC | CTC | TCC | TCG | AAC | CAG | ACG | GCG | CAG | CTC | GAC | AAG | TGG | AAT | 4443 |
| Met | Glu | Tyr | Leu | Ser | Ser | Asn | Gln | Thr | Ala | Gln | Leu | Asp | Lys | Trp | Asn | |
| | | | 1340 | | | | | 1345 | | | | | 1350 | | | |
| GCC | ACC | GCC | TTC | GAG | TAC | CCC | AAC | ACC | ACA | CTG | CAC | GCC | ATG | TTC | GAG | 4491 |
| Ala | Thr | Ala | Phe | Glu | Tyr | Pro | Asn | Thr | Thr | Leu | His | Ala | Met | Phe | Glu | |
| | | 1355 | | | | | 1360 | | | | | 1365 | | | | |
| TCC | GAG | GCG | CAG | CAG | AAG | CCG | GAC | AAG | GTG | GCC | GTG | GTG | TAC | GAG | GAT | 4539 |
| Ser | Glu | Ala | Gln | Gln | Lys | Pro | Asp | Lys | Val | Ala | Val | Val | Tyr | Glu | Asp | |
| | 1370 | | | | | 1375 | | | | | 1380 | | | | | |
| ATC | AGG | CTG | ACC | TAC | CGC | GAG | CTC | AAC | AGC | CGT | GCC | AAT | GCC | CTG | GCG | 4587 |
| Ile | Arg | Leu | Thr | Tyr | Arg | Glu | Leu | Asn | Ser | Arg | Ala | Asn | Ala | Leu | Ala | |
| 1385 | | | | | 1390 | | | | | 1395 | | | | | 1400 | |
| TTC | TAC | CTC | CTC | TCC | CAG | GCG | GCT | ATC | CAA | CCG | AAC | AAG | CTG | GTC | GGG | 4635 |
| Phe | Tyr | Leu | Leu | Ser | Gln | Ala | Ala | Ile | Gln | Pro | Asn | Lys | Leu | Val | Gly | |
| | | | | 1405 | | | | | 1410 | | | | | 1415 | | |
| CTG | ATC | ATG | GAC | AAG | AGC | GAG | CAC | ATG | ATC | ACG | AGC | ATC | CTC | GCG | GTC | 4683 |
| Leu | Ile | Met | Asp | Lys | Ser | Glu | His | Met | Ile | Thr | Ser | Ile | Leu | Ala | Val | |
| | | | 1420 | | | | | 1425 | | | | | 1430 | | | |
| TGG | AAA | ACG | GGT | GGA | GCC | TAC | GTC | CCG | ATC | GAC | CCT | CGA | TAC | CCT | GAC | 4731 |
| Trp | Lys | Thr | Gly | Gly | Ala | Tyr | Val | Pro | Ile | Asp | Pro | Arg | Tyr | Pro | Asp | |
| | | 1435 | | | | | 1440 | | | | | 1445 | | | | |
| CAG | CGT | ATC | CAG | TAT | ATC | CTG | GAG | GAT | ACG | GCG | GCT | CTC | GCA | GTC | ATC | 4779 |
| Gln | Arg | Ile | Gln | Tyr | Ile | Leu | Glu | Asp | Thr | Ala | Ala | Leu | Ala | Val | Ile | |
| | | | 1450 | | | | | 1455 | | | | | 1460 | | | |
| ACG | GAC | AGT | CCT | CAT | ATT | GAC | CGT | CTG | CGC | AGC | ATC | ACC | AAC | AAC | CGC | 4827 |
| Thr | Asp | Ser | Pro | His | Ile | Asp | Arg | Leu | Arg | Ser | Ile | Thr | Asn | Asn | Arg | |
| 1465 | | | | | 1470 | | | | | 1475 | | | | | 1480 | |
| CTT | CCT | GTT | ATC | CAG | TCG | GAC | TTT | GCT | CTC | CAA | CTC | CCG | CCC | AGC | CCA | 4875 |
| Leu | Pro | Val | Ile | Gln | Ser | Asp | Phe | Ala | Leu | Gln | Leu | Pro | Pro | Ser | Pro | |
| | | | | 1485 | | | | | 1490 | | | | | 1495 | | |
| GTT | CAT | CCC | GTC | TCA | AAC | TGC | AAG | CCA | AGC | GAC | CTC | GCC | TAC | ATC | ATG | 4923 |
| Val | His | Pro | Val | Ser | Asn | Cys | Lys | Pro | Ser | Asp | Leu | Ala | Tyr | Ile | Met | |
| | | | | 1500 | | | | | 1505 | | | | | 1510 | | |
| TAC | ACA | TCC | GGC | ACC | ACT | GGC | AAC | CCC | AAG | GGT | GTC | ATG | GTG | GAG | CAC | 4971 |
| Tyr | Thr | Ser | Gly | Thr | Thr | Gly | Asn | Pro | Lys | Gly | Val | Met | Val | Glu | His | |
| | | | 1515 | | | | | 1520 | | | | | 1525 | | | |
| CAC | GGT | GTA | GTG | AAT | CTG | TGC | GTT | TCA | CTC | TGC | CGG | CTC | TTC | GGC | CTT | 5019 |
| His | Gly | Val | Val | Asn | Leu | Cys | Val | Ser | Leu | Cys | Arg | Leu | Phe | Gly | Leu | |
| | | | 1530 | | | | | 1535 | | | | | 1540 | | | |
| CGG | AAC | ACA | GAT | GAC | GAG | GTC | ATC | CTC | TCG | TTC | TCG | AAC | TAC | GTC | TTC | 5067 |
| Arg | Asn | Thr | Asp | Asp | Glu | Val | Ile | Leu | Ser | Phe | Ser | Asn | Tyr | Val | Phe | |
| 1545 | | | | | 1550 | | | | | 1555 | | | | | 1560 | |
| GAC | CAC | TTT | GTC | GAG | CAG | ATG | ACG | GAT | GCC | CTT | CTC | AAC | GGT | CAG | ACT | 5115 |
| Asp | His | Phe | Val | Glu | Gln | Met | Thr | Asp | Ala | Leu | Leu | Asn | Gly | Gln | Thr | |
| | | | | 1565 | | | | | 1570 | | | | | 1575 | | |

```
CTT GTG GTC CTC AAC GAC GAG ATG CGT GGC GAC AAG GAG AGG CTT TAC      5163
Leu Val Val Leu Asn Asp Glu Met Arg Gly Asp Lys Glu Arg Leu Tyr
        1580                1585                1590

AGA TAC ATC GAG ACC AAC CGC GTC ACG TAC CTC TCG GGG ACA CCT TCC      5211
Arg Tyr Ile Glu Thr Asn Arg Val Thr Tyr Leu Ser Gly Thr Pro Ser
    1595                1600                1605

GTC ATC TCC ATG TAC GAG TTC GAC CGG TTC CGC GAC CAC CTG CGG CGC      5259
Val Ile Ser Met Tyr Glu Phe Asp Arg Phe Arg Asp His Leu Arg Arg
1610                1615                1620

GTG GAT TGC GTC GGC GAG GCC TTC AGC GAG CCG GTA TTC GAC AAG ATC      5307
Val Asp Cys Val Gly Glu Ala Phe Ser Glu Pro Val Phe Asp Lys Ile
1625                1630                1635                1640

CGC GAG ACG TTC CCG GGT CTC ATC ATC AAC GGT TAT GGC CCG ACT GAG      5355
Arg Glu Thr Phe Pro Gly Leu Ile Ile Asn Gly Tyr Gly Pro Thr Glu
                1645                1650                1655

GTG TCT ATC ACT ACC CAC AAG CGG CCC TAC CCG TTC CCG GAG CGC CGC      5403
Val Ser Ile Thr Thr His Lys Arg Pro Tyr Pro Phe Pro Glu Arg Arg
            1660                1665                1670

ACA GAC AAG AGC ATC GGT TGC CAG CTG GAC AAC AGC ACG AGC TAC GTC      5451
Thr Asp Lys Ser Ile Gly Cys Gln Leu Asp Asn Ser Thr Ser Tyr Val
        1675                1680                1685

CTC AAC GAT GAC ATG AAG CGC GTG CCC ATC GGG GCC GTG GGA GAG CTG      5499
Leu Asn Asp Asp Met Lys Arg Val Pro Ile Gly Ala Val Gly Glu Leu
    1690                1695                1700

TAC CTT GGT GGC GAT GGC GTC GCT CGC GGA TAC CAC AAC CGG CCA GAC      5547
Tyr Leu Gly Gly Asp Gly Val Ala Arg Gly Tyr His Asn Arg Pro Asp
1705                1710                1715                1720

CTG ACG GCT GAC CGG TTC CCT GCC AAC CCC TTC CAG ACG GAG CAG GAG      5595
Leu Thr Ala Asp Arg Phe Pro Ala Asn Pro Phe Gln Thr Glu Gln Glu
                1725                1730                1735

AGA CTT GAG GGC CGA AAT GCG CGT CTG TAT AAG ACT GGT GAC TTG GTT      5643
Arg Leu Glu Gly Arg Asn Ala Arg Leu Tyr Lys Thr Gly Asp Leu Val
            1740                1745                1750

CGC TGG ATC CAC AAT GCA AAC GGC GAT GGT GAG ATC GAG TAC CTC GGC      5691
Arg Trp Ile His Asn Ala Asn Gly Asp Gly Glu Ile Glu Tyr Leu Gly
        1755                1760                1765

CGC AAC GAC TTC CAG GTC AAG ATT CGA GGC CAG AGA ATC GAG CTG GGA      5739
Arg Asn Asp Phe Gln Val Lys Ile Arg Gly Gln Arg Ile Glu Leu Gly
    1770                1775                1780

GAG ATC GAG GCC GTG CTT TCA TCC TAT CCG GGC ATC AAA CAA TCC GTC      5787
Glu Ile Glu Ala Val Leu Ser Ser Tyr Pro Gly Ile Lys Gln Ser Val
1785                1790                1795                1800

GTC CTG GCC AAG GAC CGC AAG AAT GAC GGG CAG AAG TAC CTC GTC GGC      5835
Val Leu Ala Lys Asp Arg Lys Asn Asp Gly Gln Lys Tyr Leu Val Gly
                1805                1810                1815

TAC TTC GTC TCC TCA GCA GGG TCC CTG TCC GCC CAG GCC ATC CGC CGC      5883
Tyr Phe Val Ser Ser Ala Gly Ser Leu Ser Ala Gln Ala Ile Arg Arg
            1820                1825                1830

TTC ATG CTC ACG AGC CTG CCC GAT TAC ATG GTT CCT GCG CAG CTG GTG      5931
Phe Met Leu Thr Ser Leu Pro Asp Tyr Met Val Pro Ala Gln Leu Val
        1835                1840                1845

CCC ATC GCC AAG TTC CCC GTC ACC GTG AGC GGG AAG CTC GAT GCC AAG      5979
Pro Ile Ala Lys Phe Pro Val Thr Val Ser Gly Lys Leu Asp Ala Lys
    1850                1855                1860

GCC TTG CCC GTG CCA GAC GAT ACA GTC GAG GAT GAC ATT GTG CCA CCG      6027
Ala Leu Pro Val Pro Asp Asp Thr Val Glu Asp Asp Ile Val Pro Pro
1865                1870                1875                1880

CGT ACC GAG GTT GAG CGC ATC CTA GCT GGG ATC TGG TCT GAG CTG TTG      6075
Arg Thr Glu Val Glu Arg Ile Leu Ala Gly Ile Trp Ser Glu Leu Leu
                1885                1890                1895
```

```
GAG ATA CCG GTC GAC AGG ATC AGC ATC TAC AGT GAC TTC TTC AGT CTG       6123
Glu Ile Pro Val Asp Arg Ile Ser Ile Tyr Ser Asp Phe Phe Ser Leu
        1900                    1905                    1910

GGC GGC GAC AGT CTC AAG AGT ACC AAG CTG TCC TTT GCT GCC ACT CGG       6171
Gly Gly Asp Ser Leu Lys Ser Thr Lys Leu Ser Phe Ala Ala Thr Arg
        1915                    1920                    1925

GCT CTC GGT GTG GCC GTC AGT GTC CGC AAC TTG TTC AGC CAT CCG ACT       6219
Ala Leu Gly Val Ala Val Ser Val Arg Asn Leu Phe Ser His Pro Thr
        1930                    1935                    1940

ATC GAA GCC TTG TCT CAG TGG ATT ATC AGG GGT CGA AAC GAG GTC AAG       6267
Ile Glu Ala Leu Ser Gln Trp Ile Ile Arg Gly Ser Asn Glu Val Lys
1945            1950                    1955                    1960

GAT GTG GCT GTG GTG AAG GGC GGT GCC AGT CTT GAT ATC CCC CTA TCC       6315
Asp Val Ala Val Val Lys Gly Gly Ala Ser Leu Asp Ile Pro Leu Ser
                1965                    1970                    1975

CCT GCC CAG GAA AGA CTC ATG TTC ATC CAC GAG TTC GGC CAT AGC GGC       6363
Pro Ala Gln Glu Arg Leu Met Phe Ile His Glu Phe Gly His Ser Gly
        1980                    1985                    1990

GAG GAT ACT GGT GCT TAC AAT GTG CCT TTG CAG CTG CAG CTT CAC CAT       6411
Glu Asp Thr Gly Ala Tyr Asn Val Pro Leu Gln Leu Gln Leu His His
        1995                    2000                    2005

GAT GTC TGT CTC GAG TCG CTT GAG AAG GCT CTG CGG GAT GTC GTC TCG       6459
Asp Val Cys Leu Glu Ser Leu Glu Lys Ala Leu Arg Asp Val Val Ser
2010                    2015                    2020

AGA CAC GAG GCT CTC CGG ACC TTG ATC ACC AGG ACC CAG AAG TCC TCC       6507
Arg His Glu Ala Leu Arg Thr Leu Ile Thr Arg Thr Gln Lys Ser Ser
2025            2030                    2035                    2040

GTG CAC TGC CAG AAG ATC CTC GAC GCC GAA GAA GCG CAA AAG CTC TTC       6555
Val His Cys Gln Lys Ile Leu Asp Ala Glu Glu Ala Gln Lys Leu Phe
                2045                    2050                    2055

TCT GTT GAT GTT CTG CGC CTG ACC TCG GAG ACG GAG ATG CAG GGC AGG       6603
Ser Val Asp Val Leu Arg Leu Thr Ser Glu Thr Glu Met Gln Gly Arg
        2060                    2065                    2070

ATG GCC GAG AGT ACC GCC CAC GCC TTC AAG CTC GAC GAG GAA CTC CCG       6651
Met Ala Glu Ser Thr Ala His Ala Phe Lys Leu Asp Glu Glu Leu Pro
        2075                    2080                    2085

ATT CAT GTA CGC CTG TAC CAG GTT GTA CGT GAT GGC CGC ACG CTC AGC       6699
Ile His Val Arg Leu Tyr Gln Val Val Arg Asp Gly Arg Thr Leu Ser
        2090                    2095                    2100

TTT GCC AGC ATC GTC TGC CAC CAT CTG GCG TTT GAC GCG TGG TCA TGG       6747
Phe Ala Ser Ile Val Cys His His Leu Ala Phe Asp Ala Trp Ser Trp
2105                    2110                    2115            2120

GAT GTG TTC CAG AGG GAC TTG GAC GCC TTC TAT GCC GTC CAT ACG AAG       6795
Asp Val Phe Gln Arg Asp Leu Asp Ala Phe Tyr Ala Val His Thr Lys
                2125                    2130                    2135

CAC AAG GCT GCC GCC AAC CTG CCA ACC CTC CGC GTG CAA TAT AAG GAG       6843
His Lys Ala Ala Ala Asn Leu Pro Thr Leu Arg Val Gln Tyr Lys Glu
                2140                    2145                    2150

TAT GCG ATA GAG CAC CGC CGG GCT CTC CGC GCT GAG CAA CAC CGT GTT       6891
Tyr Ala Ile Glu His Arg Arg Ala Leu Arg Ala Glu Gln His Arg Val
        2155                    2160                    2165

CTC GCG GAC TAC TGG CTG CGC AAG CTC AGT GAC ATG GAG GCG TCT TAT       6939
Leu Ala Asp Tyr Trp Leu Arg Lys Leu Ser Asp Met Glu Ala Ser Tyr
        2170                    2175                    2180

CTG GTC CCC GAT CGC CCT CGA CCG GCG CAG TTT GAC TAT ACC GGG AAC       6987
Leu Val Pro Asp Arg Pro Arg Pro Ala Gln Phe Asp Tyr Thr Gly Asn
2185                    2190                    2195                    2200

GAT CTC CAG TTC TCA ACT ACT CCC GAG ACC ACC GCG CAG TTG AAG GAG       7035
Asp Leu Gln Phe Ser Thr Thr Pro Glu Thr Thr Ala Gln Leu Lys Glu
        2205                    2210                    2215
```

| | | | | | | | | | | | | | | | | |
|---|---|---|---|---|---|---|---|---|---|---|---|---|---|---|---|---|
| CTG | GCC | AAG | CGC | GAG | GGT | TCA | AGC | CTC | TAC | ACC | GTT | GTG | GCG | GCG | GCG | 7083 |
| Leu | Ala | Lys | Arg | Glu | Gly | Ser | Ser | Leu | Tyr | Thr | Val | Val | Ala | Ala | Ala | |
| | | | 2220 | | | | 2225 | | | | | 2230 | | | | |
| TAC | TTT | CTG | CTT | CTC | TAC | GTG | TAC | ACC | AAC | CAG | CGG | GAT | ATC | ACG | ATT | 7131 |
| Tyr | Phe | Leu | Leu | Leu | Tyr | Val | Tyr | Thr | Asn | Gln | Arg | Asp | Ile | Thr | Ile | |
| | | 2235 | | | | | 2240 | | | | | 2245 | | | | |
| GGT | ATT | CCC | GTT | GCG | CAC | CGT | AAC | CAT | CCG | GAC | TTT | GAG | TCG | GTT | GTC | 7179 |
| Gly | Ile | Pro | Val | Ala | His | Arg | Asn | His | Pro | Asp | Phe | Glu | Ser | Val | Val | |
| | | 2250 | | | | | 2255 | | | | | 2260 | | | | |
| GGC | TTC | TTT | GTC | AAC | TTG | CTC | CCT | CTG | CGG | GTC | AAC | GTG | TCT | CAG | TCG | 7227 |
| Gly | Phe | Phe | Val | Asn | Leu | Leu | Pro | Leu | Arg | Val | Asn | Val | Ser | Gln | Ser | |
| 2265 | | | | | 2270 | | | | | 2275 | | | | | 2280 | |
| GAC | ATT | CAT | GGA | CTT | ATC | CAG | GCA | GTG | CAG | AAA | GAG | CTT | GTC | GAT | GCC | 7275 |
| Asp | Ile | His | Gly | Leu | Ile | Gln | Ala | Val | Gln | Lys | Glu | Leu | Val | Asp | Ala | |
| | | | | 2285 | | | | | 2290 | | | | | 2295 | | |
| CAG | ATC | CAT | CAG | GAC | TTG | CCA | TTC | CAG | GAG | ATC | ACC | AAG | CTT | CTT | CAT | 7323 |
| Gln | Ile | His | Gln | Asp | Leu | Pro | Phe | Gln | Glu | Ile | Thr | Lys | Leu | Leu | His | |
| | | | | 2300 | | | | | 2305 | | | | | 2310 | | |
| GTG | CAG | CAC | GAT | CCA | AGC | CGC | CAT | CCC | CTT | CTC | CAG | GCC | GTG | TTC | AAC | 7371 |
| Val | Gln | His | Asp | Pro | Ser | Arg | His | Pro | Leu | Leu | Gln | Ala | Val | Phe | Asn | |
| | | | 2315 | | | | | 2320 | | | | | 2325 | | | |
| TGG | GAA | AAC | GTA | CCC | GCC | AAT | GTC | CAC | GAG | GAG | CAG | CTG | CTT | CAG | GAG | 7419 |
| Trp | Glu | Asn | Val | Pro | Ala | Asn | Val | His | Glu | Glu | Gln | Leu | Leu | Gln | Glu | |
| | | 2330 | | | | | 2335 | | | | | 2340 | | | | |
| TAC | AAG | CCG | CCC | TCG | CCT | CTG | CCT | TCG | GCG | GCC | AAG | TTT | GAT | CTC | AAC | 7467 |
| Tyr | Lys | Pro | Pro | Ser | Pro | Leu | Pro | Ser | Ala | Ala | Lys | Phe | Asp | Leu | Asn | |
| 2345 | | | | | 2350 | | | | | 2355 | | | | | 2360 | |
| GTC | ACG | GTG | AAA | GAG | AGC | GTC | AAT | TCG | CTC | AAC | GTC | AAC | TTC | AAC | TAT | 7515 |
| Val | Thr | Val | Lys | Glu | Ser | Val | Asn | Ser | Leu | Asn | Val | Asn | Phe | Asn | Tyr | |
| | | | | 2365 | | | | | 2370 | | | | | 2375 | | |
| CCT | ACC | AGC | CTC | TTC | GAG | GAG | GAG | ACC | GTT | CAG | GGG | TTC | ATG | GAA | ACC | 7563 |
| Pro | Thr | Ser | Leu | Phe | Glu | Glu | Glu | Thr | Val | Gln | Gly | Phe | Met | Glu | Thr | |
| | | | | 2380 | | | | | 2385 | | | | | 2390 | | |
| TTC | CAT | CTC | CTT | CTT | CGA | CAA | CTG | GCC | CAC | AAC | AAG | GCT | AGC | ACA | AGC | 7611 |
| Phe | His | Leu | Leu | Leu | Arg | Gln | Leu | Ala | His | Asn | Lys | Ala | Ser | Thr | Ser | |
| | | | 2395 | | | | | 2400 | | | | | 2405 | | | |
| CTC | TCG | AAG | CTG | TCG | GTT | GAA | GAT | GGA | GTG | TTG | AAT | CCA | GAG | CCG | ACT | 7659 |
| Leu | Ser | Lys | Leu | Ser | Val | Glu | Asp | Gly | Val | Leu | Asn | Pro | Glu | Pro | Thr | |
| | | 2410 | | | | | 2415 | | | | | 2420 | | | | |
| AAC | CTT | CAG | CCC | TCA | AGC | CGG | GAC | AGC | GGA | AAT | TCA | CTC | CAT | GGG | CTC | 7707 |
| Asn | Leu | Gln | Pro | Ser | Ser | Arg | Asp | Ser | Gly | Asn | Ser | Leu | His | Gly | Leu | |
| 2425 | | | | | 2430 | | | | | 2435 | | | | | 2440 | |
| TTC | GAG | GAC | ATC | GTG | GCC | TCG | ACC | CCG | GAC | CGC | ATC | GCA | ATT | GCT | GAC | 7755 |
| Phe | Glu | Asp | Ile | Val | Ala | Ser | Thr | Pro | Asp | Arg | Ile | Ala | Ile | Ala | Asp | |
| | | | | 2445 | | | | | 2450 | | | | | 2455 | | |
| GGC | ACC | AGG | AGT | CTC | TCG | TAC | TCC | GAA | CTC | AAC | GAG | CGG | GCA | AAC | CAG | 7803 |
| Gly | Thr | Arg | Ser | Leu | Ser | Tyr | Ser | Glu | Leu | Asn | Glu | Arg | Ala | Asn | Gln | |
| | | | 2460 | | | | | 2465 | | | | | 2470 | | | |
| CTC | GTA | CAT | TTG | ATC | ATC | TCT | TCT | GCC | AGT | ATT | GTA | GCA | GAC | GAC | CGC | 7851 |
| Leu | Val | His | Leu | Ile | Ile | Ser | Ser | Ala | Ser | Ile | Val | Ala | Asp | Asp | Arg | |
| | | | 2475 | | | | | 2480 | | | | | 2485 | | | |
| ATC | GCT | CTT | CTT | TTG | GAC | AAG | AGC | ATC | GAT | ATG | GTG | ATT | GCT | CTC | CTG | 7899 |
| Ile | Ala | Leu | Leu | Leu | Asp | Lys | Ser | Ile | Asp | Met | Val | Ile | Ala | Leu | Leu | |
| | | 2490 | | | | | 2495 | | | | | 2500 | | | | |
| GCA | GTT | TGG | AAG | GCC | GGT | GCC | GCA | TAT | GTG | CCC | CTT | GAC | CCG | ACA | TAT | 7947 |
| Ala | Val | Trp | Lys | Ala | Gly | Ala | Ala | Tyr | Val | Pro | Leu | Asp | Pro | Thr | Tyr | |
| 2505 | | | | | 2510 | | | | | 2515 | | | | | 2520 | |
| CCG | TCG | CAG | AGG | ACT | GAG | CTC | ATC | TTG | GAG | GAA | TCT | AGT | GCC | AGG | ACG | 7995 |
| Pro | Ser | Gln | Arg | Thr | Glu | Leu | Ile | Leu | Glu | Glu | Ser | Ser | Ala | Arg | Thr | |
| | | | | 2525 | | | | | 2530 | | | | | 2535 | | |

```
CTC ATC ACC ACT AGA AAG CAC ACG CCG AGG GGA GGA ACA GTC GCA AAT     8043
Leu Ile Thr Thr Arg Lys His Thr Pro Arg Gly Gly Thr Val Ala Asn
            2540                    2545                2550

GTT CCA NNN GTG GTC CTT GAC AGC CCC GAG ACC CTA GCC TGC CTC AAC     8091
Val Pro Ser Val Val Leu Asp Ser Pro Glu Thr Leu Ala Cys Leu Asn
        2555                    2560                2565

CAG CAG TCA AAG GAA AAC CCG ACA ACG TCA ACG CAG AAA CCG TCC GAC     8139
Gln Gln Ser Lys Glu Asn Pro Thr Thr Ser Thr Gln Lys Pro Ser Asp
        2570                    2575                2580

CTC GCA TAT GTC ATC TTC ACC TCG GGA ACC ACA GGC AAG CCC AAG GGG     8187
Leu Ala Tyr Val Ile Phe Thr Ser Gly Thr Thr Gly Lys Pro Lys Gly
2585                    2590                2595                2600

GTT CTG GTG GAG CAC CAG AGC GTA GTC CAG CTG CGC AAT TCC CTC ATC     8235
Val Leu Val Glu His Gln Ser Val Val Gln Leu Arg Asn Ser Leu Ile
                    2605                2610                2615

GAG CGA TAC TTC GGC GAG ACC AAC GGG TCT CAC GCC GTG CTC TTC CTG     8283
Glu Arg Tyr Phe Gly Glu Thr Asn Gly Ser His Ala Val Leu Phe Leu
                2620                2625                2630

TCC AAC TAC GTC TTC GAC TTC TCT CTT GAA CAG CTC TGT CTC TCA GTC     8331
Ser Asn Tyr Val Phe Asp Phe Ser Leu Glu Gln Leu Cys Leu Ser Val
            2635                2640                2645

TTG GGT GGA AAC AAG CTC ATC ATT CCA CCA GAG GAG GGT CTC ACG CAC     8379
Leu Gly Gly Asn Lys Leu Ile Ile Pro Pro Glu Glu Gly Leu Thr His
        2650                    2655                2660

GAG GCA TTC TAC GAC ATC GGC CGC AGG GAG AAG CTA TCC TAT CTC AGC     8427
Glu Ala Phe Tyr Asp Ile Gly Arg Arg Glu Lys Leu Ser Tyr Leu Ser
2665                    2670                2675                2680

GGG ACG CCC TCG GTG CTG CAG CAG ATT GAG CTC TCC CGT CTG CCG CAT     8475
Gly Thr Pro Ser Val Leu Gln Gln Ile Glu Leu Ser Arg Leu Pro His
                    2685                2690                2695

CTT CAC ATG GTC ACC GCT GCG GGC GAG GAG TTC CAC GCT AGT CAG TTT     8523
Leu His Met Val Thr Ala Ala Gly Glu Glu Phe His Ala Ser Gln Phe
                2700                2705                2710

GAG AAG ATG CGC TCC CAG TTC GCG GGC CAG ATC AAC AAC GCC TAT GGT     8571
Glu Lys Met Arg Ser Gln Phe Ala Gly Gln Ile Asn Asn Ala Tyr Gly
            2715                2720                2725

ATC ACT GAG ACG ACC GTG TAC AAC ATC ATC ACC ACG TTC AAG GGC GAT     8619
Ile Thr Glu Thr Thr Val Tyr Asn Ile Ile Thr Thr Phe Lys Gly Asp
        2730                    2735                2740

GCC CCC TTT ACC AAG GCA CTC TGC CAC GGG ATC CCC GGA AGT CAC GTC     8667
Ala Pro Phe Thr Lys Ala Leu Cys His Gly Ile Pro Gly Ser His Val
2745                    2750                2755                2760

TAC GTC CTG AAC GAC CGA CTT CAG CGT GTT CCT TTC AAC GCT GTT GGC     8715
Tyr Val Leu Asn Asp Arg Leu Gln Arg Val Pro Phe Asn Ala Val Gly
                    2765                2770                2775

GAG CTC TAC TTG GGC GGT GAC TGC CTT GCT CGC GGG TAC CTC AAC CAG     8763
Glu Leu Tyr Leu Gly Gly Asp Cys Leu Ala Arg Gly Tyr Leu Asn Gln
                2780                2785                2790

GAT GCC CTG ACC AAC GAG CGA TTC ATC CCC AAC CCT TTC TAC GAG CCG     8811
Asp Ala Leu Thr Asn Glu Arg Phe Ile Pro Asn Pro Phe Tyr Glu Pro
            2795                2800                2805

AAA CAG GCA AGT GAC AGT CGT CCC CAG AGA CTC TAC AAG ACT GGA GAT     8859
Lys Gln Ala Ser Asp Ser Arg Pro Gln Arg Leu Tyr Lys Thr Gly Asp
        2810                    2815                2820

CTG GTG CGC TTC CGT GGA CCC CAC CAT CTC GAG TAT CTC GGC CGC AAG     8907
Leu Val Arg Phe Arg Gly Pro His His Leu Glu Tyr Leu Gly Arg Lys
2825                    2830                2835                2840

GAC CAG CAG GTC AAG CTG AGG GGC TTC CGC ATC GAG CTC TCC GAG GTG     8955
Asp Gln Gln Val Lys Leu Arg Gly Phe Arg Ile Glu Leu Ser Glu Val
                    2845                2850                2855
```

```
CGG  GAT  GCC  GTC  CTA  GCC  ATC  TCT  GCT  GTT  AAG  GAG  GCT  GCC  GTC  ATC        9003
Arg  Asp  Ala  Val  Leu  Ala  Ile  Ser  Ala  Val  Lys  Glu  Ala  Ala  Val  Ile
               2860                    2865                    2870

CCC  AAG  TAT  GAC  GAG  GAT  GGC  TCC  GAT  TCA  CGA  AGG  GTC  AGC  GCC  ATC        9051
Pro  Lys  Tyr  Asp  Glu  Asp  Gly  Ser  Asp  Ser  Arg  Arg  Val  Ser  Ala  Ile
               2875                    2880                    2885

GTC  TGC  TAC  TAC  ACG  CTC  AAC  GCC  GGA  ACT  GTG  TGC  GAA  GCA  TCG  AGT        9099
Val  Cys  Tyr  Tyr  Thr  Leu  Asn  Ala  Gly  Thr  Val  Cys  Glu  Ala  Ser  Ser
               2890                    2895                    2900

ATC  CGT  GAC  CAC  CTG  CAC  GCC  AAC  CTT  CCC  CCG  TAC  ATG  GTC  CCA  AGT        9147
Ile  Arg  Asp  His  Leu  His  Ala  Asn  Leu  Pro  Pro  Tyr  Met  Val  Pro  Ser
2905                    2910                    2915                    2920

CAG  ATC  CAC  CAG  TTG  GAG  GGA  TCT  CTC  CCC  GTG  ACC  GTC  AAT  GGG  AAG        9195
Gln  Ile  His  Gln  Leu  Glu  Gly  Ser  Leu  Pro  Val  Thr  Val  Asn  Gly  Lys
               2925                    2930                    2935

CTC  GAC  CTG  AAC  AGG  CTC  TCC  ACA  ACT  CAA  GTC  TCG  CAG  CCA  GAG  CTT        9243
Leu  Asp  Leu  Asn  Arg  Leu  Ser  Thr  Thr  Gln  Val  Ser  Gln  Pro  Glu  Leu
               2940                    2945                    2950

TAC  ACC  GCT  CCA  CGA  AAT  TCG  ACA  GAG  GAA  ACC  TTG  TGC  CAG  CTT  TGG        9291
Tyr  Thr  Ala  Pro  Arg  Asn  Ser  Thr  Glu  Glu  Thr  Leu  Cys  Gln  Leu  Trp
               2955                    2960                    2965

GCA  TCT  CTC  CTA  GGC  GTC  GAC  CAC  TGC  GGC  ATT  GAC  GAC  GAC  CTG  TTT        9339
Ala  Ser  Leu  Leu  Gly  Val  Asp  His  Cys  Gly  Ile  Asp  Asp  Asp  Leu  Phe
2970                    2975                    2980

GCC  CGA  GGC  GGC  GAC  AGC  ATC  TCC  TCT  CTC  CGA  CTA  GTG  GGT  GAC  ATC        9387
Ala  Arg  Gly  Gly  Asp  Ser  Ile  Ser  Ser  Leu  Arg  Leu  Val  Gly  Asp  Ile
2985                    2990                    2995                    3000

TAC  CGC  GCG  CTA  GGA  CGC  AAG  GTC  ACC  GTC  AAG  GAC  ATC  TAC  CTC  CAC        9435
Tyr  Arg  Ala  Leu  Gly  Arg  Lys  Val  Thr  Val  Lys  Asp  Ile  Tyr  Leu  His
               3005                    3010                    3015

CGC  AGC  GTC  CGA  GCC  CTA  AGC  GAA  AAT  GTC  CTG  ACC  GAC  CAG  AAG  GAT        9483
Arg  Ser  Val  Arg  Ala  Leu  Ser  Glu  Asn  Val  Leu  Thr  Asp  Gln  Lys  Asp
               3020                    3025                    3030

AAG  GGT  ACT  CTG  CCA  GCG  TCT  CCT  CCC  CTC  CAG  CGA  GCG  GAG  CAG  GGC        9531
Lys  Gly  Thr  Leu  Pro  Ala  Ser  Pro  Pro  Leu  Gln  Arg  Ala  Glu  Gln  Gly
               3035                    3040                    3045

CAG  GTT  GAG  GGC  GAC  GCA  CCG  CTT  CTC  CCC  ATC  CAG  GAC  TGG  TTC  CTT        9579
Gln  Val  Glu  Gly  Asp  Ala  Pro  Leu  Leu  Pro  Ile  Gln  Asp  Trp  Phe  Leu
               3050                    3055                    3060

TCC  AAG  CCC  CTG  GAT  AAC  CCC  GCT  TAC  TGG  AAC  CAC  TGC  TTC  ACC  ATT        9627
Ser  Lys  Pro  Leu  Asp  Asn  Pro  Ala  Tyr  Trp  Asn  His  Cys  Phe  Thr  Ile
3065                    3070                    3075                    3080

CGA  ACC  GGG  GCA  CTC  TCC  GTC  GAA  GGG  CTC  CGG  GGT  GCT  CTG  AAG  CTG        9675
Arg  Thr  Gly  Ala  Leu  Ser  Val  Glu  Gly  Leu  Arg  Gly  Ala  Leu  Lys  Leu
               3085                    3090                    3095

CTG  CAG  GAG  CGC  CAC  GAC  GTG  CTG  CGT  CTG  AGA  CTG  CAA  CGC  CGG  GAC        9723
Leu  Gln  Glu  Arg  His  Asp  Val  Leu  Arg  Leu  Arg  Leu  Gln  Arg  Arg  Asp
               3100                    3105                    3110

GAA  GGT  CGC  CAT  GTT  CAG  ACC  TTT  GCG  CGT  GAC  TGC  GCG  CAA  CCT  CGC        9771
Glu  Gly  Arg  His  Val  Gln  Thr  Phe  Ala  Arg  Asp  Cys  Ala  Gln  Pro  Arg
               3115                    3120                    3125

TTG  ACT  GTG  CTA  GAC  CGA  CGA  AGC  TTC  GAG  GAC  GCA  GAG  GAT  GTA  CAG        9819
Leu  Thr  Val  Leu  Asp  Arg  Arg  Ser  Phe  Glu  Asp  Ala  Glu  Asp  Val  Gln
               3130                    3135                    3140

GAG  GCT  CTC  TGC  GAG  ATC  CAA  TCT  CAT  TTC  GAC  CTC  GAG  AAT  GGA  CCC        9867
Glu  Ala  Leu  Cys  Glu  Ile  Gln  Ser  His  Phe  Asp  Leu  Glu  Asn  Gly  Pro
3145                    3150                    3155                    3160

CTC  TAC  ACA  GTG  GCG  TAC  ATC  CAC  GGT  TAC  GAG  GAC  GGC  TCC  GCC  CGA        9915
Leu  Tyr  Thr  Val  Ala  Tyr  Ile  His  Gly  Tyr  Glu  Asp  Gly  Ser  Ala  Arg
               3165                    3170                    3175
```

```
GTG TGG TTT GCC TGC CAT CAC GTC ATG GTC GAC ACT GTG AGC TGG AAC         9963
Val Trp Phe Ala Cys His His Val Met Val Asp Thr Val Ser Trp Asn
        3180              3185                  3190

ATT ATA CTG CAA GAC CTG CAG GCT CTC TAT CAT GGA GAC AGC CTT GGT        10011
Ile Ile Leu Gln Asp Leu Gln Ala Leu Tyr His Gly Asp Ser Leu Gly
        3195              3200                  3205

CCC AAG AGC AGC AGC GTG CAG CAG TGG TCG CTA GCT GTC AGC GAC TAC        10059
Pro Lys Ser Ser Ser Val Gln Gln Trp Ser Leu Ala Val Ser Asp Tyr
        3210              3215                  3220

AAA ATG CCA CTG TCG GAG AGG GCG CAT TGG AAT GTG CTC AGG AAG ACA        10107
Lys Met Pro Leu Ser Glu Arg Ala His Trp Asn Val Leu Arg Lys Thr
3225            3230              3235                  3240

GTC GCC CAG AGC TTC GAG ACC CTG CCT ATC TGC ATG GGC GGC GTG CTC        10155
Val Ala Gln Ser Phe Glu Thr Leu Pro Ile Cys Met Gly Gly Val Leu
            3245              3250                  3255

CAG TGC CAG GAG AAG TTC TCG AGG GAA ACG ACA ACA GCT CTG CTC TCC        10203
Gln Cys Gln Glu Lys Phe Ser Arg Glu Thr Thr Thr Ala Leu Leu Ser
            3260              3265                  3270

AAG GCC TGC CCT GCC TTG GAC TCC GGT ATG CAT GAG ATC CTT CTC ATG        10251
Lys Ala Cys Pro Ala Leu Asp Ser Gly Met His Glu Ile Leu Leu Met
        3275              3280                  3285

GCC GTG GGC TCC GCG CTG CAG AAG GCG GCA GGG GAT GTC CCT CAG GTC        10299
Ala Val Gly Ser Ala Leu Gln Lys Ala Ala Gly Asp Val Pro Gln Val
        3290              3295                  3300

GTC ACG ATA GAG GGT CAC GGG CGC GAA GAT ACT ATC GAC GCA ACT CTG        10347
Val Thr Ile Glu Gly His Gly Arg Glu Asp Thr Ile Asp Ala Thr Leu
3305            3310              3315                  3320

GAC GTC AGC CGG ACA GTC GGC TGG TTC ACG AGC ATG TAC CCC TTC GAG        10395
Asp Val Ser Arg Thr Val Gly Trp Phe Thr Ser Met Tyr Pro Phe Glu
            3325              3330                  3335

ATC CCC AAA GTG ACC GAC CCC GCT CAG GGC GTC GTC GAT GTC AAG GAG        10443
Ile Pro Lys Val Thr Asp Pro Ala Gln Gly Val Val Asp Val Lys Glu
        3340              3345                  3350

GCG ATG CGT CGC GTG CCG AAT AGG GGT GTC GGT TAC GGT CCA GCC TAC        10491
Ala Met Arg Arg Val Pro Asn Arg Gly Val Gly Tyr Gly Pro Ala Tyr
            3355              3360                  3365

GGA TAC GGC GGA TCG TGC CTG CCC GCG GTG AGC TTC AAC TAC CTT GGT        10539
Gly Tyr Gly Gly Ser Cys Leu Pro Ala Val Ser Phe Asn Tyr Leu Gly
        3370              3375                  3380

CGC CTG GAC CAG GCT TCC TCG GGG GCT CAA AGG GAC TGG ACG CTG GTC        10587
Arg Leu Asp Gln Ala Ser Ser Gly Ala Gln Arg Asp Trp Thr Leu Val
3385            3390              3395                  3400

ATG GAT GAA GAC GAG TAT CCG GTC GGA CTG TGC ACC AGC GCT GAG GAC        10635
Met Asp Glu Asp Glu Tyr Pro Val Gly Leu Cys Thr Ser Ala Glu Asp
            3405              3410                  3415

TCG GGA CGA AGC TCC TCC ATG GTG GAT TTC ACC TTC TCT ATC TCT GGC        10683
Ser Gly Arg Ser Ser Ser Met Val Asp Phe Thr Phe Ser Ile Ser Gly
            3420              3425                  3430

GGC CAG CTT GTC ATG GAT ATG AGT AGC AGC TGG GGC CAC GGC GCA CGA        10731
Gly Gln Leu Val Met Asp Met Ser Ser Ser Trp Gly His Gly Ala Arg
        3435              3440                  3445

AAT GAA TTC GTT CGC ACA GTT CGT AAC ACA CTA GAT GAC TTG ATC AAA        10779
Asn Glu Phe Val Arg Thr Val Arg Asn Thr Leu Asp Asp Leu Ile Lys
        3450              3455                  3460

ACA ACG AGC AGC AGG GAC TTC AGC GCA CCT CTG CCT CCG TCG GAT CAG        10827
Thr Thr Ser Ser Arg Asp Phe Ser Ala Pro Leu Pro Pro Ser Asp Gln
3465            3470              3475                  3480

GAG TCC AGC TTC ACC CCT TAT TTT GTC TTC GAA GAG GGC GAG CGA CAC        10875
Glu Ser Ser Phe Thr Pro Tyr Phe Val Phe Glu Glu Gly Glu Arg His
            3485              3490                  3495
```

```
GGC GCT CCG CTC TTC CTG CTC CCA CCT GGC GAA GGC GGA GCG GAG AGC        10923
Gly Ala Pro Leu Phe Leu Leu Pro Pro Gly Glu Gly Gly Ala Glu Ser
        3500                    3505                    3510

TAC TTC CAC AAC ATT GTC AAG GGT CTC CCG AAC CGC AAT CTT GTC GTG        10971
Tyr Phe His Asn Ile Val Lys Gly Leu Pro Asn Arg Asn Leu Val Val
        3515                    3520                    3525

TTC AAC AAT CAT TAC CGC GAG GAG AAG ACG CTC CGG ACC ATC GAG GCG        11019
Phe Asn Asn His Tyr Arg Glu Glu Lys Thr Leu Arg Thr Ile Glu Ala
        3530                    3535                    3540

CTG GCC GAG TAC TAC CTG TCG CAC ATC CGA TCC ATC CAG CCG GAG GGG        11067
Leu Ala Glu Tyr Tyr Leu Ser His Ile Arg Ser Ile Gln Pro Glu Gly
3545                    3550                    3555                    3560

CCA TAC CAC ATC CTC GGC TGG AGT TTC GGA GGC ATC CTC GGT CTC GAG        11115
Pro Tyr His Ile Leu Gly Trp Ser Phe Gly Gly Ile Leu Gly Leu Glu
                3565                    3570                    3575

GCG GCA AAG CGA TTG ACT GGC GAG GGT CAC AAG ATT GCC ACG CTG GCA        11163
Ala Ala Lys Arg Leu Thr Gly Glu Gly His Lys Ile Ala Thr Leu Ala
        3580                    3585                    3590

CTT ATC GAT CCG TAC TTT GAC ATC CCG TCC GCG TCC AAG GCC ATC GGC        11211
Leu Ile Asp Pro Tyr Phe Asp Ile Pro Ser Ala Ser Lys Ala Ile Gly
        3595                    3600                    3605

CAA CCT GAC GAT GCC TGC GTC TTG GAC CCC ATA TAC CAC GTC TAC CAC        11259
Gln Pro Asp Asp Ala Cys Val Leu Asp Pro Ile Tyr His Val Tyr His
        3610                    3615                    3620

CCG TCG CCG GAG AGC TTC AGG ACG GTG TCA TCT CTC ACT AAT CAC ATA        11307
Pro Ser Pro Glu Ser Phe Arg Thr Val Ser Ser Leu Thr Asn His Ile
3625                    3630                    3635                    3640

GCC CTG TTC AAG GCT ACC GAG ACG AAT GAC CAG CAT GGC AAT GCC ACG        11355
Ala Leu Phe Lys Ala Thr Glu Thr Asn Asp Gln His Gly Asn Ala Thr
                3645                    3650                    3655

CAG CAG GCC CTG TAT GAG TGG TTT GCC ACG TGC CCT TTG AAC AAC CTG        11403
Gln Gln Ala Leu Tyr Glu Trp Phe Ala Thr Cys Pro Leu Asn Asn Leu
        3660                    3665                    3670

GAC AAG TTT TTG GCG GCC GAC ACG ATC AAG GTG GTT CCT CTG GAG GGT        11451
Asp Lys Phe Leu Ala Ala Asp Thr Ile Lys Val Val Pro Leu Glu Gly
        3675                    3680                    3685

ACA CAT TTT ACC TGG GTG CAC CAC CCG GAG CAG GTG CGC TCA ATG TGC        11499
Thr His Phe Thr Trp Val His His Pro Glu Gln Val Arg Ser Met Cys
        3690                    3695                    3700

ACT ATG CTG GAT GAA TGG CTT GGG TGAACGAGGC AGTTGCTGTG AGAGAATGAG       11553
Thr Met Leu Asp Glu Trp Leu Gly
3705                    3710

AATGAGACAC AAAACGCGGG CGGAAGAGAG ACTTCCTCGG ACGGCGGG                   11601
```

( 2 ) INFORMATION FOR SEQ ID NO:25:

( i ) SEQUENCE CHARACTERISTICS:
        ( A ) LENGTH: 3712 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Val Ala Leu Glu Gln Trp Lys Thr Thr Val Gln Ser Val Ser Glu Arg
 1               5                  10                  15

Cys Asp Leu Ser Gly Leu Ser Gln His Pro Thr Asp Tyr Gln Leu Ala
            20                  25                  30

Ser Thr Gly Val Lys Gly Ala Gly Gly Ser Ser Ile Glu Glu Arg Ser
        35                  40                  45
```

| Ala | Ile | Val | Ser | Asp | Glu | Leu | Phe | Ser | Ser | Leu | Arg | Asp | Val | Cys | Ser |
| --- | --- | --- | --- | --- | --- | --- | --- | --- | --- | --- | --- | --- | --- | --- | --- |
| | 50 | | | | | 55 | | | | | 60 | | | | |
| Gln | Arg | Gln | Leu | Asp | Pro | Arg | Ser | Leu | Met | Leu | Phe | Ser | Val | His | Gln |
| 65 | | | | | 70 | | | | | 75 | | | | | 80 |
| Met | Leu | Lys | Arg | Phe | Gly | Asn | Gly | Ser | His | Thr | Val | Val | Ala | Ser | Leu |
| | | | | 85 | | | | | 90 | | | | | 95 | |
| Val | Thr | Ser | Ser | Glu | Gly | Cys | Pro | Ser | Thr | Ser | Ala | Trp | Arg | Ala | Ile |
| | | | 100 | | | | | 105 | | | | | 110 | | |
| Pro | Ser | Val | Ile | His | His | Ile | Glu | Gly | Gly | Asp | Asn | Asn | Asn | Thr | Val |
| | | | 115 | | | | 120 | | | | | 125 | | | |
| Ala | Ser | Ala | Val | Glu | Gln | Ala | Ala | Asn | Leu | Leu | Asn | Ser | Glu | Gly | Ser |
| | 130 | | | | | 135 | | | | | 140 | | | | |
| Gly | Gln | Asp | Leu | Leu | Ile | Pro | Ile | Gly | Leu | Thr | Glu | Leu | Val | Lys | Ser |
| 145 | | | | | 150 | | | | | 155 | | | | | 160 |
| Glu | Leu | Ile | Asp | Leu | Leu | Val | Ile | Phe | Asp | Asp | Glu | Thr | Asn | Asn | Ile |
| | | | | 165 | | | | | 170 | | | | | 175 | |
| Arg | Leu | Pro | Gln | Asp | Phe | Pro | Leu | Ile | Leu | Arg | Ile | His | Gln | Arg | Gln |
| | | | 180 | | | | | 185 | | | | | 190 | | |
| Asp | His | Trp | Gln | Leu | Ser | Val | Arg | Tyr | Pro | Ser | Pro | Leu | Phe | Asp | Thr |
| | | 195 | | | | | 200 | | | | | 205 | | | |
| Met | Val | Ile | Asp | Ser | Phe | Leu | Ser | Ala | Leu | His | Asn | Leu | Leu | Ser | Ala |
| | 210 | | | | | 215 | | | | | 220 | | | | |
| Val | Thr | Lys | Pro | Ser | Gln | Leu | Val | Arg | Asp | Ile | Glu | Leu | Leu | Pro | Glu |
| 225 | | | | | 230 | | | | | 235 | | | | | 240 |
| Tyr | Gln | Val | Ala | Gln | Leu | Glu | Lys | Trp | Asn | Asn | Thr | Asp | Gly | Asp | Tyr |
| | | | | 245 | | | | | 250 | | | | | 255 | |
| Pro | Thr | Glu | Lys | Arg | Leu | His | His | Leu | Phe | Glu | Glu | Ala | Ala | Val | Arg |
| | | | 260 | | | | | 265 | | | | | 270 | | |
| Arg | Pro | Gln | His | Val | Ala | Leu | Ile | Cys | Gly | Asp | Lys | Arg | Ile | Thr | Tyr |
| | | 275 | | | | | 280 | | | | | 285 | | | |
| Glu | Glu | Leu | Asn | Ala | Met | Ala | Asn | Arg | Leu | Ala | His | His | Leu | Val | Ser |
| | 290 | | | | | 295 | | | | | 300 | | | | |
| Ser | Gly | Ile | Gln | Thr | Glu | Gln | Leu | Val | Gly | Leu | Phe | Leu | Asp | Lys | Thr |
| 305 | | | | | 310 | | | | | 315 | | | | | 320 |
| Glu | Leu | Met | Ile | Ala | Thr | Ile | Leu | Gly | Ile | Trp | Lys | Ser | Gly | Ala | Ala |
| | | | | 325 | | | | | 330 | | | | | 335 | |
| His | Val | Pro | Ile | Asp | Pro | Gly | Tyr | Pro | Asp | Glu | Arg | Val | Lys | Phe | Val |
| | | | 340 | | | | | 345 | | | | | 350 | | |
| Leu | Asn | Asp | Thr | Lys | Ala | Gln | Val | Val | Ile | Ala | Ser | Gln | Arg | His | Val |
| | | 355 | | | | | 360 | | | | | 365 | | | |
| Asp | Arg | Leu | Arg | Ala | Glu | Val | Gly | Gly | Gln | His | Leu | Arg | Ile | Ile |
| | 370 | | | | | 375 | | | | | 380 | | | | |
| Gly | Leu | Glu | Ser | Leu | Phe | Asp | Asn | Leu | Ala | Gln | Gln | Thr | Gln | His | Ser |
| 385 | | | | | 390 | | | | | 395 | | | | | 400 |
| Pro | Glu | Thr | Ser | Gly | Asn | Leu | Thr | His | Leu | Pro | Leu | Asn | Ser | Lys | Gln |
| | | | | 405 | | | | | 410 | | | | | 415 | |
| Leu | Ala | Tyr | Val | Thr | Tyr | Thr | Ser | Gly | Thr | Thr | Gly | Phe | Pro | Lys | Gly |
| | | | 420 | | | | | 425 | | | | | 430 | | |
| Ile | Tyr | Lys | Glu | His | Thr | Ser | Val | Val | Asn | Ser | Ile | Thr | Asp | Leu | Ser |
| | | 435 | | | | | 440 | | | | | 445 | | | |
| Ala | Arg | Tyr | Gly | Val | Ala | Gly | Glu | Asp | Asp | Glu | Val | Ile | Leu | Val | Phe |
| | 450 | | | | | 455 | | | | | 460 | | | | |
| Ser | Ala | Tyr | Val | Phe | Glu | Pro | Phe | Val | Arg | Gln | Met | Leu | Met | Ala | Leu |
| 465 | | | | | 470 | | | | | 475 | | | | | 480 |

```
Thr Thr Gly Asn Ser Leu Ala Ile Ile Ser Asp Glu Asp Lys Phe Asp
            485                     490                 495
Pro Asp Thr Leu Ile Pro Phe Ile Gln Lys His Lys Val Thr Tyr Ile
            500                 505                     510
His Ala Thr Ser Ser Val Leu Gln Glu Tyr Asp Phe Gly Ser Cys Pro
            515             520                 525
Ser Leu Lys Arg Met Ile Leu Val Gly Glu Asn Leu Thr Glu Pro Arg
    530                 535                 540
Tyr Glu Ala Leu Arg Gln Arg Phe Lys Ser Arg Ile Leu Asn Glu Tyr
545                 550                 555                 560
Gly Phe Thr Glu Ser Ala Phe Val Thr Ala Leu Asn Ile Phe Glu Pro
                565                 570                 575
Thr Ser Gln Arg Lys Asp Met Ser Leu Gly Arg Pro Val Arg Asn Val
            580                 585                 590
Lys Cys Tyr Ile Leu Asp Ala Asn Leu Lys Arg Val Pro Ile Gly Val
            595                 600                 605
Thr Gly Glu Leu His Ile Gly Gly Leu Gly Ile Ser Arg Gly Tyr Met
    610                 615                 620
Asn Arg Glu Glu Leu Thr Arg Gln Lys Phe Leu Pro Asn Pro Tyr Gln
625                 630                 635                 640
Thr Asp Lys Glu Arg Gln Arg Gly Val Asn Ser Thr Met Tyr Lys Thr
                645                 650                 655
Gly Asp Leu Ala Arg Trp Leu Pro Ser Gly Glu Val Glu Tyr Leu Gly
                660                 665                 670
Arg Ala Asp Phe Gln Ile Lys Leu Arg Gly Ile Arg Ile Glu Pro Gly
            675                 680                 685
Glu Ile Glu Ser Thr Leu Ala Met Tyr Pro Gly Ile Arg Ala Ser Ile
    690                 695                 700
Val Val Ser Lys Lys Leu Leu Ser Gln Gly Gln Glu Thr Ile Gln Asp
705                 710                 715                 720
His Leu Val Gly Tyr Tyr Val Cys Asp Glu Gly His Ile Pro Glu Gly
                725                 730                 735
Asp Leu Leu Ser Phe Leu Glu Lys Lys Leu Pro Arg Tyr Met Val Pro
            740                 745                 750
Thr Arg Leu Val Gln Leu Ala Gln Ile Pro Thr Asn Ile Asn Gly Lys
        755                 760                 765
Ala Asp Leu Arg Ala Leu Pro Ala Val Glu Val Ala Val Ala Pro Thr
    770                 775                 780
His Lys Gln Asp Gly Glu Arg Gly Asn Gln Leu Glu Ser Asp Leu Ala
785                 790                 795                 800
Ala Ile Trp Gly Asn Ile Leu Ser Val Pro Ala Gln Asp Ile Gly Ser
                805                 810                 815
Glu Ser Asn Phe Phe Arg Leu Gly Gly His Ser Ile Ala Cys Ile Gln
            820                 825                 830
Leu Ile Ala Arg Val Arg Gln Gln Leu Gly Gln Gly Ile Thr Leu Glu
        835                 840                 845
Glu Val Phe Gln Thr Lys Thr Leu Arg Ala Met Ala Ala Leu Leu Ser
    850                 855                 860
Glu Lys Tyr Thr Lys Ala Ser Asn Gly Thr Asn Gly Val Thr Asn Gly
865                 870                 875                 880
Thr Ala His Val Asn Gly His Ala Ala Asn Gly His Val Ser Asp Ser
                885                 890                 895
Tyr Val Ala Ser Ser Leu Gln Gln Gly Phe Val Tyr His Ser Leu Lys
```

```
                              900                     905                     910
Asn  Glu  Leu  Ser  Glu  Ala  Tyr  Thr  Met  Gln  Ser  Met  Ile  His  Tyr  Gly
               915                      920                     925

Val  Pro  Leu  Lys  Arg  Asp  Ile  Tyr  Gln  Ala  Ala  Trp  Gln  Arg  Val  Gln
930                      935                     940

Gly  Glu  His  Pro  Ala  Leu  Arg  Leu  Arg  Phe  Thr  Trp  Glu  Ala  Glu  Val
945                           950                     955                     960

Met  Gln  Ile  Val  Asp  Pro  Lys  Ser  Glu  Leu  Asp  Trp  Arg  Val  Val  Asp
                    965                     970                     975

Trp  Thr  Asp  Val  Ser  Ser  Arg  Glu  Lys  Gln  Leu  Val  Ala  Leu  Glu  Gln
               980                      985                     990

Leu  Gln  Thr  Glu  Asp  Leu  Ala  Lys  Val  Tyr  His  Leu  Asp  Lys  Gly  Pro
          995                      1000                    1005

Leu  Met  Arg  Leu  Tyr  Leu  Ile  Leu  Leu  Pro  Asp  Ser  Lys  Tyr  Ser  Cys
          1010                     1015                    1020

Leu  Phe  Ser  Cys  His  His  Ala  Ile  Leu  Asp  Gly  Trp  Ser  Leu  Pro  Leu
1025                     1030                    1035                         1040

Leu  Phe  Asn  Asn  Val  His  Gln  Ala  Tyr  Leu  Asp  Leu  Val  Glu  Gly  Thr
                    1045                    1050                    1055

Ala  Ser  Pro  Val  Glu  Gln  Asp  Ala  Thr  Tyr  Leu  Leu  Gly  Gln  Gln  Tyr
                    1060                    1065                    1070

Leu  Gln  Ser  His  Arg  Asp  Asp  His  Leu  Asp  Phe  Trp  Ala  Glu  Gln  Ile
               1075                     1080                    1085

Gly  Arg  Ile  Glu  Glu  Arg  Cys  Asp  Met  Asn  Ala  Leu  Leu  Asn  Glu  Ala
          1090                     1095                    1100

Ser  Arg  Tyr  Lys  Val  Pro  Leu  Ala  Asp  Tyr  Asp  Gln  Val  Arg  Glu  Gln
1105                     1110                    1115                         1120

Arg  Gln  Gln  Thr  Ile  Ser  Leu  Pro  Trp  Asn  Asn  Ser  Met  Asp  Ala  Gly
               1125                     1130                    1135

Val  Arg  Glu  Glu  Leu  Ser  Ser  Arg  Gly  Ile  Thr  Leu  His  Ser  Ile  Leu
                    1140                    1145                    1150

Gln  Thr  Val  Trp  His  Leu  Val  Leu  His  Ser  Tyr  Gly  Gly  Gly  Thr  His
               1155                     1160                    1165

Thr  Ile  Thr  Gly  Thr  Thr  Ile  Ser  Gly  Arg  His  Leu  Pro  Val  Pro  Gly
          1170                     1175                    1180

Ile  Glu  Arg  Ser  Val  Gly  Leu  Phe  Ile  Asn  Thr  Leu  Pro  Met  Ile  Phe
1185                     1190                    1195                         1200

Asp  His  Thr  Val  Cys  Gln  Asp  Met  Thr  Ala  Leu  Glu  Ala  Ile  Glu  His
               1205                     1210                    1215

Val  Gln  Gly  Gln  Val  Asn  Ala  Met  Asn  Ser  Arg  Gly  Asn  Val  Glu  Leu
               1220                     1225                    1230

Gly  Arg  Met  Ser  Lys  Asn  Asp  Leu  Lys  His  Gly  Leu  Phe  Asp  Thr  Leu
               1235                     1240                    1245

Phe  Val  Leu  Glu  Asn  Tyr  Pro  Asn  Leu  Asp  Thr  Glu  Gln  Arg  Glu  Lys
          1250                     1255                    1260

His  Glu  Glu  Lys  Leu  Lys  Phe  Thr  Ile  Lys  Gly  Gly  Thr  Glu  Lys  Leu
1265                     1270                    1275                         1280

Ser  Tyr  Pro  Leu  Ala  Val  Ile  Ala  Gln  Glu  Asp  Gly  Asp  Ser  Gly  Cys
                    1285                    1290                    1295

Ser  Phe  Thr  Leu  Cys  Tyr  Ala  Gly  Glu  Leu  Phe  Thr  Asp  Glu  Ser  Ile
          1300                     1305                    1310

Gln  Ala  Leu  Leu  Asp  Thr  Val  Arg  Asp  Thr  Leu  Ser  Asp  Ile  Leu  Gly
          1315                     1320                    1325
```

```
Asn  Ile  His  Ala  Pro  Ile  Arg  Asn  Met  Glu  Tyr  Leu  Ser  Ser  Asn  Gln
     1330                1335                1340

Thr  Ala  Gln  Leu  Asp  Lys  Trp  Asn  Ala  Thr  Ala  Phe  Glu  Tyr  Pro  Asn
1345                1350                1355                               1360

Thr  Thr  Leu  His  Ala  Met  Phe  Glu  Ser  Ala  Gln  Gln  Lys  Pro  Asp
                1365                1370                     1375

Lys  Val  Ala  Val  Val  Tyr  Glu  Asp  Ile  Arg  Leu  Thr  Tyr  Arg  Glu  Leu
               1380                1385                     1390

Asn  Ser  Arg  Ala  Asn  Ala  Leu  Ala  Phe  Tyr  Leu  Leu  Ser  Gln  Ala  Ala
               1395                1400                     1405

Ile  Gln  Pro  Asn  Lys  Leu  Val  Gly  Leu  Ile  Met  Asp  Lys  Ser  Glu  His
     1410                1415                1420

Met  Ile  Thr  Ser  Ile  Leu  Ala  Val  Trp  Lys  Thr  Gly  Gly  Ala  Tyr  Val
1425                1430                1435                               1440

Pro  Ile  Asp  Pro  Arg  Tyr  Pro  Asp  Gln  Arg  Ile  Gln  Tyr  Ile  Leu  Glu
               1445                1450                     1455

Asp  Thr  Ala  Ala  Leu  Ala  Val  Ile  Thr  Asp  Ser  Pro  His  Ile  Asp  Arg
               1460                1465                     1470

Leu  Arg  Ser  Ile  Thr  Asn  Asn  Arg  Leu  Pro  Val  Ile  Gln  Ser  Asp  Phe
               1475                1480                     1485

Ala  Leu  Gln  Leu  Pro  Pro  Ser  Pro  Val  His  Pro  Val  Ser  Asn  Cys  Lys
     1490                1495                1500

Pro  Ser  Asp  Leu  Ala  Tyr  Ile  Met  Tyr  Thr  Ser  Gly  Thr  Thr  Gly  Asn
1505                1510                1515                               1520

Pro  Lys  Gly  Val  Met  Val  Glu  His  His  Gly  Val  Val  Asn  Leu  Cys  Val
                    1525                1530                     1535

Ser  Leu  Cys  Arg  Leu  Phe  Gly  Leu  Arg  Asn  Thr  Asp  Asp  Glu  Val  Ile
               1540                1545                     1550

Leu  Ser  Phe  Ser  Asn  Tyr  Val  Phe  Asp  His  Phe  Val  Glu  Gln  Met  Thr
               1555                1560                     1565

Asp  Ala  Leu  Leu  Asn  Gly  Gln  Thr  Leu  Val  Val  Leu  Asn  Asp  Glu  Met
               1570                1575                     1580

Arg  Gly  Asp  Lys  Glu  Arg  Leu  Tyr  Arg  Tyr  Ile  Glu  Thr  Asn  Arg  Val
1585                1590                1595                               1600

Thr  Tyr  Leu  Ser  Gly  Thr  Pro  Ser  Val  Ile  Ser  Met  Tyr  Glu  Phe  Asp
                    1605                1610                     1615

Arg  Phe  Arg  Asp  His  Leu  Arg  Arg  Val  Asp  Cys  Val  Gly  Glu  Ala  Phe
                    1620                1625                     1630

Ser  Glu  Pro  Val  Phe  Asp  Lys  Ile  Arg  Glu  Thr  Phe  Pro  Gly  Leu  Ile
               1635                1640                     1645

Ile  Asn  Gly  Tyr  Gly  Pro  Thr  Glu  Val  Ser  Ile  Thr  Thr  His  Lys  Arg
     1650                1655                1660

Pro  Tyr  Pro  Phe  Pro  Glu  Arg  Arg  Thr  Asp  Lys  Ser  Ile  Gly  Cys  Gln
1665                1670                1675                               1680

Leu  Asp  Asn  Ser  Thr  Ser  Tyr  Val  Leu  Asn  Asp  Asp  Met  Lys  Arg  Val
                    1685                1690                     1695

Pro  Ile  Gly  Ala  Val  Gly  Glu  Leu  Tyr  Leu  Gly  Gly  Asp  Gly  Val  Ala
                    1700                1705                     1710

Arg  Gly  Tyr  His  Asn  Arg  Pro  Asp  Leu  Thr  Ala  Asp  Arg  Phe  Pro  Ala
                    1715                1720                     1725

Asn  Pro  Phe  Gln  Thr  Glu  Gln  Glu  Arg  Leu  Glu  Gly  Arg  Asn  Ala  Arg
                    1730                1735                     1740

Leu  Tyr  Lys  Thr  Gly  Asp  Leu  Val  Arg  Trp  Ile  His  Asn  Ala  Asn  Gly
     1745                1750                1755                          1760
```

```
Asp  Gly  Glu  Ile  Glu  Tyr  Leu  Gly  Arg  Asn  Asp  Phe  Gln  Val  Lys  Ile
               1765                     1770                     1775

Arg  Gly  Gln  Arg  Ile  Glu  Leu  Gly  Glu  Ile  Glu  Ala  Val  Leu  Ser  Ser
               1780                     1785                     1790

Tyr  Pro  Gly  Ile  Lys  Gln  Ser  Val  Val  Leu  Ala  Lys  Asp  Arg  Lys  Asn
               1795                     1800                     1805

Asp  Gly  Gln  Lys  Tyr  Leu  Val  Gly  Tyr  Phe  Val  Ser  Ser  Ala  Gly  Ser
               1810                     1815                     1820

Leu  Ser  Ala  Gln  Ala  Ile  Arg  Arg  Phe  Met  Leu  Thr  Ser  Leu  Pro  Asp
1825                    1830                     1835                     1840

Tyr  Met  Val  Pro  Ala  Gln  Leu  Val  Pro  Ile  Ala  Lys  Phe  Pro  Val  Thr
                    1845                     1850                     1855

Val  Ser  Gly  Lys  Leu  Asp  Ala  Lys  Ala  Leu  Pro  Val  Pro  Asp  Asp  Thr
                    1860                     1865                     1870

Val  Glu  Asp  Asp  Ile  Val  Pro  Pro  Arg  Thr  Glu  Val  Glu  Arg  Ile  Leu
                    1875                     1880                     1885

Ala  Gly  Ile  Trp  Ser  Glu  Leu  Leu  Glu  Ile  Pro  Val  Asp  Arg  Ile  Ser
                    1890                     1895                     1900

Ile  Tyr  Ser  Asp  Phe  Phe  Ser  Leu  Gly  Gly  Asp  Ser  Leu  Lys  Ser  Thr
1905                    1910                     1915                     1920

Lys  Leu  Ser  Phe  Ala  Ala  Thr  Arg  Ala  Leu  Gly  Val  Ala  Val  Ser  Val
                    1925                     1930                     1935

Arg  Asn  Leu  Phe  Ser  His  Pro  Thr  Ile  Glu  Ala  Leu  Ser  Gln  Trp  Ile
                    1940                     1945                     1950

Ile  Arg  Gly  Ser  Asn  Glu  Val  Lys  Asp  Val  Ala  Val  Val  Lys  Gly  Gly
                    1955                     1960                     1965

Ala  Ser  Leu  Asp  Ile  Pro  Leu  Ser  Pro  Ala  Gln  Glu  Arg  Leu  Met  Phe
     1970                    1975                     1980

Ile  His  Glu  Phe  Gly  His  Ser  Gly  Glu  Asp  Thr  Gly  Ala  Tyr  Asn  Val
1985                    1990                     1995                     2000

Pro  Leu  Gln  Leu  Gln  Leu  His  His  Asp  Val  Cys  Leu  Glu  Ser  Leu  Glu
                    2005                     2010                     2015

Lys  Ala  Leu  Arg  Asp  Val  Val  Ser  Arg  His  Glu  Ala  Leu  Arg  Thr  Leu
                    2020                     2025                     2030

Ile  Thr  Arg  Thr  Gln  Lys  Ser  Ser  Val  His  Cys  Gln  Lys  Ile  Leu  Asp
                    2035                     2040                     2045

Ala  Glu  Glu  Ala  Gln  Lys  Leu  Phe  Ser  Val  Asp  Val  Leu  Arg  Leu  Thr
     2050                    2055                     2060

Ser  Glu  Thr  Glu  Met  Gln  Gly  Arg  Met  Ala  Glu  Ser  Thr  Ala  His  Ala
2065                    2070                     2075                     2080

Phe  Lys  Leu  Asp  Glu  Glu  Leu  Pro  Ile  His  Val  Arg  Leu  Tyr  Gln  Val
                    2085                     2090                     2095

Val  Arg  Asp  Gly  Arg  Thr  Leu  Ser  Phe  Ala  Ser  Ile  Val  Cys  His  His
                    2100                     2105                     2110

Leu  Ala  Phe  Asp  Ala  Trp  Ser  Trp  Asp  Val  Phe  Gln  Arg  Asp  Leu  Asp
                    2115                     2120                     2125

Ala  Phe  Tyr  Ala  Val  His  Thr  Lys  His  Lys  Ala  Ala  Ala  Asn  Leu  Pro
                    2130                     2135                     2140

Thr  Leu  Arg  Val  Gln  Tyr  Lys  Glu  Tyr  Ala  Ile  Glu  His  Arg  Arg  Ala
2145                    2150                     2155                     2160

Leu  Arg  Ala  Glu  Gln  His  Arg  Val  Leu  Ala  Asp  Tyr  Trp  Leu  Arg  Lys
                    2165                     2170                     2175

Leu  Ser  Asp  Met  Glu  Ala  Ser  Tyr  Leu  Val  Pro  Asp  Arg  Pro  Arg  Pro
```

|      |      |      |      |      | 2180 |      |      |      |      | 2185 |      |      |      |      | 2190 |      |
|------|------|------|------|------|------|------|------|------|------|------|------|------|------|------|------|------|

Ala Gln Phe Asp Tyr Thr Gly Asn Asp Leu Gln Phe Ser Thr Thr Pro
             2195                    2200                    2205

Glu Thr Thr Ala Gln Leu Lys Glu Leu Ala Lys Arg Glu Gly Ser Ser
    2210                    2215                    2220

Leu Tyr Thr Val Val Ala Ala Ala Tyr Phe Leu Leu Leu Tyr Val Tyr
2225                    2230                    2235                    2240

Thr Asn Gln Arg Asp Ile Thr Ile Gly Ile Pro Val Ala His Arg Asn
             2245                    2250                    2255

His Pro Asp Phe Glu Ser Val Val Gly Phe Phe Val Asn Leu Leu Pro
             2260                    2265                    2270

Leu Arg Val Asn Val Ser Gln Ser Asp Ile His Gly Leu Ile Gln Ala
             2275                    2280                    2285

Val Gln Lys Glu Leu Val Asp Ala Gln Ile His Gln Asp Leu Pro Phe
             2290                    2295                    2300

Gln Glu Ile Thr Lys Leu Leu His Val Gln His Asp Pro Ser Arg His
2305                    2310                    2315                    2320

Pro Leu Leu Gln Ala Val Phe Asn Trp Glu Asn Val Pro Ala Asn Val
                  2325                    2330                    2335

His Glu Glu Gln Leu Leu Gln Glu Tyr Lys Pro Pro Ser Pro Leu Pro
                  2340                    2345                    2350

Ser Ala Ala Lys Phe Asp Leu Asn Val Thr Val Lys Glu Ser Val Asn
             2355                    2360                    2365

Ser Leu Asn Val Asn Phe Asn Tyr Pro Thr Ser Leu Phe Glu Glu Glu
    2370                    2375                    2380

Thr Val Gln Gly Phe Met Glu Thr Phe His Leu Leu Leu Arg Gln Leu
2385                    2390                    2395                    2400

Ala His Asn Lys Ala Ser Thr Ser Leu Ser Lys Leu Ser Val Glu Asp
                  2405                    2410                    2415

Gly Val Leu Asn Pro Glu Pro Thr Asn Leu Gln Pro Ser Ser Arg Asp
                  2420                    2425                    2430

Ser Gly Asn Ser Leu His Gly Leu Phe Glu Asp Ile Val Ala Ser Thr
             2435                    2440                    2445

Pro Asp Arg Ile Ala Ile Ala Asp Gly Thr Arg Ser Leu Ser Tyr Ser
             2450                    2455                    2460

Glu Leu Asn Glu Arg Ala Asn Gln Leu Val His Leu Ile Ile Ser Ser
2465                    2470                    2475                    2480

Ala Ser Ile Val Ala Asp Asp Arg Ile Ala Leu Leu Leu Asp Lys Ser
                  2485                    2490                    2495

Ile Asp Met Val Ile Ala Leu Leu Ala Val Trp Lys Ala Gly Ala Ala
             2500                    2505                    2510

Tyr Val Pro Leu Asp Pro Thr Tyr Pro Ser Gln Arg Thr Glu Leu Ile
             2515                    2520                    2525

Leu Glu Glu Ser Ser Ala Arg Thr Leu Ile Thr Thr Arg Lys His Thr
    2530                    2535                    2540

Pro Arg Gly Gly Thr Val Ala Asn Val Pro Ser Val Val Leu Asp Ser
2545                    2550                    2555                    2560

Pro Glu Thr Leu Ala Cys Leu Asn Gln Gln Ser Lys Glu Asn Pro Thr
                  2565                    2570                    2575

Thr Ser Thr Gln Lys Pro Ser Asp Leu Ala Tyr Val Ile Phe Thr Ser
             2580                    2585                    2590

Gly Thr Thr Gly Lys Pro Lys Gly Val Leu Val Glu His Gln Ser Val
             2595                    2600                    2605

-continued

```
Val Gln Leu Arg Asn Ser Leu Ile Glu Arg Tyr Phe Gly Glu Thr Asn
    2610            2615                2620
Gly Ser His Ala Val Leu Phe Leu Ser Asn Tyr Val Phe Asp Phe Ser
2625            2630            2635                    2640
Leu Glu Gln Leu Cys Leu Ser Val Leu Gly Gly Asn Lys Leu Ile Ile
            2645            2650                2655
Pro Pro Glu Glu Gly Leu Thr His Glu Ala Phe Tyr Asp Ile Gly Arg
        2660            2665            2670
Arg Glu Lys Leu Ser Tyr Leu Ser Gly Thr Pro Ser Val Leu Gln Gln
        2675            2680            2685
Ile Glu Leu Ser Arg Leu Pro His Leu His Met Val Thr Ala Ala Gly
    2690            2695            2700
Glu Glu Phe His Ala Ser Gln Phe Glu Lys Met Arg Ser Gln Phe Ala
2705            2710            2715                    2720
Gly Gln Ile Asn Asn Ala Tyr Gly Ile Thr Glu Thr Thr Val Tyr Asn
            2725            2730                2735
Ile Ile Thr Thr Phe Lys Gly Asp Ala Pro Phe Thr Lys Ala Leu Cys
            2740            2745            2750
His Gly Ile Pro Gly Ser His Val Tyr Val Leu Asn Asp Arg Leu Gln
            2755            2760            2765
Arg Val Pro Phe Asn Ala Val Gly Glu Leu Tyr Leu Gly Gly Asp Cys
    2770            2775            2780
Leu Ala Arg Gly Tyr Leu Asn Gln Asp Ala Leu Thr Asn Glu Arg Phe
2785            2790            2795                    2800
Ile Pro Asn Pro Phe Tyr Glu Pro Lys Gln Ala Ser Asp Ser Arg Pro
            2805            2810            2815
Gln Arg Leu Tyr Lys Thr Gly Asp Leu Val Arg Phe Arg Gly Pro His
        2820            2825            2830
His Leu Glu Tyr Leu Gly Arg Lys Asp Gln Gln Val Lys Leu Arg Gly
        2835            2840            2845
Phe Arg Ile Glu Leu Ser Glu Val Arg Asp Ala Val Leu Ala Ile Ser
    2850            2855            2860
Ala Val Lys Glu Ala Ala Val Ile Pro Lys Tyr Asp Glu Asp Gly Ser
2865            2870            2875                    2880
Asp Ser Arg Arg Val Ser Ala Ile Val Cys Tyr Tyr Thr Leu Asn Ala
            2885            2890            2895
Gly Thr Val Cys Glu Ala Ser Ser Ile Arg Asp His Leu His Ala Asn
            2900            2905            2910
Leu Pro Pro Tyr Met Val Pro Ser Gln Ile His Gln Leu Glu Gly Ser
            2915            2920            2925
Leu Pro Val Thr Val Asn Gly Lys Leu Asp Leu Asn Arg Leu Ser Thr
    2930            2935            2940
Thr Gln Val Ser Gln Pro Glu Leu Tyr Thr Ala Pro Arg Asn Ser Thr
2945            2950            2955                    2960
Glu Glu Thr Leu Cys Gln Leu Trp Ala Ser Leu Leu Gly Val Asp His
            2965            2970            2975
Cys Gly Ile Asp Asp Asp Leu Phe Ala Arg Gly Gly Asp Ser Ile Ser
            2980            2985            2990
Ser Leu Arg Leu Val Gly Asp Ile Tyr Arg Ala Leu Gly Arg Lys Val
            2995            3000            3005
Thr Val Lys Asp Ile Tyr Leu His Arg Ser Val Arg Ala Leu Ser Glu
            3010            3015            3020
Asn Val Leu Thr Asp Gln Lys Asp Lys Gly Thr Leu Pro Ala Ser Pro
3025            3030            3035                    3040
```

| | | | | | | | | | | | | | | |
|---|---|---|---|---|---|---|---|---|---|---|---|---|---|---|
|Pro|Leu|Gln|Arg|Ala|Glu|Gln|Gly|Gln|Val|Glu|Gly|Asp|Ala|Pro|Leu|
| | | | |3045| | | |3050| | | |3055| | |

```
Pro  Leu  Gln  Arg  Ala  Glu  Gln  Gly  Gln  Val  Glu  Gly  Asp  Ala  Pro  Leu
                    3045                    3050                    3055

Leu  Pro  Ile  Gln  Asp  Trp  Phe  Leu  Ser  Lys  Pro  Leu  Asp  Asn  Pro  Ala
                    3060                    3065                    3070

Tyr  Trp  Asn  His  Cys  Phe  Thr  Ile  Arg  Thr  Gly  Ala  Leu  Ser  Val  Glu
                    3075                    3080                    3085

Gly  Leu  Arg  Gly  Ala  Leu  Lys  Leu  Leu  Gln  Glu  Arg  His  Asp  Val  Leu
                    3090                    3095                    3100

Arg  Leu  Arg  Leu  Gln  Arg  Arg  Asp  Glu  Gly  Arg  His  Val  Gln  Thr  Phe
3105                    3110                    3115                    3120

Ala  Arg  Asp  Cys  Ala  Gln  Pro  Arg  Leu  Thr  Val  Leu  Asp  Arg  Arg  Ser
                    3125                    3130                    3135

Phe  Glu  Asp  Ala  Glu  Asp  Val  Gln  Glu  Ala  Leu  Cys  Glu  Ile  Gln  Ser
                    3140                    3145                    3150

His  Phe  Asp  Leu  Glu  Asn  Gly  Pro  Leu  Tyr  Thr  Val  Ala  Tyr  Ile  His
                    3155                    3160                    3165

Gly  Tyr  Glu  Asp  Gly  Ser  Ala  Arg  Val  Trp  Phe  Ala  Cys  His  His  Val
                    3170                    3175                    3180

Met  Val  Asp  Thr  Val  Ser  Trp  Asn  Ile  Ile  Leu  Gln  Asp  Leu  Gln  Ala
3185                    3190                    3195                    3200

Leu  Tyr  His  Gly  Asp  Ser  Leu  Gly  Pro  Lys  Ser  Ser  Ser  Val  Gln  Gln
                    3205                    3210                    3215

Trp  Ser  Leu  Ala  Val  Ser  Asp  Tyr  Lys  Met  Pro  Leu  Ser  Glu  Arg  Ala
                    3220                    3225                    3230

His  Trp  Asn  Val  Leu  Arg  Lys  Thr  Val  Ala  Gln  Ser  Phe  Glu  Thr  Leu
                    3235                    3240                    3245

Pro  Ile  Cys  Met  Gly  Gly  Val  Leu  Gln  Cys  Gln  Glu  Lys  Phe  Ser  Arg
                    3250                    3255                    3260

Glu  Thr  Thr  Thr  Ala  Leu  Leu  Ser  Lys  Ala  Cys  Pro  Ala  Leu  Asp  Ser
3265                    3270                    3275                    3280

Gly  Met  His  Glu  Ile  Leu  Leu  Met  Ala  Val  Gly  Ser  Ala  Leu  Gln  Lys
                    3285                    3290                    3295

Ala  Ala  Gly  Asp  Val  Pro  Gln  Val  Val  Thr  Ile  Glu  Gly  His  Gly  Arg
                    3300                    3305                    3310

Glu  Asp  Thr  Ile  Asp  Ala  Thr  Leu  Asp  Val  Ser  Arg  Thr  Val  Gly  Trp
                    3315                    3320                    3325

Phe  Thr  Ser  Met  Tyr  Pro  Phe  Glu  Ile  Pro  Lys  Val  Thr  Asp  Pro  Ala
                    3330                    3335                    3340

Gln  Gly  Val  Val  Asp  Val  Lys  Glu  Ala  Met  Arg  Arg  Val  Pro  Asn  Arg
3345                    3350                    3355                    3360

Gly  Val  Gly  Tyr  Gly  Pro  Ala  Tyr  Gly  Tyr  Gly  Gly  Ser  Cys  Leu  Pro
                    3365                    3370                    3375

Ala  Val  Ser  Phe  Asn  Tyr  Leu  Gly  Arg  Leu  Asp  Gln  Ala  Ser  Ser  Gly
                    3380                    3385                    3390

Ala  Gln  Arg  Asp  Trp  Thr  Leu  Val  Met  Asp  Glu  Asp  Glu  Tyr  Pro  Val
                    3395                    3400                    3405

Gly  Leu  Cys  Thr  Ser  Ala  Glu  Asp  Ser  Gly  Arg  Ser  Ser  Ser  Met  Val
                    3410                    3415                    3420

Asp  Phe  Thr  Phe  Ser  Ile  Ser  Gly  Gly  Gln  Leu  Val  Met  Asp  Met  Ser
3425                    3430                    3435                    3440

Ser  Ser  Trp  Gly  His  Gly  Ala  Arg  Asn  Glu  Phe  Val  Arg  Thr  Val  Arg
                    3445                    3450                    3455

Asn  Thr  Leu  Asp  Asp  Leu  Ile  Lys  Thr  Thr  Ser  Ser  Arg  Asp  Phe  Ser
```

```
                                  3460                          3465                          3470
        Ala  Pro  Leu  Pro  Pro  Ser  Asp  Gln  Glu  Ser  Ser  Phe  Thr  Pro  Tyr  Phe
                      3475                          3480                          3485
        Val  Phe  Glu  Glu  Gly  Glu  Arg  His  Gly  Ala  Pro  Leu  Phe  Leu  Leu  Pro
                 3490                          3495                          3500
        Pro  Gly  Glu  Gly  Gly  Ala  Glu  Ser  Tyr  Phe  His  Asn  Ile  Val  Lys  Gly
        3505                          3510                          3515                          3520
        Leu  Pro  Asn  Arg  Asn  Leu  Val  Val  Phe  Asn  Asn  His  Tyr  Arg  Glu  Glu
                           3525                          3530                          3535
        Lys  Thr  Leu  Arg  Thr  Ile  Glu  Ala  Leu  Ala  Glu  Tyr  Tyr  Leu  Ser  His
                      3540                          3545                          3550
        Ile  Arg  Ser  Ile  Gln  Pro  Glu  Gly  Pro  Tyr  His  Ile  Leu  Gly  Trp  Ser
                 3555                          3560                          3565
        Phe  Gly  Gly  Ile  Leu  Gly  Leu  Glu  Ala  Ala  Lys  Arg  Leu  Thr  Gly  Glu
                 3570                          3575                          3580
        Gly  His  Lys  Ile  Ala  Thr  Leu  Ala  Leu  Ile  Asp  Pro  Tyr  Phe  Asp  Ile
        3585                          3590                          3595                          3600
        Pro  Ser  Ala  Ser  Lys  Ala  Ile  Gly  Gln  Pro  Asp  Asp  Ala  Cys  Val  Leu
                           3605                          3610                          3615
        Asp  Pro  Ile  Tyr  His  Val  Tyr  His  Pro  Ser  Pro  Glu  Ser  Phe  Arg  Thr
                      3620                          3625                          3630
        Val  Ser  Ser  Leu  Thr  Asn  His  Ile  Ala  Leu  Phe  Lys  Ala  Thr  Glu  Thr
                 3635                          3640                          3645
        Asn  Asp  Gln  His  Gly  Asn  Ala  Thr  Gln  Gln  Ala  Leu  Tyr  Glu  Trp  Phe
                 3650                          3655                          3660
        Ala  Thr  Cys  Pro  Leu  Asn  Asn  Leu  Asp  Lys  Phe  Leu  Ala  Ala  Asp  Thr
        3665                          3670                          3675                          3680
        Ile  Lys  Val  Val  Pro  Leu  Glu  Gly  Thr  His  Phe  Thr  Trp  Val  His  His
                           3685                          3690                          3695
        Pro  Glu  Gln  Val  Arg  Ser  Met  Cys  Thr  Met  Leu  Asp  Glu  Trp  Leu  Gly
                      3700                          3705                          3710
```

( 2 ) INFORMATION FOR SEQ ID NO:26:

( i ) SEQUENCE CHARACTERISTICS:
        ( A ) LENGTH: 11444 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

```
GTCGACAGTT  GACAGAGCCA  ATGGCATCGG  ATCTGCCCTA  GACCGTGCTA  GACGAAAGTC           60

TCCATCTTGT  CTGCGGGCAG  TTCTTCAGTC  GCCCAGATTC  TCGATGGAGA  TTGGCCAGGT          120

CAGCCATATA  TACCCTGCAA  TGGCAGACCA  ATGCAGCAGG  CCCAGTATAA  GGAATTCCCC          180

TCGAGCTTGT  CTGTGATTGC  GTTTTTTCTA  ACACTTGTTG  TTGCATCCGA  TCCGTCGCTA          240

CCAATTATTG  GTCATTGACA  GAC ATG ACT CAA CTG AAG CCA CCG AAC GGA                 290
                            Met Thr Gln Leu Lys Pro Pro Asn Gly
                              1               5

ACC ACG CCG ATA GGC TTC TCG GCC ACT ACA TCC CTG AAC GCC AGT GGG                 338
Thr Thr Pro Ile Gly Phe Ser Ala Thr Thr Ser Leu Asn Ala Ser Gly
 10              15                  20                      25

AGC TCG AGT GTG AAA AAT GGG ACC ATC AAA CCC AGC AAT GGC ATC TTC                 386
Ser Ser Ser Val Lys Asn Gly Thr Ile Lys Pro Ser Asn Gly Ile Phe
             30                  35                      40
```

| | | | | | | | | | | | | | | | | |
|---|---|---|---|---|---|---|---|---|---|---|---|---|---|---|---|---|
| AAG | CCC | AGC | ACT | AGG | GAC | ACC | ATG | GAC | CCT | TGC | AGT | GGG | AAT | GCG | GCC | 434 |
| Lys | Pro | Ser | Thr | Arg | Asp | Thr | Met | Asp | Pro | Cys | Ser | Gly | Asn | Ala | Ala | |
| | | | 45 | | | | 50 | | | | | 55 | | | | |
| GAT | GGC | AGT | ATC | CGC | GTC | CGT | TTC | CGT | GGA | GGA | ATC | GAA | CGG | TGG | AAG | 482 |
| Asp | Gly | Ser | Ile | Arg | Val | Arg | Phe | Arg | Gly | Gly | Ile | Glu | Arg | Trp | Lys | |
| | | 60 | | | | 65 | | | | | 70 | | | | | |
| GAG | TGC | GTC | AAC | CAG | GTC | CCC | GAG | CGC | TGC | GAC | CTG | AGT | GGT | CTG | ACA | 530 |
| Glu | Cys | Val | Asn | Gln | Val | Pro | Glu | Arg | Cys | Asp | Leu | Ser | Gly | Leu | Thr | |
| | 75 | | | | | 80 | | | | | 85 | | | | | |
| ACC | GAC | TCC | ACG | CGA | TAT | CAG | CTC | GCA | TCG | ACT | GGG | TTC | GGT | GAC | GCG | 578 |
| Thr | Asp | Ser | Thr | Arg | Tyr | Gln | Leu | Ala | Ser | Thr | Gly | Phe | Gly | Asp | Ala | |
| 90 | | | | | 95 | | | | | 100 | | | | | 105 | |
| AGC | GCT | GCG | TAC | CAG | GAG | CGC | TTG | ATG | ACG | GTC | CCT | GTT | GAC | GTA | CAT | 626 |
| Ser | Ala | Ala | Tyr | Gln | Glu | Arg | Leu | Met | Thr | Val | Pro | Val | Asp | Val | His | |
| | | | | 110 | | | | | 115 | | | | | 120 | | |
| GCC | GCG | CTC | CAA | GAG | CTG | TGC | CTA | GAA | CGC | CGT | GTG | AGC | GTG | GGA | TCC | 674 |
| Ala | Ala | Leu | Gln | Glu | Leu | Cys | Leu | Glu | Arg | Arg | Val | Ser | Val | Gly | Ser | |
| | | | 125 | | | | | 130 | | | | | 135 | | | |
| GTC | ATT | AAT | TTC | TCC | GTG | CAC | CAG | ATG | CTG | AAA | GGG | TTT | GGA | AAT | GGC | 722 |
| Val | Ile | Asn | Phe | Ser | Val | His | Gln | Met | Leu | Lys | Gly | Phe | Gly | Asn | Gly | |
| | | 140 | | | | | 145 | | | | | 150 | | | | |
| ACA | CAC | ACT | ATC | ACC | GCC | TCT | CTG | CAC | CGT | GAG | CAG | AAT | TTG | CAG | AAT | 770 |
| Thr | His | Thr | Ile | Thr | Ala | Ser | Leu | His | Arg | Glu | Gln | Asn | Leu | Gln | Asn | |
| | 155 | | | | | 160 | | | | | 165 | | | | | |
| TCT | TCG | CCA | TCC | TGG | GTA | GTC | TCC | CCC | ACA | ATC | GTC | ACC | CAT | GAG | AAC | 818 |
| Ser | Ser | Pro | Ser | Trp | Val | Val | Ser | Pro | Thr | Ile | Val | Thr | His | Glu | Asn | |
| 170 | | | | | 175 | | | | | 180 | | | | | 185 | |
| AGA | GAC | GGA | TGG | TCC | GTC | GCG | CAG | GCG | GTC | GAG | AGT | ATC | GAA | GCG | GCG | 866 |
| Arg | Asp | Gly | Trp | Ser | Val | Ala | Gln | Ala | Val | Glu | Ser | Ile | Glu | Ala | Ala | |
| | | | | 190 | | | | | 195 | | | | | 200 | | |
| CGC | GGT | TCC | GAG | AAG | GAG | TCA | GTG | ACT | GCG | ATT | GAC | TCC | GCG | TCA | AGT | 914 |
| Arg | Gly | Ser | Glu | Lys | Glu | Ser | Val | Thr | Ala | Ile | Asp | Ser | Ala | Ser | Ser | |
| | | | | 205 | | | | | 210 | | | | | 215 | | |
| CTC | GTG | AAA | ATG | GGG | TTA | TTT | GAC | TTA | CTC | GTC | AGC | TTT | GTC | GAT | GCA | 962 |
| Leu | Val | Lys | Met | Gly | Leu | Phe | Asp | Leu | Leu | Val | Ser | Phe | Val | Asp | Ala | |
| | | 220 | | | | | 225 | | | | | 230 | | | | |
| GAC | GAT | GCT | CGT | ATT | CCA | TGT | TTC | GAC | TTT | CCC | CTC | GCA | GTG | ATA | GTG | 1010 |
| Asp | Asp | Ala | Arg | Ile | Pro | Cys | Phe | Asp | Phe | Pro | Leu | Ala | Val | Ile | Val | |
| | | 235 | | | | | 240 | | | | | 245 | | | | |
| CGT | GAG | TGT | GAT | GCC | AAC | CTC | TCG | CTG | ACT | CTG | CGT | TTC | TCC | GAC | TGT | 1058 |
| Arg | Glu | Cys | Asp | Ala | Asn | Leu | Ser | Leu | Thr | Leu | Arg | Phe | Ser | Asp | Cys | |
| 250 | | | | | 255 | | | | | 260 | | | | | 265 | |
| CTC | TTC | AAC | GAG | GAG | ACG | ATA | TGC | AAT | TTT | ACC | GAT | GCC | CTA | AAC | ATC | 1106 |
| Leu | Phe | Asn | Glu | Glu | Thr | Ile | Cys | Asn | Phe | Thr | Asp | Ala | Leu | Asn | Ile | |
| | | | | 270 | | | | | 275 | | | | | 280 | | |
| TTG | CTC | GCC | GAA | GCA | GTG | ATA | GGA | AGA | GTG | ACC | CCG | GTT | GCC | GAT | ATC | 1154 |
| Leu | Leu | Ala | Glu | Ala | Val | Ile | Gly | Arg | Val | Thr | Pro | Val | Ala | Asp | Ile | |
| | | | 285 | | | | | 290 | | | | | 295 | | | |
| GAA | CTA | CTA | TCC | GCG | GAG | CAG | AAG | CAG | CAG | CTG | GAA | GAG | TGG | AAC | AAC | 1202 |
| Glu | Leu | Leu | Ser | Ala | Glu | Gln | Lys | Gln | Gln | Leu | Glu | Glu | Trp | Asn | Asn | |
| | | 300 | | | | | 305 | | | | | 310 | | | | |
| ACG | GAT | GGC | GAG | TAC | CCT | TCA | TCA | AAG | CGA | CTG | CAC | CAT | CTC | ATT | GAA | 1250 |
| Thr | Asp | Gly | Glu | Tyr | Pro | Ser | Ser | Lys | Arg | Leu | His | His | Leu | Ile | Glu | |
| | 315 | | | | | 320 | | | | | 325 | | | | | |
| GAG | GTG | GTT | GAA | CGG | CAT | GAA | GAC | AAA | ATA | GCC | GTT | GTC | TGC | GAC | GAG | 1298 |
| Glu | Val | Val | Glu | Arg | His | Glu | Asp | Lys | Ile | Ala | Val | Val | Cys | Asp | Glu | |
| 330 | | | | | 335 | | | | | 340 | | | | | 345 | |
| CGA | GAG | CTC | ACT | TAC | GGC | GAG | CTC | AAT | GCC | CAA | GGC | AAC | AGC | CTC | GCA | 1346 |
| Arg | Glu | Leu | Thr | Tyr | Gly | Glu | Leu | Asn | Ala | Gln | Gly | Asn | Ser | Leu | Ala | |
| | | | | 350 | | | | | 355 | | | | | 360 | | |

| | | | | | | | | | | | | | | | | |
|---|---|---|---|---|---|---|---|---|---|---|---|---|---|---|---|---|
| CGC | TAT | CTC | CGT | TCC | ATT | GGT | ATC | CTG | CCC | GAG | CAG | CTA | GTC | GCA | TTG | 1394 |
| Arg | Tyr | Leu | Arg 365 | Ser | Ile | Gly | Ile | Leu 370 | Pro | Glu | Gln | Leu | Val 375 | Ala | Leu | |
| TTT | CTA | GAT | AAG | AGC | GAG | AAG | CTC | ATT | GTT | ACC | ATC | CTC | GGC | GTG | TGG | 1442 |
| Phe | Leu | Asp 380 | Lys | Ser | Glu | Lys | Leu 385 | Ile | Val | Thr | Ile | Leu 390 | Gly | Val | Trp | |
| AAA | TCC | GGC | GCC | GCC | TAC | GTG | CCC | ATC | GAC | CCG | ACT | TAT | CCG | GAT | GAG | 1490 |
| Lys | Ser 395 | Gly | Ala | Ala | Tyr | Val 400 | Pro | Ile | Asp | Pro | Thr 405 | Tyr | Pro | Asp | Glu | |
| CGA | GTG | CGC | TTC | GTG | CTG | GAT | GAC | ACC | AAG | GCA | CGG | GCC | ATC | ATC | GCC | 1538 |
| Arg 410 | Val | Arg | Phe | Val | Leu 415 | Asp | Asp | Thr | Lys | Ala 420 | Arg | Ala | Ile | Ile | Ala 425 | |
| AGT | AAT | CAA | CAT | GTG | GAG | AGG | CTC | CAG | CGA | GAG | GTC | ATC | GGC | GAT | AGA | 1586 |
| Ser | Asn | Gln | His | Val 430 | Glu | Arg | Leu | Gln | Arg 435 | Glu | Val | Ile | Gly | Asp 440 | Arg | |
| AAC | CTA | TGC | ATT | ATC | CGT | CTG | GAG | CCC | TTG | TTG | GCC | TCC | CTT | GCT | CAG | 1634 |
| Asn | Leu | Cys | Ile 445 | Ile | Arg | Leu | Glu | Pro 450 | Leu | Leu | Ala | Ser | Leu 455 | Ala | Gln | |
| GAT | TCC | TCA | AAA | TTC | CCC | GCG | CAT | AAC | TTG | GAC | GAC | CTA | CCC | CTC | ACA | 1682 |
| Asp | Ser | Ser 460 | Lys | Phe | Pro | Ala | His 465 | Asn | Leu | Asp | Asp | Leu 470 | Pro | Leu | Thr | |
| AGC | CAG | CAG | CTC | GCC | TAT | GTG | ACT | TAC | ACC | TCT | GGG | ACC | ACT | GGT | TTC | 1730 |
| Ser | Gln 475 | Gln | Leu | Ala | Tyr | Val 480 | Thr | Tyr | Thr | Ser | Gly 485 | Thr | Thr | Gly | Phe | |
| CCA | AAG | GGC | ATA | TTT | AAA | CAA | CAC | ACC | AAT | GTG | GTG | AAC | AGT | ATT | ACC | 1778 |
| Pro 490 | Lys | Gly | Ile | Phe | Lys 495 | Gln | His | Thr | Asn | Val 500 | Val | Asn | Ser | Ile | Thr 505 | |
| GAC | CTG | TCT | GCA | AGG | TAC | GGG | GTG | GCC | GGG | CAG | CAC | CAC | GAA | GCC | ATT | 1826 |
| Asp | Leu | Ser | Ala | Arg 510 | Tyr | Gly | Val | Ala | Gly 515 | Gln | His | His | Glu | Ala 520 | Ile | |
| CTG | CTT | TTC | TCG | GCC | TGC | GTG | TTC | GAG | CCG | TTC | GTT | CGA | CAG | ACG | CTC | 1874 |
| Leu | Leu | Phe | Ser 525 | Ala | Cys | Val | Phe | Glu 530 | Pro | Phe | Val | Arg | Gln 535 | Thr | Leu | |
| ATG | GCA | CTC | GTG | AAT | GGC | CAT | CTC | CTC | GCA | GTT | ATC | AAT | GAC | GTG | GAA | 1922 |
| Met | Ala | Leu 540 | Val | Asn | Gly | His | Leu 545 | Leu | Ala | Val | Ile | Asn 550 | Asp | Val | Glu | |
| AAA | TAT | GAT | GCC | GAT | ACG | CTC | CTG | CCG | TTC | ATA | CGC | AGA | CAC | AGC | ATC | 1970 |
| Lys | Tyr 555 | Asp | Ala | Asp | Thr | Leu 560 | Leu | Pro | Phe | Ile | Arg 565 | Arg | His | Ser | Ile | |
| ACC | TAC | CTC | AAT | GGT | ACT | GCC | TCT | GTC | TTG | CAA | GAG | TAC | GAC | TTT | TCC | 2018 |
| Thr 570 | Tyr | Leu | Asn | Gly | Thr 575 | Ala | Ser | Val | Leu | Gln 580 | Glu | Tyr | Asp | Phe | Ser 585 | |
| GAC | TGC | CCA | TCA | CTG | AAT | CGG | ATA | ATC | CTG | GTG | GGT | GAG | AAC | CTG | ACA | 2066 |
| Asp | Cys | Pro | Ser | Leu 590 | Asn | Arg | Ile | Ile | Leu 595 | Val | Gly | Glu | Asn | Leu 600 | Thr | |
| GAA | GCC | CGG | TAT | CTG | GCG | CTG | CGC | CAG | CGG | TTC | AAG | AAT | CGC | ATC | CTC | 2114 |
| Glu | Ala | Arg | Tyr 605 | Leu | Ala | Leu | Arg | Gln 610 | Arg | Phe | Lys | Asn | Arg 615 | Ile | Leu | |
| AAC | GAG | TAT | GGT | TTT | ACC | GAG | TCA | GCC | TTT | GTA | ACG | GCC | CTC | AAG | ATT | 2162 |
| Asn | Glu | Tyr 620 | Gly | Phe | Thr | Glu | Ser 625 | Ala | Phe | Val | Thr | Ala 630 | Leu | Lys | Ile | |
| TTC | GAC | CCG | GAG | TCG | ACC | CGT | AAG | GAC | ACG | AGT | CTG | GGG | AGA | CCG | GTG | 2210 |
| Phe | Asp | Pro 635 | Glu | Ser | Thr | Arg | Lys 640 | Asp | Thr | Ser | Leu | Gly 645 | Arg | Pro | Val | |
| CGC | AAC | GTC | AAG | TGC | TAC | ATC | CTC | AAT | CCA | TCC | CTT | AAA | CGT | GTC | CCG | 2258 |
| Arg 650 | Asn | Val | Lys | Cys | Tyr 655 | Ile | Leu | Asn | Pro | Ser 660 | Leu | Lys | Arg | Val | Pro 665 | |
| ATT | GGA | GCT | ACG | GGT | GAG | TTG | CAT | ATC | GGA | GGG | TTG | GGC | ATT | TCC | AAG | 2306 |
| Ile | Gly | Ala | Thr | Gly 670 | Glu | Leu | His | Ile | Gly 675 | Gly | Leu | Gly | Ile | Ser 680 | Lys | |

```
GGA  TAC  CTC  AAC  CGC  CCC  GAA  CTC  ACG  CCG  CAC  CGC  TTC  ATT  CCC  AAC      2354
Gly  Tyr  Leu  Asn  Arg  Pro  Glu  Leu  Thr  Pro  His  Arg  Phe  Ile  Pro  Asn
          685                      690                      695

CCC  TTC  CAA  ACG  GAT  TGC  GAG  AAG  CAG  CTC  GGG  ATC  AAC  AGC  TTG  ATG      2402
Pro  Phe  Gln  Thr  Asp  Cys  Glu  Lys  Gln  Leu  Gly  Ile  Asn  Ser  Leu  Met
          700                      705                      710

TAC  AAG  ACC  GGT  GAC  CTG  GCC  CGC  TGG  CTT  CCG  AAC  GGC  GAG  GTT  GAG      2450
Tyr  Lys  Thr  Gly  Asp  Leu  Ala  Arg  Trp  Leu  Pro  Asn  Gly  Glu  Val  Glu
     715                      720                      725

TAT  CTC  GGA  CGC  GCA  GAT  TTC  CAG  ATC  AAA  CTG  CGA  GGT  ATT  CGA  ATT      2498
Tyr  Leu  Gly  Arg  Ala  Asp  Phe  Gln  Ile  Lys  Leu  Arg  Gly  Ile  Arg  Ile
730                      735                      740                      745

GAA  CCT  GGT  GAA  ATT  GAG  ACG  ATG  CTG  GCT  ATG  TAC  CCT  AGG  GTC  CGG      2546
Glu  Pro  Gly  Glu  Ile  Glu  Thr  Met  Leu  Ala  Met  Tyr  Pro  Arg  Val  Arg
                         750                      755                      760

ACC  AGT  TTA  GTG  GTG  TCC  AAA  AAG  CTC  CGC  AAC  GGT  CCA  GAG  GAA  ACT      2594
Thr  Ser  Leu  Val  Val  Ser  Lys  Lys  Leu  Arg  Asn  Gly  Pro  Glu  Glu  Thr
               765                      770                      775

ACC  AAC  GAG  CAC  CTC  GTG  GGT  TAT  TAT  GTT  TGT  GAT  AGC  GCC  TCA  GTG      2642
Thr  Asn  Glu  His  Leu  Val  Gly  Tyr  Tyr  Val  Cys  Asp  Ser  Ala  Ser  Val
          780                      785                      790

TCC  GAG  GCA  GAC  CTG  CTG  TCA  TTT  TTA  GAG  AAG  AAA  CTG  CCT  CGA  TAC      2690
Ser  Glu  Ala  Asp  Leu  Leu  Ser  Phe  Leu  Glu  Lys  Lys  Leu  Pro  Arg  Tyr
795                      800                      805

ATG  ATT  CCC  ACG  CGG  TTG  GTA  CAG  CTG  TCG  CAG  ATC  CCA  GTG  AAT  GTG      2738
Met  Ile  Pro  Thr  Arg  Leu  Val  Gln  Leu  Ser  Gln  Ile  Pro  Val  Asn  Val
810                      815                      820                      825

AAC  GGG  AAG  GCG  GAC  CTA  CGC  GCC  TTG  CCG  GCC  GTC  GAT  ATC  TCC  AAT      2786
Asn  Gly  Lys  Ala  Asp  Leu  Arg  Ala  Leu  Pro  Ala  Val  Asp  Ile  Ser  Asn
                         830                      835                      840

TCC  ACG  GAG  GTG  CGT  TCC  GAC  CTT  CGA  GGC  GAT  ACG  GAA  ATC  GCC  CTC      2834
Ser  Thr  Glu  Val  Arg  Ser  Asp  Leu  Arg  Gly  Asp  Thr  Glu  Ile  Ala  Leu
               845                      850                      855

GGG  GAA  ATC  TGG  GCC  GAC  GTG  TTG  GGA  GCC  CGC  CAG  AGA  TCC  GTC  TCT      2882
Gly  Glu  Ile  Trp  Ala  Asp  Val  Leu  Gly  Ala  Arg  Gln  Arg  Ser  Val  Ser
          860                      865                      870

CGC  AAC  GAC  AAC  TTC  TTC  CGC  CTA  GGA  GGG  CAC  AGC  ATC  ACC  TGC  ATC      2930
Arg  Asn  Asp  Asn  Phe  Phe  Arg  Leu  Gly  Gly  His  Ser  Ile  Thr  Cys  Ile
875                      880                      885

CAA  CTG  ATC  GCT  CGC  ATC  CGA  CAA  CGA  CAA  CGA  CTC  TCG  GTC  AGC  ATC      2978
Gln  Leu  Ile  Ala  Arg  Ile  Arg  Gln  Arg  Gln  Arg  Leu  Ser  Val  Ser  Ile
890                      895                      900                      905

TCC  GTC  GAA  GAT  GTT  TTT  GCA  ACA  AGG  ACA  CTT  GAG  CGC  ATG  GCA  GAC      3026
Ser  Val  Glu  Asp  Val  Phe  Ala  Thr  Arg  Thr  Leu  Glu  Arg  Met  Ala  Asp
                         910                      915                      920

CTT  CTA  CAG  AAC  AAG  CAG  CAG  GAG  AAA  TGC  GAC  AAA  CCC  CAT  GAG  GCG      3074
Leu  Leu  Gln  Asn  Lys  Gln  Gln  Glu  Lys  Cys  Asp  Lys  Pro  His  Glu  Ala
               925                      930                      935

CCG  ACA  GAG  CTG  CTT  GAG  GAG  AAT  GCA  GCA  ACG  GAC  AAT  ATC  TAT  CTG      3122
Pro  Thr  Glu  Leu  Leu  Glu  Glu  Asn  Ala  Ala  Thr  Asp  Asn  Ile  Tyr  Leu
          940                      945                      950

GCA  AAC  AGT  CTT  CAG  CAG  GGC  TTC  GTC  TAC  CAT  TAC  CTC  AAG  AGC  ATG      3170
Ala  Asn  Ser  Leu  Gln  Gln  Gly  Phe  Val  Tyr  His  Tyr  Leu  Lys  Ser  Met
955                      960                      965

GAA  CAA  TCC  GAC  GCC  TAT  GTA  ATG  CAG  TCC  GTT  CTT  CGG  TAC  AAC  ACC      3218
Glu  Gln  Ser  Asp  Ala  Tyr  Val  Met  Gln  Ser  Val  Leu  Arg  Tyr  Asn  Thr
970                      975                      980                      985

ACA  TTG  TCT  CCA  GAT  CTG  TTT  CAG  AGA  GCC  TGG  AAG  CAT  GCA  CAG  CAG      3266
Thr  Leu  Ser  Pro  Asp  Leu  Phe  Gln  Arg  Ala  Trp  Lys  His  Ala  Gln  Gln
                         990                      995                      1000
```

| | | | | | | | | | | | | | | | | |
|---|---|---|---|---|---|---|---|---|---|---|---|---|---|---|---|---|
| TCC | TTT | CCA | GCG | CTG | CGG | CTG | CGG | TTC | TCA | TGG | GAA | AAG | GAG | GTT | TTC | 3314 |
| Ser | Phe | Pro | Ala | Leu | Arg | Leu | Arg | Phe | Ser | Trp | Glu | Lys | Glu | Val | Phe | |
| | | | 1005 | | | | 1010 | | | | | 1015 | | | | |
| CAA | CTG | CTC | GAT | CAG | GAT | CCA | CCA | TTG | GAC | TGG | CGT | TTC | CTC | TAC | TTC | 3362 |
| Gln | Leu | Leu | Asp | Gln | Asp | Pro | Pro | Leu | Asp | Trp | Arg | Phe | Leu | Tyr | Phe | |
| | | | 1020 | | | | 1025 | | | | | 1030 | | | | |
| ACC | GAC | GTT | GCC | GCG | GGT | GCT | GTC | GAG | GAC | CGG | AAA | TTG | GAA | GAC | TTG | 3410 |
| Thr | Asp | Val | Ala | Ala | Gly | Ala | Val | Glu | Asp | Arg | Lys | Leu | Glu | Asp | Leu | |
| | | | 1035 | | | | 1040 | | | | | 1045 | | | | |
| CGG | CGC | CAA | GAC | CTT | ACG | GAG | AGA | TTC | AAG | CTG | GAT | GTT | GGC | AGA | CTG | 3458 |
| Arg | Arg | Gln | Asp | Leu | Thr | Glu | Arg | Phe | Lys | Leu | Asp | Val | Gly | Arg | Leu | |
| 1050 | | | | | 1055 | | | | | 1060 | | | | | 1065 | |
| TTC | CGC | GTC | TAT | CTG | ATT | AAA | CAC | AGC | GAG | AAT | CGC | TTC | ACG | TGT | CTT | 3506 |
| Phe | Arg | Val | Tyr | Leu | Ile | Lys | His | Ser | Glu | Asn | Arg | Phe | Thr | Cys | Leu | |
| | | | 1070 | | | | 1075 | | | | | 1080 | | | | |
| TTC | AGC | TGC | CAT | CAT | GCA | ATC | CTC | GAT | GGT | TGG | AGT | CTG | CCA | CTC | TTG | 3554 |
| Phe | Ser | Cys | His | His | Ala | Ile | Leu | Asp | Gly | Trp | Ser | Leu | Pro | Leu | Leu | |
| | | | 1085 | | | | 1090 | | | | | 1095 | | | | |
| TTC | GAA | AAG | GTT | CAC | GAG | ACC | TAC | CTG | CAA | CTG | CTG | CAT | GGG | GAC | AAT | 3602 |
| Phe | Glu | Lys | Val | His | Glu | Thr | Tyr | Leu | Gln | Leu | Leu | His | Gly | Asp | Asn | |
| | | | 1100 | | | | 1105 | | | | | 1110 | | | | |
| CTC | ACT | TCG | TCC | ATG | GAT | GAC | CCT | TAC | ACT | CGC | ACC | CAG | CGG | TAT | CTC | 3650 |
| Leu | Thr | Ser | Ser | Met | Asp | Asp | Pro | Tyr | Thr | Arg | Thr | Gln | Arg | Tyr | Leu | |
| | | | 1115 | | | | 1120 | | | | | 1125 | | | | |
| CAC | GCT | CAC | CGT | GAG | GAT | CAC | CTC | GAC | TTT | TGG | GCC | GGT | GTG | GTT | CAA | 3698 |
| His | Ala | His | Arg | Glu | Asp | His | Leu | Asp | Phe | Trp | Ala | Gly | Val | Val | Gln | |
| 1130 | | | | | 1135 | | | | | 1140 | | | | | 1145 | |
| AAG | ATC | AAC | GAA | CGG | TGT | GAT | ATG | AAC | GCC | TTG | TTG | AAC | GAG | CGC | AGT | 3746 |
| Lys | Ile | Asn | Glu | Arg | Cys | Asp | Met | Asn | Ala | Leu | Leu | Asn | Glu | Arg | Ser | |
| | | | 1150 | | | | 1155 | | | | | 1160 | | | | |
| CGT | TAC | AAA | GTC | CAG | CTG | GCA | GAC | TAT | GAC | CAG | GTG | CAG | GAG | CAG | CGA | 3794 |
| Arg | Tyr | Lys | Val | Gln | Leu | Ala | Asp | Tyr | Asp | Gln | Val | Gln | Glu | Gln | Arg | |
| | | | 1165 | | | | 1170 | | | | | 1175 | | | | |
| CAC | GTG | ACA | ATT | GCT | CTC | TCT | GGA | GAC | GCA | TGG | CTA | GCA | GAC | CTT | CGT | 3842 |
| His | Val | Thr | Ile | Ala | Leu | Ser | Gly | Asp | Ala | Trp | Leu | Ala | Asp | Leu | Arg | |
| | | | 1180 | | | | 1185 | | | | | 1190 | | | | |
| CAG | ACC | TGC | TCC | GCC | CAG | GGT | ATT | ACC | TTA | CAT | TCG | ATT | CTC | CAA | TTT | 3890 |
| Gln | Thr | Cys | Ser | Ala | Gln | Gly | Ile | Thr | Leu | His | Ser | Ile | Leu | Gln | Phe | |
| | | | 1195 | | | | 1200 | | | | | 1205 | | | | |
| GTT | TGG | CAC | GCC | GTG | CTG | CAC | GCT | TAT | GGC | GGT | GGC | ACC | CAC | ACC | ATA | 3938 |
| Val | Trp | His | Ala | Val | Leu | His | Ala | Tyr | Gly | Gly | Gly | Thr | His | Thr | Ile | |
| 1210 | | | | | 1215 | | | | | 1220 | | | | | 1225 | |
| ACC | GGC | ACG | ACC | ATT | TCT | GGA | AGG | AAC | CTG | CCC | ATC | TTG | GGA | ATT | GAA | 3986 |
| Thr | Gly | Thr | Thr | Ile | Ser | Gly | Arg | Asn | Leu | Pro | Ile | Leu | Gly | Ile | Glu | |
| | | | 1230 | | | | 1235 | | | | | 1240 | | | | |
| CGA | GCA | GTT | GGT | CCG | TAT | ATC | AAC | ACT | CTA | CCG | CTG | GTA | CTC | GAT | CAT | 4034 |
| Arg | Ala | Val | Gly | Pro | Tyr | Ile | Asn | Thr | Leu | Pro | Leu | Val | Leu | Asp | His | |
| | | | 1245 | | | | 1250 | | | | | 1255 | | | | |
| TCG | ACG | TTC | AAG | GAT | AAG | ACA | ATC | ATG | GAG | GCC | ATC | GAG | GAT | GTG | CAG | 4082 |
| Ser | Thr | Phe | Lys | Asp | Lys | Thr | Ile | Met | Glu | Ala | Ile | Glu | Asp | Val | Gln | |
| | | | 1260 | | | | 1265 | | | | | 1270 | | | | |
| GCC | AAG | GTA | AAC | GTC | ATG | AAC | AGC | CGG | GGC | AAT | GTG | GAA | CTG | GGC | CGT | 4130 |
| Ala | Lys | Val | Asn | Val | Met | Asn | Ser | Arg | Gly | Asn | Val | Glu | Leu | Gly | Arg | |
| | | | 1275 | | | | 1280 | | | | | 1285 | | | | |
| TTG | CAC | AAA | ACC | GAC | TTA | AAG | CAC | GGA | TTA | TTC | GAT | TCT | TTA | TTC | GTG | 4178 |
| Leu | His | Lys | Thr | Asp | Leu | Lys | His | Gly | Leu | Phe | Asp | Ser | Leu | Phe | Val | |
| 1290 | | | | | 1295 | | | | | 1300 | | | | | 1305 | |
| CTT | GAA | AAC | TAC | CCG | AAT | TTG | GAC | AAA | TCG | CGA | ACA | CTT | GAG | CAC | CAG | 4226 |
| Leu | Glu | Asn | Tyr | Pro | Asn | Leu | Asp | Lys | Ser | Arg | Thr | Leu | Glu | His | Gln | |
| | | | 1310 | | | | 1315 | | | | | 1320 | | | | |

```
ACT GAA CTG GGG TAT TCG ATT GAA GGC GGC ACT GAG AAG CTG AAT TAT     4274
Thr Glu Leu Gly Tyr Ser Ile Glu Gly Gly Thr Glu Lys Leu Asn Tyr
        1325                1330                1335

CCA CTG GCT GTC ATC GCG CGC GAA GTC GAG ACG ACT GGC GGA TTC ACA     4322
Pro Leu Ala Val Ile Ala Arg Glu Val Glu Thr Thr Gly Gly Phe Thr
    1340                1345                1350

GTA TCC ATC TGC TAC GCC AGT GAG CTA TTT GAG GAG GTT ATG ATC TCC     4370
Val Ser Ile Cys Tyr Ala Ser Glu Leu Phe Glu Glu Val Met Ile Ser
1355                1360                1365

GAG CTT CTT CAT ATG GTC CAG GAC ACA CTG ATG CAG GTT GCC CGA GGT     4418
Glu Leu Leu His Met Val Gln Asp Thr Leu Met Gln Val Ala Arg Gly
1370                1375                1380                1385

TTG AAT GAA CCC GTC GGC AGC CTG GAG TAT CTC TCA TCT ATC CAA TTG     4466
Leu Asn Glu Pro Val Gly Ser Leu Glu Tyr Leu Ser Ser Ile Gln Leu
        1390                1395                1400

GAG CAA CTC GCC GCG TGG AAT GCC ACG GAA GCT GAG TTT CCC GAT ACC     4514
Glu Gln Leu Ala Ala Trp Asn Ala Thr Glu Ala Glu Phe Pro Asp Thr
    1405                1410                1415

ACG CTT CAT GAG ATG TTT GAA AAC GAA GCG AGC CAG AAG CCG GAC AAG     4562
Thr Leu His Glu Met Phe Glu Asn Glu Ala Ser Gln Lys Pro Asp Lys
1420                1425                1430

ATA GCA GTG GTC TAT GAG GAG ACG TCC TTG ACT TAC CGC GAG TTG AAT     4610
Ile Ala Val Val Tyr Glu Glu Thr Ser Leu Thr Tyr Arg Glu Leu Asn
1435                1440                1445

GAG CGG GCG AAC CGT ATG GCA CAT CAG CTA AGG TCC GAC GTC AGC CCC     4658
Glu Arg Ala Asn Arg Met Ala His Gln Leu Arg Ser Asp Val Ser Pro
1450                1455                1460                1465

AAC CCC AAC GAG GTC ATT GCG CTG GTG ATG GAC AAG AGC GAG CAT ATG     4706
Asn Pro Asn Glu Val Ile Ala Leu Val Met Asp Lys Ser Glu His Met
        1470                1475                1480

ATC GTC AAC ATT CTG GCC GTA TGG AAG AGC GGC GGT GCC TAT GTC CCC     4754
Ile Val Asn Ile Leu Ala Val Trp Lys Ser Gly Gly Ala Tyr Val Pro
    1485                1490                1495

ATT GAC CCT GGA TAT CCT AAC GAC CGC ATT CAA TAT ATC CTA GAG GAC     4802
Ile Asp Pro Gly Tyr Pro Asn Asp Arg Ile Gln Tyr Ile Leu Glu Asp
1500                1505                1510

ACA CAA GCC CTC GCA GTC ATC GCG GAC TCC TGC TAT CTG CCT CGC ATC     4850
Thr Gln Ala Leu Ala Val Ile Ala Asp Ser Cys Tyr Leu Pro Arg Ile
1515                1520                1525

AAG GGA ATG GCT GCC TCC GGC ACG CTT CTT TAT CCC TCT GTC TTG CCT     4898
Lys Gly Met Ala Ala Ser Gly Thr Leu Leu Tyr Pro Ser Val Leu Pro
1530                1535                1540                1545

GCC AAT CCG GAT TCC AAG TGG AGC GTA TCG AAC CCT TCA CCG TTG AGT     4946
Ala Asn Pro Asp Ser Lys Trp Ser Val Ser Asn Pro Ser Pro Leu Ser
        1550                1555                1560

CGG AGC ACG GAC TTA GCT TAT ATC ATC TAT ACC TCT GGA ACG ACA GGT     4994
Arg Ser Thr Asp Leu Ala Tyr Ile Ile Tyr Thr Ser Gly Thr Thr Gly
    1565                1570                1575

CGG CCC AAG GGC GTC ACG GTA GAG CAT CAT GGA GTG GTC AAC CTG CAG     5042
Arg Pro Lys Gly Val Thr Val Glu His His Gly Val Val Asn Leu Gln
1580                1585                1590

GTG TCG CTA TCC AAA GTA TTC GGA CTA CGG GAT ACG GAC GAC GAG GTA     5090
Val Ser Leu Ser Lys Val Phe Gly Leu Arg Asp Thr Asp Asp Glu Val
1595                1600                1605

ATT CTC TCC TTT TCC AAC TAT GTG TTC GAC CAT TTC GTG GAG CAG ATG     5138
Ile Leu Ser Phe Ser Asn Tyr Val Phe Asp His Phe Val Glu Gln Met
1610                1615                1620                1625

ACC GAC GCC ATT CTC AAT GGC CAA ACC CTC CTG GTC CTC AAC GAT GGA     5186
Thr Asp Ala Ile Leu Asn Gly Gln Thr Leu Leu Val Leu Asn Asp Gly
        1630                1635                1640
```

```
ATG CGC GGG GAC AAA GAG CGA CTC TAC AGA TAC ATT GAG AAG AAC CGA         5234
Met Arg Gly Asp Lys Glu Arg Leu Tyr Arg Tyr Ile Glu Lys Asn Arg
             1645                1650                1655

GTG ACC TAC TTG TCT GGC ACC CCA TCC GTG GTC TCC ATG TAC GAA TTT         5282
Val Thr Tyr Leu Ser Gly Thr Pro Ser Val Val Ser Met Tyr Glu Phe
        1660                1665                1670

AGC CGG TTC AAG GAC CAT CTA CGC CGT GTG GAC TGC GTG GGG GAG GCG         5330
Ser Arg Phe Lys Asp His Leu Arg Arg Val Asp Cys Val Gly Glu Ala
    1675                1680                1685

TTC AGC GAA CCG GTC TTC GAC AAG ATC CGC GAA ACG TTC CAT GGC CTC         5378
Phe Ser Glu Pro Val Phe Asp Lys Ile Arg Glu Thr Phe His Gly Leu
1690                1695                1700                1705

GTT ATC AAC GGC TAC GGC CCA ACT GAA GTT TCC ATC ACC ACC CAC AAG         5426
Val Ile Asn Gly Tyr Gly Pro Thr Glu Val Ser Ile Thr Thr His Lys
        1710                1715                1720

CGG CTC TAT CCA TTC CCA GAG CGG CGA ATG GAC AAA AGT ATT GGC CAA         5474
Arg Leu Tyr Pro Phe Pro Glu Arg Arg Met Asp Lys Ser Ile Gly Gln
    1725                1730                1735

CAG GTC CAC AAT AGC ACG AGC TAT GTG CTG AAC GAG GAC ATG AAG CGC         5522
Gln Val His Asn Ser Thr Ser Tyr Val Leu Asn Glu Asp Met Lys Arg
    1740                1745                1750

ACC CCC ATA GGG GCT GTC GGC GAG CTC TAC CTG GGT GGT GAA GGA GTG         5570
Thr Pro Ile Gly Ala Val Gly Glu Leu Tyr Leu Gly Gly Glu Gly Val
    1755                1760                1765

GTA CGG GGA TAT CAC AAT CGC GCA GAT GTG ACC GCG GAG CGT TTT ATT         5618
Val Arg Gly Tyr His Asn Arg Ala Asp Val Thr Ala Glu Arg Phe Ile
1770                1775                1780                1785

CCT AAT CCA TTC CAG TCG GAA GAA GAT AAG CGA GAA GGT CGT AAC TCC         5666
Pro Asn Pro Phe Gln Ser Glu Glu Asp Lys Arg Glu Gly Arg Asn Ser
        1790                1795                1800

CGT TTG TAC AAG ACC GGT GAC CTG GTA CGC TGG ATT CCT GGA AGC AGC         5714
Arg Leu Tyr Lys Thr Gly Asp Leu Val Arg Trp Ile Pro Gly Ser Ser
    1805                1810                1815

GGG GAG GTC GAG TAT CTA GGT CGT AAT GAC TTC CAG GTC AAG ATT CGC         5762
Gly Glu Val Glu Tyr Leu Gly Arg Asn Asp Phe Gln Val Lys Ile Arg
    1820                1825                1830

GGA CTG CGC ATC GAA GTA GGC GAG ATT GAG GCC ATC CTA TCG TCT TAT         5810
Gly Leu Arg Ile Glu Val Gly Glu Ile Glu Ala Ile Leu Ser Ser Tyr
    1835                1840                1845

CAC GGA ATC AAA CAG TCT GTG GTG ATT GCC AAG GAT TGC AGA GAA GGG         5858
His Gly Ile Lys Gln Ser Val Val Ile Ala Lys Asp Cys Arg Glu Gly
    1850                1855                1860                1865

GCC CAG AAA TTC CTG GTT GGT TAC TAT GTC GCC GAT GCA GCG CTG CCG         5906
Ala Gln Lys Phe Leu Val Gly Tyr Tyr Val Ala Asp Ala Ala Leu Pro
        1870                1875                1880

TCC GCT GCC ATT CGG CGC TTC ATG CAG TCT CGG CTC CCT GGC TAC ATG         5954
Ser Ala Ala Ile Arg Arg Phe Met Gln Ser Arg Leu Pro Gly Tyr Met
        1885                1890                1895

GTG CCC TCT CGT CTC ATT CTC GTC AGC AAG TTC CCC GTC ACT CCT AGT         6002
Val Pro Ser Arg Leu Ile Leu Val Ser Lys Phe Pro Val Thr Pro Ser
    1900                1905                1910

GGA AAA TTA GAC ACC AAG GCT TTG CCC CCA GCC GAG GAA GAG AGC GAG         6050
Gly Lys Leu Asp Thr Lys Ala Leu Pro Pro Ala Glu Glu Glu Ser Glu
    1915                1920                1925

ATT GAC GTG GTG CCG CCG CGT AGT GAA ATC GAA CGC TCC TTG TGT GAC         6098
Ile Asp Val Val Pro Pro Arg Ser Glu Ile Glu Arg Ser Leu Cys Asp
1930                1935                1940                1945

ATC TGG GCG GAA CTA CTC GAG ATG CAC CCA GAG GAG ATC GGC ATT TAC         6146
Ile Trp Ala Glu Leu Leu Glu Met His Pro Glu Glu Ile Gly Ile Tyr
        1950                1955                1960
```

| | | | | | | | | | | | | | | | | |
|---|---|---|---|---|---|---|---|---|---|---|---|---|---|---|---|---|
| AGC | GAT | TTC | TTC | AGC | CTG | GGA | GGT | GAC | AGC | CTA | AAG | AGC | ACA | AAG | CTT | 6194 |
| Ser | Asp | Phe | Phe | Ser | Leu | Gly | Gly | Asp | Ser | Leu | Lys | Ser | Thr | Lys | Leu | |
| | | | 1965 | | | | 1970 | | | | | 1975 | | | | |
| TCC | TTC | ATG | ATT | CAC | GAG | TCC | TTT | AAC | CGC | GCC | GTC | TCA | GTC | AGC | GCC | 6242 |
| Ser | Phe | Met | Ile | His | Glu | Ser | Phe | Asn | Arg | Ala | Val | Ser | Val | Ser | Ala | |
| | | 1980 | | | | | 1985 | | | | | 1990 | | | | |
| CTT | TTC | TGT | CAC | CGG | ACA | GTT | GAA | GCC | CAG | ACG | CAC | TTG | ATC | CTG | AAC | 6290 |
| Leu | Phe | Cys | His | Arg | Thr | Val | Glu | Ala | Gln | Thr | His | Leu | Ile | Leu | Asn | |
| | 1995 | | | | | 2000 | | | | | 2005 | | | | | |
| GAT | GCT | GCA | GAT | GTG | CAC | GAA | ATT | ACT | CCC | ATA | GAT | TGC | AAT | GAT | ACG | 6338 |
| Asp | Ala | Ala | Asp | Val | His | Glu | Ile | Thr | Pro | Ile | Asp | Cys | Asn | Asp | Thr | |
| 2010 | | | | | 2015 | | | | | 2020 | | | | | 2025 | |
| CAG | ATG | ATT | CCC | GTG | TCC | CGT | GCC | CAG | GAG | CGA | CTC | CTC | TTC | ATC | CAC | 6386 |
| Gln | Met | Ile | Pro | Val | Ser | Arg | Ala | Gln | Glu | Arg | Leu | Leu | Phe | Ile | His | |
| | | | | 2030 | | | | | 2035 | | | | | 2040 | | |
| GAA | TTT | GAG | AAT | GGC | AGC | AAT | GCA | TAC | AAT | ATC | GAC | GCT | GCA | TTT | GAA | 6434 |
| Glu | Phe | Glu | Asn | Gly | Ser | Asn | Ala | Tyr | Asn | Ile | Asp | Ala | Ala | Phe | Glu | |
| | | | | 2045 | | | | | 2050 | | | | | 2055 | | |
| CTG | CCT | GGC | TCG | GTT | GAC | GCG | TCG | CTT | CTC | GAG | CAG | GCG | CTG | CGT | GGA | 6482 |
| Leu | Pro | Gly | Ser | Val | Asp | Ala | Ser | Leu | Leu | Glu | Gln | Ala | Leu | Arg | Gly | |
| | | 2060 | | | | | 2065 | | | | | 2070 | | | | |
| AAC | CTT | GCT | CGA | CAT | GAG | GCG | TTG | AGA | ACT | TTA | CTG | GTC | AAG | GAT | CAC | 6530 |
| Asn | Leu | Ala | Arg | His | Glu | Ala | Leu | Arg | Thr | Leu | Leu | Val | Lys | Asp | His | |
| | 2075 | | | | | 2080 | | | | | 2085 | | | | | |
| GCA | ACC | GGC | ATC | TAT | CTT | CAG | AAG | GTA | TTG | AGT | CCC | GAT | GAA | GCC | CAG | 6578 |
| Ala | Thr | Gly | Ile | Tyr | Leu | Gln | Lys | Val | Leu | Ser | Pro | Asp | Glu | Ala | Gln | |
| 2090 | | | | | 2095 | | | | | 2100 | | | | | 2105 | |
| GGC | ATG | TTC | TCC | GTC | AAC | GTG | GAC | ACA | GCC | AAG | CAG | GTG | GAG | CGG | CTG | 6626 |
| Gly | Met | Phe | Ser | Val | Asn | Val | Asp | Thr | Ala | Lys | Gln | Val | Glu | Arg | Leu | |
| | | | | 2110 | | | | | 2115 | | | | | 2120 | | |
| GAC | CAG | GAG | ATA | GCC | AGT | CTA | TCC | CAG | CAT | GTT | TTC | CGC | CTC | GAT | GAT | 6674 |
| Asp | Gln | Glu | Ile | Ala | Ser | Leu | Ser | Gln | His | Val | Phe | Arg | Leu | Asp | Asp | |
| | | | 2125 | | | | | 2130 | | | | | 2135 | | | |
| GAA | CTG | CCT | TGG | GAG | GCC | CGC | ATC | CTT | AAA | CTC | GAA | TCC | GGC | GGC | CTG | 6722 |
| Glu | Leu | Pro | Trp | Glu | Ala | Arg | Ile | Leu | Lys | Leu | Glu | Ser | Gly | Gly | Leu | |
| | | | 2140 | | | | | 2145 | | | | | 2150 | | | |
| TAT | CTC | ATT | CTG | GCG | TTC | CAC | CAT | ACC | TGC | TTC | GAT | GCA | TGG | TCA | TTG | 6770 |
| Tyr | Leu | Ile | Leu | Ala | Phe | His | His | Thr | Cys | Phe | Asp | Ala | Trp | Ser | Leu | |
| | 2155 | | | | | 2160 | | | | | | 2165 | | | | |
| AAA | GTC | TTC | GAG | CAA | GAG | CTT | CGG | GCC | TTG | TAC | GCA | GCG | CTC | CAG | AAA | 6818 |
| Lys | Val | Phe | Glu | Gln | Glu | Leu | Arg | Ala | Leu | Tyr | Ala | Ala | Leu | Gln | Lys | |
| 2170 | | | | | 2175 | | | | | 2180 | | | | | 2185 | |
| ACC | AAA | AGT | GCA | GCG | AAC | TTA | CCA | GCC | CTC | AAA | GCG | CAG | TAC | AAG | GAA | 6866 |
| Thr | Lys | Ser | Ala | Ala | Asn | Leu | Pro | Ala | Leu | Lys | Ala | Gln | Tyr | Lys | Glu | |
| | | | | 2190 | | | | | 2195 | | | | | 2200 | | |
| TAC | GCG | CTC | TAC | CAT | CGC | CGG | CAG | CTG | TCT | GGC | GAT | CGC | ATG | CGC | AAC | 6914 |
| Tyr | Ala | Leu | Tyr | His | Arg | Arg | Gln | Leu | Ser | Gly | Asp | Arg | Met | Arg | Asn | |
| | | | 2205 | | | | | 2210 | | | | | 2215 | | | |
| CTG | TCA | GAC | TTT | TGG | CTG | CGG | AAA | CTC | ATT | GGC | TTG | GAA | CCA | TTG | CAG | 6962 |
| Leu | Ser | Asp | Phe | Trp | Leu | Arg | Lys | Leu | Ile | Gly | Leu | Glu | Pro | Leu | Gln | |
| | | | 2220 | | | | | 2225 | | | | | 2230 | | | |
| CTG | ATC | ACG | GAC | CGC | CCA | CGT | CCT | GTG | CAA | TTC | AAA | TAC | GAC | GGT | GAC | 7010 |
| Leu | Ile | Thr | Asp | Arg | Pro | Arg | Pro | Val | Gln | Phe | Lys | Tyr | Asp | Gly | Asp | |
| | | 2235 | | | | | 2240 | | | | | 2245 | | | | |
| GAC | CTC | AGT | ATC | GAA | CTG | AGC | AAG | AAG | GAA | ACG | GAG | AAC | CTG | AGG | GGG | 7058 |
| Asp | Leu | Ser | Ile | Glu | Leu | Ser | Lys | Lys | Glu | Thr | Glu | Asn | Leu | Arg | Gly | |
| 2250 | | | | | 2255 | | | | | 2260 | | | | | 2265 | |
| GTG | GCC | AAA | CGT | TGC | AAG | TCG | AGT | CTG | TAC | GTC | GTG | TTG | GTT | TCC | GTT | 7106 |
| Val | Ala | Lys | Arg | Cys | Lys | Ser | Ser | Leu | Tyr | Val | Val | Leu | Val | Ser | Val | |
| | | | | 2270 | | | | | 2275 | | | | | 2280 | | |

```
TAT  TGC  GTT  ATG  CTA  GCC  TCG  TAC  GCG  AAC  CAG  TCC  GAT  GTT  TCC  GTG      7154
Tyr  Cys  Val  Met  Leu  Ala  Ser  Tyr  Ala  Asn  Gln  Ser  Asp  Val  Ser  Val
               2285                    2290                    2295

GGT  ATC  CCA  GTC  AGC  CAC  CGA  ACG  CAT  CCT  CAG  TTC  CAA  TCG  GTC  ATT      7202
Gly  Ile  Pro  Val  Ser  His  Arg  Thr  His  Pro  Gln  Phe  Gln  Ser  Val  Ile
2300                    2305                    2310

GGA  TTC  TTC  GTC  AAC  CTT  GTG  GTG  CTA  AGG  GTG  GAT  ATT  TCT  CAG  TCA      7250
Gly  Phe  Phe  Val  Asn  Leu  Val  Val  Leu  Arg  Val  Asp  Ile  Ser  Gln  Ser
     2315                    2320                    2325

GCC  ATT  TGC  GGG  CTC  ATC  AGA  AGG  GTA  ATG  AAA  GAG  CTC  GTG  GAC  GCC      7298
Ala  Ile  Cys  Gly  Leu  Ile  Arg  Arg  Val  Met  Lys  Glu  Leu  Val  Asp  Ala
2330                    2335                    2340                    2345

CAA  CTG  CAC  CAA  GAC  ATG  CCG  TTC  CAG  GAA  GTG  ACG  AAG  CTG  CTG  CAG      7346
Gln  Leu  His  Gln  Asp  Met  Pro  Phe  Gln  Glu  Val  Thr  Lys  Leu  Leu  Gln
               2350                    2355                    2360

GTG  GAT  AAT  GAC  CCC  AGC  CGG  CAT  CCG  CTG  GTA  CAG  AAC  GTG  TTC  AAC      7394
Val  Asp  Asn  Asp  Pro  Ser  Arg  His  Pro  Leu  Val  Gln  Asn  Val  Phe  Asn
               2365                    2370                    2375

TTC  GAA  TCC  CGT  GCG  AAC  GGA  GAA  CAC  GAT  GCC  AGG  TCG  GAG  GAT  GAA      7442
Phe  Glu  Ser  Arg  Ala  Asn  Gly  Glu  His  Asp  Ala  Arg  Ser  Glu  Asp  Glu
               2380                    2385                    2390

GGA  TCG  CTT  GCA  TTC  AAT  CAA  TAC  CGG  CCG  GTT  CAG  CCC  GTG  GAT  TCC      7490
Gly  Ser  Leu  Ala  Phe  Asn  Gln  Tyr  Arg  Pro  Val  Gln  Pro  Val  Asp  Ser
     2395                    2400                    2405

GTT  GCG  AAG  TTC  GAT  CTG  AAC  GCA  ACG  GTC  ACG  GAA  TTG  GAG  TCG  GGA      7538
Val  Ala  Lys  Phe  Asp  Leu  Asn  Ala  Thr  Val  Thr  Glu  Leu  Glu  Ser  Gly
2410                    2415                    2420                    2425

TTG  AGA  GTC  AAC  TTC  AAC  TAT  GCG  ACC  AGC  CTA  TTC  AAC  AAA  AGC  ACG      7586
Leu  Arg  Val  Asn  Phe  Asn  Tyr  Ala  Thr  Ser  Leu  Phe  Asn  Lys  Ser  Thr
               2430                    2435                    2440

ATC  CAG  GGT  TTT  TTG  CAT  ACC  TAT  GAG  TAT  CTC  CTG  CGC  CAG  CTG  TCC      7634
Ile  Gln  Gly  Phe  Leu  His  Thr  Tyr  Glu  Tyr  Leu  Leu  Arg  Gln  Leu  Ser
               2445                    2450                    2455

GAA  CTG  AGT  GCA  GAA  GGG  ATC  AAT  GAG  GAT  ACG  CAG  CTG  TCG  TTA  GTT      7682
Glu  Leu  Ser  Ala  Glu  Gly  Ile  Asn  Glu  Asp  Thr  Gln  Leu  Ser  Leu  Val
               2460                    2465                    2470

CGC  CCG  ACA  GAG  AAT  GGC  GAT  CTG  CAC  TTG  CCA  TTG  GCA  CAG  TCC  CCG      7730
Arg  Pro  Thr  Glu  Asn  Gly  Asp  Leu  His  Leu  Pro  Leu  Ala  Gln  Ser  Pro
               2475                    2480                    2485

CTT  GCG  ACG  ACT  GCT  GAG  GAG  CAG  AAA  GTA  GCG  TCG  TTG  AAC  CAG  GCC      7778
Leu  Ala  Thr  Thr  Ala  Glu  Glu  Gln  Lys  Val  Ala  Ser  Leu  Asn  Gln  Ala
2490                    2495                    2500                    2505

TTT  GAG  CGC  GAA  GCT  TTC  CTT  GCC  GCA  GAG  AAG  ATT  GCC  GTC  GTG  CAG      7826
Phe  Glu  Arg  Glu  Ala  Phe  Leu  Ala  Ala  Glu  Lys  Ile  Ala  Val  Val  Gln
               2510                    2515                    2520

GGA  GAT  AGA  GCA  CTT  AGT  TAT  GCT  GAT  CTT  AAC  GGG  CAG  GCT  AAC  CAG      7874
Gly  Asp  Arg  Ala  Leu  Ser  Tyr  Ala  Asp  Leu  Asn  Gly  Gln  Ala  Asn  Gln
               2525                    2530                    2535

CTC  GCC  CGG  TAC  ATA  CAG  TCC  GTG  TCC  TGT  ATT  GGG  GCA  GAC  GAC  GGA      7922
Leu  Ala  Arg  Tyr  Ile  Gln  Ser  Val  Ser  Cys  Ile  Gly  Ala  Asp  Asp  Gly
               2540                    2545                    2550

ATA  GCT  TTG  ATG  CTG  GAA  AAG  AGT  ATC  GAC  ACG  ATT  ATT  TGC  ATT  CTC      7970
Ile  Ala  Leu  Met  Leu  Glu  Lys  Ser  Ile  Asp  Thr  Ile  Ile  Cys  Ile  Leu
     2555                    2560                    2565

GCG  ATT  TGG  AAG  GCT  GGT  GCA  GCA  TAC  GTG  CCC  TTG  GAT  CCG  ACT  TAC      8018
Ala  Ile  Trp  Lys  Ala  Gly  Ala  Ala  Tyr  Val  Pro  Leu  Asp  Pro  Thr  Tyr
2570                    2575                    2580                    2585

CCA  CCC  GGA  CGC  GTC  CAG  CTG  ATT  CTG  GAG  GAG  ATT  AAA  GCG  AAG  GCT      8066
Pro  Pro  Gly  Arg  Val  Gln  Leu  Ile  Leu  Glu  Glu  Ile  Lys  Ala  Lys  Ala
               2590                    2595                    2600
```

```
GTC  CTT  GTG  CAC  TCC  AGT  CAT  GCT  TCG  AAA  TGT  GAA  CGC  CAT  GGC  GCG      8114
Val  Leu  Val  His  Ser  Ser  His  Ala  Ser  Lys  Cys  Glu  Arg  His  Gly  Ala
               2605                2610                2615

AAG  GTG  ATT  GCA  GTC  GAC  TCG  CCC  GCC  ATC  GAG  ACG  GCG  GTC  AGC  CAA      8162
Lys  Val  Ile  Ala  Val  Asp  Ser  Pro  Ala  Ile  Glu  Thr  Ala  Val  Ser  Gln
          2620                2625                2630

CAG  TCA  GCT  GCT  GAC  CTG  CCC  ACA  ATT  GCT  AGC  CTC  GGC  AAT  CTA  GCG      8210
Gln  Ser  Ala  Ala  Asp  Leu  Pro  Thr  Ile  Ala  Ser  Leu  Gly  Asn  Leu  Ala
     2635                2640                2645

TAT  ATA  ATC  TTT  ACT  TCA  GGC  ACT  TCC  GGT  AAG  CCA  AAG  GGA  GTC  CTA      8258
Tyr  Ile  Ile  Phe  Thr  Ser  Gly  Thr  Ser  Gly  Lys  Pro  Lys  Gly  Val  Leu
2650                2655                2660                          2665

GTT  GAG  CAA  AAG  GCA  GTT  CTT  CTT  CTA  CGC  GAT  GCC  CTC  CGG  GAG  CGG      8306
Val  Glu  Gln  Lys  Ala  Val  Leu  Leu  Leu  Arg  Asp  Ala  Leu  Arg  Glu  Arg
                    2670                2675                2680

TAT  TTC  GGT  CGA  GAC  TGT  ACC  AAG  CAT  CAT  GGC  GTC  CTG  TTC  CTG  TCC      8354
Tyr  Phe  Gly  Arg  Asp  Cys  Thr  Lys  His  His  Gly  Val  Leu  Phe  Leu  Ser
               2685                2690                2695

AAC  TAC  GTC  TTC  GAC  TTC  TCC  GTC  GAA  CAA  CTT  GTG  TTG  TCG  GTG  CTC      8402
Asn  Tyr  Val  Phe  Asp  Phe  Ser  Val  Glu  Gln  Leu  Val  Leu  Ser  Val  Leu
          2700                2705                2710

AGC  GGA  CAC  AAG  CTG  ATC  GTT  CCC  CCA  GCT  GAG  TTC  GTC  GCA  GAT  GAT      8450
Ser  Gly  His  Lys  Leu  Ile  Val  Pro  Pro  Ala  Glu  Phe  Val  Ala  Asp  Asp
     2715                2720                2725

GAA  TTT  TAC  AGA  ATG  GCC  AGC  ACG  CAC  GGT  CTC  TCC  TAT  CTC  AGC  GGC      8498
Glu  Phe  Tyr  Arg  Met  Ala  Ser  Thr  His  Gly  Leu  Ser  Tyr  Leu  Ser  Gly
2730                2735                2740                          2745

ACA  CCA  TCC  TTA  CTG  CAG  AAG  ATC  GAT  CTG  GCA  CGA  CTG  GAC  CAT  CTG      8546
Thr  Pro  Ser  Leu  Leu  Gln  Lys  Ile  Asp  Leu  Ala  Arg  Leu  Asp  His  Leu
                    2750                2755                2760

CAG  GTT  GTT  ACC  GCC  GCG  GGC  GAA  GAG  CTT  CAC  GCC  ACC  CAG  TAC  GAG      8594
Gln  Val  Val  Thr  Ala  Ala  Gly  Glu  Glu  Leu  His  Ala  Thr  Gln  Tyr  Glu
               2765                2770                2775

AAG  ATG  CGC  CGC  CGA  TTC  AAC  GGT  CCC  ATC  TAC  AAT  GCC  TAT  GGT  GTC      8642
Lys  Met  Arg  Arg  Arg  Phe  Asn  Gly  Pro  Ile  Tyr  Asn  Ala  Tyr  Gly  Val
          2780                2785                2790

ACC  GAG  ACC  ACG  GTG  TAC  AAC  ATT  ATC  GCG  GAA  TTC  ACA  ACG  AAT  TCG      8690
Thr  Glu  Thr  Thr  Val  Tyr  Asn  Ile  Ile  Ala  Glu  Phe  Thr  Thr  Asn  Ser
     2795                2800                2805

ATA  TTT  GAG  AAT  GCT  CTT  CGG  GAA  GTG  CTC  CCT  GGT  ACC  CGA  GCG  TAT      8738
Ile  Phe  Glu  Asn  Ala  Leu  Arg  Glu  Val  Leu  Pro  Gly  Thr  Arg  Ala  Tyr
2810                2815                2820                          2825

GTG  CTG  ACC  GCG  GCA  CTT  CAG  CCC  GTC  CCC  TTC  GAT  GCT  GTC  GGA  GAA      8786
Val  Leu  Thr  Ala  Ala  Leu  Gln  Pro  Val  Pro  Phe  Asp  Ala  Val  Gly  Glu
                    2830                2835                2840

CTC  TAT  CTT  GCC  GGC  GAC  ACG  GTT  ACG  CGT  GGT  TAT  CTC  AAC  CAA  CCT      8834
Leu  Tyr  Leu  Ala  Gly  Asp  Thr  Val  Thr  Arg  Gly  Tyr  Leu  Asn  Gln  Pro
               2845                2850                2855

CTT  CTA  ACG  GAT  CAG  CGA  TTC  ATT  CCC  AAC  CCT  TTC  TGC  AAA  GAG  GAG      8882
Leu  Leu  Thr  Asp  Gln  Arg  Phe  Ile  Pro  Asn  Pro  Phe  Cys  Lys  Glu  Glu
          2860                2865                2870

GAC  ATC  GCT  ATG  GGG  CGC  TTC  GCG  CGG  CTC  TAC  AAG  ACC  GGC  GAC  CTG      8930
Asp  Ile  Ala  Met  Gly  Arg  Phe  Ala  Arg  Leu  Tyr  Lys  Thr  Gly  Asp  Leu
     2875                2880                2885

GTT  CGA  TCG  CGT  TTC  AAC  CGT  CAG  CAG  CAG  CCG  CAG  CTG  GAA  TAC  CTA      8978
Val  Arg  Ser  Arg  Phe  Asn  Arg  Gln  Gln  Gln  Pro  Gln  Leu  Glu  Tyr  Leu
2890                2895                2900                          2905

GGA  AGA  GGC  GAT  CTG  CAG  ATC  AAG  ATG  AGG  GGA  TAC  CGG  ATC  GAG  ATT      9026
Gly  Arg  Gly  Asp  Leu  Gln  Ile  Lys  Met  Arg  Gly  Tyr  Arg  Ile  Glu  Ile
                    2910                2915                2920
```

| | | | | | | | | | | | | | | | | |
|---|---|---|---|---|---|---|---|---|---|---|---|---|---|---|---|---|
| TCT | GAA | GTT | CAG | AAC | GTG | CTC | ACT | TCA | AGT | CCC | GGT | GTC | CGG | GAG | GGT | 9074 |
| Ser | Glu | Val | Gln | Asn | Val | Leu | Thr | Ser | Ser | Pro | Gly | Val | Arg | Glu | Gly | |
| | | | 2925 | | | | 2930 | | | | | | 2935 | | | |
| GCA | GTC | GTT | GCC | AAG | TAT | GAG | AAC | AAC | GAT | ACC | TAT | TCC | CGG | ACC | GCT | 9122 |
| Ala | Val | Val | Ala | Lys | Tyr | Glu | Asn | Asn | Asp | Thr | Tyr | Ser | Arg | Thr | Ala | |
| | | 2940 | | | | 2945 | | | | | 2950 | | | | | |
| CAC | TCT | CTG | GTC | GGT | TAC | TAT | ACC | ACG | GAC | AAT | GAA | ACA | GTA | TCG | GAA | 9170 |
| His | Ser | Leu | Val | Gly | Tyr | Tyr | Thr | Thr | Asp | Asn | Glu | Thr | Val | Ser | Glu | |
| | 2955 | | | | | 2960 | | | | | 2965 | | | | | |
| GCC | GAT | ATT | CTC | ACT | TTC | ATG | AAA | GCA | AGG | CTT | CCA | ACG | TAC | ATG | GTG | 9218 |
| Ala | Asp | Ile | Leu | Thr | Phe | Met | Lys | Ala | Arg | Leu | Pro | Thr | Tyr | Met | Val | |
| 2970 | | | | | 2975 | | | | | 2980 | | | | | 2985 | |
| CCA | AGC | CAC | CTC | TGC | TGT | CTG | GAA | GGC | GCA | CTG | CCT | GTG | ACG | ATT | AAC | 9266 |
| Pro | Ser | His | Leu | Cys | Cys | Leu | Glu | Gly | Ala | Leu | Pro | Val | Thr | Ile | Asn | |
| | | | 2990 | | | | | 2995 | | | | | 3000 | | | |
| GGA | AAG | CTC | GAC | GTC | CGG | AGA | TTG | CCG | GAG | ATT | ATC | AAC | GAC | TCC | GCG | 9314 |
| Gly | Lys | Leu | Asp | Val | Arg | Arg | Leu | Pro | Glu | Ile | Ile | Asn | Asp | Ser | Ala | |
| | | | 3005 | | | | 3010 | | | | | 3015 | | | | |
| CAG | TCC | TCG | TAC | AGC | CCA | CCA | AGG | AAC | ATA | ATC | GAG | GCC | AAG | ATG | TGC | 9362 |
| Gln | Ser | Ser | Tyr | Ser | Pro | Pro | Arg | Asn | Ile | Ile | Glu | Ala | Lys | Met | Cys | |
| | | 3020 | | | | 3025 | | | | | 3030 | | | | | |
| AGA | CTG | TGG | GAA | TCC | GCC | TTG | GGA | ATG | GAG | CGA | TGC | GGT | ATC | GAC | GAC | 9410 |
| Arg | Leu | Trp | Glu | Ser | Ala | Leu | Gly | Met | Glu | Arg | Cys | Gly | Ile | Asp | Asp | |
| | 3035 | | | | | 3040 | | | | | 3045 | | | | | |
| GAC | CTG | TTC | AAA | CTG | GGT | GGC | GAC | AGC | ATC | ACA | TCT | TTG | CAT | CTC | GTG | 9458 |
| Asp | Leu | Phe | Lys | Leu | Gly | Gly | Asp | Ser | Ile | Thr | Ser | Leu | His | Leu | Val | |
| 3050 | | | | | 3055 | | | | | 3060 | | | | | 3065 | |
| GCC | CAG | ATT | CAC | AAC | CAG | GTG | GGC | TGC | AAG | ATC | ACC | GTT | CGG | GAT | ATA | 9506 |
| Ala | Gln | Ile | His | Asn | Gln | Val | Gly | Cys | Lys | Ile | Thr | Val | Arg | Asp | Ile | |
| | | | | 3070 | | | | 3075 | | | | | 3080 | | | |
| TTT | GAA | CAT | CGT | ACC | GCC | CGA | GCC | CTC | CAT | GAT | CAC | GTC | TTC | ATG | AAG | 9554 |
| Phe | Glu | His | Arg | Thr | Ala | Arg | Ala | Leu | His | Asp | His | Val | Phe | Met | Lys | |
| | | | 3085 | | | | 3090 | | | | | 3095 | | | | |
| GAC | TCC | GAC | CGG | AGT | AAT | GTG | ACT | CAG | TTC | CGA | ACC | GAA | CAA | GGG | CCG | 9602 |
| Asp | Ser | Asp | Arg | Ser | Asn | Val | Thr | Gln | Phe | Arg | Thr | Glu | Gln | Gly | Pro | |
| | | | 3100 | | | | 3105 | | | | | 3110 | | | | |
| GTC | ATC | GGC | GAG | GCG | CCC | CTA | CTG | CCG | ATT | CAA | GAC | TGG | TTT | TTG | TCA | 9650 |
| Val | Ile | Gly | Glu | Ala | Pro | Leu | Leu | Pro | Ile | Gln | Asp | Trp | Phe | Leu | Ser | |
| | | 3115 | | | | 3120 | | | | | 3125 | | | | | |
| AAG | GCT | CTG | CAG | CAT | CCG | ATG | TAT | TGG | AAT | CAC | ACT | TTC | TAC | GTC | CGA | 9698 |
| Lys | Ala | Leu | Gln | His | Pro | Met | Tyr | Trp | Asn | His | Thr | Phe | Tyr | Val | Arg | |
| 3130 | | | | | 3135 | | | | | 3140 | | | | | 3145 | |
| ACG | CCA | GAG | CTG | GAT | GTT | GAT | TCC | TTA | AGC | GCT | GCT | GTC | AGG | GAC | TTG | 9746 |
| Thr | Pro | Glu | Leu | Asp | Val | Asp | Ser | Leu | Ser | Ala | Ala | Val | Arg | Asp | Leu | |
| | | | | 3150 | | | | 3155 | | | | | 3160 | | | |
| CAA | CAG | TAT | CAC | GAT | GTT | TTC | CGC | ATG | CGA | CTC | AAG | CGC | GAG | GAA | GTC | 9794 |
| Gln | Gln | Tyr | His | Asp | Val | Phe | Arg | Met | Arg | Leu | Lys | Arg | Glu | Glu | Val | |
| | | | 3165 | | | | 3170 | | | | | 3175 | | | | |
| GGA | TTC | GTG | CAG | TCC | TTT | GCT | GAG | GAC | TTC | TCT | CCT | GCC | CAG | CTT | CGG | 9842 |
| Gly | Phe | Val | Gln | Ser | Phe | Ala | Glu | Asp | Phe | Ser | Pro | Ala | Gln | Leu | Arg | |
| | | | 3180 | | | | 3185 | | | | | 3190 | | | | |
| GTG | CTG | AAC | GTA | AAA | GAT | GTT | GAC | GGG | TCC | GCG | GCC | GTC | AAC | GAG | ATA | 9890 |
| Val | Leu | Asn | Val | Lys | Asp | Val | Asp | Gly | Ser | Ala | Ala | Val | Asn | Glu | Ile | |
| | | 3195 | | | | 3200 | | | | | 3205 | | | | | |
| TTG | GAT | GGG | TGG | CAG | TCT | GGC | TTC | AAC | CTT | GAG | AAC | GGA | CCC | ATT | GGT | 9938 |
| Leu | Asp | Gly | Trp | Gln | Ser | Gly | Phe | Asn | Leu | Glu | Asn | Gly | Pro | Ile | Gly | |
| 3210 | | | | | 3215 | | | | | 3220 | | | | | 3225 | |
| TCC | ATT | GGC | TAC | CTA | CAT | GGG | TAT | GAA | GAC | CGA | TCC | GCG | CGA | GTC | TGG | 9986 |
| Ser | Ile | Gly | Tyr | Leu | His | Gly | Tyr | Glu | Asp | Arg | Ser | Ala | Arg | Val | Trp | |
| | | | | 3230 | | | | 3235 | | | | | 3240 | | | |

```
TTC TCC GTT CAC CAT ATG GCC ATT GAC ACC GTC AGC TGG CAG ATC CTT      10034
Phe Ser Val His His Met Ala Ile Asp Thr Val Ser Trp Gln Ile Leu
        3245            3250            3255

GTC CGT GAC CTG CAG ACG CTG TAC CGA AAT GGA AGC CTC GGA AGC AAG      10082
Val Arg Asp Leu Gln Thr Leu Tyr Arg Asn Gly Ser Leu Gly Ser Lys
        3260            3265            3270

GGC AGC AGT TTC CGG CAG TGG GCT GAA GCC ATC CAA AAT TAC AAG GCG      10130
Gly Ser Ser Phe Arg Gln Trp Ala Glu Ala Ile Gln Asn Tyr Lys Ala
        3275            3280            3285

TCA GAC TCT GAG AGG AAC CAT TGG AAT AAG CTC GTC ATG GAA ACA GCT      10178
Ser Asp Ser Glu Arg Asn His Trp Asn Lys Leu Val Met Glu Thr Ala
3290            3295            3300            3305

TCC AGC ATA TCC GCA TTG CCT ACG TCA ACC GGT TCG CGC GTG CGC CTG      10226
Ser Ser Ile Ser Ala Leu Pro Thr Ser Thr Gly Ser Arg Val Arg Leu
                3310            3315            3320

AGC AGA AGT TTG AGC CCT GAG AAG ACA GCC TCA CTG ATC CAA GGA GGA      10274
Ser Arg Ser Leu Ser Pro Glu Lys Thr Ala Ser Leu Ile Gln Gly Gly
            3325            3330            3335

ATC GAT CGA CAG GAT GTC TCC GTG TAC GAC TCC CTC CTG ACT TCA GTT      10322
Ile Asp Arg Gln Asp Val Ser Val Tyr Asp Ser Leu Leu Thr Ser Val
        3340            3345            3350

GGA TTG GCG CTC CAA CAT ATC GCT CCA ACC GGC CCA AGT ATG GTT ACG      10370
Gly Leu Ala Leu Gln His Ile Ala Pro Thr Gly Pro Ser Met Val Thr
        3355            3360            3365

ATC GAG GGA CAT GGC CGT GAA GAA GTG GAT CAG ACA CTG GAT GTG AGC      10418
Ile Glu Gly His Gly Arg Glu Glu Val Asp Gln Thr Leu Asp Val Ser
3370            3375            3380            3385

CGC ACC ATG GGT TGG TTC ACC ACC ATG TAT CCA TTT GAA ATT CCC CGT      10466
Arg Thr Met Gly Trp Phe Thr Thr Met Tyr Pro Phe Glu Ile Pro Arg
                3390            3395            3400

CTC AGC ACC GAG AAC ATT GTT CAA GGA GTC GTC GCT GTG AGC GAA CGG      10514
Leu Ser Thr Glu Asn Ile Val Gln Gly Val Val Ala Val Ser Glu Arg
                3405            3410            3415

TTC AGA CAG GTG CCT GCC CGT GGC GTC GGG TAT GGA ACC TTG TAC GGC      10562
Phe Arg Gln Val Pro Ala Arg Gly Val Gly Tyr Gly Thr Leu Tyr Gly
        3420            3425            3430

TAT ACT CAA CAC CCG CTG CCC CAG GTG ACC GTC AAC TAC CTG GGC CAG      10610
Tyr Thr Gln His Pro Leu Pro Gln Val Thr Val Asn Tyr Leu Gly Gln
        3435            3440            3445

CTC GCC CGC AAG CAA TCG AAG CCA AAG GAA TGG GTC CTC GCG GTG GGC      10658
Leu Ala Arg Lys Gln Ser Lys Pro Lys Glu Trp Val Leu Ala Val Gly
3450            3455            3460            3465

GAC AAC GAA TTT GAA TAC GGA CTC ATG ACT AGC CCA GAG GAC AAA GAC      10706
Asp Asn Glu Phe Glu Tyr Gly Leu Met Thr Ser Pro Glu Asp Lys Asp
                3470            3475            3480

CGG AGC TCT TCT GCC GTC GAC GTC ACG GCC GTG TGT ATT GAC GGC ACT      10754
Arg Ser Ser Ser Ala Val Asp Val Thr Ala Val Cys Ile Asp Gly Thr
            3485            3490            3495

ATG ATC ATC GAT GTG GAC AGT GCT TGG AGC CTT GAG GAG AGC GAG CAA      10802
Met Ile Ile Asp Val Asp Ser Ala Trp Ser Leu Glu Glu Ser Glu Gln
        3500            3505            3510

TTC ATC TCG AGC ATC GAG GAA GGA CTG AAC AAG ATC CTC GAC GGC AGG      10850
Phe Ile Ser Ser Ile Glu Glu Gly Leu Asn Lys Ile Leu Asp Gly Arg
        3515            3520            3525

GCA AGT CAG CAA ACC TCG CGA TTC CCG GAT GTT CCT CAA CCG GCG GAG      10898
Ala Ser Gln Gln Thr Ser Arg Phe Pro Asp Val Pro Gln Pro Ala Glu
3530            3535            3540            3545

ACA TAT ACG CCG TAT TTC GAG TAT CTG GAA CCT CCA CGA CAG GGA CCG      10946
Thr Tyr Thr Pro Tyr Phe Glu Tyr Leu Glu Pro Pro Arg Gln Gly Pro
                3550            3555            3560
```

| | | | | | | | | | | | | | | | | |
|---|---|---|---|---|---|---|---|---|---|---|---|---|---|---|---|---|
| ACG | CTG | TTC | CTG | CTG | CCG | CCG | GGC | GAA | GGA | GGC | GCC | GAG | AGT | TAC | TTC | 10994 |
| Thr | Leu | Phe | Leu | Leu | Pro | Pro | Gly | Glu | Gly | Gly | Ala | Glu | Ser | Tyr | Phe | |
| | | | 3565 | | | | 3570 | | | | | 3575 | | | | |
| AAC | AAC | ATC | GTC | AAG | CGC | CTG | CGT | CAG | ACA | AAT | ATG | GTG | GTC | TTC | AAC | 11042 |
| Asn | Asn | Ile | Val | Lys | Arg | Leu | Arg | Gln | Thr | Asn | Met | Val | Val | Phe | Asn | |
| | | 3580 | | | | 3585 | | | | | 3590 | | | | | |
| AAC | TAC | TAC | TTG | CAC | AGC | AAA | CGC | CTG | CGC | ACG | TTC | GAG | GAG | CTG | GCG | 11090 |
| Asn | Tyr | Tyr | Leu | His | Ser | Lys | Arg | Leu | Arg | Thr | Phe | Glu | Glu | Leu | Ala | |
| | 3595 | | | | 3600 | | | | | 3605 | | | | | | |
| GAA | ATG | TAT | CTC | GAC | CAA | GTA | CGC | GGC | ATC | CAA | CCA | CAC | GGA | CCG | TAC | 11138 |
| Glu | Met | Tyr | Leu | Asp | Gln | Val | Arg | Gly | Ile | Gln | Pro | His | Gly | Pro | Tyr | |
| 3610 | | | | 3615 | | | | 3620 | | | | | 3625 | | | |
| CAC | TTC | ATC | GGA | TGG | AGC | TTC | GGA | GGA | ATT | CTC | GCA | ATG | GAA | ATG | TCG | 11186 |
| His | Phe | Ile | Gly | Trp | Ser | Phe | Gly | Gly | Ile | Leu | Ala | Met | Glu | Met | Ser | |
| | | | | 3630 | | | | | 3635 | | | | | 3640 | | |
| CGG | CGA | CTG | GTA | GCC | TCG | GAC | GAG | AAG | ATT | GGC | TTC | CTC | GGT | ATT | ATC | 11234 |
| Arg | Arg | Leu | Val | Ala | Ser | Asp | Glu | Lys | Ile | Gly | Phe | Leu | Gly | Ile | Ile | |
| | | | 3645 | | | | 3650 | | | | | 3655 | | | | |
| GAC | ACC | TAT | TTC | AAC | GTG | CGG | GGA | GCG | ACA | CGC | ACC | ATT | GGC | TTG | GGG | 11282 |
| Asp | Thr | Tyr | Phe | Asn | Val | Arg | Gly | Ala | Thr | Arg | Thr | Ile | Gly | Leu | Gly | |
| | | 3660 | | | | 3665 | | | | | 3670 | | | | | |
| GAC | ACT | GAG | ATT | CTG | GAC | CCG | ATC | CAT | CAC | ATC | TAC | AAT | CCC | GAT | CCG | 11330 |
| Asp | Thr | Glu | Ile | Leu | Asp | Pro | Ile | His | His | Ile | Tyr | Asn | Pro | Asp | Pro | |
| | 3675 | | | | 3680 | | | | | 3685 | | | | | | |
| GCC | AAC | TTC | CAA | CGC | CTG | CCC | TCT | GCA | ACA | GAT | CGC | ATT | GTG | CTG | TTC | 11378 |
| Ala | Asn | Phe | Gln | Arg | Leu | Pro | Ser | Ala | Thr | Asp | Arg | Ile | Val | Leu | Phe | |
| 3690 | | | | 3695 | | | | 3700 | | | | | 3705 | | | |
| AAG | GCC | ATG | AGG | CCG | AAC | AAC | AAG | TAC | GAA | TCC | GAG | AAC | CAG | CGT | CGC | 11426 |
| Lys | Ala | Met | Arg | Pro | Asn | Asn | Lys | Tyr | Glu | Ser | Glu | Asn | Gln | Arg | Arg | |
| | | | | 3710 | | | | 3715 | | | | | 3720 | | | |
| CTG | TAC | GAG | TAC | TAT | GAC | | 11444 | | | | | | | | | |
| Leu | Tyr | Glu | Tyr | Tyr | Asp | | | | | | | | | | | |

(2) INFORMATION FOR SEQ ID NO:27:

(i) SEQUENCE CHARACTERISTICS:
        (A) LENGTH: 3727 amino acids
        (B) TYPE: amino acid
        (D) TOPOLOGY: linear (ii) MOLECULE TYPE: protein (xi) SEQUENCE DESCRIPTION: SEQ ID NO:27:

| | | | | | | | | | | | | | | |
|---|---|---|---|---|---|---|---|---|---|---|---|---|---|---|
| Met | Thr | Gln | Leu | Lys | Pro | Pro | Asn | Gly | Thr | Thr | Pro | Ile | Gly | Phe | Ser |
| 1 | | | | 5 | | | | | 10 | | | | | 15 | |
| Ala | Thr | Thr | Ser | Leu | Asn | Ala | Ser | Gly | Ser | Ser | Val | Lys | Asn | Gly | |
| | | | 20 | | | | | 25 | | | | | 30 | | |
| Thr | Ile | Lys | Pro | Ser | Asn | Gly | Ile | Phe | Lys | Pro | Ser | Thr | Arg | Asp | Thr |
| | | 35 | | | | | 40 | | | | | 45 | | | |
| Met | Asp | Pro | Cys | Ser | Gly | Asn | Ala | Ala | Asp | Gly | Ser | Ile | Arg | Val | Arg |
| | 50 | | | | | 55 | | | | | 60 | | | | |
| Phe | Arg | Gly | Gly | Ile | Glu | Arg | Trp | Lys | Glu | Cys | Val | Asn | Gln | Val | Pro |
| 65 | | | | | 70 | | | | | 75 | | | | | 80 |
| Glu | Arg | Cys | Asp | Leu | Ser | Gly | Leu | Thr | Thr | Asp | Ser | Thr | Arg | Tyr | Gln |
| | | | | 85 | | | | | 90 | | | | | 95 | |
| Leu | Ala | Ser | Thr | Gly | Phe | Gly | Asp | Ala | Ser | Ala | Ala | Tyr | Gln | Glu | Arg |
| | | | 100 | | | | | 105 | | | | | 110 | | |
| Leu | Met | Thr | Val | Pro | Val | Asp | Val | His | Ala | Ala | Leu | Gln | Glu | Leu | Cys |
| | | | 115 | | | | | 120 | | | | | 125 | | |
| Leu | Glu | Arg | Arg | Val | Ser | Val | Gly | Ser | Val | Ile | Asn | Phe | Ser | Val | His |

|     |     |     |     | 130 |     |     |     |     | 135 |     |     |     |     | 140 |     |
| --- | --- | --- | --- | --- | --- | --- | --- | --- | --- | --- | --- | --- | --- | --- | --- |
| Gln | Met | Leu | Lys | Gly | Phe | Gly | Asn | Gly | Thr | His | Thr | Ile | Thr | Ala | Ser |
| 145 |     |     |     |     | 150 |     |     |     |     | 155 |     |     |     |     | 160 |
| Leu | His | Arg | Glu | Gln | Asn | Leu | Gln | Asn | Ser | Ser | Pro | Ser | Trp | Val | Val |
|     |     |     |     | 165 |     |     |     |     | 170 |     |     |     |     | 175 |     |
| Ser | Pro | Thr | Ile | Val | Thr | His | Glu | Asn | Arg | Asp | Gly | Trp | Ser | Val | Ala |
|     |     |     |     | 180 |     |     |     |     | 185 |     |     |     |     | 190 |     |
| Gln | Ala | Val | Glu | Ser | Ile | Glu | Ala | Ala | Arg | Gly | Ser | Glu | Lys | Glu | Ser |
|     |     |     | 195 |     |     |     |     | 200 |     |     |     |     | 205 |     |     |
| Val | Thr | Ala | Ile | Asp | Ser | Ala | Ser | Ser | Leu | Val | Lys | Met | Gly | Leu | Phe |
|     |     |     | 210 |     |     |     |     | 215 |     |     |     |     | 220 |     |     |
| Asp | Leu | Leu | Val | Ser | Phe | Val | Asp | Ala | Asp | Ala | Arg | Ile | Pro | Cys |     |
| 225 |     |     |     |     | 230 |     |     |     |     | 235 |     |     |     |     | 240 |
| Phe | Asp | Phe | Pro | Leu | Ala | Val | Ile | Val | Arg | Glu | Cys | Asp | Ala | Asn | Leu |
|     |     |     |     | 245 |     |     |     |     | 250 |     |     |     |     | 255 |     |
| Ser | Leu | Thr | Leu | Arg | Phe | Ser | Asp | Cys | Leu | Phe | Asn | Glu | Glu | Thr | Ile |
|     |     |     |     | 260 |     |     |     |     | 265 |     |     |     |     | 270 |     |
| Cys | Asn | Phe | Thr | Asp | Ala | Leu | Asn | Ile | Leu | Leu | Ala | Glu | Ala | Val | Ile |
|     |     |     | 275 |     |     |     |     | 280 |     |     |     |     | 285 |     |     |
| Gly | Arg | Val | Thr | Pro | Val | Ala | Asp | Ile | Glu | Leu | Leu | Ser | Ala | Glu | Gln |
|     |     | 290 |     |     |     |     | 295 |     |     |     |     | 300 |     |     |     |
| Lys | Gln | Gln | Leu | Glu | Glu | Trp | Asn | Asn | Thr | Asp | Gly | Glu | Tyr | Pro | Ser |
| 305 |     |     |     |     | 310 |     |     |     |     | 315 |     |     |     |     | 320 |
| Ser | Lys | Arg | Leu | His | His | Leu | Ile | Glu | Glu | Val | Val | Glu | Arg | His | Glu |
|     |     |     |     | 325 |     |     |     |     | 330 |     |     |     |     | 335 |     |
| Asp | Lys | Ile | Ala | Val | Val | Cys | Asp | Glu | Arg | Glu | Leu | Thr | Tyr | Gly | Glu |
|     |     |     | 340 |     |     |     |     | 345 |     |     |     |     | 350 |     |     |
| Leu | Asn | Ala | Gln | Gly | Asn | Ser | Leu | Ala | Arg | Tyr | Leu | Arg | Ser | Ile | Gly |
|     |     |     | 355 |     |     |     |     | 360 |     |     |     |     | 365 |     |     |
| Ile | Leu | Pro | Glu | Gln | Leu | Val | Ala | Leu | Phe | Leu | Asp | Lys | Ser | Glu | Lys |
|     | 370 |     |     |     |     | 375 |     |     |     |     | 380 |     |     |     |     |
| Leu | Ile | Val | Thr | Ile | Leu | Gly | Val | Trp | Lys | Ser | Gly | Ala | Ala | Tyr | Val |
| 385 |     |     |     |     | 390 |     |     |     |     | 395 |     |     |     |     | 400 |
| Pro | Ile | Asp | Pro | Thr | Tyr | Pro | Asp | Glu | Arg | Val | Arg | Phe | Val | Leu | Asp |
|     |     |     |     | 405 |     |     |     |     | 410 |     |     |     |     | 415 |     |
| Asp | Thr | Lys | Ala | Arg | Ala | Ile | Ile | Ala | Ser | Asn | Gln | His | Val | Glu | Arg |
|     |     |     | 420 |     |     |     |     | 425 |     |     |     |     | 430 |     |     |
| Leu | Gln | Arg | Glu | Val | Ile | Gly | Asp | Arg | Asn | Leu | Cys | Ile | Ile | Arg | Leu |
|     |     | 435 |     |     |     |     | 440 |     |     |     |     | 445 |     |     |     |
| Glu | Pro | Leu | Leu | Ala | Ser | Leu | Ala | Gln | Asp | Ser | Ser | Lys | Phe | Pro | Ala |
|     | 450 |     |     |     |     | 455 |     |     |     |     | 460 |     |     |     |     |
| His | Asn | Leu | Asp | Asp | Leu | Pro | Leu | Thr | Ser | Gln | Gln | Leu | Ala | Tyr | Val |
| 465 |     |     |     |     | 470 |     |     |     |     | 475 |     |     |     |     | 480 |
| Thr | Tyr | Thr | Ser | Gly | Thr | Thr | Gly | Phe | Pro | Lys | Gly | Ile | Phe | Lys | Gln |
|     |     |     |     | 485 |     |     |     |     | 490 |     |     |     |     | 495 |     |
| His | Thr | Asn | Val | Val | Asn | Ser | Ile | Thr | Asp | Leu | Ser | Ala | Arg | Tyr | Gly |
|     |     |     | 500 |     |     |     |     | 505 |     |     |     |     | 510 |     |     |
| Val | Ala | Gly | Gln | His | His | Glu | Ala | Ile | Leu | Leu | Phe | Ser | Ala | Cys | Val |
|     |     |     | 515 |     |     |     |     | 520 |     |     |     |     | 525 |     |     |
| Phe | Glu | Pro | Phe | Val | Arg | Gln | Thr | Leu | Met | Ala | Leu | Val | Asn | Gly | His |
|     |     | 530 |     |     |     |     | 535 |     |     |     |     | 540 |     |     |     |
| Leu | Leu | Ala | Val | Ile | Asn | Asp | Val | Glu | Lys | Tyr | Asp | Ala | Asp | Thr | Leu |
| 545 |     |     |     |     | 550 |     |     |     |     | 555 |     |     |     |     | 560 |

| | | | | | | | | | | | | | | |
|---|---|---|---|---|---|---|---|---|---|---|---|---|---|---|
| Leu | Pro | Phe | Ile | Arg<br>565 | Arg | His | Ser | Ile<br>570 | Thr | Tyr | Leu | Asn | Gly<br>575 | Thr | Ala |
| Ser | Val | Leu | Gln<br>580 | Glu | Tyr | Asp | Phe | Ser<br>585 | Asp | Cys | Pro | Ser | Leu<br>590 | Asn | Arg |
| Ile | Ile | Leu<br>595 | Val | Gly | Glu | Asn | Leu<br>600 | Thr | Glu | Ala | Arg | Tyr<br>605 | Leu | Ala | Leu |
| Arg | Gln<br>610 | Arg | Phe | Lys | Asn | Arg<br>615 | Ile | Leu | Asn | Glu | Tyr<br>620 | Gly | Phe | Thr | Glu |
| Ser<br>625 | Ala | Phe | Val | Thr | Ala<br>630 | Leu | Lys | Ile | Phe | Asp<br>635 | Pro | Glu | Ser | Thr | Arg<br>640 |
| Lys | Asp | Thr | Ser | Leu<br>645 | Gly | Arg | Pro | Val | Arg<br>650 | Asn | Val | Lys | Cys | Tyr<br>655 | Ile |
| Leu | Asn | Pro | Ser<br>660 | Leu | Lys | Arg | Val | Pro<br>665 | Ile | Gly | Ala | Thr | Gly<br>670 | Glu | Leu |
| His | Ile | Gly<br>675 | Gly | Leu | Gly | Ile | Ser<br>680 | Lys | Gly | Tyr | Leu | Asn<br>685 | Arg | Pro | Glu |
| Leu | Thr<br>690 | Pro | His | Arg | Phe | Ile<br>695 | Pro | Asn | Pro | Phe | Gln<br>700 | Thr | Asp | Cys | Glu |
| Lys<br>705 | Gln | Leu | Gly | Ile | Asn<br>710 | Ser | Leu | Met | Tyr | Lys<br>715 | Thr | Gly | Asp | Leu | Ala<br>720 |
| Arg | Trp | Leu | Pro | Asn<br>725 | Gly | Glu | Val | Glu | Tyr<br>730 | Leu | Gly | Arg | Ala | Asp<br>735 | Phe |
| Gln | Ile | Lys | Leu<br>740 | Arg | Gly | Ile | Arg | Ile<br>745 | Glu | Pro | Gly | Glu | Ile<br>750 | Glu | Thr |
| Met | Leu | Ala<br>755 | Met | Tyr | Pro | Arg | Val<br>760 | Arg | Thr | Ser | Leu | Val<br>765 | Val | Ser | Lys |
| Lys | Leu<br>770 | Arg | Asn | Gly | Pro | Glu<br>775 | Glu | Thr | Thr | Asn | Glu<br>780 | His | Leu | Val | Gly |
| Tyr<br>785 | Tyr | Val | Cys | Asp | Ser<br>790 | Ala | Ser | Val | Ser | Glu<br>795 | Ala | Asp | Leu | Leu | Ser<br>800 |
| Phe | Leu | Glu | Lys | Lys<br>805 | Leu | Pro | Arg | Tyr | Met<br>810 | Ile | Pro | Thr | Arg | Leu<br>815 | Val |
| Gln | Leu | Ser | Gln<br>820 | Ile | Pro | Val | Asn | Val<br>825 | Asn | Gly | Lys | Ala | Asp<br>830 | Leu | Arg |
| Ala | Leu | Pro<br>835 | Ala | Val | Asp | Ile | Ser<br>840 | Asn | Ser | Thr | Glu | Val<br>845 | Arg | Ser | Asp |
| Leu | Arg<br>850 | Gly | Asp | Thr | Glu | Ile<br>855 | Ala | Leu | Gly | Glu | Ile<br>860 | Trp | Ala | Asp | Val |
| Leu | Gly<br>865 | Ala | Arg | Gln | Arg<br>870 | Ser | Val | Ser | Arg | Asn<br>875 | Asp | Asn | Phe | Phe<br>880 | Arg |
| Leu | Gly | Gly | His | Ser<br>885 | Ile | Thr | Cys | Ile | Gln<br>890 | Leu | Ile | Ala | Arg | Ile<br>895 | Arg |
| Gln | Arg | Gln | Arg<br>900 | Leu | Ser | Val | Ser | Ile<br>905 | Ser | Val | Glu | Asp | Val<br>910 | Phe | Ala |
| Thr | Arg | Thr<br>915 | Leu | Glu | Arg | Met | Ala<br>920 | Asp | Leu | Leu | Gln | Asn<br>925 | Lys | Gln | Gln |
| Glu | Lys<br>930 | Cys | Asp | Lys | Pro | His<br>935 | Glu | Ala | Pro | Thr | Glu<br>940 | Leu | Leu | Glu | Glu |
| Asn<br>945 | Ala | Ala | Thr | Asp | Asn<br>950 | Ile | Tyr | Leu | Ala | Asn<br>955 | Ser | Leu | Gln | Gln | Gly<br>960 |
| Phe | Val | Tyr | His | Tyr<br>965 | Leu | Lys | Ser | Met | Glu<br>970 | Gln | Ser | Asp | Ala | Tyr<br>975 | Val |
| Met | Gln | Ser | Val<br>980 | Leu | Arg | Tyr | Asn | Thr<br>985 | Thr | Leu | Ser | Pro | Asp<br>990 | Leu | Phe |

```
Gln Arg Ala Trp Lys His Ala Gln Gln Ser Phe Pro Ala Leu Arg Leu
        995                 1000                1005
Arg Phe Ser Trp Glu Lys Glu Val Phe Gln Leu Leu Asp Gln Asp Pro
        1010                1015                1020
Pro Leu Asp Trp Arg Phe Leu Tyr Phe Thr Asp Val Ala Ala Gly Ala
1025                1030                1035                1040
Val Glu Asp Arg Lys Leu Glu Asp Leu Arg Arg Gln Asp Leu Thr Glu
        1045                1050                1055
Arg Phe Lys Leu Asp Val Gly Arg Leu Phe Arg Val Tyr Leu Ile Lys
        1060                1065                1070
His Ser Glu Asn Arg Phe Thr Cys Leu Phe Ser Cys His His Ala Ile
        1075                1080                1085
Leu Asp Gly Trp Ser Leu Pro Leu Leu Phe Glu Lys Val His Glu Thr
        1090                1095                1100
Tyr Leu Gln Leu Leu His Gly Asp Asn Leu Thr Ser Ser Met Asp Asp
1105                1110                1115                1120
Pro Tyr Thr Arg Thr Gln Arg Tyr Leu His Ala His Arg Glu Asp His
        1125                1130                1135
Leu Asp Phe Trp Ala Gly Val Val Gln Lys Ile Asn Glu Arg Cys Asp
        1140                1145                1150
Met Asn Ala Leu Leu Asn Glu Arg Ser Arg Tyr Lys Val Gln Leu Ala
        1155                1160                1165
Asp Tyr Asp Gln Val Gln Glu Gln Arg His Val Thr Ile Ala Leu Ser
        1170                1175                1180
Gly Asp Ala Trp Leu Ala Asp Leu Arg Gln Thr Cys Ser Ala Gln Gly
1185                1190                1195                1200
Ile Thr Leu His Ser Ile Leu Gln Phe Val Trp His Ala Val Leu His
        1205                1210                1215
Ala Tyr Gly Gly Gly Thr His Thr Ile Thr Gly Thr Thr Ile Ser Gly
        1220                1225                1230
Arg Asn Leu Pro Ile Leu Gly Ile Glu Arg Ala Val Gly Pro Tyr Ile
        1235                1240                1245
Asn Thr Leu Pro Leu Val Leu Asp His Ser Thr Phe Lys Asp Lys Thr
        1250                1255                1260
Ile Met Glu Ala Ile Glu Asp Val Gln Ala Lys Val Asn Val Met Asn
1265                1270                1275                1280
Ser Arg Gly Asn Val Glu Leu Gly Arg Leu His Lys Thr Asp Leu Lys
        1285                1290                1295
His Gly Leu Phe Asp Ser Leu Phe Val Leu Glu Asn Tyr Pro Asn Leu
        1300                1305                1310
Asp Lys Ser Arg Thr Leu Glu His Gln Thr Glu Leu Gly Tyr Ser Ile
        1315                1320                1325
Glu Gly Gly Thr Glu Lys Leu Asn Tyr Pro Leu Ala Val Ile Ala Arg
        1330                1335                1340
Glu Val Glu Thr Thr Gly Gly Phe Thr Val Ser Ile Cys Tyr Ala Ser
1345                1350                1355                1360
Glu Leu Phe Glu Glu Val Met Ile Ser Glu Leu Leu His Met Val Gln
        1365                1370                1375
Asp Thr Leu Met Gln Val Ala Arg Gly Leu Asn Glu Pro Val Gly Ser
        1380                1385                1390
Leu Glu Tyr Leu Ser Ser Ile Gln Leu Glu Gln Leu Ala Ala Trp Asn
        1395                1400                1405
Ala Thr Glu Ala Glu Phe Pro Asp Thr Thr Leu His Glu Met Phe Glu
```

```
                    1410                    1415                         1420
Asn  Glu  Ala  Ser  Gln  Lys  Pro  Asp  Lys  Ile  Ala  Val  Val  Tyr  Glu  Glu
1425                     1430                         1435                     1440

Thr  Ser  Leu  Thr  Tyr  Arg  Glu  Leu  Asn  Glu  Arg  Ala  Asn  Arg  Met  Ala
                    1445                        1450                      1455

His  Gln  Leu  Arg  Ser  Asp  Val  Ser  Pro  Asn  Pro  Asn  Glu  Val  Ile  Ala
                    1460                        1465                      1470

Leu  Val  Met  Asp  Lys  Ser  Glu  His  Met  Ile  Val  Asn  Ile  Leu  Ala  Val
                    1475                        1480                      1485

Trp  Lys  Ser  Gly  Gly  Ala  Tyr  Val  Pro  Ile  Asp  Pro  Gly  Tyr  Pro  Asn
                    1490                        1495                      1500

Asp  Arg  Ile  Gln  Tyr  Ile  Leu  Glu  Asp  Thr  Gln  Ala  Leu  Ala  Val  Ile
1505                     1510                         1515                     1520

Ala  Asp  Ser  Cys  Tyr  Leu  Pro  Arg  Ile  Lys  Gly  Met  Ala  Ala  Ser  Gly
                    1525                        1530                      1535

Thr  Leu  Leu  Tyr  Pro  Ser  Val  Leu  Pro  Ala  Asn  Pro  Asp  Ser  Lys  Trp
                    1540                        1545                      1550

Ser  Val  Ser  Asn  Pro  Ser  Pro  Leu  Ser  Arg  Ser  Thr  Asp  Leu  Ala  Tyr
                    1555                        1560                      1565

Ile  Ile  Tyr  Thr  Ser  Gly  Thr  Thr  Gly  Arg  Pro  Lys  Gly  Val  Thr  Val
                    1570                        1575                      1580

Glu  His  His  Gly  Val  Val  Asn  Leu  Gln  Val  Ser  Leu  Ser  Lys  Val  Phe
1585                     1590                         1595                     1600

Gly  Leu  Arg  Asp  Thr  Asp  Asp  Glu  Val  Ile  Leu  Ser  Phe  Ser  Asn  Tyr
                    1605                        1610                      1615

Val  Phe  Asp  His  Phe  Val  Glu  Gln  Met  Thr  Asp  Ala  Ile  Leu  Asn  Gly
                    1620                        1625                      1630

Gln  Thr  Leu  Leu  Val  Leu  Asn  Asp  Gly  Met  Arg  Gly  Asp  Lys  Glu  Arg
                    1635                        1640                      1645

Leu  Tyr  Arg  Tyr  Ile  Glu  Lys  Asn  Arg  Val  Thr  Tyr  Leu  Ser  Gly  Thr
                    1650                        1655                      1660

Pro  Ser  Val  Val  Ser  Met  Tyr  Glu  Phe  Ser  Arg  Phe  Lys  Asp  His  Leu
1665                     1670                         1675                     1680

Arg  Arg  Val  Asp  Cys  Val  Gly  Glu  Ala  Phe  Ser  Glu  Pro  Val  Phe  Asp
                    1685                        1690                      1695

Lys  Ile  Arg  Glu  Thr  Phe  His  Gly  Leu  Val  Ile  Asn  Gly  Tyr  Gly  Pro
                    1700                        1705                      1710

Thr  Glu  Val  Ser  Ile  Thr  Thr  His  Lys  Arg  Leu  Tyr  Pro  Phe  Pro  Glu
                    1715                        1720                      1725

Arg  Arg  Met  Asp  Lys  Ser  Ile  Gly  Gln  Gln  Val  His  Asn  Ser  Thr  Ser
1730                     1735                         1740

Tyr  Val  Leu  Asn  Glu  Asp  Met  Lys  Arg  Thr  Pro  Ile  Gly  Ala  Val  Gly
1745                     1750                         1755                     1760

Glu  Leu  Tyr  Leu  Gly  Gly  Glu  Gly  Val  Val  Arg  Gly  Tyr  His  Asn  Arg
                    1765                        1770                      1775

Ala  Asp  Val  Thr  Ala  Glu  Arg  Phe  Ile  Pro  Asn  Pro  Phe  Gln  Ser  Glu
                    1780                        1785                      1790

Glu  Asp  Lys  Arg  Glu  Gly  Arg  Asn  Ser  Arg  Leu  Tyr  Lys  Thr  Gly  Asp
                    1795                        1800                      1805

Leu  Val  Arg  Trp  Ile  Pro  Gly  Ser  Ser  Gly  Glu  Val  Glu  Tyr  Leu  Gly
                    1810                        1815                      1820

Arg  Asn  Asp  Phe  Gln  Val  Lys  Ile  Arg  Gly  Leu  Arg  Ile  Glu  Val  Gly
1825                     1830                         1835                     1840
```

```
Glu Ile Glu Ala Ile Leu Ser Ser Tyr His Gly Ile Lys Gln Ser Val
                1845                1850                1855
Val Ile Ala Lys Asp Cys Arg Glu Gly Ala Gln Lys Phe Leu Val Gly
                1860                1865                1870
Tyr Tyr Val Ala Asp Ala Ala Leu Pro Ser Ala Ala Ile Arg Arg Phe
                1875                1880                1885
Met Gln Ser Arg Leu Pro Gly Tyr Met Val Pro Ser Arg Leu Ile Leu
                1890                1895                1900
Val Ser Lys Phe Pro Val Thr Pro Ser Gly Lys Leu Asp Thr Lys Ala
1905                1910                1915                1920
Leu Pro Pro Ala Glu Glu Glu Ser Glu Ile Asp Val Val Pro Pro Arg
                1925                1930                1935
Ser Glu Ile Glu Arg Ser Leu Cys Asp Ile Trp Ala Glu Leu Leu Glu
                1940                1945                1950
Met His Pro Glu Glu Ile Gly Ile Tyr Ser Asp Phe Phe Ser Leu Gly
                1955                1960                1965
Gly Asp Ser Leu Lys Ser Thr Lys Leu Ser Phe Met Ile His Glu Ser
                1970                1975                1980
Phe Asn Arg Ala Val Ser Val Ser Ala Leu Phe Cys His Arg Thr Val
1985                1990                1995                2000
Glu Ala Gln Thr His Leu Ile Leu Asn Asp Ala Ala Asp Val His Glu
                2005                2010                2015
Ile Thr Pro Ile Asp Cys Asn Asp Thr Gln Met Ile Pro Val Ser Arg
                2020                2025                2030
Ala Gln Glu Arg Leu Leu Phe Ile His Glu Phe Glu Asn Gly Ser Asn
                2035                2040                2045
Ala Tyr Asn Ile Asp Ala Ala Phe Glu Leu Pro Gly Ser Val Asp Ala
                2050                2055                2060
Ser Leu Leu Glu Gln Ala Leu Arg Gly Asn Leu Ala Arg His Glu Ala
2065                2070                2075                2080
Leu Arg Thr Leu Leu Val Lys Asp His Ala Thr Gly Ile Tyr Leu Gln
                2085                2090                2095
Lys Val Leu Ser Pro Asp Glu Ala Gln Gly Met Phe Ser Val Asn Val
                2100                2105                2110
Asp Thr Ala Lys Gln Val Glu Arg Leu Asp Gln Glu Ile Ala Ser Leu
                2115                2120                2125
Ser Gln His Val Phe Arg Leu Asp Asp Glu Leu Pro Trp Glu Ala Arg
                2130                2135                2140
Ile Leu Lys Leu Glu Ser Gly Gly Leu Tyr Leu Ile Leu Ala Phe His
2145                2150                2155                2160
His Thr Cys Phe Asp Ala Trp Ser Leu Lys Val Phe Glu Gln Glu Leu
                2165                2170                2175
Arg Ala Leu Tyr Ala Ala Leu Gln Lys Thr Lys Ser Ala Ala Asn Leu
                2180                2185                2190
Pro Ala Leu Lys Ala Gln Tyr Lys Glu Tyr Ala Leu Tyr His Arg Arg
                2195                2200                2205
Gln Leu Ser Gly Asp Arg Met Arg Asn Leu Ser Asp Phe Trp Leu Arg
                2210                2215                2220
Lys Leu Ile Gly Leu Glu Pro Leu Gln Leu Ile Thr Asp Arg Pro Arg
2225                2230                2235                2240
Pro Val Gln Phe Lys Tyr Asp Gly Asp Asp Leu Ser Ile Glu Leu Ser
                2245                2250                2255
Lys Lys Glu Thr Glu Asn Leu Arg Gly Val Ala Lys Arg Cys Lys Ser
                2260                2265                2270
```

```
Ser Leu Tyr Val Val Leu Val Ser Val Tyr Cys Val Met Leu Ala Ser
        2275                2280                2285

Tyr Ala Asn Gln Ser Asp Val Ser Val Gly Ile Pro Val Ser His Arg
        2290                2295                2300

Thr His Pro Gln Phe Gln Ser Val Ile Gly Phe Phe Val Asn Leu Val
2305                2310                2315                2320

Val Leu Arg Val Asp Ile Ser Gln Ser Ala Ile Cys Gly Leu Ile Arg
                2325                2330                2335

Arg Val Met Lys Glu Leu Val Asp Ala Gln Leu His Gln Asp Met Pro
            2340                2345                2350

Phe Gln Glu Val Thr Lys Leu Leu Gln Val Asp Asn Asp Pro Ser Arg
        2355                2360                2365

His Pro Leu Val Gln Asn Val Phe Asn Phe Glu Ser Arg Ala Asn Gly
        2370                2375                2380

Glu His Asp Ala Arg Ser Glu Asp Glu Gly Ser Leu Ala Phe Asn Gln
2385                2390                2395                2400

Tyr Arg Pro Val Gln Pro Val Asp Ser Val Ala Lys Phe Asp Leu Asn
                2405                2410                2415

Ala Thr Val Thr Glu Leu Glu Ser Gly Leu Arg Val Asn Phe Asn Tyr
            2420                2425                2430

Ala Thr Ser Leu Phe Asn Lys Ser Thr Ile Gln Gly Phe Leu His Thr
        2435                2440                2445

Tyr Glu Tyr Leu Leu Arg Gln Leu Ser Glu Leu Ser Ala Glu Gly Ile
        2450                2455                2460

Asn Glu Asp Thr Gln Leu Ser Leu Val Arg Pro Thr Glu Asn Gly Asp
2465                2470                2475                2480

Leu His Leu Pro Leu Ala Gln Ser Pro Leu Ala Thr Thr Ala Glu Glu
                2485                2490                2495

Gln Lys Val Ala Ser Leu Asn Gln Ala Phe Glu Arg Glu Ala Phe Leu
            2500                2505                2510

Ala Ala Glu Lys Ile Ala Val Val Gln Gly Asp Arg Ala Leu Ser Tyr
        2515                2520                2525

Ala Asp Leu Asn Gly Gln Ala Asn Gln Leu Ala Arg Tyr Ile Gln Ser
        2530                2535                2540

Val Ser Cys Ile Gly Ala Asp Asp Gly Ile Ala Leu Met Leu Glu Lys
2545                2550                2555                2560

Ser Ile Asp Thr Ile Ile Cys Ile Leu Ala Ile Trp Lys Ala Gly Ala
                2565                2570                2575

Ala Tyr Val Pro Leu Asp Pro Thr Tyr Pro Pro Gly Arg Val Gln Leu
            2580                2585                2590

Ile Leu Glu Glu Ile Lys Ala Lys Ala Val Leu Val His Ser Ser His
        2595                2600                2605

Ala Ser Lys Cys Glu Arg His Gly Ala Lys Val Ile Ala Val Asp Ser
        2610                2615                2620

Pro Ala Ile Glu Thr Ala Val Ser Gln Gln Ser Ala Ala Asp Leu Pro
2625                2630                2635                2640

Thr Ile Ala Ser Leu Gly Asn Leu Ala Tyr Ile Ile Phe Thr Ser Gly
                2645                2650                2655

Thr Ser Gly Lys Pro Lys Gly Val Leu Val Glu Gln Lys Ala Val Leu
            2660                2665                2670

Leu Leu Arg Asp Ala Leu Arg Glu Arg Tyr Phe Gly Arg Asp Cys Thr
        2675                2680                2685

Lys His His Gly Val Leu Phe Leu Ser Asn Tyr Val Phe Asp Phe Ser
```

-continued

```
                       2690                      2695                           2700
Val  Glu  Gln  Leu  Val  Leu  Ser  Val  Leu  Ser  Gly  His  Lys  Leu  Ile  Val
2705                      2710                      2715                      2720

Pro  Pro  Ala  Glu  Phe  Val  Ala  Asp  Asp  Glu  Phe  Tyr  Arg  Met  Ala  Ser
                       2725                      2730                      2735

Thr  His  Gly  Leu  Ser  Tyr  Leu  Ser  Gly  Thr  Pro  Ser  Leu  Leu  Gln  Lys
                       2740                      2745                      2750

Ile  Asp  Leu  Ala  Arg  Leu  Asp  His  Leu  Gln  Val  Val  Thr  Ala  Ala  Gly
                       2755                      2760                      2765

Glu  Glu  Leu  His  Ala  Thr  Gln  Tyr  Glu  Lys  Met  Arg  Arg  Arg  Phe  Asn
                       2770                      2775                      2780

Gly  Pro  Ile  Tyr  Asn  Ala  Tyr  Gly  Val  Thr  Glu  Thr  Thr  Val  Tyr  Asn
2785                      2790                      2795                      2800

Ile  Ile  Ala  Glu  Phe  Thr  Thr  Asn  Ser  Ile  Phe  Glu  Asn  Ala  Leu  Arg
                       2805                      2810                      2815

Glu  Val  Leu  Pro  Gly  Thr  Arg  Ala  Tyr  Val  Leu  Thr  Ala  Ala  Leu  Gln
                       2820                      2825                      2830

Pro  Val  Pro  Phe  Asp  Ala  Val  Gly  Glu  Leu  Tyr  Leu  Ala  Gly  Asp  Thr
                       2835                      2840                      2845

Val  Thr  Arg  Gly  Tyr  Leu  Asn  Gln  Pro  Leu  Leu  Thr  Asp  Gln  Arg  Phe
                       2850                      2855                      2860

Ile  Pro  Asn  Pro  Phe  Cys  Lys  Glu  Glu  Asp  Ile  Ala  Met  Gly  Arg  Phe
2865                      2870                      2875                      2880

Ala  Arg  Leu  Tyr  Lys  Thr  Gly  Asp  Leu  Val  Arg  Ser  Arg  Phe  Asn  Arg
                       2885                      2890                      2895

Gln  Gln  Gln  Pro  Gln  Leu  Glu  Tyr  Leu  Gly  Arg  Gly  Asp  Leu  Gln  Ile
                       2900                      2905                      2910

Lys  Met  Arg  Gly  Tyr  Arg  Ile  Glu  Ile  Ser  Glu  Val  Gln  Asn  Val  Leu
                       2915                      2920                      2925

Thr  Ser  Ser  Pro  Gly  Val  Arg  Glu  Gly  Ala  Val  Val  Ala  Lys  Tyr  Glu
                       2930                      2935                      2940

Asn  Asn  Asp  Thr  Tyr  Ser  Arg  Thr  Ala  His  Ser  Leu  Val  Gly  Tyr  Tyr
2945                      2950                      2955                      2960

Thr  Thr  Asp  Asn  Glu  Thr  Val  Ser  Glu  Ala  Asp  Ile  Leu  Thr  Phe  Met
                       2965                      2970                      2975

Lys  Ala  Arg  Leu  Pro  Thr  Tyr  Met  Val  Pro  Ser  His  Leu  Cys  Cys  Leu
                       2980                      2985                      2990

Glu  Gly  Ala  Leu  Pro  Val  Thr  Ile  Asn  Gly  Lys  Leu  Asp  Val  Arg  Arg
                       2995                      3000                      3005

Leu  Pro  Glu  Ile  Ile  Asn  Asp  Ser  Ala  Gln  Ser  Ser  Tyr  Ser  Pro  Pro
                       3010                      3015                      3020

Arg  Asn  Ile  Ile  Glu  Ala  Lys  Met  Cys  Arg  Leu  Trp  Glu  Ser  Ala  Leu
3025                      3030                      3035                      3040

Gly  Met  Glu  Arg  Cys  Gly  Ile  Asp  Asp  Asp  Leu  Phe  Lys  Leu  Gly  Gly
                       3045                      3050                      3055

Asp  Ser  Ile  Thr  Ser  Leu  His  Leu  Val  Ala  Gln  Ile  His  Asn  Gln  Val
                       3060                      3065                      3070

Gly  Cys  Lys  Ile  Thr  Val  Arg  Asp  Ile  Phe  Glu  His  Arg  Thr  Ala  Arg
                       3075                      3080                      3085

Ala  Leu  His  Asp  His  Val  Phe  Met  Lys  Asp  Ser  Asp  Arg  Ser  Asn  Val
                       3090                      3095                      3100

Thr  Gln  Phe  Arg  Thr  Glu  Gln  Gly  Pro  Val  Ile  Gly  Glu  Ala  Pro  Leu
3105                      3110                      3115                      3120
```

```
Leu Pro Ile Gln Asp Trp Phe Leu Ser Lys Ala Leu Gln His Pro Met
         3125                3130                3135

Tyr Trp Asn His Thr Phe Tyr Val Arg Thr Pro Glu Leu Asp Val Asp
         3140                3145                3150

Ser Leu Ser Ala Ala Val Arg Asp Leu Gln Gln Tyr His Asp Val Phe
         3155                3160                3165

Arg Met Arg Leu Lys Arg Glu Glu Val Gly Phe Val Gln Ser Phe Ala
         3170                3175                3180

Glu Asp Phe Ser Pro Ala Gln Leu Arg Val Leu Asn Val Lys Asp Val
3185                3190                3195                3200

Asp Gly Ser Ala Ala Val Asn Glu Ile Leu Asp Gly Trp Gln Ser Gly
                3205                3210                3215

Phe Asn Leu Glu Asn Gly Pro Ile Gly Ser Ile Gly Tyr Leu His Gly
                3220                3225                3230

Tyr Glu Asp Arg Ser Ala Arg Val Trp Phe Ser Val His His Met Ala
                3235                3240                3245

Ile Asp Thr Val Ser Trp Gln Ile Leu Val Arg Asp Leu Gln Thr Leu
                3250                3255                3260

Tyr Arg Asn Gly Ser Leu Gly Ser Lys Gly Ser Ser Phe Arg Gln Trp
3265                3270                3275                3280

Ala Glu Ala Ile Gln Asn Tyr Lys Ala Ser Asp Ser Glu Arg Asn His
                3285                3290                3295

Trp Asn Lys Leu Val Met Glu Thr Ala Ser Ser Ile Ser Ala Leu Pro
                3300                3305                3310

Thr Ser Thr Gly Ser Arg Val Arg Leu Ser Arg Ser Leu Ser Pro Glu
                3315                3320                3325

Lys Thr Ala Ser Leu Ile Gln Gly Gly Ile Asp Arg Gln Asp Val Ser
                3330                3335                3340

Val Tyr Asp Ser Leu Leu Thr Ser Val Gly Leu Ala Leu Gln His Ile
3345                3350                3355                3360

Ala Pro Thr Gly Pro Ser Met Val Thr Ile Glu Gly His Gly Arg Glu
                3365                3370                3375

Glu Val Asp Gln Thr Leu Asp Val Ser Arg Thr Met Gly Trp Phe Thr
                3380                3385                3390

Thr Met Tyr Pro Phe Glu Ile Pro Arg Leu Ser Thr Glu Asn Ile Val
                3395                3400                3405

Gln Gly Val Val Ala Val Ser Glu Arg Phe Arg Gln Val Pro Ala Arg
                3410                3415                3420

Gly Val Gly Tyr Gly Thr Leu Tyr Gly Tyr Thr Gln His Pro Leu Pro
3425                3430                3435                3440

Gln Val Thr Val Asn Tyr Leu Gly Gln Leu Ala Arg Lys Gln Ser Lys
                3445                3450                3455

Pro Lys Glu Trp Val Leu Ala Val Gly Asp Asn Glu Phe Glu Tyr Gly
                3460                3465                3470

Leu Met Thr Ser Pro Glu Asp Lys Asp Arg Ser Ser Ser Ala Val Asp
                3475                3480                3485

Val Thr Ala Val Cys Ile Asp Gly Thr Met Ile Ile Asp Val Asp Ser
                3490                3495                3500

Ala Trp Ser Leu Glu Glu Ser Glu Gln Phe Ile Ser Ser Ile Glu Glu
3505                3510                3515                3520

Gly Leu Asn Lys Ile Leu Asp Gly Arg Ala Ser Gln Gln Thr Ser Arg
                3525                3530                3535

Phe Pro Asp Val Pro Gln Pro Ala Glu Thr Tyr Thr Pro Tyr Phe Glu
                3540                3545                3550
```

-continued

| | | | | | | | | | | | | | | |
|---|---|---|---|---|---|---|---|---|---|---|---|---|---|---|
| Tyr | Leu | Glu | Pro | Pro | Arg | Gln | Gly | Pro | Thr | Leu | Phe | Leu | Leu | Pro | Pro |
| | | 3555 | | | | | 3560 | | | | | 3565 | | | |
| Gly | Glu | Gly | Gly | Ala | Glu | Ser | Tyr | Phe | Asn | Asn | Ile | Val | Lys | Arg | Leu |
| | | 3570 | | | | 3575 | | | | | 3580 | | | | |
| Arg | Gln | Thr | Asn | Met | Val | Val | Phe | Asn | Asn | Tyr | Tyr | Leu | His | Ser | Lys |
| 3585 | | | | | 3590 | | | | | 3595 | | | | | 3600 |
| Arg | Leu | Arg | Thr | Phe | Glu | Glu | Leu | Ala | Glu | Met | Tyr | Leu | Asp | Gln | Val |
| | | | | 3605 | | | | | 3610 | | | | | 3615 | |
| Arg | Gly | Ile | Gln | Pro | His | Gly | Pro | Tyr | His | Phe | Ile | Gly | Trp | Ser | Phe |
| | | | 3620 | | | | | 3625 | | | | | 3630 | | |
| Gly | Gly | Ile | Leu | Ala | Met | Glu | Met | Ser | Arg | Arg | Leu | Val | Ala | Ser | Asp |
| | | | 3635 | | | | 3640 | | | | | 3645 | | | |
| Glu | Lys | Ile | Gly | Phe | Leu | Gly | Ile | Ile | Asp | Thr | Tyr | Phe | Asn | Val | Arg |
| | | 3650 | | | | 3655 | | | | | 3660 | | | | |
| Gly | Ala | Thr | Arg | Thr | Ile | Gly | Leu | Gly | Asp | Thr | Glu | Ile | Leu | Asp | Pro |
| 3665 | | | | | 3670 | | | | | 3675 | | | | | 3680 |
| Ile | His | His | Ile | Tyr | Asn | Pro | Asp | Pro | Ala | Asn | Phe | Gln | Arg | Leu | Pro |
| | | | | 3685 | | | | | 3690 | | | | | 3695 | |
| Ser | Ala | Thr | Asp | Arg | Ile | Val | Leu | Phe | Lys | Ala | Met | Arg | Pro | Asn | Asn |
| | | | 3700 | | | | | 3705 | | | | | 3710 | | |
| Lys | Tyr | Glu | Ser | Glu | Asn | Gln | Arg | Arg | Leu | Tyr | Glu | Tyr | Tyr | Asp | |
| | | 3715 | | | | | 3720 | | | | | 3725 | | | |

Figure 3:
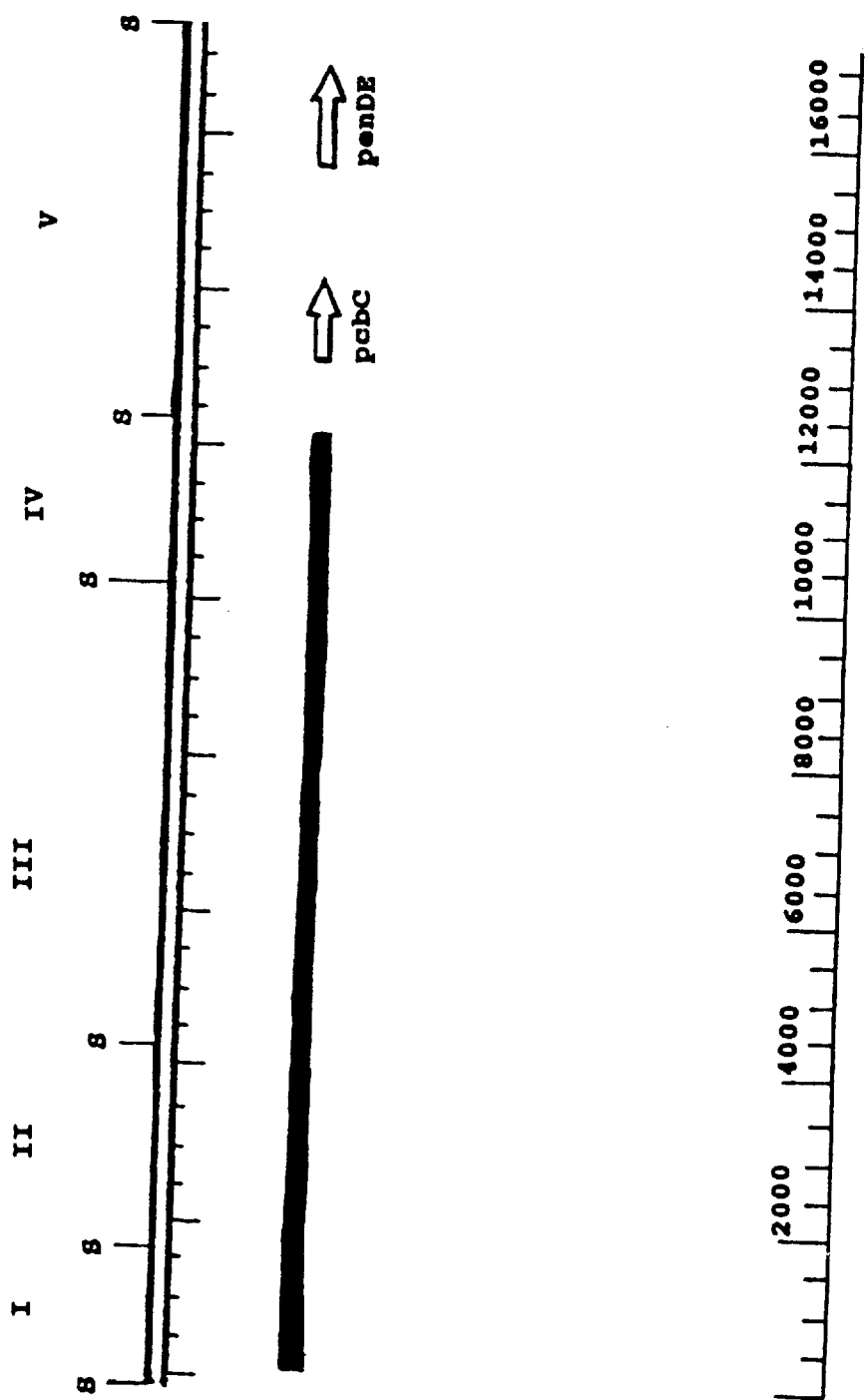
FIG. 3 shows a restriction site and functional map of the chromosomal region containing the ACV synthetase gene in *P. chrysogenum*. Probes that have been used for Northern hybridizations are indicated. The region containing the pcbAB gene is shaded. S=SalI.
Figure 4A:
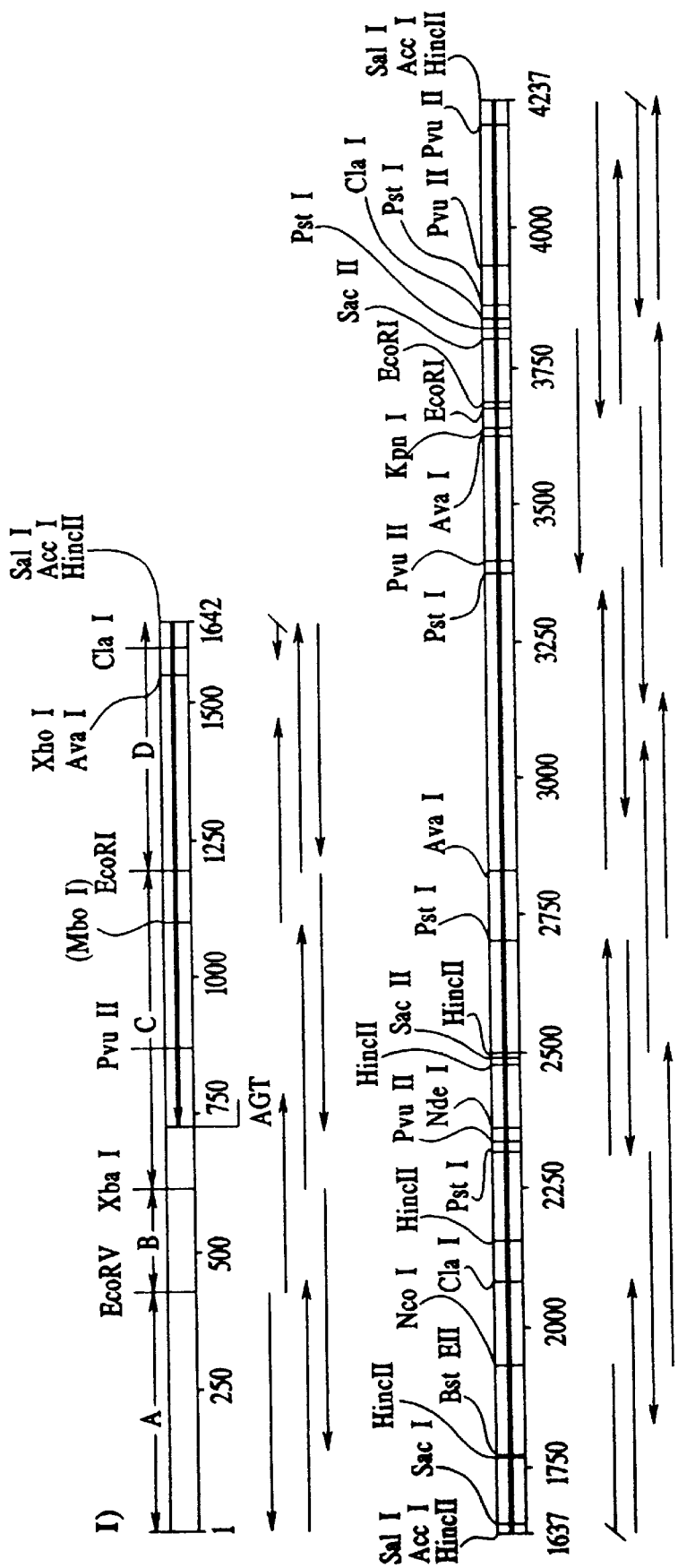
FIGS. 4A–4D show a detailed physical map of the region encoding the ACV synthetase gene in *P. chrysogenum*, including the sequencing strategy.
Figure 4B:
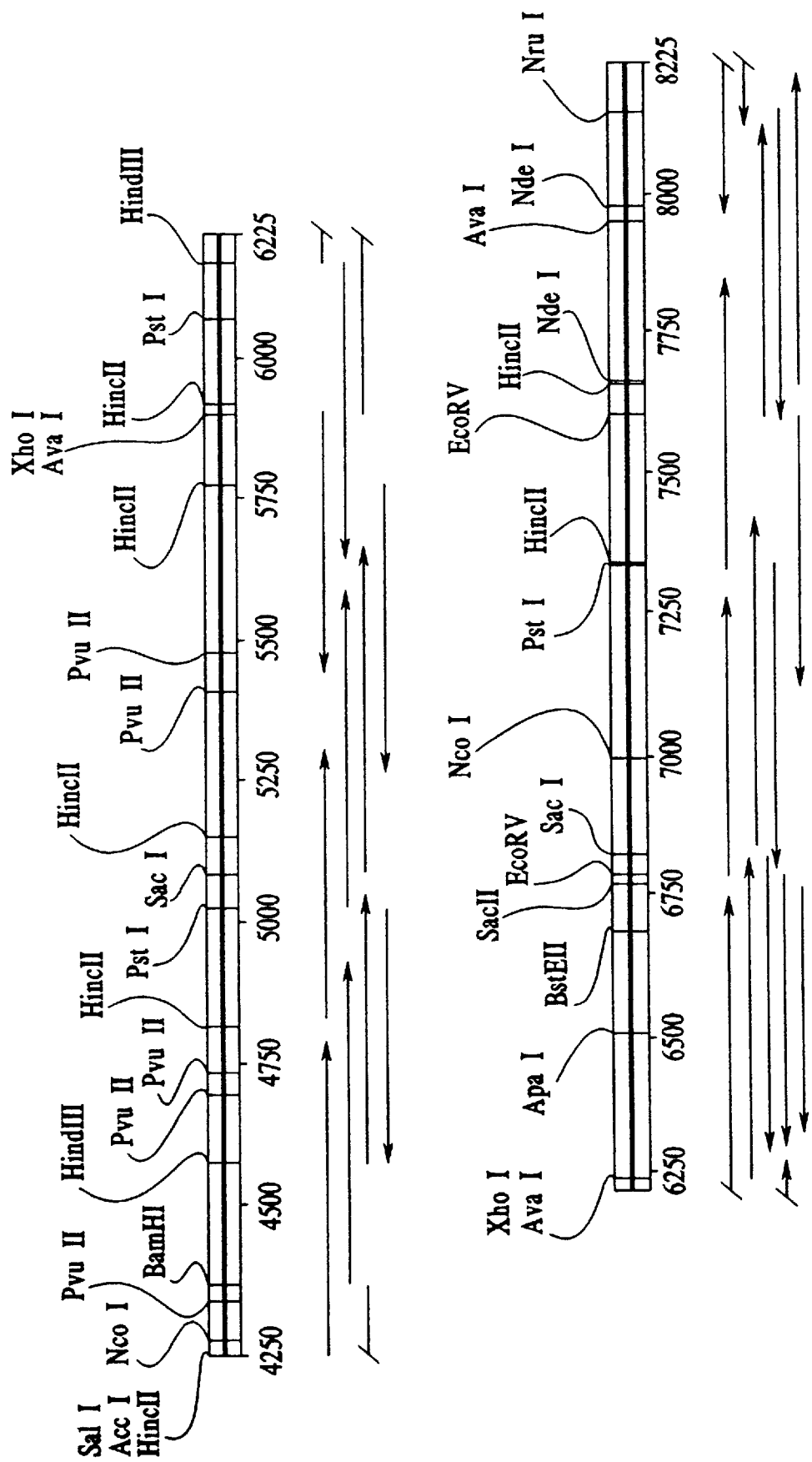
Figure 4C:
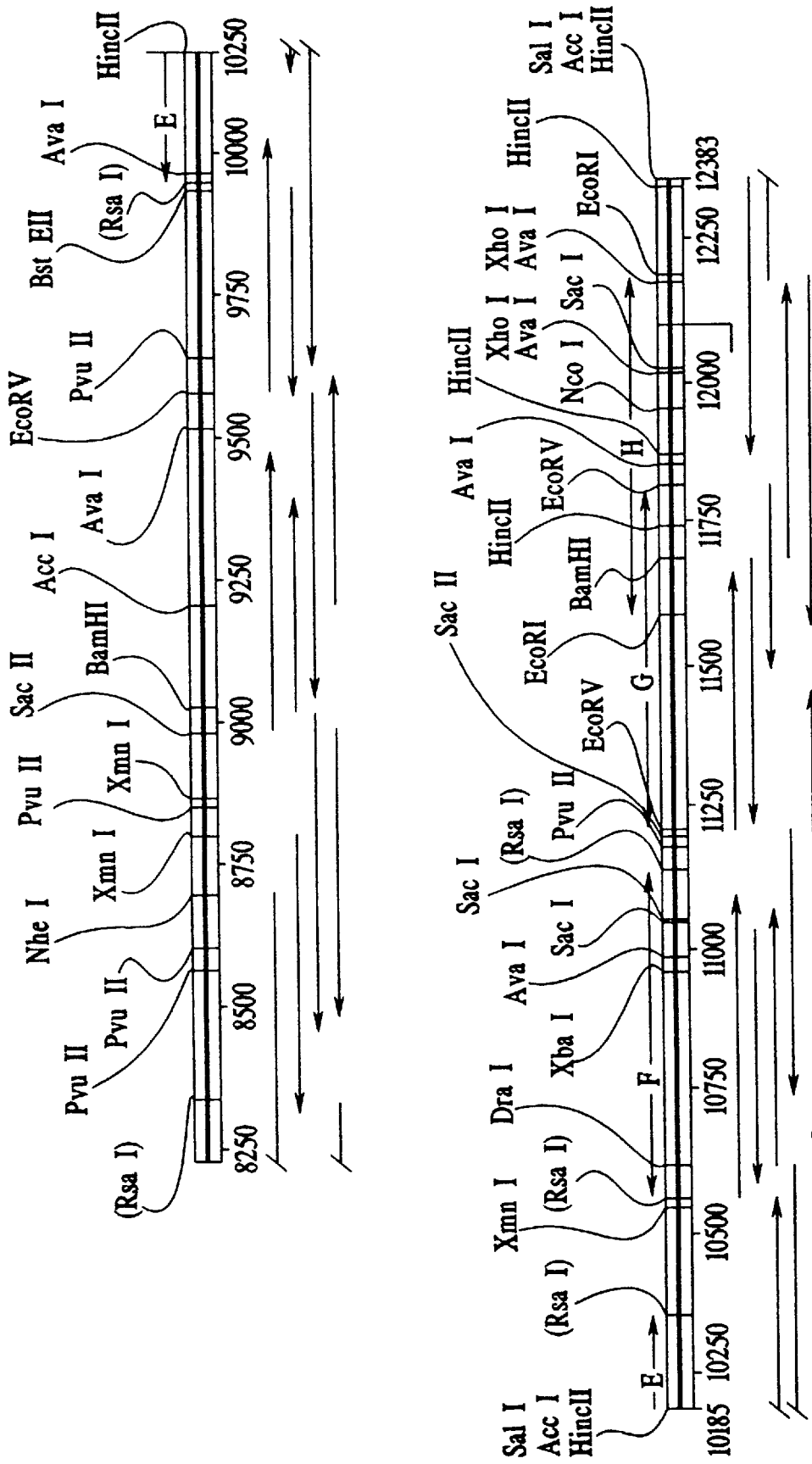
Figure 4D:
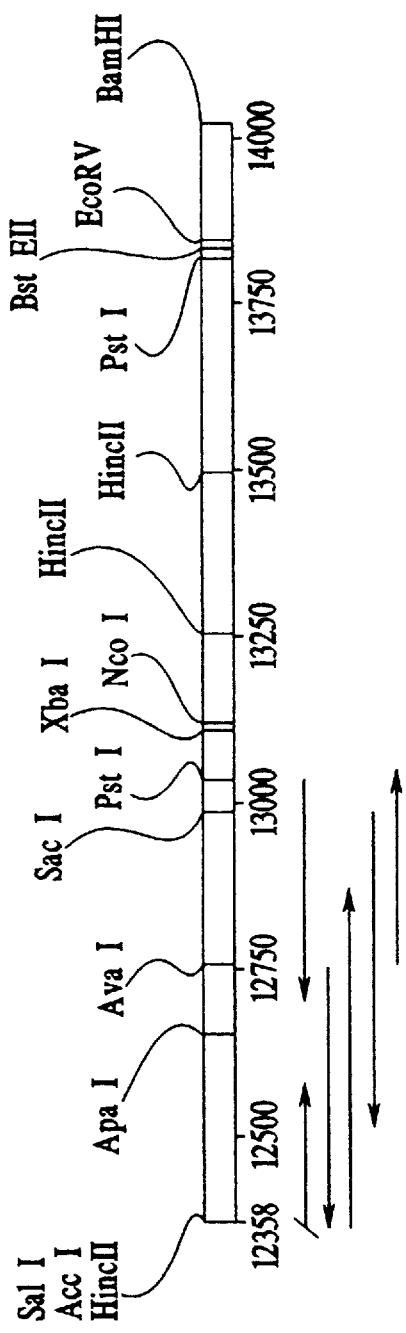

What is claimed is:

1. An expression cassette comprising as operably linked components, in the direction of transcription;
   (a) a promoter functional in a host cell;
   (b) a DNA of fewer than 15 kbp consisting essentially of an open reading frame encoding the enzyme δ-(L-α-aminoadipyl)-L-cysteinyl-D-valine synthetase which
       (i) has a restriction map as indicated in FIG. 3, FIG. 4, or FIG. 16,
   or (ii) encodes the sequence of SEQ ID NO: 25,
   or (iii) is contained in a vector selected from the group consisting of HM193, pPCV02, pSLACV-01, pSLACV-03A, and pSLACV-03B;
   and (c) a terminator functional in a host cell;
   wherein expression of said synthetase is under regulatory control of said promoter and terminator.

2. The expression cassette according to claim 1, wherein said promoter is active in the presence of glucose.

3. The expression cassette according to claim 1, wherein said promoter is selected from the group consisting of a *Penicillium chrysogenum* pgk promoter, an *E. coli* trp promoter, a Streptomyces aph promoter, and a tyrosinase promoter.

4. The expression cassette according to claim 1, wherein said promoter is functional in a filamentous fungus or a prokaryotic cell.

5. The expression cassette according to claim 1, wherein said enzyme encoded by said open reading frame exhibits δ-(L-α-aminoadipyl)-L-cysteinyl-D-valine synthetase activity.

6. A transformed host cell comprising:
   an expression cassette according to claim 1.

7. The cell according to claim 6, wherein said cell is selected from the group consisting of a prokaryotic cell and a filamentous fingus.

8. The cell according to claim 6, wherein said promoter is active in the presence of glucose.

9. The cell according to claim 6, wherein said promoter is selected from the group consisting of a *Penicillium chrysogenum* pgk promoter, an *E. coli* trp promoter, a Streptomyces aph promoter and a tyrosinase promoter.

10. The cell according to claim 6, wherein said cell is selected from the group consisting of a *Penicillium chrysogenum, Acremonium chrysogenum, Aspergillus nidulans*, and Streptomyces cell.

11. The cell according to claim 6, wherein said DNA is transcribed to RNA, and said RNA is translated.

12. A method for producing a β-lactam antibiotic, said method comprising:
    growing the transformed host cell according to claim 11 under industrial fermentation conditions to produce said β-lactam antibiotic, and optionally isolating said β-lactam antibiotic.

13. A method for increasing production of β-lactam antibiotics in a microbial host cell, said method comprising:
    transforming a host cell capable of producing β-lactam antibiotics with the expression cassette of claim 1 whereby transformed cells are obtained;
    selecting said transformed cells by means of a selection marker on said expression cassette;
    identifying as enhanced expressers said transformed cells producing increased amounts of β-lactam antibiotics as compared to untransformed cells and isolating said enhanced expressers;
    growing said enhanced expressers whereby enhanced production of β-lactam antibiotics in a microbial host is obtained;
    and optionally isolating said β-lactam antibiotics.

14. A method for producing δ-(L-α-aminoadipyl)-L-cysteinyl-D-valine synthetase in a host cell, said method comprising:

growing the transformed host cell of claim 11 under conditions whereby said ACVS is produced and optionally isolated.

15. The method according to any one of claims 12, 13, or 14, wherein said host cell is a Streptomyces or a filamentous fungus.

16. The method according to claim 15, wherein said filamentous fungus is selected from the group consisting of *Penicillium chrysogenum, Acremonium chrysogenum,* and *Aspergillus nidulans*.

17. In a method for in vitro synthesis of δ-(L-α-aminoadipyl)-L-cysteinyl-D-valine using a cell-free extract obtained from cells which produce β-lactam antibiotics, the improvement which comprises:

adding δ-(L-α-aminoadipyl)-L-cysteinyl-D-valine synthetase obtained according to the method of claim 14 to said cell-free extract.

18. An isolated DNA of fewer than 15 kbp consisting essentially of an open reading frame encoding the enzyme δ-(L-α-aminoadipyl)-L-cysteinyl-D-valine synthetase which has a restriction map as indicated in FIG. 3 or FIG. 4.

19. An isolated DNA of fewer than 15 kbp consisting essentially of an open reading frame encoding the enzyme δ-(L-α-aminoadipyl)-L-cysteinyl-D-valine synthetase which has a restriction map as indicated in FIG. 16.

20. An isolated DNA of fewer than 15 kbp consisting essentially of an open reading frame encoding the enzyme δ-(L-α-aminoadipyl)-L-cysteinyl-D-valine synthetase wherein said DNA encodes the sequence of SEQ ID NO: 25.

21. An isolated DNA of fewer than 15 kbp consisting essentially of an open reading frame encoding the enzyme δ-(L-α-aminoadipyl)-L-cysteinyl-D-valine synthetase which is contained in a vector selected from the group consisting of HM193, pPCV02, pSLACV-01, pSLACV-03A, and pSLACV-03B.

22. The DNA according to any of claims 18, 19, 20 or 21, wherein said DNA is obtained from a filamentous fungus species selected from the group consisting of *Penicillium chrysogenum, Acremonium chrysogenum,* and *Aspergillus nidulans*.

23. The DNA according to any one of claims 18, 19, 20 or 21, wherein said DNA is obtained from a bacterium belonging to the genus Flavobacterium or Streptomyces.

24. The DNA according to any one of claims 18, 19, 20 or 21, wherein said enzyme encoded by said open reading frame exhibits δ-(L-α-aminoadipyl)-L-cysteinyl-D-valine synthetase activity.

25. An isolated DNA comprising:

(a) a DNA according to any one of claims 18, 19, 20 or 21; and (b) a promoter selected from the group consisting of a *Penicillium chrysogenum* pgk promoter, a trp promoter, a Streptomyces aph promoter, and a tyrosinase promoter.

26. Plasmid pPCV02, pPCV03, pMA-ACVS, pSLACV-01, pSLACV-03A or pSLACV-03B.

27. A transformed *E. coli* cell comprising plasmid pMA-ACVS.

28. A transformed Streptomyces cell comprising plasmid pSLACV-01, pSLACV-03A or pSLACV-03B.

29. A transformed *Penicillium chrysogenum* cell or *Acremonium chrysogenum* or *Aspergillus nidulans* cell comprising plasmid pPCV02 or pPCV03.

30. The cell according to claim 6, wherein said cell is a eukaryotic cell.

* * * * *